US010196391B2

(12) United States Patent
Cheng et al.

(10) Patent No.: US 10,196,391 B2
(45) Date of Patent: Feb. 5, 2019

(54) TETRAHYDROPYRIDOPYRIMIDINES AND TETRAHYDROPYRIDOPYRIDINES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Zhanling Cheng, Shanghai (CN); Min Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/639,966

(22) Filed: Jun. 30, 2017

(65) Prior Publication Data

US 2017/0298067 A1    Oct. 19, 2017

Related U.S. Application Data

(63) Continuation of application No. PCT/EP2015/081257, filed on Dec. 28, 2015.

(30) Foreign Application Priority Data

Dec. 30, 2014   (WO) ................. PCT/CN2014/095480
Nov. 6, 2015    (WO) ................. PCT/CN2015/093954

(51) Int. Cl.
| | | |
|---|---|---|
| *A61K 31/506* | (2006.01) | |
| *A61K 31/519* | (2006.01) | |
| *C07D 471/04* | (2006.01) | |
| *A61K 31/444* | (2006.01) | |

(52) U.S. Cl.
CPC .......... *C07D 471/04* (2013.01); *A61K 31/444* (2013.01); *A61K 31/506* (2013.01); *A61K 31/519* (2013.01)

(58) Field of Classification Search
CPC .................................................. C07D 471/04
USPC .................................................. 514/1, 264.1
See application file for complete search history.

(56) References Cited

U.S. PATENT DOCUMENTS

| | | | | |
|---|---|---|---|---|
| 8,492,392 | B2 * | 7/2013 | Breslin ................. | C07D 519/00 |
| | | | | 514/264.1 |
| 9,845,322 | B2 * | 12/2017 | Cheng ................... | C07D 471/04 |
| 2015/0197519 | A1 | 7/2015 | Bifulco, Jr. et al. | |

FOREIGN PATENT DOCUMENTS

| | | |
|---|---|---|
| WO | 02/064574 A2 | 8/2002 |
| WO | 2005/035526 A1 | 4/2005 |
| WO | 2006/035061 A1 | 4/2006 |
| WO | 2009/042193 A1 | 2/2009 |
| WO | 2010/138430 A1 | 2/2010 |
| WO | 2011/022213 A1 | 2/2011 |
| WO | 2013016197 A1 | 1/2013 |
| WO | 2013/049352 A2 | 4/2013 |
| WO | 2014/106019 A2 | 3/2014 |

OTHER PUBLICATIONS

Acs et al., Proc Natl Acad Sci USA 84:4641-4644 ( 1987).
Ansel et al., "Pharmaceutical Dosage Forms and Drug Delivery Systems" 6th Ed.:456-457 (1995).
Bastin et al., "Salt Selection and Optimisation Procedures for Pharmaceutical New Chemical Entitites"Organic Process Research & Development 4:427-435 (2000).
Belloni et al., "IFN-αinhibits HBV transcription and replication in cell culture and in humanized mice by targeting the epigenetic regulation of the nuclear cccDNa minichromosome" J Clin Invest 122(2):529-537 (Feb. 2012).
Buster et al., "Peginterferon alpha-2b is safe and effective in HBeAg-Positive chronic hepatitis B patients with advanced fibrosis"Hepatology 46:388-394 ( 2007).
Fisicaro et al., "Antiviral intrahepatic T-cell responses can be restored by blocking programmed death-1 pathway in chronic hepatitis B"Gastroenterology 138:682-693 ( 2010).
Geng et al., "Small-molecule inhibitors for the treatment of hepatitis B virus documented in patents" Mini Reviews in Medicinal Chemistry 13(5):749-776 (Apr. 1, 2013).
Janssen et al., "Pegylated interferon alfa-2b alone or in combination with lamivudine for HBeAg-positive chronic hepatitis B: a randomised trial" Lancet 365:123-129 (Jan. 8, 2005).
Kondo et al., "Hepatitis B surface antigen could contribute to the immunopathogenesis of hepatitis B virus infection" ISRN Gastroenterology (Article ID 935295), 2013.
Kondo et al., "Recovery of functional cytotoxic T lymphocytes during lamivudine therapy by acquiring muti-specificity" J Med Virol 74:425-433 ( 2004).
Kumar et al., "Hepatitis B virus regulatory HBx protein binds to adaptor protein IPS-1 and inhibits the activation of beta interferon" J Virol 85(2):987-995 (Jan. 2011).

(Continued)

*Primary Examiner* — My-Chau T. Tran
(74) *Attorney, Agent, or Firm* — Brian Buckwalter

(57) ABSTRACT

The invention provides novel compounds having the general formula:

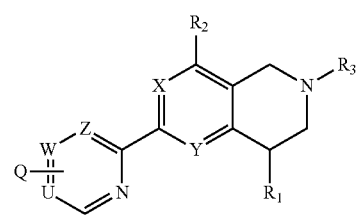

wherein $R^1$, $R^2$, $R^3$, Q, U, W, Z, X and Y are as described herein, compositions including the compounds and methods of using the compounds. These compounds are HbsAg inhibitors and are useful as medicaments for the treatment or prophylaxis of HBV infection.

12 Claims, No Drawings

(56) References Cited

OTHER PUBLICATIONS

Lambert et al., "Posttranslational N-glycosylation of the hepatitis B virus large envelope protein" Virol J 4( Suppl 1-9):45 (May 2007).

Locarnini, S., "Molecular virology and the development of resistant mutants: implications for therapy" Semin Liver Dis 25( Suppl 1):9-19 ( 2005).

Mao et al., "Indoleamine 2,3-dioxygenase mediates the antiviral effect of gagamma interferon against hepatitis B virus in human hepatocyte-derived cells" J Virol 85(2):1048-1057 (Jan. 2011).

Mao et al., "Inhibition of hepatitis B virus replication by the host zinc finger antiviral protein" PLoS Pathogens 9(7 Suppl 1-18):e1003494 (Jul. 2013).

Marcellin et al., "Peginterferon alfa-2a alone, lamivudine alone, and the two in combination in patients with HBeAg-negative chronic hepatitis B" New E J Med 351(12):1206-1217 (Sep. 16, 2004).

Nayersina et al., "HLA A2 restricted cytotoxic T lymphocyte responses to multiple hepatitis B surface antigen epitopes during hepatitis B virus infection" J Immunol 150:4659-4671 (May 15, 1993).

Op den Brouw et al., "Hepatitis B virus surface antigen impairs myeloid dendritic cell function: a possible immune escape mechanism of hepatitis B virus" Immunol 126:280-290 ( 2008).

Quasdorff et al., "Control of hepatitis B virus at the level of transcription" J Viral Hepatitis 17:527-536 ( 2010).

Schulze et al., "Hepatitis B virus infection initiates with a large surface protein-dependent binding to heparan sulfate proteoglycans" Hepatology 46:1759-1768 ( 2007).

Shi et al., "Hepatitis B virus suppresses the functional interaction between natural killer cells and plasmacytoid dendritic cells" J Viral Hepatitis 19:e26-e33 ( 2012).

Wieland et al., "Stealth and cunning: hepatitis B and hepatitis C viruses" J Virol 79(15):9369-9380 (Aug. 2005).

Woltman et al., "Hepatitis B virus lacks immune activating capacity, but actively inhibits plasmacytoid dendritic cell function" PLoS ONE 6(1 Suppl 1-14):e15324 (Jan. 2011).

Yan et al., "Molecular determinants of hepatitis B and D virus entry restriction in mouse sodium taurocholate cotransporting polypeptide" J Virol 87(14):7977-7991 (Jul. 2013).

CAS Registry Database, 338791-44-9, May 29, 2001.

\* cited by examiner

TETRAHYDROPYRIDOPYRIMIDINES AND TETRAHYDROPYRIDOPYRIDINES FOR THE TREATMENT AND PROPHYLAXIS OF HEPATITIS B VIRUS INFECTION

The present invention relates to organic compounds useful for therapy and/or prophylaxis in a mammal, and in particular HBsAg (HBV Surface antigen) inhibitors useful for treating HBV infection.

FIELD OF THE INVENTION

The present invention relates to novel tetrahydropyridopyrimidines and tetrahydropyridopyridines having pharmaceutical activity, their manufacture, pharmaceutical compositions containing them and their potential use as medicaments.

The present invention relates to compounds of formula I

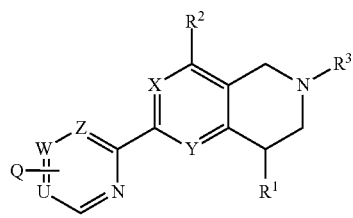

(I)

wherein $R^1$ to $R^3$, Q, U, W, X, Y and Z are as described below, or to pharmaceutically acceptable salts, or to enantiomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

The present invention relates to the use of a compound of formula I,

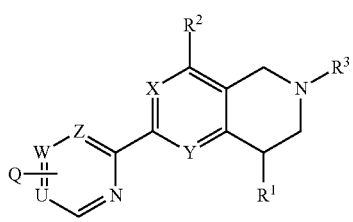

wherein
$R^1$ is hydrogen, $C_{1-6}$alkyl, or halo$C_{1-6}$alkyl;
$R^2$ is $C_{1-6}$alkyl, $C_{2-6}$alkenyl, $C_{1-6}$alkoxy, hydrogen, hydroxy, halo$C_{1-6}$alkyl, phenyl$C_{1-6}$alkoxy, amino, $C_{1-6}$alkylamino or di$C_{1-6}$alkylamino;
$R^3$ is phenyl; phenyl substituted by one, two or three substituents independently selected from $C_{1-6}$alkyl, $C_{3-7}$cycloalkyl, halogen, halo$C_{1-6}$alkyl, cyano, nitro, —C(=O)O$R^4$, —O$R^5$, —SO$_2R^6$ and —C(=O)N$R^7R^8$; thiophenyl; thiophenyl substituted by one, two or three substituents independently selected from $C_{1-6}$alkyl, $C_{1-6}$alkyoxy and halogen; furanyl; furanyl substituted by one, two or three substituents independently selected from $C_{1-6}$alky, $C_{1-6}$alkyoxy and halogen; N-containing heteroaryl; or N-containing heteroaryl substituted with one, two or three substituents independently selected from $C_{1-6}$alky, $C_{1-6}$alkyoxy, halogen, halo$C_{1-6}$alkyl, cyano, nitro, —C(=O)O$R^4$, —O$R^5$ and —SO$_2R^6$; wherein,
$R^4$ is hydrogen or $C_{1-6}$alkyl;
$R^5$ is hydrogen, $C_{1-6}$alkyl, halo$C_{1-6}$alkyl, hydroxy$C_{1-6}$alkyl, $C_{1-6}$alkoxy$C_{1-6}$alkyl or phenyl$C_{1-6}$alkyl;
$R^6$ is $C_{1-6}$alkyl, halo$C_{1-6}$alkyl, amino, $C_{1-6}$alkyamino or di$C_{1-6}$alkyamino;
$R^7$ and $R^8$ are independently selected from hydrogen, $C_{1-6}$alkyl, halo$C_{1-6}$alkyl, hydroxy$C_{1-6}$alkyl and $C_{1-6}$alkoxy$C_{1-6}$alkyl;
Q is hydrogen, $C_{1-6}$alkyl, $C_{1-6}$alkoxy, halogen, or halo$C_{1-6}$alkyl;
U, W and Z are independently selected from C and N;
one of X and Y is N, and the other one is C or N;

or pharmaceutically acceptable salts, or enantiomers for the preparation of a medicament for the treatment or prophylaxis of HBV infection.

The present invention also relates to a compound of formula I, wherein
$R^1$ is hydrogen, $C_{1-6}$alkyl, or halo$C_{1-6}$alkyl;
$R^2$ is $C_{1-6}$alkyl, $C_{2-6}$alkenyl, $C_{1-6}$alkoxy, hydrogen, hydroxy, halo$C_{1-6}$alkyl, phenyl$C_{1-6}$alkoxy, amino, $C_{1-6}$alkylamino or di$C_{1-6}$alkylamino;
$R^3$ is phenyl; phenyl substituted by one, two or three substituents independently selected from $C_{1-6}$alkyl, $C_{3-7}$cycloalkyl, halogen, halo$C_{1-6}$alkyl, cyano, nitro, —C(=O)O$R^4$, —O$R^5$, —SO$_2R^6$ and —C(=O)N$R^7R^8$; thiophenyl; thiophenyl substituted by one, two or three substituents independently selected from $C_{1-6}$alkyl, $C_{1-6}$alkyoxy and halogen; furanyl; furanyl substituted by one, two or three substituents independently selected from $C_{1-6}$alky, $C_{1-6}$alkyoxy and halogen; N-containing heteroaryl; or N-containing heteroaryl substituted with one, two or three substituents independently selected from $C_{1-6}$alky, $C_{1-6}$alkyoxy, halogen, halo$C_{1-6}$alkyl, cyano, nitro, —C(=O)O$R^4$, —O$R^5$ and —SO$_2R^6$; wherein,
$R^4$ is hydrogen or $C_{1-6}$alkyl;
$R^5$ is hydrogen, $C_{1-6}$alkyl, halo$C_{1-6}$alkyl, hydroxy$C_{1-6}$alkyl, $C_{1-6}$alkoxy$C_{1-6}$alkyl or phenyl$C_{1-6}$alkyl;
$R^6$ is $C_{1-6}$alkyl, halo$C_{1-6}$alkyl, amino, $C_{1-6}$alkyamino or di$C_{1-6}$alkyamino;
$R^7$ and $R^8$ are independently selected from hydrogen, $C_{1-6}$alkyl, halo$C_{1-6}$alkyl, hydroxy$C_{1-6}$alkyl and $C_{1-6}$alkoxy$C_{1-6}$alkyl;
Q is hydrogen, $C_{1-6}$alkyl, $C_{1-6}$alkoxy, halogen, or halo$C_{1-6}$alkyl;
U, W and Z are independently selected from C and N;
one of X and Y is N, and the other one is C or N;
with the proviso that 6-(4-nitrophenyl)-2-(2-pyridyl)-7,8-dihydro-5H-pyrido[4,3-d]pyrimidine is excluded;
or pharmaceutically acceptable salts, or enantiomers thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy.

The term "halogen" means fluorine, chlorine, bromine or iodine.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "haloC$_{1-6}$alkyl" group is difluoromethyl or trifluoromethyl.

The term "C$_{2-6}$alkenyl" denotes a monovalent linear or branched hydrocarbon group of 2 to 6 carbon atoms with at least one double bond. In particular embodiments, C$_{2-6}$alkenyl has 2 to 4 carbon atoms with at least one double bond. Examples of C$_{2-6}$alkenyl include ethenyl, propenyl, prop-2-enyl, isopropenyl, n-butenyl, and iso-butenyl. Particular "C$_{2-6}$alkenyl" group is propenyl or ethenyl.

The term "amino" denotes a group of the formula —NR'R" wherein R' and R" are independently hydrogen, C$_{1-6}$alkyl, C$_{1-6}$alkoxy, C$_{3-7}$cycloalkyl, heteroC$_{3-7}$cycloalkyl, aryl or heteroaryl. Alternatively, R' and R", together with the nitrogen to which they are attached, can form a heteroC$_{3-7}$cycloalkyl. The term "C$_{1-6}$alkylamino" denotes a group wherein R' is hydrogen and R" is a C$_{1-6}$alkyl. Examples of C$_{1-6}$alkylamino groups include methylamino and ethylamino. The term "diC$_{1-6}$alkylamino" denotes a group wherein R' and R" are both C$_{1-6}$alkyl. Examples of diC$_{1-6}$alkylamino groups include dimethylamino, methylethylamino, diethylamino and di(1-methylethyl)amino.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "N-containing heteroaryl" refers to a heteroaryl group as defined above wherein at least one of the heteroatoms is N. Examples for "N-containing heteroaryl" include pyrrolyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, isothiazolyl, indolyl, isoindolyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular "N-containing heteroaryl" is pyridinyl, pyrimidinyl, thiazolyl, isoquinolinyl or quinolinyl. More particularly "N-containing heteroaryl" is pyridinyl The term "enantiomer" denotes two stereoisomers of a compound which are non-superimposable mirror images of one another.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides organic compounds useful for therapy and/or prophylaxis in a mammal, and in particular to HBsAg (HBV Surface antigen) inhibitors useful for treating HBV infection.

One embodiment of the present is (i) the use of a compound of formula I

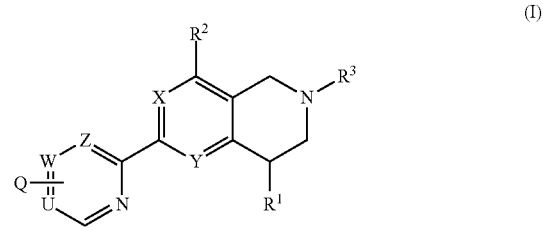

(I)

wherein
R$^1$ is hydrogen, C$_{1-6}$alkyl, or haloC$_{1-6}$alkyl;
R$^2$ is C$_{1-6}$alkyl, C$_{2-6}$alkenyl, C$_{1-6}$alkoxy, hydrogen, hydroxy, haloC$_{1-6}$alkyl, phenylC$_{1-6}$alkoxy, amino, C$_{1-6}$alkylamino or diC$_{1-6}$alkylamino;
R$^3$ is phenyl; phenyl substituted by one, two or three substituents independently selected from C$_{1-6}$alkyl, C$_{3-7}$cycloalkyl, halogen, haloC$_{1-6}$alkyl, cyano, nitro, —C(=O)OR$^4$, —OR$^5$, —SO$_2$R$^6$ and —C(=O)NR$^7$R$^8$; thiophenyl; thiophenyl substituted by one, two or three substituents independently selected from C$_{1-6}$alkyl, C$_{1-6}$alkyoxy and halogen; furanyl; furanyl substituted by one, two or three substituents independently selected from C$_{1-6}$alky, C$_{1-6}$alkyoxy and halogen; N-containing heteroaryl; or N-containing heteroaryl substituted with one, two or three substituents independently selected from C$_{1-6}$alky, C$_{1-6}$alkyoxy, halogen, haloC$_{1-6}$alkyl, cyano, nitro, —C(=O)OR$^4$, —OR$^5$ and —SO$_2$R$^6$; wherein,
R$^4$ is hydrogen or C$_{1-6}$alkyl;
R$^5$ is hydrogen, C$_{1-6}$alkyl, haloC$_{1-6}$alkyl, hydroxyC$_{1-6}$alkyl, C$_{1-6}$alkoxyC$_{1-6}$alkyl or phenylC$_{1-6}$alkyl;
R$^6$ is C$_{1-6}$alkyl, haloC$_{1-6}$alkyl, amino, C$_{1-6}$alkyamino or diC$_{1-6}$alkyamino;
R$^7$ and R$^8$ are independently selected from hydrogen, C$_{1-6}$alkyl, haloC$_{1-6}$alkyl, hydroxyC$_{1-6}$alkyl and C$_{1-6}$alkoxyC$_{1-6}$alkyl;

Q is hydrogen, $C_{1-6}$alkyl, $C_{1-6}$alkoxy, halogen, or halo$C_{1-6}$alkyl;

U, W and Z are independently selected from C and N;

one of X and Y is N, and the other one is C or N;

or pharmaceutically acceptable salts, or enantiomers for the preparation of a medicament for the treatment or prophylaxis of HBV infection.

Another embodiment of the present invention is (ii) a compound of formula I, wherein $R^1$ is hydrogen, $C_{1-6}$alkyl, or halo $C_{1-6}$alkyl;

$R^2$ is $C_{1-6}$alkyl, $C_{2-6}$alkenyl, $C_{1-6}$alkoxy, hydrogen, hydroxy, halo$C_{1-6}$alkyl, phenyl$C_{1-6}$alkoxy, amino, $C_{1-6}$alkylamino or di$C_{1-6}$alkylamino;

$R^3$ is phenyl; phenyl substituted by one, two or three substituents independently selected from $C_{1-6}$alkyl, $C_{3-7}$cycloalkyl, halogen, halo $C_{1-6}$alkyl, cyano, nitro, —C(=O)OR$^4$, —OR$^5$, —SO$_2$R$^6$ and —C(=O)NR$^7$R$^8$; thiophenyl; thiophenyl substituted by one, two or three substituents independently selected from $C_{1-6}$alkyl, $C_{1-6}$alkyoxy and halogen; furanyl; furanyl substituted by one, two or three substituents independently selected from $C_{1-6}$alky, $C_{1-6}$alkyoxy and halogen; N-containing heteroaryl; or N-containing heteroaryl substituted with one, two or three substituents independently selected from $C_{1-6}$alky, $C_{1-6}$alkyoxy, halogen, halo $C_{1-6}$alkyl, cyano, nitro, —C(=O)OR$^4$, —OR$^5$ and —SO$_2$R$^6$; wherein, $R^4$ is hydrogen or $C_{1-6}$alkyl;

$R^5$ is hydrogen, $C_{1-6}$alkyl, halo$C_{1-6}$alkyl, hydroxy $C_{1-6}$alkyl, $C_{1-6}$alkoxy $C_{1-6}$alkyl or phenyl $C_{1-6}$alkyl;

$R^6$ is $C_{1-6}$alkyl, halo $C_{1-6}$alkyl, amino, $C_{1-6}$alkyamino or di$C_{1-6}$alkyamino;

$R^7$ and $R^8$ are independently selected from hydrogen, $C_{1-6}$alkyl, halo $C_{1-6}$alkyl, hydroxy$C_{1-6}$alkyl and $C_{1-6}$alkoxy $C_{1-6}$alkyl;

Q is hydrogen, $C_{1-6}$alkyl, $C_{1-6}$alkoxy, halogen, or halo $C_{1-6}$alkyl;

U, W and Z are independently selected from C and N;

one of X and Y is N, and the other one is C or N;

with the proviso that 6-(4-nitrophenyl)-2-(2-pyridyl)-7,8-dihydro-5H-pyrido[4,3-d]pyrimidine is excluded;

or pharmaceutically acceptable salts, or enantiomers thereof.

A further embodiment of present invention is (iii) a compound of formula I according to embodiment (ii), wherein $R^1$ is hydrogen or $C_{1-6}$alkyl;

$R^2$ is $C_{1-6}$alkyl, $C_{2-6}$alkenyl, $C_{1-6}$alkoxy, hydrogen, hydroxy, phenyl $C_{1-6}$alkoxy or $C_{1-6}$alkylamino;

$R^3$ is phenyl; phenyl substituted by one, two or three substituents independently selected from $C_{1-6}$alkyl, $C_{3-7}$cycloalkyl, halogen, halo $C_{1-6}$alkyl, cyano, nitro, —C(=O)OR$^4$, —OR$^5$, —SO$_2$R$^6$ and —C(=O)NR$^7$R$^8$; thiazolyl; quinolyl substituted by $C_{1-6}$alkoxy; isoquinolyl substituted by $C_{1-6}$alkoxy; pyrimidinyl substituted with one or two substituents independently selected from $C_{1-6}$alkyoxy and halogen; pyridinyl; or pyridinyl substituted with one or two substituents independently selected from $C_{1-6}$alkyoxy and halogen; wherein, $R^4$ is hydrogen or $C_{1-6}$alkyl;

$R^5$ is hydrogen, $C_{1-6}$alkyl, halo $C_{1-6}$alkyl, hydroxy $C_{1-6}$alkyl, $C_{1-6}$alkoxy $C_{1-6}$alkyl or phenyl $C_{1-6}$alkyl;

$R^6$ is $C_{1-6}$alkyl, halo $C_{1-6}$alkyl, $C_{1-6}$alkyamino or di$C_{1-6}$alkyamino;

$R^7$ and $R^8$ are independently selected from hydrogen, $C_{1-6}$alkyl, halo $C_{1-6}$alkyl, hydroxy$C_{1-6}$alkyl and $C_{1-6}$alkoxy $C_{1-6}$alkyl;

Q is hydrogen, $C_{1-6}$alkyl, $C_{1-6}$alkoxy or halogen;

U is C, W is C, and Z is C; or one of U, W and Z is N, and the other two are C; one of X and Y is N, and the other one is C or N;

or pharmaceutically acceptable salts, or enantiomers thereof.

A further embodiment of the present invention is (iv) a compound of formula I according to embodiment (ii) or (iii), or pharmaceutically acceptable salts, or enantiomers thereof, wherein U is C;

W is C;

X is N;

Y is C or N;

Z is C or N.

Another embodiment of the present invention is (v) a compound of formula I according to embodiments (ii) to (iv), or pharmaceutically acceptable salts, or enantiomers thereof, wherein $R^1$ is hydrogen, $R^2$ is hydrogen, Q is hydrogen.

Another embodiment of the present invention is (vi) a compound of formula I according to anyone of embodiments (ii) to (v), or pharmaceutically acceptable salts, or enantiomers thereof, wherein $R^3$ is phenyl substituted by one, two or three substituents independently selected from halogen, cyano, nitro, carboxy, —OR$^5$ and —SO$_2$R$^6$, wherein $R^5$ is $C_{1-6}$alkyl, halo $C_{1-6}$alkyl, hydroxy $C_{1-6}$alkyl, $C_{1-6}$alkoxy $C_{1-6}$alkyl or phenyl $C_{1-6}$alkyl; $R^6$ is $C_{1-6}$alkyl; or pyridinyl substituted by one or two substituents independently selected from halogen and $C_{1-6}$alkoxy.

A further embodiment of the present invention is (vii) a compound of formula I according to anyone of embodiments (ii) to (vi), or pharmaceutically acceptable salts, or enantiomers thereof, wherein $R^3$ is phenyl substituted by one, two or three substituents independently selected from fluoro, chloro, cyano, nitro, carboxy, methoxy, ethoxy, propoxy, difluoromethoxy, trifluoromethoxy, hydroxyethoxy, hydroxypropoxy, methoxyethoxy, methoxypropoxy, benzyloxy and methylsulfonyl; or pyridinyl substituted by one or two substituents independently selected from fluoro, chloro and methoxy.

Another embodiment of the present invention is (viii) a compound of formula I according to embodiment (ii) or (iii), wherein $R^1$ is hydrogen;

$R^2$ is hydrogen;

$R^3$ is phenyl substituted by one, two or three substituents independently selected from halogen, cyano and —OR$^5$, wherein $R^5$ is $C_{1-6}$alkyl, hydroxy $C_{1-6}$alkyl or $C_{1-6}$alkoxy $C_{1-6}$alkyl; or pyridinyl substituted by one or two substituents independently selected from halogen and $C_{1-6}$alkoxy;

Q is hydrogen;

U is C;

W is C, Z is C; or one of W and Z is N, and the other one is C;

X is N;

Y is C or N;

or pharmaceutically acceptable salts, or enantiomers thereof.

A further embodiment of present invention is (ix) a compound of formula I according to embodiment (ii), (iii) or (viii), wherein $R^1$ is hydrogen;

$R^2$ is hydrogen;

$R^3$ is phenyl substituted by one, two or three substituents independently selected from fluoro, chloro, cyano, methoxy, ethoxy, hydroxypropoxy and methoxypropoxy; or pyridinyl substituted by one or two substituents independently selected from fluoro, chloro and methoxy;

Q is hydrogen;

U is C;
W is C, Z is C; or one of W and Z is N, and the other one is C;
X is N;
Y is C or N;
or pharmaceutically acceptable salts, or enantiomers thereof.

Another embodiment of the present invention is (x) the use of a compound having the general formula I:

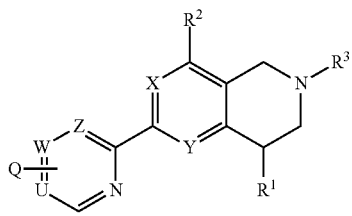

(I)

wherein
$R^1$ is hydrogen, $C_{1-6}$alkyl, or halo $C_{1-6}$alkyl;
$R^2$ is $C_{1-6}$alkyl, $C_{2-6}$alkenyl, $C_{1-6}$alkoxy, hydrogen, hydroxy, halo $C_{1-6}$alkyl, phenyl $C_{1-6}$alkoxy, amino, $C_{1-6}$alkylamino or di$C_{1-6}$alkylamino;
$R^3$ is phenyl; phenyl substituted by one, two or three groups independently selected from $C_{1-6}$alkyl, $C_{3-7}$cycloalkyl, halogen, halo $C_{1-6}$alkyl, cyano, nitro, —C(=O)OR$^4$, —OR$^5$ and —SO$_2$R$^6$; thiophenyl; thiophenyl substituted by one, two or three groups independently selected from $C_{1-6}$alkyl, $C_{1-6}$alkyoxy and halogen; furanyl; furanyl substituted by one, two or three groups independently selected from $C_{1-6}$alky, $C_{1-6}$alkyoxy and halogen; N-containing heteroaryl; or N-containing heteroaryl substituted with one, two or three groups independently selected from $C_{1-6}$alky, $C_{1-6}$alkyoxy, halogen, halo $C_{1-6}$alkyl, cyano, nitro, C(=O)OR$^4$, OR$^5$ and —SO$_2$R$^6$; wherein,
$R^4$ is hydrogen or $C_{1-6}$alkyl;
$R^5$ is hydrogen, $C_{1-6}$alkyl, halo $C_{1-6}$alkyl, hydroxy $C_{1-6}$alkyl, $C_{1-6}$alkoxy $C_{1-6}$alkyl or phenyl $C_{1-6}$alkyl;
$R^6$ is $C_{1-6}$alkyl, halo $C_{1-6}$alkyl, amino, $C_{1-6}$alkyamino or di$C_{1-6}$alkyamino;
Q is hydrogen, $C_{1-6}$alkyl, $C_{1-6}$alkoxy, halogen, or halo $C_{1-6}$alkyl;
U, W and Z are independently selected from C and N;
one of X and Y is N, and the other one is C or N;
or pharmaceutically acceptable salts, or enantiomers for the preparation of a medicament for the treatment or prophylaxis of HBV infection.

A further embodiment of the present invention is (xi) a compound of formula I, wherein
$R^1$ is hydrogen, $C_{1-6}$alkyl, or halo $C_{1-6}$alkyl;
$R^2$ is $C_{1-6}$alkyl, $C_{2-6}$alkenyl, $C_{1-6}$alkoxy, hydrogen, hydroxy, halo$C_{1-6}$alkyl, phenyl$C_{1-6}$alkoxy, amino, $C_{1-6}$alkylamino or di$C_{1-6}$alkylamino;
$R^3$ is phenyl; phenyl substituted by one, two or three groups independently selected from $C_{1-6}$alkyl, $C_{3-7}$cycloalkyl, halogen, halo $C_{1-6}$alkyl, cyano, nitro, —C(=O)OR$^4$, —OR$^5$ and —SO$_2$R$^6$; thiophenyl; thiophenyl substituted by one, two or three groups independently selected from $C_{1-6}$alkyl, $C_{1-6}$alkyoxy and halogen; furanyl; furanyl substituted by one, two or three groups independently selected from $C_{1-6}$alky, $C_{1-6}$alkyoxy and halogen; N-containing heteroaryl; or N-containing heteroaryl substituted with one, two or three groups independently selected from $C_{1-6}$alky, $C_{1-6}$alkyoxy, halogen, halo $C_{1-6}$alkyl, cyano, nitro, C(=O)OR$^4$, OR$^5$ and —SO$_2$R$^6$; wherein,
$R^4$ is hydrogen or $C_{1-6}$alkyl;
$R^5$ is hydrogen, $C_{1-6}$alkyl, halo $C_{1-6}$alkyl, hydroxy $C_{1-6}$alkyl, $C_{1-6}$alkoxy $C_{1-6}$alkyl or phenyl $C_{1-6}$alkyl;
$R^6$ is $C_{1-6}$alkyl, halo $C_{1-6}$alkyl, amino, $C_{1-6}$alkyamino or di$C_{1-6}$alkyamino;
Q is hydrogen, $C_{1-6}$alkyl, $C_{1-6}$alkoxy, halogen, or halo $C_{1-6}$alkyl;
U, W and Z are independently selected from C and N;
one of X and Y is N, and the other one is C or N;
with the proviso that 6-(4-nitrophenyl)-2-(2-pyridyl)-7,8-dihydro-5H-pyrido[4,3-d]pyrimidine is excluded;
or pharmaceutically acceptable salts, or enantiomers thereof.

Another embodiment of present invention is (xii) a compound of formula I according to embodiment (xi), wherein
$R^1$ is hydrogen or $C_{1-6}$alkyl;
$R^2$ is $C_{1-6}$ alkyl, $C_{2-6}$alkenyl, $C_{1-6}$alkoxy, hydrogen, hydroxy, phenyl$C_{1-6}$alkoxy or $C_{1-6}$alkylamino;
$R^3$ is phenyl; phenyl substituted by one, two or three groups independently selected from $C_{1-6}$alkyl, $C_{3-7}$cycloalkyl, halogen, cyano, nitro, —C(=O)OR$^4$, —OR$^5$ and —SO$_2$R$^6$; N-containing heteroaryl; or N-containing heteroaryl substituted with one or two groups independently selected from $C_{1-6}$alkyoxy and halogen; wherein,
$R^4$ is hydrogen or $C_{1-6}$alkyl;
$R^5$ is hydrogen, $C_{1-6}$alkyl, halo $C_{1-6}$alkyl, hydroxy $C_{1-6}$alkyl, $C_{1-6}$alkoxy $C_{1-6}$alkyl or phenyl $C_{1-6}$alkyl;
$R^6$ is $C_{1-6}$alkyl, halo $C_{1-6}$alkyl, $C_{1-6}$alkyamino or di$C_{1-6}$ alkyamino;
Q is hydrogen, $C_{1-6}$alkyl, $C_{1-6}$alkoxy or halogen;
U is C, W is C, and Z is C; or one of U, W and Z is N, and the other two are C;
one of X and Y is N, and the other one is C or N;
with the proviso that 6-(4-nitrophenyl)-2-(2-pyridyl)-7,8-dihydro-5H-pyrido[4,3-d]pyrimidine is excluded;
or pharmaceutically acceptable salts, or enantiomers thereof.

A further embodiment of the present invention is (xiii) a compound of formula I according to embodiment (xi) or (xii), or pharmaceutically acceptable salts, or enantiomers thereof, wherein
U is C;
W is C;
X is N;
Y is C or N;
Z is C or N.

Another embodiment of the present invention is (xiv) a compound of formula I according to anyone of embodiments (xi) to (xiii), or pharmaceutically acceptable salts, or enantiomers thereof, wherein $R^1$ is hydrogen, $R^2$ is hydrogen, Q is hydrogen.

Another embodiment of the present invention is (xv) a compound of formula I according to anyone of embodiments (xi) to (xiv), or pharmaceutically acceptable salts, or enantiomers thereof, wherein $R^3$ is phenyl substituted by one, two or three groups independently selected from halogen, cyano, nitro, carboxy, —OR$^5$ and —SO$_2$R$^6$, wherein $R^5$ is $C_{1-6}$alkyl, halo$C_{1-6}$alkyl, hydroxy$C_{1-6}$alkyl, $C_{1-6}$alkoxy$C_{1-6}$alkyl or phenyl $C_{1-6}$alkyl; $R^6$ is $C_{1-6}$alkyl.

A further embodiment of the present invention is (xvi) a compound of formula I according to anyone of embodiments (xi) to (xv), or pharmaceutically acceptable salts, or enantiomers thereof, wherein $R^3$ is phenyl substituted by one, two or three groups independently selected from fluoro, chloro, cyano, nitro, carboxy, methoxy, ethoxy, propoxy, difluoromethoxy, trifluoromethoxy, hydroxyethoxy, hydroxypropoxy, methoxyethoxy, methoxypropoxy, benzyloxy and methyl sulfonyl.

Another embodiment of the present invention is (xvii) a compound of formula I according to embodiment (xi) or (xii), wherein
$R^1$ is hydrogen;
$R^2$ is hydrogen;
$R^3$ is phenyl substituted by one, two or three groups independently selected from halogen, cyano and —$OR^5$, wherein $R^5$ is $C_{1-6}$alkyl, hydroxy $C_{1-6}$alkyl or $C_{1-6}$alkoxy $C_{1-6}$alkyl; or pyridinyl substituted by halogen and $C_{1-6}$alkoxy;
Q is hydrogen;
U is C;
W is C, Z is C; or one of W and Z is N, and the other one is C;
X is N;
Y is C or N;
or pharmaceutically acceptable salts, or enantiomers thereof.

A further embodiment of present invention is (xviii) a compound of formula I according to embodiment (xi), (xii) or (xvii), wherein
$R^1$ is hydrogen;
$R^2$ is hydrogen;
$R^3$ is phenyl substituted by one, two or three groups independently selected from fluoro, chloro, cyano, methoxy, ethoxy, hydroxypropoxy and methoxypropoxy; or pyridinyl substituted by fluoro and methoxy;
Q is hydrogen;
U is C;
W is C, Z is C; or one of W and Z is N, and the other one is C;
X is N;
Y is C or N;
or pharmaceutically acceptable salts, or enantiomers thereof.

Particular compounds of formula I according to the invention are the following:
6-(4-Methylsulfonylphenyl)-2-(2-pyridyl)-7,8-dihydro-5H-pyrido[4,3-d]pyrimidine;
2-(5-Fluoro-2-pyridyl)-6-(4-methylsulfonylphenyl)-7,8-dihydro-5H-pyrido[4,3-d]pyrimidine;
2-(5-Methyl-2-pyridyl)-6-(4-methylsulfonylphenyl)-7,8-dihydro-5H-pyrido[4,3-d]pyrimidine;
2-(3-Methyl-2-pyridyl)-6-(4-methylsulfonylphenyl)-7,8-dihydro-5H-pyrido[4,3-d]pyrimidine;
2-(5-Methoxy-2-pyridyl)-6-(4-methylsulfonylphenyl)-7,8-dihydro-5H-pyrido[4,3-d]pyrimidine;
2-(5-Chloro-2-pyridyl)-6-(4-methylsulfonylphenyl)-7,8-dihydro-5H-pyrido[4,3-d]pyrimidine;
8-Ethyl-6-(4-methylsulfonylphenyl)-2-(2-pyridyl)-7,8-dihydro-5H-pyrido[4,3-d]pyrimidine;
N-Methyl-4-[2-(2-pyridyl)-7,8-dihydro-5H-pyrido[4,3-d]pyrimidin-6-yl]benzenesulfonamide;
N,N-Dimethyl-4-[2-(2-pyridyl)-7,8-dihydro-5H-pyrido[4,3-d]pyrimidin-6-yl]benzenesulfonamide;
6-(3,4-Difluorophenyl)-2-(2-pyridyl)-7,8-dihydro-5H-pyrido[4,3-d]pyrimidine;
6-(3-Methyl sulfonylphenyl)-2-(2-pyridyl)-7,8-dihydro-5H-pyrido[4,3-d]pyrimidine;
2-(2-Pyridyl)-6-[4-(trifluoromethylsulfonyl)phenyl]-7,8-dihydro-5H-pyrido[4,3-d]pyrimidine;
6-(3,5-Difluorophenyl)-2-(2-pyridyl)-7,8-dihydro-5H-pyrido[4,3-d]pyrimidine;
6-(2,4-Difluorophenyl)-2-(2-pyridyl)-7,8-dihydro-5H-pyrido[4,3-d]pyrimidine;
Methyl 2-fluoro-4-[2-(2-pyridyl)-7,8-dihydro-5H-pyrido[4,3-d]pyrimidin-6-yl]benzoate;
Methyl 5-bromo-2-[2-(2-pyridyl)-7,8-dihydro-5H-pyrido[4,3-d]pyrimidin-6-yl]benzoate;
6-(3,4-Difluoro-5-methoxy-phenyl)-2-(2-pyridyl)-7,8-dihydro-5H-pyrido[4,3-d]pyrimidine;
2,3-Difluoro-5-[2-(2-pyridyl)-7,8-dihydro-5H-pyrido[4,3-d]pyrimidin-6-yl]phenol;
6-[3,4-Difluoro-5-(3-methoxypropoxy)phenyl]-2-(2-pyridyl)-7,8-dihydro-5H-pyrido[4,3-d]pyrimidine;
6-(3-Benzyloxy-4,5-difluoro-phenyl)-2-(2-pyridyl)-7,8-dihydro-5H-pyrido[4,3-d]pyrimidine;
6-(3-Ethoxy-4,5-difluoro-phenyl)-2-(2-pyridyl)-7,8-dihydro-5H-pyrido[4,3-d]pyrimidine;
6-(3,4-Difluoro-5-propoxy-phenyl)-2-(2-pyridyl)-7,8-dihydro-5H-pyrido[4,3-d]pyrimidine;
6-[3,4-Difluoro-5-(2-methoxyethoxy)phenyl]-2-(2-pyridyl)-7,8-dihydro-5H-pyrido[4,3-d]pyrimidine;
6-(3,4-Difluoro-5-methoxy-phenyl)-2-(4-methoxy-2-pyridyl)-7,8-dihydro-5H-pyrido[4,3-d]pyrimidine;
6-(3,4-Difluoro-5-methoxy-phenyl)-2-(6-methoxy-2-pyridyl)-7,8-dihydro-5H-pyrido[4,3-d]pyrimidine;
6-(3,4-Difluoro-5-methoxy-phenyl)-2-pyrimidin-2-yl-7,8-dihydro-5H-pyrido[4,3-d]pyrimidine;
6-(4,5-Difluoro-2-methoxy-phenyl)-2-(2-pyridyl)-7,8-dihydro-5H-pyrido[4,3-d]pyrimidine;
6-(3,4-Difluoro-5-methoxy-phenyl)-2-pyrazin-2-yl-7,8-dihydro-5H-pyrido[4,3-d]pyrimidine
6-(3,4-Difluoro-5-methoxy-phenyl)-2-pyrimidin-4-yl-7,8-dihydro-5H-pyrido[4,3-d]pyrimidine;
6-(3,4-Difluoro-2-methoxy-phenyl)-2-(2-pyridyl)-7,8-dihydro-5H-pyrido[4,3-d]pyrimidine;
Ethyl 4-[2-(2-pyridyl)-7,8-dihydro-5H-pyrido[4,3-d]pyrimidin-6-yl]benzoate;
4-[2-(2-Pyridyl)-7,8-dihydro-5H-pyrido[4,3-d]pyrimidin-6-yl]benzoic acid;
6-(2-Nitrophenyl)-2-(2-pyridyl)-7,8-dihydro-5H-pyrido[4,3-d]pyrimidine;
6-(2-Methoxy-4-nitro-phenyl)-2-(2-pyridyl)-7,8-dihydro-5H-pyrido[4,3-d]pyrimidine
2,6-Bis(2-pyridyl)-7,8-dihydro-5H-pyrido[4,3-d]pyrimidine;
6-(5-Chloro-2-pyridyl)-2-(2-pyridyl)-7,8-dihydro-5H-pyrido[4,3-d]pyrimidine;
2-(2-Pyridyl)-6-pyrimidin-2-yl-7,8-dihydro-5H-pyrido[4,3-d]pyrimidine;
6-(2-Benzyloxy-4-fluoro-phenyl)-2-(2-pyridyl)-7,8-dihydro-5H-pyrido[4,3-d]pyrimidine;
2-(2-Pyridyl)-6-(3-pyridyl)-7,8-dihydro-5H-pyrido[4,3-d]pyrimidine;
6-(3-Fluoro-5-methyl-phenyl)-2-(2-pyridyl)-7,8-dihydro-5H-pyrido[4,3-d]pyrimidine;
6-(3-Bromo-5-fluoro-phenyl)-2-pyrimidin-2-yl-7,8-dihydro-5H-pyrido[4,3-d]pyrimidine;
6-(3-Cyclopropyl-5-fluoro-phenyl)-2-pyrimidin-2-yl-7,8-dihydro-5H-pyrido[4,3-d]pyrimidine;
2-Pyrimidin-2-yl-6-[3-(trifluoromethoxy)phenyl]-7,8-dihydro-5H-pyrido[4,3-d]pyrimidine;
6-[3-Methoxy-4-(3-methoxypropoxy)phenyl]-2-(2-pyridyl)-7,8-dihydro-5H-pyrido[4,3-d]pyrimidine;
6-(4-Chlorophenyl)-2-(2-pyridyl)-7,8-dihydro-5H-pyrido[4,3-d]pyrimidine;
6-(4-Benzyloxyphenyl)-2-(2-pyridyl)-7,8-dihydro-5H-pyrido[4,3-d]pyrimidine;
6-(p-Tolyl)-2-(2-pyridyl)-7,8-dihydro-5H-pyrido[4,3-d]pyrimidine;

8-Methyl-6-(4-nitrophenyl)-2-(2-pyridyl)-7,8-dihydro-5H-pyrido[4,3-d]pyrimidine;
6-(3,4-Dichlorophenyl)-2-(2-pyridyl)-7,8-dihydro-5H-pyrido[4,3-d]pyrimidine;
6-(4-Methoxyphenyl)-2-(2-pyridyl)-7,8-dihydro-5H-pyrido[4,3-d]pyrimidine;
6-(3-Bromo-4-fluoro-phenyl)-2-(2-pyridyl)-7,8-dihydro-5H-pyrido[4,3-d]pyrimidine;
6-(4-Bromo-3-fluoro-phenyl)-2-(2-pyridyl)-7,8-dihydro-5H-pyrido[4,3-d]pyrimidine;
6-(4-Benzyloxy-3-fluoro-phenyl)-2-(2-pyridyl)-7,8-dihydro-5H-pyrido[4,3-d]pyrimidine;
6-(4-Ethoxy-3-fluoro-phenyl)-2-(2-pyridyl)-7,8-dihydro-5H-pyrido[4,3-d]pyrimidine;
6-(3-Fluoro-4-propoxy-phenyl)-2-(2-pyridyl)-7,8-dihydro-5H-pyrido[4,3-d]pyrimidine;
6-[3-Fluoro-4-(3-methoxypropoxy)phenyl]-2-(2-pyridyl)-7,8-dihydro-5H-pyrido[4,3-d]pyrimidine;
6-[3-Methoxy-4-(2-methoxyethoxy)phenyl]-2-(2-pyridyl)-7,8-dihydro-5H-pyrido[4,3-d]pyrimidine;
6-[4-Methoxy-3-(2-methoxyethoxy)phenyl]-2-(2-pyridyl)-7,8-dihydro-5H-pyrido[4,3-d]pyrimidine;
6-(3,4-Dimethoxyphenyl)-2-(2-pyridyl)-7,8-dihydro-5H-pyrido[4,3-d]pyrimidine;
2-Methoxy-4-[2-(2-pyridyl)-7,8-dihydro-5H-pyrido[4,3-d]pyrimidin-6-yl]benzonitrile;
6-(2,3-Difluoro-4-methoxy-phenyl)-2-pyrimidin-2-yl-7,8-dihydro-5H-pyrido[4,3-d]pyrimidine;
6-(4-Chloro-3-methoxy-phenyl)-2-(2-pyridyl)-7,8-dihydro-5H-pyrido[4,3-d]pyrimidine;
6-[3-(Difluoromethoxy)phenyl]-2-pyrimidin-2-yl-7,8-dihydro-5H-pyrido[4,3-d]pyrimidine;
6-(4-Benzyloxy-3,5-difluoro-phenyl)-2-(2-pyridyl)-7,8-dihydro-5H-pyrido[4,3-d]pyrimidine;
2-Methoxy-4-[2-(2-pyridyl)-7,8-dihydro-5H-pyrido[4,3-d]pyrimidin-6-yl]benzoic acid;
2-Ethoxy-4-[2-(2-pyridyl)-7,8-dihydro-5H-pyrido[4,3-d]pyrimidin-6-yl]benzoic acid;
2-Butoxy-4-[2-(2-pyridyl)-7,8-dihydro-5H-pyrido[4,3-d]pyrimidin-6-yl]benzoic acid;
6-(5-Chloro-4-methoxy-pyrimidin-2-yl)-2-(2-pyridyl)-7,8-dihydro-5H-pyrido[4,3-d]pyrimidine;
6-(5-Chloro-2-methoxy-pyrimidin-4-yl)-2-(2-pyridyl)-7,8-dihydro-5H-pyrido[4,3-d]pyrimidine;
6-(3-Fluoro-4-methoxy-2-pyridyl)-2-(2-pyridyl)-7,8-dihydro-5H-pyrido[4,3-d]pyrimidine;
6-(5-Fluoro-4-methoxy-2-pyridyl)-2-(2-pyridyl)-7,8-dihydro-5H-pyrido[4,3-d]pyrimidine;
6-(5-Fluoro-6-methoxy-2-pyridyl)-2-pyrimidin-2-yl-7,8-dihydro-5H-pyrido[4,3-d]pyrimidine;
6-(3,5-Dimethoxyphenyl)-2-pyrimidin-2-yl-7,8-dihydro-5H-pyrido[4,3-d]pyrimidine;
6-(8-Methoxy-3-isoquinolyl)-2-pyrimidin-2-yl-7,8-dihydro-5H-pyrido[4,3-d]pyrimidine;
6-(2-Methoxy-7-quinolyl)-2-pyrimidin-2-yl-7,8-dihydro-5H-pyrido[4,3-d]pyrimidine;
3-Methoxy-5-(2-pyrimidin-2-yl-7,8-dihydro-5H-pyrido[4,3-d]pyrimidin-6-yl)benzonitrile;
2-Fluoro-6-methoxy-4-(2-pyrimidin-2-yl-7,8-dihydro-5H-pyrido[4,3-d]pyrimidin-6-yl)benzonitrile;
6-(4-Chloro-3-fluoro-5-methoxy-phenyl)-2-pyrimidin-2-yl-7,8-dihydro-5H-pyrido[4,3-d]pyrimidine;
6-(3-Chloro-4-fluoro-5-methoxy-phenyl)-2-pyrimidin-2-yl-7,8-dihydro-5H-pyrido[4,3-d]pyrimidine;
6-(4-Methylsulfonylphenyl)-2-(2-pyridyl)-3,5,7,8-tetrahydropyrido[4,3-d]pyrimidin-4-one;
4-Methoxy-6-(4-methylsulfonylphenyl)-2-pyrimidin-2-yl-7,8-dihydro-5H-pyrido[4,3-d]pyrimidine;
4-Ethoxy-6-(4-methylsulfonylphenyl)-2-pyrimidin-2-yl-7,8-dihydro-5H-pyrido[4,3-d]pyrimidine;
4-Benzyloxy-6-(4-methylsulfonylphenyl)-2-pyrimidin-2-yl-7,8-dihydro-5H-pyrido[4,3-d]pyrimidine;
6-(4-Methylsulfonylphenyl)-4-[(E)-prop-1-enyl]-2-pyrimidin-2-yl-7,8-dihydro-5H-pyrido[4,3-d]pyrimidine;
6-(4-Methylsulfonylphenyl)-4-propyl-2-pyrimidin-2-yl-7,8-dihydro-5H-pyrido[4,3-d]pyrimidine;
4-Ethyl-6-(4-methylsulfonylphenyl)-2-pyrimidin-2-yl-7,8-dihydro-5H-pyrido[4,3-d]pyrimidine;
4-Methyl-6-(4-methylsulfonylphenyl)-2-pyrimidin-2-yl-7,8-dihydro-5H-pyrido[4,3-d]pyrimidine;
N-Methyl-6-(4-methylsulfonylphenyl)-2-pyrimidin-2-yl-7,8-dihydro-5H-pyrido[4,3-d]pyrimidin-4-amine;
6-(4-Methylsulfonylphenyl)-2-(2-pyridyl)-7,8-dihydro-5H-1,6-naphthyridine;
6-(4-Fluoro-3-methoxy-phenyl)-2-(2-pyridyl)-7,8-dihydro-5H-pyrido[4,3-d]pyrimidine;
6-(3-Fluoro-5-methoxy-phenyl)-2-(2-pyridyl)-7,8-dihydro-5H-pyrido[4,3-d]pyrimidine;
6-(3-Methoxyphenyl)-2-(2-pyridyl)-7,8-dihydro-5H-pyrido[4,3-d]pyrimidine;
3-[2,3-Difluoro-5-[2-(2-pyridyl)-7,8-dihydro-5H-pyrido[4,3-d]pyrimidin-6-yl]phenoxy]propan-1-ol;
2-[2,3-Difluoro-5-[2-(2-pyridyl)-7,8-dihydro-5H-pyrido[4,3-d]pyrimidin-6-yl]phenoxy]ethanol;
2-(3,4-Difluoro-5-methoxy-phenyl)-6-pyrimidin-2-yl-3,4-dihydro-1H-2,7-naphthyridine;
2-(3,4-Difluoro-5-methoxy-phenyl)-6-(2-pyridyl)-3,4-dihydro-1H-2,7-naphthyridine;
6-(3,4-Difluoro-5-methoxy-phenyl)-2-pyrimidin-2-yl-7,8-dihydro-5H-1,6-naphthyridine;
6-(3-Chloro-5-methoxy-phenyl)-2-pyrimidin-2-yl-7,8-dihydro-5H-pyrido[4,3-d]pyrimidine;
6-(6-Fluoro-4-methoxy-2-pyridyl)-2-pyrimidin-2-yl-7,8-dihydro-5H-pyrido[4,3-d]pyrimidine;
6-[3-Methoxy-5-(trifluoromethyl)phenyl]-2-pyrimidin-2-yl-7,8-dihydro-5H-pyrido[4,3-d]pyrimidine;
3-Fluoro-5-(2-pyrimidin-2-yl-7,8-dihydro-5H-pyrido[4,3-d]pyrimidin-6-yl)benzonitrile;
Methyl 3-fluoro-5-(2-pyrimidin-2-yl-7,8-dihydro-5H-pyrido[4,3-d]pyrimidin-6-yl)benzoate;
3-Fluoro-N-methyl-5-(2-pyrimidin-2-yl-7,8-dihydro-5H-pyrido[4,3-d]pyrimidin-6-yl)benzamide;
3-Fluoro-5-(2-pyrimidin-2-yl-7,8-dihydro-5H-pyrido[4,3-d]pyrimidin-6-yl)-N-(2,2,2-trifluoroethyl)benzamide;
3-Fluoro-5-(2-pyrimidin-2-yl-7,8-dihydro-5H-pyrido[4,3-d]pyrimidin-6-yl)benzamide;
3-Fluoro-N-(3-methoxypropyl)-5-(2-pyrimidin-2-yl-7,8-dihydro-5H-pyrido[4,3-d]pyrimidin-6-yl)benzamide;
3-Fluoro-N-(5-hydroxypentyl)-5-(2-pyrimidin-2-yl-7,8-dihydro-5H-pyrido[4,3-d]pyrimidin-6-yl)benzamide;
6-(6-Chloro-4-methoxy-2-pyridyl)-2-pyrimidin-2-yl-7,8-dihydro-5H-pyrido[4,3-d]pyrimidine;
6-(2,6-Difluoro-4-pyridyl)-2-pyrimidin-2-yl-7,8-dihydro-5H-pyrido[4,3-d]pyrimidine;
6-(4,6-Difluoro-2-pyridyl)-2-pyrimidin-2-yl-7,8-dihydro-5H-pyrido[4,3-d]pyrimidine;
6-(4-Fluoro-6-methoxy-2-pyridyl)-2-pyrimidin-2-yl-7,8-dihydro-5H-pyrido[4,3-d]pyrimidine;
6-(2-Fluoro-6-methoxy-4-pyridyl)-2-pyrimidin-2-yl-7,8-dihydro-5H-pyrido[4,3-d]pyrimidine;
6-(4,6-Dichloro-2-pyridyl)-2-pyrimidin-2-yl-7,8-dihydro-5H-pyrido[4,3-d]pyrimidine;

6-(2,6-Dichloro-4-pyridyl)-2-pyrimidin-2-yl-7,8-dihydro-5H-pyrido[4,3-d]pyrimidine;
6-(4-Chloro-6-methoxy-2-pyridyl)-2-pyrimidin-2-yl-7,8-dihydro-5H-pyrido[4,3-d]pyrimidine;
6-(2-Chloro-6-methoxy-4-pyridyl)-2-pyrimidin-2-yl-7,8-dihydro-5H-pyrido[4,3-d]pyrimidine;
6-(3-Fluoro-5-methoxy-phenyl)-2-pyrimidin-2-yl-7,8-dihydro-5H-pyrido[4,3-d]pyrimidine;
6-[3-Fluoro-5-(trifluoromethoxy)phenyl]-2-pyrimidin-2-yl-7,8-dihydro-5H-pyrido[4,3-d]pyrimidine;
2-(2-Pyrimidin-2-yl-7,8-dihydro-5H-pyrido[4,3-d]pyrimidin-6-yl)thiazole;
or pharmaceutically acceptable salts, or enantiomers thereof.

More particularly, the invention relates to the following compounds of formula I:
6-(3,4-Difluoro-5-methoxy-phenyl)-2-(2-pyridyl)-7,8-dihydro-5H-pyrido[4,3-d]pyrimidine;
6-[3,4-Difluoro-5-(3-methoxypropoxy)phenyl]-2-(2-pyridyl)-7,8-dihydro-5H-pyrido[4,3-d]pyrimidine;
6-(3-Ethoxy-4,5-difluoro-phenyl)-2-(2-pyridyl)-7,8-dihydro-5H-pyrido[4,3-d]pyrimidine;
6-(3,4-Difluoro-5-methoxy-phenyl)-2-pyrimidin-2-yl-7,8-dihydro-5H-pyrido[4,3-d]pyrimidine;
6-(3,4-Difluoro-5-methoxy-phenyl)-2-pyrazin-2-yl-7,8-dihydro-5H-pyrido[4,3-d]pyrimidine;
2-Methoxy-4-[2-(2-pyridyl)-7,8-dihydro-5H-pyrido[4,3-d]pyrimidin-6-yl]benzonitrile;
6-(5-Fluoro-4-methoxy-2-pyridyl)-2-(2-pyridyl)-7,8-dihydro-5H-pyrido[4,3-d]pyrimidine;
2-Fluoro-6-methoxy-4-(2-pyrimidin-2-yl-7,8-dihydro-5H-pyrido[4,3-d]pyrimidin-6-yl)benzonitrile;
6-(3-Chloro-4-fluoro-5-methoxy-phenyl)-2-pyrimidin-2-yl-7,8-dihydro-5H-pyrido[4,3-d]pyrimidine;
6-(3-Fluoro-5-methoxy-phenyl)-2-(2-pyridyl)-7,8-dihydro-5H-pyrido[4,3-d]pyrimidine;
3-[2,3-Difluoro-5-[2-(2-pyridyl)-7,8-dihydro-5H-pyrido[4,3-d]pyrimidin-6-yl]phenoxy]propan-1-ol;
2-(3,4-Difluoro-5-methoxy-phenyl)-6-pyrimidin-2-yl-3,4-dihydro-1H-2,7-naphthyridine;
2-(3,4-Difluoro-5-methoxy-phenyl)-6-(2-pyridyl)-3,4-dihydro-1H-2,7-naphthyridine;
6-(3-Chloro-5-methoxy-phenyl)-2-pyrimidin-2-yl-7,8-dihydro-5H-pyrido[4,3-d]pyrimidine;
6-(6-Fluoro-4-methoxy-2-pyridyl)-2-pyrimidin-2-yl-7,8-dihydro-5H-pyrido[4,3-d]pyrimidine;
6-(6-Chloro-4-methoxy-2-pyridyl)-2-pyrimidin-2-yl-7,8-dihydro-5H-pyrido[4,3-d]pyrimidine;
6-(4,6-Dichloro-2-pyridyl)-2-pyrimidin-2-yl-7,8-dihydro-5H-pyrido[4,3-d]pyrimidine;
6-(3-Fluoro-5-methoxy-phenyl)-2-pyrimidin-2-yl-7,8-dihydro-5H-pyrido[4,3-d]pyrimidine;
or pharmaceutically acceptable salts, or enantiomers thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^3$, Q, U, W, X, Y and Z are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia (Scheme 1)

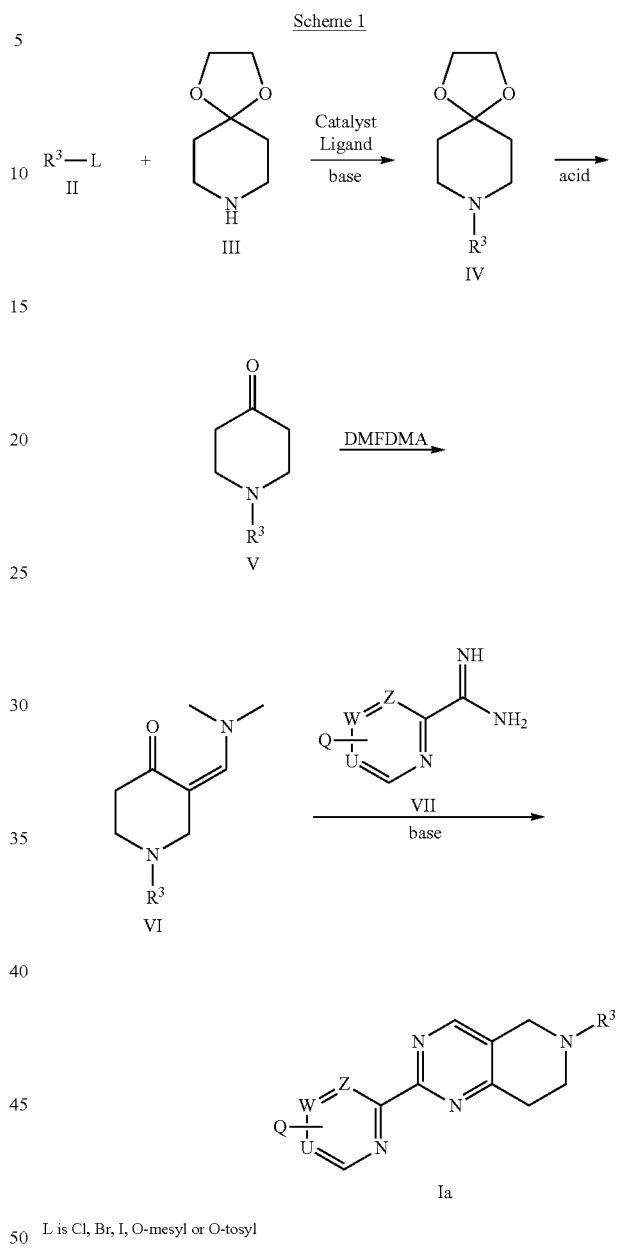

L is Cl, Br, I, O-mesyl or O-tosyl

The compound of formula Ia can be prepared according to Scheme 1.

Compound II is heated with compound III in the presence of a catalyst such as $Pd_2(dba)_3$ or $Pd(OAc)_2$, a ligand such as Ruphos, Sphos or BINAP and a base such as $Cs_2CO_3$ or t-BuONa in a suitable solvent such as 1,4-dioxane or toluene, to afford compound IV. Deprotection of compound IV under an acidic condition affords compound V. Reaction of compound V with DMFDMA in the absence or presence of a suitable solvent such as DMF or acetonitrile generates intermediate VI. Compound Ia can be obtained by cyclization of intermediate VI with compound VII in the presence of a base such as $K_2CO_3$, NaOMe or $Et_3N$, in a suitable solvent such as EtOH or MeOH.

General Synthetic Route for Compound Ib (Scheme 2)

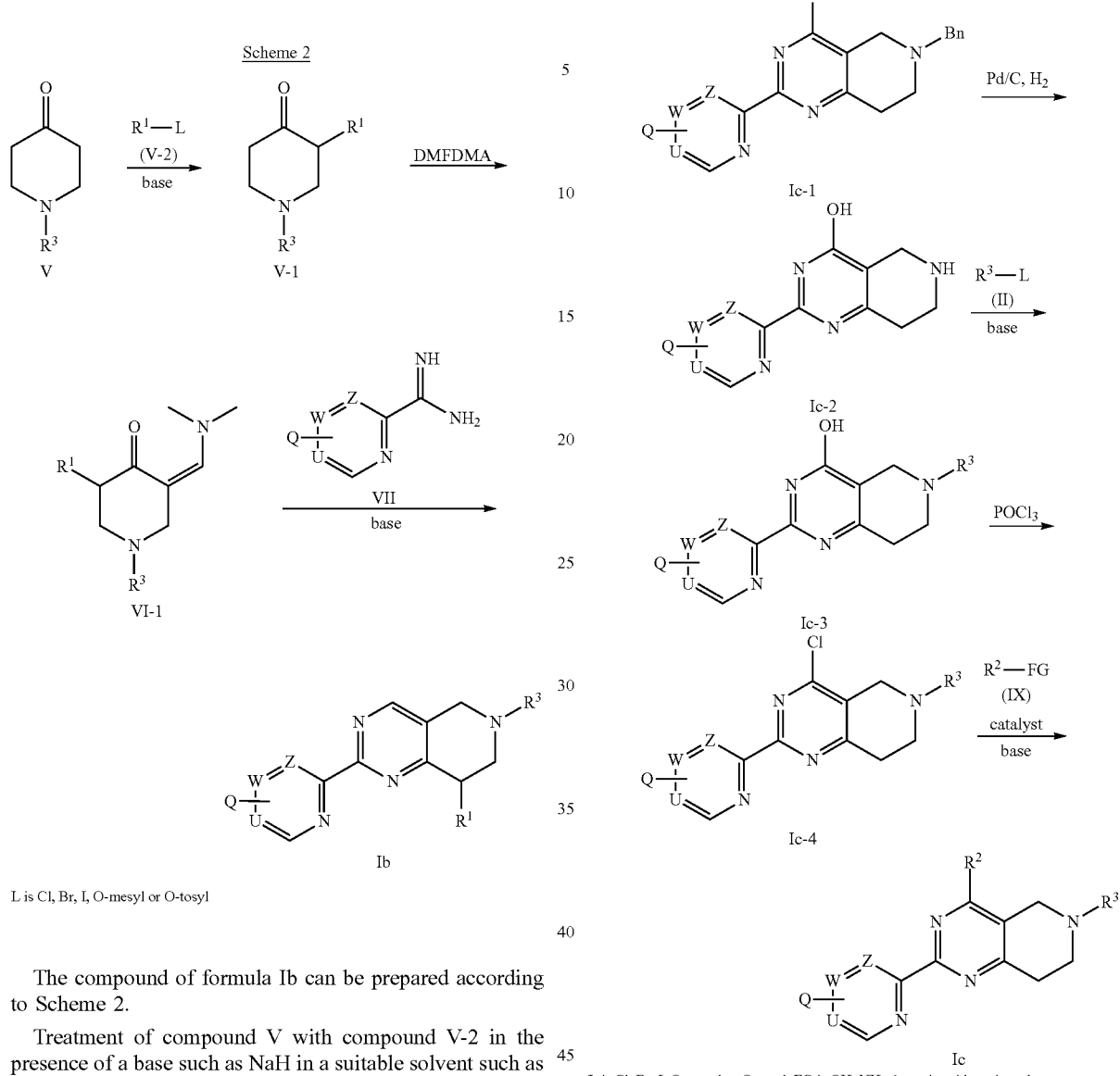

L is Cl, Br, I, O-mesyl or O-tosyl

The compound of formula Ib can be prepared according to Scheme 2.

Treatment of compound V with compound V-2 in the presence of a base such as NaH in a suitable solvent such as THF gives compound V-1. Compound V-1 can be converted to compound VI-1 by reacting with DMFDMA in a suitable solvent such as acetonitrile. Cyclization of compound VI-1 with compound VII affords compound VII-1. The reaction can be carried out under basic condition such as $K_2CO_3$, NaOMe or $Et_3N$, in a suitable solvent such as EtOH or MeOH.

General Synthetic Route for Compound Ic (Scheme 3)

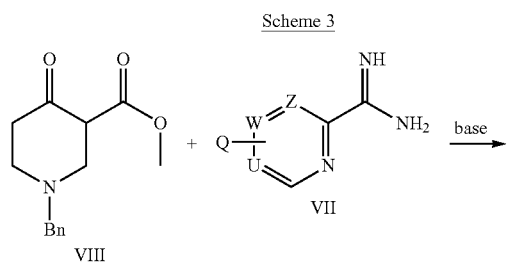

L is Cl, Br, I, O-mesyl or O-tosyl; FG is OH, $NH_2$, boronic acid or pinacol ester The compound of formula Ic can be prepared according to Scheme 3.

Cyclization of intermediate VIII with compound VII affords Compound Ic-1. The reaction can be carried out in the presence of a base such as $K_2CO_3$, NaOMe or $Et_3N$, in a suitable solvent such as EtOH or MeOH. Debenzylation under hydrogenation condition by using Pd/C in a suitable solvent such as THF, MeOH or EtOH affords compound Ic-2. Compound Ic-3 can be obtained by reaction of compound Ic-2 with compound II in the presence of a base such as $Cs_2CO_3$ or $K_2CO_3$ in a suitable solvent such as DMF or DMA. Compound Ic-3 was converted to compound Ic-4 by using $POCl_3$. Compound Ic can be obtained by reacting of compound Ic-4 with compound IX in the presence of a catalyst such as $Pd_2(dba)_3$, $Pd(OAc)_2$, $Pd(PPh_3)_4$ or $PdCl_2$(dppf) and a base such as $K_2CO_3$ or $Cs_2CO_3$, in a suitable solvent such as 1,4-dioxane, THF, 1,2-dimethoxyethane, DMF, DMA or DMSO.

General Synthetic Route for Compound Id (Scheme 4)

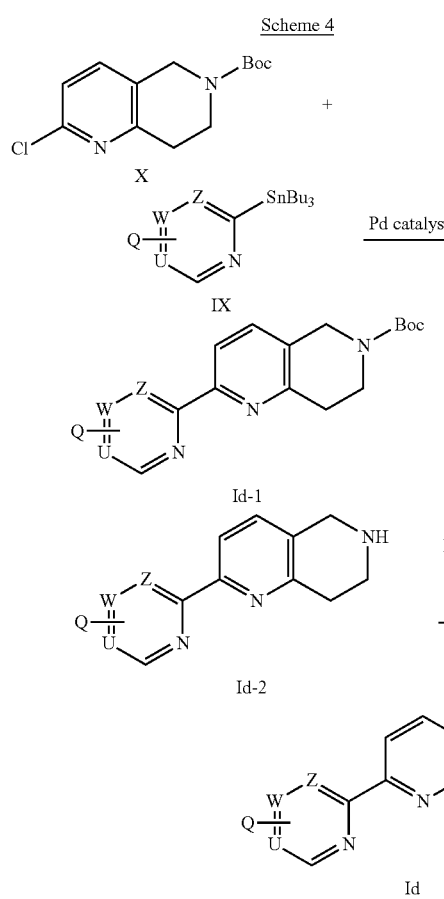

L is Cl, Br, I, O-mesyl or O-tosyl

The compound of formula Id can be prepared according to Scheme 4.

Coupling of intermediate IX with intermediate X in the presence of a catalyst such as Pd(PPh$_3$)$_4$, Pd(dppf)Cl$_2$ or Pd$_2$(dba)$_3$, in a suitable solvent such as 1,4-dioxane, CHCl$_3$ or THF can afford compound Id-1. Removal of Boc protection under acidic condition affords compound Id-2. Compound Id can be obtained by coupling of compound Id-2 with compound II in the presence of a catalyst such as Pd$_2$(dba)$_3$ or Pd(OAc)$_2$ and a base such as Cs$_2$CO$_3$ or t-BuONa, in a suitable solvent such as 1,4-dioxane, DMF or DMA.

General Synthetic Route for Compound Ie (Scheme 5)

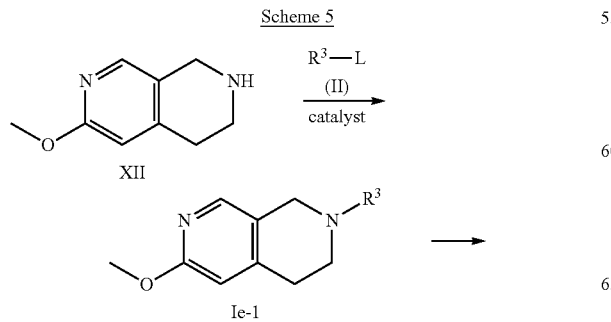

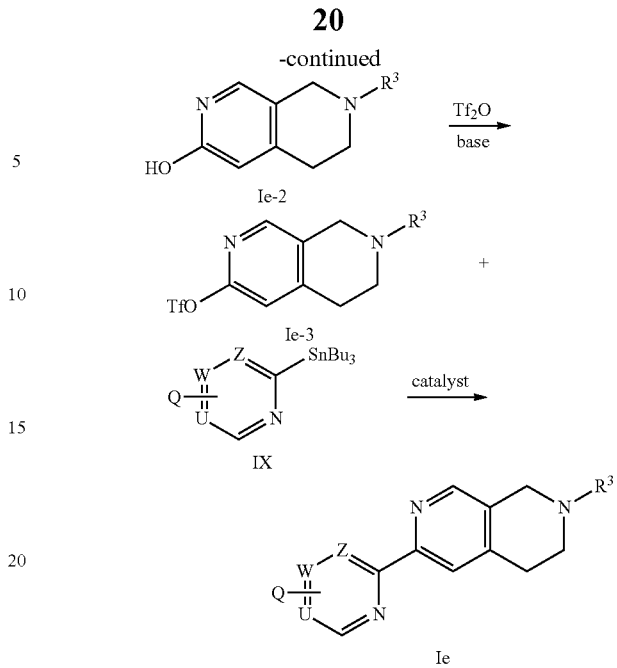

The compound of formula Ie can be prepared according to Scheme 5.

Coupling of compound XII with compound II in the presence of a catalyst such as Pd$_2$(dba)$_3$ or Pd(OAc)$_2$ and a base such as Cs$_2$CO$_3$ or t-BuONa, in a suitable solvent such as 1,4-dioxane, DMF or DMA gives compound Ie-1. Demethylation of compound Ie-1 by treating compound Ie-1 with HBr in AcOH can afford compound Ie-2. Compound Ie-2 can be converted to compound Ie-3 by reacting with trifluoromethanesulfonic anhydride in the presence of a base such as pyridine. Coupling of compound Ie-3 with compound XI in the presence of a catalyst such as Pd(PPh$_3$)$_4$, Pd(dppf)Cl$_2$ or Pd$_2$(dba)$_3$ in a suitable solvent such as 1,4-dioxane, CHCl$_3$ or THF affords compound Ie.

This invention also relates to a process for the preparation of a compound of formula I comprising (a) cyclization of a compound of formula (A)

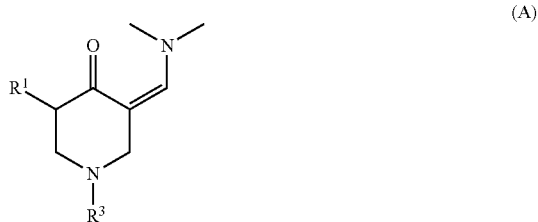

with a compound of formula (B)

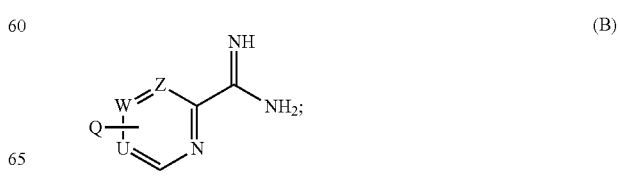

(b) coupling of a compound of formula (C)

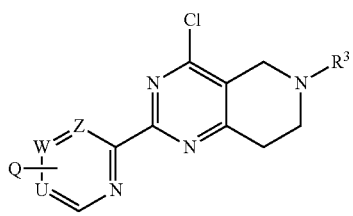

(C)

with a compound of formula (D)

R²-FG (D);

(c) coupling of a compound of formula (E)

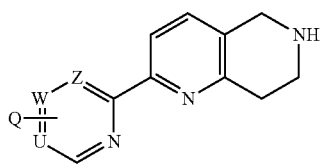

(E)

with a compound of formula (F)

R³-L (F); or (d) coupling of a compound of formula (G)

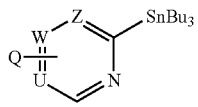

(G)

with a compound of formula (H)

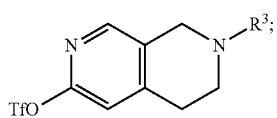

(H)

wherein R¹ to R³, Q, U, W and Z are defined as in embodiments (i) to (xviii), FG is OH, NH₂, boronic acid or pinacol ester, L is Cl, Br, I, O-mesyl or O-tosyl.

Pharmaceutical Compositions and Administration

The invention also relates to a compound of formula I for use as therapeutically active sub stance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

EXAMPLE A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

EXAMPLE B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
$(Boc)_2O$: di-tert-butyl dicarbonate
BSA: bovine serum albumin
DMF: dimethylformamide
$IC_{50}$: the half maximal inhibitory concentration
LC/MS: liquid chromatography/mass spectrometry
M: molarity
MHz: megahertz
min: minute
hr(s): hour(s)
mM: millimoles per liter
DCM: dichloromethane
EA: ethyl acetate
PE: petroleum ether
$Me_3SiCl$: chlorotrimethylsilane
MS (ESI): mass spectroscopy (electron spray ionization)
$NaBH_3CN$: sodium cyanotrihydroborate
nM: nanomoles per liter
NMR: nuclear magnetic resonance
obsd. observed
rt: room temperature
Pd/C: palladium on activated carbon
$Pd(PPh_3)_4$: tetrakis(triphenylphosphine)palladium(0)
$Pd(PPh_3)_2Cl_2$: bis(triphenylphosphine)palladium(II) chloride
$Pd(dppf)Cl_2$: [1,1'-bis(diphenylphosphino)ferrocene]dichloropalladium(II)
$Pd_2(dba)_3$: Tris(dibenzylideneacetone)dipalladium(0)
TFA: trifluoroacetic acid
δ: chemical shift
Xantphos: 4,5-bis(diphenylphosphino)-9,9-dimethylxanthene
XPhos: 2-dicyclohexylphosphino-2',4',6'-triisopropylbiphenyl
RuPhos: 2-Dicyclohexylphosphino-2',6'-diisopropoxybiphenyl
BINAP: (2,2'-bis(diphenylphosphino)-1,1'-binaphthyl)
Sphos: 2-Dicyclohexylphosphino-2',6'-dimethoxybiphenyl
DMFDMA: N,N-Dimethylformamide dimethyl acetal
t-BuONa: Sodium tert-butoxide
HATU: N-[(Dimethylamino)-1H-1,2,3-triazolo-[4,5-b]pyridin-1-ylmethylene]-N-methylmethanaminium hexafluorophosphate N-oxide General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm, ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using an Acquity Ultra Performance LC—3100 Mass Detector or Acquity Ultra Performance LC—SQ Detector. Standard LC/MS conditions were as follows (running time 3 minutes):

Acidic condition: A: 0.1% formic acid in $H_2O$; B: 0.1% formic acid in acetonitrile;

Basic condition: A: 0.05% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

Preparative Examples

Example 1: 6-(4-methylsulfonylphenyl)-2-(2-pyridyl)-7,8-dihydro-5H-pyrido[4,3-d]pyrimidine

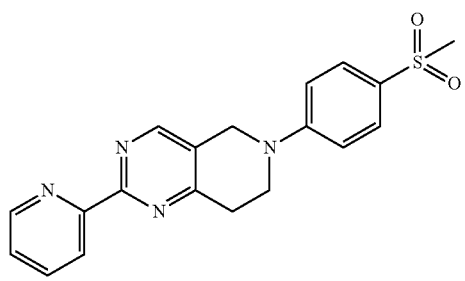 [SMILES: CS(=O)(=O)c1ccc(N2CCc3nc(-c4ccccn4)ncc3C2)cc1]

Step 1: Preparation of 8-(4-methylsulfonylphenyl)-1,4-dioxa-8-azaspiro[4.5]decane

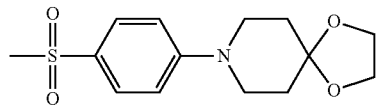

To a flask containing 1-bromo-4-methylsulfonyl-benzene (1.9 g, 8.12 mmol) and 1,4-dioxa-8-azaspiro[4.5]decane (1.39 g, 9.74 mmol) in dioxane (40 mL) was added t-BuONa (1.56 g, 16.24 mmol), $Pd_2(dba)_3$ (147 mg, 0.16 mmol) and Sphos (131 mg, 0.32 mmol) successively under $N_2$, then the reaction mixture was heated to 100° C. and stirred at 100° C. overnight. After being cooled to rt, the reaction mixture was diluted with $H_2O$ (20 mL) and extracted with EA (50 mL) for three times. The combined organic layer was washed with brine (50 mL), dried over anhydrous $Na_2SO_4$ and concentrated in vacuo to afford crude 8-(4-methylsulfonylphenyl)-1,4-dioxa-8-azaspiro[4.5]decane (2.2 g), which was used in the next step without further purification.

Step 2: Preparation of 1-(4-methylsulfonylphenyl)piperidin-4-one

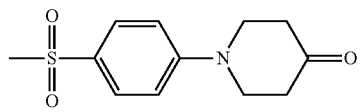 [SMILES: CS(=O)(=O)c1ccc(N2CCC(=O)CC2)cc1]

A mixture of crude 8-(4-methylsulfonylphenyl)-1,4-dioxa-8-azaspiro[4.5]decane (2.2 g, 7.48 mmol) and 44% formic acid (20 mL) was heated at 90° C. for 8 hrs. The resulting mixture was concentrated in vacuo. The residue was diluted with sat. $NaHCO_3$ (20 mL), and then extracted with EA (50 mL) for three times. The combined organic layer was washed with brine (50 mL), dried over anhydrous $Na_2SO_4$ and concentrated in vacuo to give 1-(4-methylsulfonylphenyl)piperidin-4-one (1.64 g) as brown solid, which was used in the next step without further purification.

Step 3: Preparation of 6-(4-methylsulfonylphenyl)-2-(2-pyridyl)-7,8-dihydro-5H-pyrido[4,3-d]pyrimidine

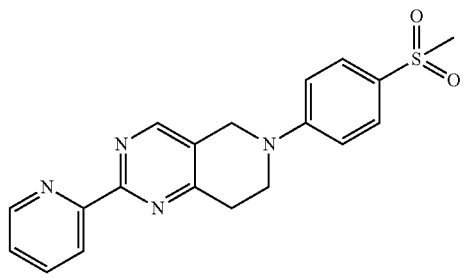 [SMILES: CS(=O)(=O)c1ccc(N2CCc3nc(-c4ccccn4)ncc3C2)cc1]

1-(4-Methylsulfonylphenyl)piperidin-4-one (1.64 g, 6.75 mmol) was heated with DMFDMA (10 mL) at 90° C. for 3 hrs. The resulting mixture was concentrated in vacuo. The residue was dissolved in EtOH (20 mL). To the solution was added pyridine-2-carboxamidine hydrochloride (1.06 g, 6.75 mmol) and $K_2CO_3$ (1.86 g, 13.5 mmol) successively. After being heated to 80° C. and stirred overnight, the resulting reaction mixture was cooled to rt and purified by prep-HPLC to give 6-(4-methylsulfonylphenyl)-2-(2-pyridyl)-7,8-dihydro-5H-pyrido[4,3-d]pyrimidine (1.0 g). $^1$H NMR (400 MHz, CDCl$_3$) δ: 8.88-8.93 (m, 1H), 8.77 (s, 1H), 8.51-8.58 (m, 1H), 7.90-7.98 (m, 1H), 7.86 (d, 2H), 7.44-7.51 (m, 1H), 7.06 (d, 2H), 4.65 (s, 2H), 3.87 (t, 2H), 3.33 (t, 2H), 3.05 (s, 3H). MS obsd. (ESI$^+$) [(M+H)$^+$]: 367.

Example 2: 2-(5-fluoro-2-pyridyl)-6-(4-methylsulfonylphenyl)-7,8-dihydro-5H-pyrido[4,3-d]pyrimidine

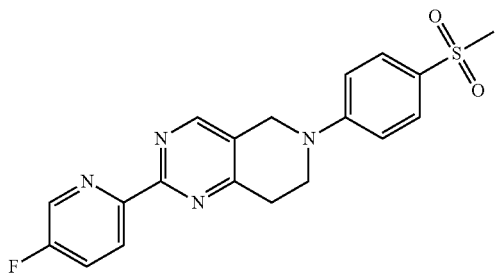 [SMILES: CS(=O)(=O)c1ccc(N2CCc3nc(-c4ccc(F)cn4)ncc3C2)cc1]

Step 1: Preparation of 5-fluoropyridine-2-carboxamidine hydrochloride

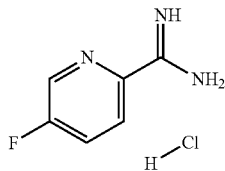

To a solution of 5-fluoropyridine-2-carbonitrile (1.0 g, 8.26 mmol) in methanol (20 mL) was added NaOCH₃ (89 mg, 1.65 mmol). The resulting mixture was stirred at rt. for 12 hrs. Then to the reaction mixture was added NH₄Cl (440 mg, 8.26 mmol). After being heated under reflux for 3 hrs, the resulting mixture was concentrated in vacuo. The residue was suspended in ethanol (30 mL) and the suspension was heated under reflux for 1 hr. The resulting mixture was filtered and the filtrate was concentrated in vacuo to afford 5-fluoropyridine-2-carboxamidine hydrochloride (1.4 g), which was used in the next step without further purification.

Step 2: Preparation of 2-(5-fluoro-2-pyridyl)-6-(4-methylsulfonylphenyl)-7,8-dihydro-5H-pyrido[4,3-d]pyrimidine

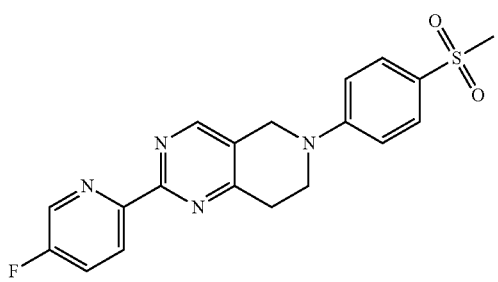 [SMILES: CS(=O)(=O)c1ccc(N2CCc3nc(-c4ccc(F)cn4)ncc3C2)cc1]

A solution of 1-(4-methylsulfonylphenyl)piperidin-4-one (100 mg, 0.39 mmol) and DMFDMA (1 ml) in acetonitrile (8 mL) was heated with stirring at 90° C. for 2 hrs. The resulting mixture was concentrated in vacuo and the residue was dissolved in EtOH (10 mL). To the solution was added 5-fluoropyridine-2-carboxamidine hydrochloride (55 mg, 0.39 mmol) and potassium carbonate (107 mg, 0.78 mmol) successively. After being heated at 90° C. overnight, the reaction mixture was cooled to rt, diluted with water (20 mL) and extracted with EA (20 mL) for three times. The combined organic layer was washed with brine, dried over anhydrous Na₂SO₄ and concentrated in vacuo. The residue was purified by prep-HPLC to give 2-(5-fluoro-2-pyridyl)-6-(4-methylsulfonylphenyl)-7,8-dihydro-5H-pyrido[4,3-d]pyrimidine (13 mg). ¹H NMR (400 MHz, CDCl₃): δ 8.74 (s, 1H), 8.70 (d, 1H), 8.59 (dd, 1H), 7.87 (d, 2H), 7.70-7.48 (m, 1H), 7.06 (d, 2H), 4.64 (s, 2H), 3.87 (t, 2H), 3.31 (t, 2H), 3.05 (s, 3H). MS obsd. (ESI⁺) [(M+H)⁺]: 385.

Example 3: 2-(5-methyl-2-pyridyl)-6-(4-methylsulfonylphenyl)-7,8-dihydro-5H-pyrido[4,3-d]pyrimidine

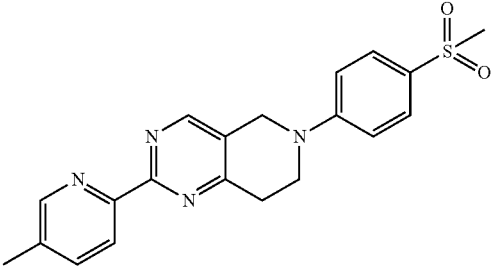 [SMILES: Cc1ccc(-c2ncc3c(n2)CCN(c2ccc(S(C)(=O)=O)cc2)C3)nc1]

Step 1: Preparation of 5-methylpyridine-2-carboxamidine hydrochloride

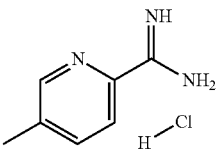

To a solution of 5-methylpyridine-2-carbonitrile (1.0 g, 8.55 mmol) in methanol (20 mL) was added NaOCH₃ (92 mg, 1.71 mmol). The resulting mixture was stirred at rt for 12 hrs. Then to the reaction mixture was added NH₄Cl (460 mg, 8.55 mmol). After being heated under reflux for 3 hrs, the resulting reaction mixture was then concentrated in vacuo. The residue was suspended in ethanol (30 mL) and the suspension was heated under reflux for 1 hr. The resulting mixture was filtered and the filtrate was concentrated in vacuo to afford crude 5-metylpyridine-2-carboxamidine hydrochloride (1.4 g), which was used in the next step without further purification.

Step 2: Preparation of 2-(5-methyl-2-pyridyl)-6-(4-methylsulfonylphenyl)-7,8-dihydro-5H-pyrido[4,3-d]pyrimidine

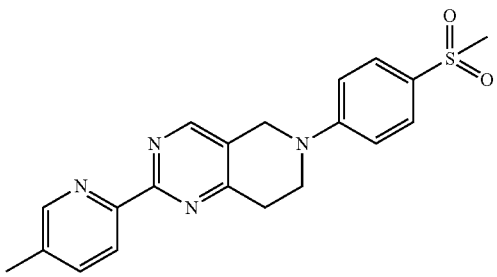

A mixture of 1-(4-methylsulfonylphenyl)piperidin-4-one (100 mg, 0.39 mmol) and DMFDMA (1 mL) in acetonitrile (8 mL) was heated with stirring at 90° C. for 2 hrs. The resulting mixture was concentrated in vacuo and the residue was dissolved in EtOH (10 mL). To the solution was added 5-methylpyridine-2-carboxamidine hydrochloride (54 mg, 0.39 mmol) and potassium carbonate (88 mg, 0.64 mmol) successively. After being heated at 90° C. overnight, the reaction mixture was cooled to rt, diluted with water (20 mL) and extracted with EA (20 mL) for three times. The combined organic layer was washed with brine, dried over anhydrous Na₂SO₄ and concentrated in vacuo. The residue was purified by prep-HPLC to give 2-(5-methyl-2-pyridyl)-6-(4-methylsulfonylphenyl)-7,8-dihydro-5H-pyrido[4,3-d]pyrimidine (9 mg). $^1$H NMR (400 MHz, CDCl₃): δ 8.73 (s, 1H), 8.69 (s, 1H), 8.43 (d, 1H), 7.88-7.83 (m, 2H), 7.69 (dd, 1H), 7.09-6.98 (m, 2H), 4.63 (s, 2H), 3.87 (t, 2H), 3.31 (t, 2H), 3.05 (s, 3H), 2.45 (s, 3H). MS obsd. (ESI⁺) [(M+H)⁺]: 381.

Example 4: 2-(3-methyl-2-pyridyl)-6-(4-methylsulfonylphenyl)-7,8-dihydro-5H-pyrido[4,3-d]pyrimidine

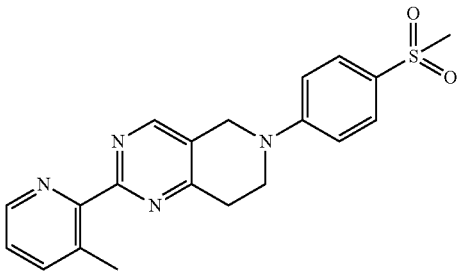

Step 1: Preparation of 3-methylpyridine-2-carboxamidine hydrochloride

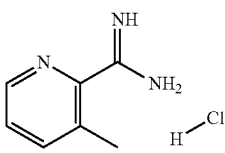

To a solution of 3-methylpyridine-2-carbonitrile (1.0 g, 8.55 mmol) in methanol (20 mL) was added NaOCH₃ (92 mg, 1.71 mmol). The resulting mixture was stirred at rt for 12 hrs. Then to the reaction mixture was added NH₄Cl (460 mg, 8.55 mmol). After being heated under reflux for 3 hrs, the resulting mixture was concentrated in vacuo. The residue was suspended in ethanol (30 mL) and the suspension was heated under reflux for 1 hr. The mixture was filtered and the filtrate was concentrated in vacuo to afford 3-metylpyridine-2-carboxamidine hydrochloride (1.4 g), which was used in the next step without further purification.

Step 2: Preparation of 2-(3-methyl-2-pyridyl)-6-(4-methylsulfonylphenyl)-7,8-dihydro-5H-pyrido[4,3-d]pyrimidine

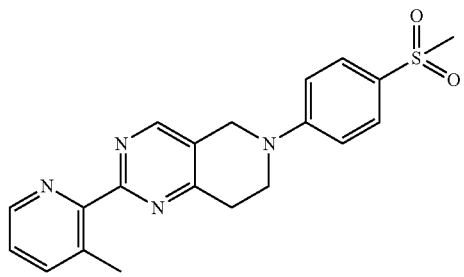 [SMILES: Cc1cccnc1-c1ncc2c(n1)CCN(c1ccc(S(C)(=O)=O)cc1)C2]

A mixture of 1-(4-methylsulfonylphenyl)piperidin-4-one (100 mg, 0.39 mmol) and DMFDMA (1 mL) in acetonitrile (8 mL) was heated with stirring at 90° C. for 2 hrs. The resulting mixture was concentrated in vacuo and the residue was dissolved in EtOH (10 mL). To the solution was added 3-methylpyridine-2-carboxamidine hydrochloride (53 mg, 0.39 mmol) and potassium carbonate (88 mg, 0.64 mmol) successively. After being heated at 90° C. overnight, the reaction mixture was cooled to rt, diluted with water (20 mL) and extracted with EA (20 mL) for three times. The combined organic layer was washed with brine, dried over anhydrous Na₂SO₄ and concentrated in vacuo. The residue was purified by prep-HPLC to give 2-(3-methyl-2-pyridyl)-6-(4-methylsulfonylphenyl)-7,8-dihydro-5H-pyrido[4,3-d]pyrimidine (20 mg). $^1$H NMR (400 MHz, CDCl₃): δ 8.75 (s, 1H), 8.64 (dd, 1H), 7.87 (d, 2H), 7.67 (d, 1H), 7.34-7.28 (m, 1H), 7.06 (d, 2H), 4.65 (s, 2H), 3.88 (t, 2H), 3.29 (t, 2H), 3.05 (s, 3H), 2.54 (s, 3H). MS obsd. (ESI⁺) [(M+H)⁺]: 381.

Example 5: 2-(5-methoxy-2-pyridyl)-6-(4-methylsulfonylphenyl)-7,8-dihydro-5H-pyrido[4,3-d]pyrimidine

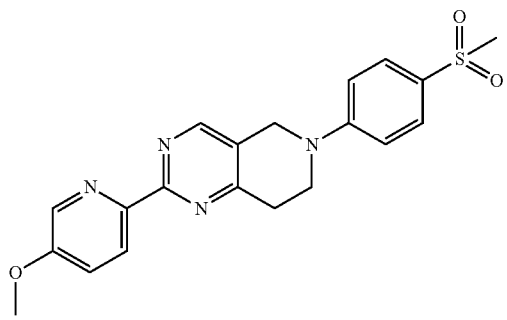 [SMILES: COc1ccc(-c2ncc3c(n2)CCN(c2ccc(S(C)(=O)=O)cc2)C3)nc1]

Step 1: Preparation of
5-methoxypyridine-2-carboxamidine hydrochloride

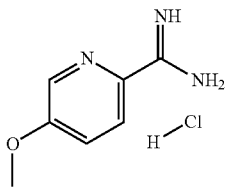

To a solution of 5-methyoxypyridine-2-carbonitrile (1.0 g, 7.46 mmol) in methanol (20 mL) was added NaOCH$_3$ (80 mg, 1.49 mmol). The mixture was stirred at rt for 12 hrs. Then to the reaction mixture was added NH$_4$Cl (399 mg, 7.46 mmol). After being heated under reflux for 3 hrs, the reaction mixture was then concentrated in vacuo. The residue was suspended in ethanol (30 mL) and the suspension was heated under reflux for 1 hr. The resulting mixture was filtered and the filtrate was concentrated in vacuo to afford 5-metyoxypyridine-2-carboxamidine hydrochloride (1.3 g), which was used in the next step without further purification.

Step 2: Preparation of 2-(5-methoxy-2-pyridyl)-6-(4-methylsulfonylphenyl)-7,8-dihydro-5H-pyrido[4,3-d]pyrimidine

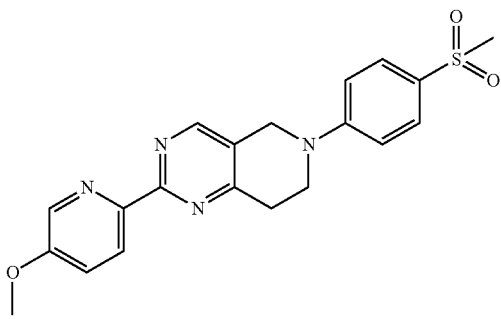

A mixture of 1-(4-methylsulfonylphenyl)piperidin-4-one (100 mg, 0.39 mmol) and DMFDMA (1 mL) in acetonitrile (8 mL) was heated with stirring at 90° C. for 2 hrs. The resulting mixture was concentrated in vacuo and the residue was dissolved in EtOH (10 mL). To the solution was added 5-methoxypyridine-2-carboxamidine hydrochloride (59 mg, 0.39 mmol) and potassium carbonate (88 mg, 0.64 mmol) successively. After being heated at 90° C. overnight, the reaction mixture was cooled to rt, diluted with water (20 mL) and extracted with EA (20 mL) for three times. The combined organic layer was washed with brine, dried over anhydrous Na$_2$SO$_4$ and concentrated in vacuo. The residue was purified by prep-HPLC to give 6-(4-methylsulfonylphenyl)-2-(2-pyridyl)-7,8-dihydro-5H-pyrido[4,3-d]pyrimidine (42 mg), $^1$H NMR (400 MHz, DMSO-d$_6$): δ 8.78 (s, 1H), 8.55-8.32 (m, 2H), 7.74 (d, 2H), 7.54 (dd, 1H), 7.22 (d, 2H), 5.77 (s, 2H), 4.69 (s, 2H), 3.97-3.83 (m, 4H), 3.11 (s, 3H). MS obsd. (ESI$^+$) [(M+H)$^+$]: 397.

Example 6: 2-(5-chloro-2-pyridyl)-6-(4-methylsulfonylphenyl)-7,8-dihydro-5H-pyrido[4,3-d]pyrimidine

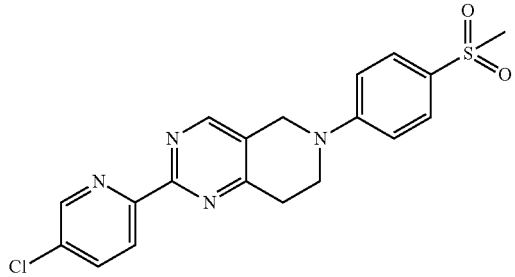 [SMILES: CS(=O)(=O)c1ccc(N2CCc3nc(-c4ccc(Cl)cn4)ncc3C2)cc1]

Step 1: Preparation of
5-chloropyridine-2-carboxamidine hydrochloride

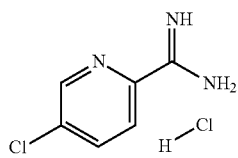

To a solution of 5-chloropyridine-2-carbonitrile (1.0 g, 7.25 mmol) in methanol (20 mL) was added NaOCH$_3$ (80 mg, 1.45 mmol). The mixture was stirred at rt for 12 hrs. To the resulting reaction mixture was added NH$_4$Cl (390 mg, 7.25 mmol). After being heated under reflux for 3 hrs, the reaction mixture was then concentrated in vacuo. The residue was suspended in ethanol (30 mL) and heated under reflux for 1 hr. The resulting mixture was filtered and the filtrate was concentrated in vacuo to afford 5-chloropyridine-2-carboxamidine hydrochloride (1.3 g), which was used in the next step without further purification.

Step 2: Preparation of 2-(5-chloro-2-pyridyl)-6-(4-methylsulfonylphenyl)-7,8-dihydro-5H-pyrido[4,3-d]pyrimidine

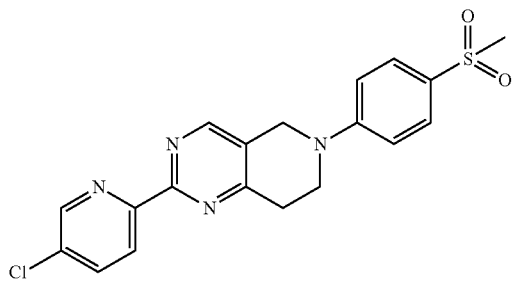 [SMILES: CS(=O)(=O)c1ccc(N2CCc3nc(-c4ccc(Cl)cn4)ncc3C2)cc1]

A mixture of 1-(4-methylsulfonylphenyl)piperidin-4-one (100 mg, 0.39 mmol) and DMFDMA (1 mL) in acetonitrile (5 mL) was heated with stirring at 90° C. for 2 hrs. The resulting mixture was concentrated in vacuo and the residue was dissolved in EtOH (10 mL). To the solution was added 5-chloropyridine-2-carboxamidine hydrochloride (74 mg, 0.39 mmol) and potassium carbonate (88 mg, 0.64 mmol) successively. After being heated at 90° C. overnight, the reaction mixture was cooled to rt, diluted with water (20 mL) and extracted with EA (20 mL) for three times. The combined organic layer was washed with brine, dried over anhydrous Na$_2$SO$_4$ and concentrated in vacuo. The residue was purified by prep-HPLC to afford 2-(5-chloro-2-pyridyl)-6-(4-methylsulfonylphenyl)-7,8-dihydro-5H-pyrido[4,3-d]pyrimidine (10 mg). $^1$H NMR (400 MHz, CDCl$_3$): δ 3.05 (s, 3H), 3.32 (t, 2H), 3.88 (t, 2H), 4.65 (s, 2H), 7.00-7.11 (m, 2H), 7.83-7.92 (m, 3H), 8.48-8.57 (m, 1H), 8.73-8.86 (m, 2H). MS obsd. (ESI$^+$) [(M+H)$^+$]: 401.

Example 7: 8-ethyl-6-(4-methylsulfonylphenyl)-2-(2-pyridyl)-7,8-dihydro-5H-pyrido[4,3-d]pyrimidine

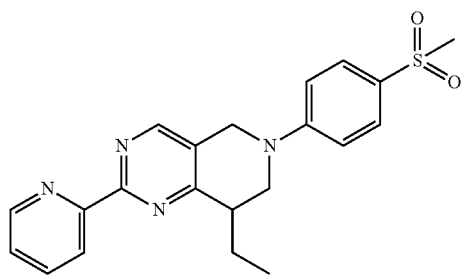 [SMILES: CCC1CN(c2ccc(S(C)(=O)=O)cc2)Cc2cnc(-c3ccccn3)nc21]

Step 1: Preparation of 3-ethyl-1-(4-methylsulfonylphenyl)piperidin-4-one

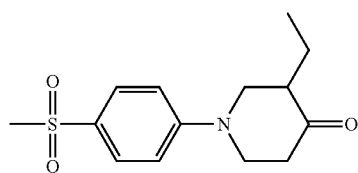 [SMILES: CCC1CN(c2ccc(S(C)(=O)=O)cc2)CCC1=O]

To a solution of 1-(4-methylsulfonylphenyl)piperidin-4-one (1.0 g, 3.93 mmol) in THF (15 mL) was added sodium hydride (104 mg, 4.43 mmol) at 0° C. under N$_2$ atmosphere. The mixture was stirred for 0.5 hr at 0° C. To the resulting mixture was added ethyl iodide (3.5 ml, 4.33 mmol) and the reaction mixture was heated under reflux overnight. Then the reaction was quenched with H$_2$O and the resulting mixture was extracted with EA (40 mL) for three times. The combined organic layer was washed with brine, dried over anhydrous Na$_2$SO$_4$ and concentrated in vacuo. The residue was purified by column chromatography (eluting with 20% EA in PE) to give 3-ethyl-1-(4-methylsulfonylphenyl)-piperidin-4-one (1.0 g), which was used in the next step without further purification.

Step 2: Preparation of 8-ethyl-6-(4-methylsulfonylphenyl)-2-(2-pyridyl)-7,8-dihydro-5H-pyrido[4,3-d]pyrimidine

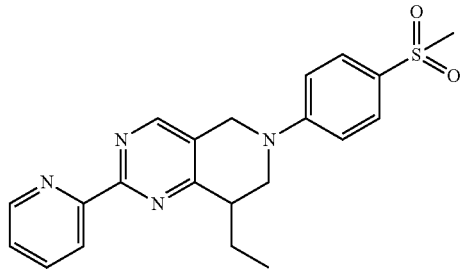 [SMILES: CCC1CN(c2ccc(S(C)(=O)=O)cc2)Cc2cnc(-c3ccccn3)nc21]

A mixture of 3-ethyl-1-(4-methylsulfonylphenyl)piperidin-4-one (1.0 g, 3.54 mmol) and DMFDMA (2 mL) in acetonitrile (8 mL) was heated with stirring at 90° C. for 2 hrs. The resulting mixture was concentrated in vacuo and the residue was dissolved in EtOH (20 mL). To the solution was added pyridine-2-carboxamidine hydrochloride (560 mg, 3.54 mmol) and potassium carbonate (980 mg, 7.08 mmol) successively. After being heated with stirring at 90° C. overnight, the reaction mixture was cooled to rt, diluted with water (20 mL) and extracted with EA (50 mL) for three times. The combined organic layers were washed with brine, dried over anhydrous Na$_2$SO$_4$ and concentrated in vacuo. The residue was purified by prep-HPLC to give 8-ethyl-6-(4-methylsulfonylphenyl)-2-(2-pyridyl)-7,8-dihydro-5H-pyrido[4,3-d]pyrimidine (6 mg). $^1$H NMR (400 MHz, CDCl$_3$): δ 8.92-8.83 (m, 1H), 8.78 (s, 1H), 8.56 (d, 1H), 7.99-7.83 (m, 3H), 7.44 (ddd, 1H), 7.08-6.98 (m, 2H), 4.68 (d, 1H), 4.54 (d, 1H), 3.89 (dd, 1H), 3.72 (dd, 1H), 3.17 (dd, 1H), 3.06 (s, 3H), 2.16 (m, 1H), 1.78 (m, 1H), 1.19 (t, 3H). MS obsd. (ESI+) [(M+H)$^+$]: 395.

Example 8: N-methyl-4-[2-(2-pyridyl)-7,8-dihydro-5H-pyrido[4,3-d]pyrimidin-6-yl]benzenesulfonamide

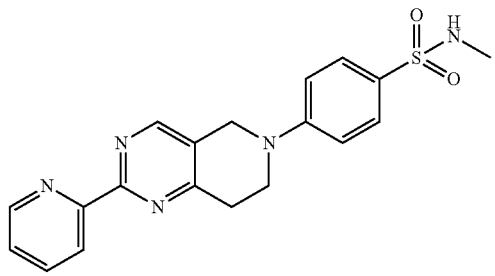 [SMILES: CNS(=O)(=O)c1ccc(N2CCc3nc(-c4ccccn4)ncc3C2)cc1]

Step 1: Preparation of 4-(1,4-dioxa-8-azaspiro[4.5]decan-8-yl)-N-methyl-benzenesulfonamide

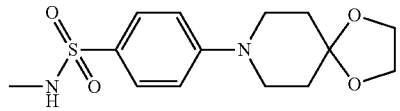 [SMILES: CNS(=O)(=O)c1ccc(N2CCC3(CC2)OCCO3)cc1]

A mixture of 4-fluoro-N-methyl-benzenesulfonamide (0.50 g, 2.64 mmol), 1,4-dioxa-8-azaspiro[4.5]decane (0.76 g, 5.28 mmol) and potassium carbonate (0.73 g, 5.28 mmol) in a mixed solvent of acetonitrile (10 mL) and 1,3-dimethylhexahydropyrimidin-2-one (20 mL) was heated with stirring at 65° C. for 3 hrs. The resulting reaction mixture was cooled to rt, diluted with water (50 mL) and extracted with EA (30 mL) for three times. The combined organic layer was washed with brine, dried over anhydrous Na₂SO₄ and concentrated in vacuo to give crude 4-(1,4-dioxa-8-azaspiro [4.5]decan-8-yl)-N-methyl-benzenesulfonamide (0.60 g), which was used in the next step without further purification.

Step 2: Preparation of N-methyl-4-(4-oxo-1-piperidyl)benzenesulfonamide

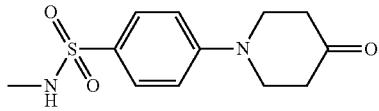

A solution of 4-(1,4-dioxa-8-azaspiro[4.5]decan-8-yl)-N-methyl-benzenesulfonamide (0.60 g, 1.91 mmol) in a mixture of H₂O (5 mL) and formic acid (5 mL) was heated with stirring at 90° C. overnight. The resulting reaction mixture was cooled to rt and concentrated in vacuo. The residue was diluted with sat. aqueous solution of NaHCO₃ and extracted with EA (30 mL) for three times. The combined organic layers were washed with brine, dried over anhydrous Na₂SO₄ and concentrated in vacuo. The residue was purified by column chromatography (2.5% MeOH in DCM) to give N-methyl-4-(4-oxo-1-piperidyl)benzenesulfonamide (0.45 g).

Step 3: Preparation of N-methyl-4-[2-(2-pyridyl)-7,8-dihydro-5H-pyrido[4,3-d]pyrimidin-6-yl]benzenesulfonamide

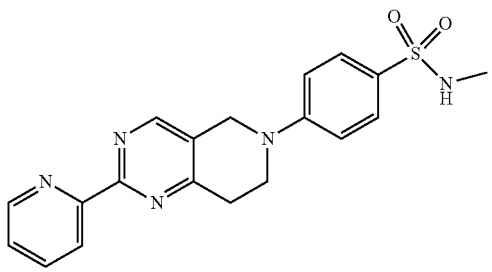 [SMILES: CNS(=O)(=O)c1ccc(N2CCc3nc(-c4ccccn4)ncc3C2)cc1]

A mixture of N-methyl-4-(4-oxo-1-piperidyl)benzenesulfonamide (0.45 g, 1.67 mmol) and DMFDMA (2 mL) in acetonitrile (8 mL) was heated with stirring at 90° C. for 2 hrs. The resulting reaction mixture was concentrated in vacuo and the residue was dissolved in EtOH (10 mL). To the solution was added pyridine-2-carboxamidine (0.15 g, 1.23 mmol) and potassium carbonate (0.34 g, 2.46 mmol) successively. After being heated with stirring at 90° C. overnight, the resulting reaction mixture was cooled to rt, diluted with water (20 mL) and extracted with EA (20 mL) for three times. The combined organic layer was washed with brine, dried over anhydrous Na₂SO₄ and concentrated in vacuo. The residue was purified by prep-PLC to give N-methyl-4-[2-(2-pyridyl)-7,8-dihydro-5H-pyrido[4,3-d] pyrimidin-6-yl]benzenesulfonamide (7 mg). ¹H NMR (400 MHz, CDCl₃): δ 8.87 (d, 1H), 8.80-8.70 (m, 1H), 8.53 (d, 1H), 7.89 (dt, 1H), 7.80 (d, 2H), 7.44 (ddd, 1H), 7.06-6.97 (m, 2H), 4.63 (s, 2H), 3.86 (t, 2H), 3.32 (t, 2H), 2.67 (s, 3H). MS obsd. (ESI⁺) [(M+H)⁺]: 382.

Example 9: N,N-dimethyl-4-[2-(2-pyridyl)-7,8-dihydro-5H-pyrido[4,3-d]pyrimidin-6-yl]benzenesulfonamide

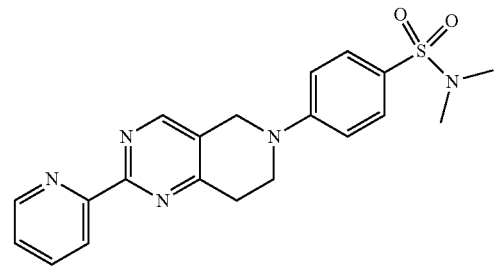 [SMILES: CN(C)S(=O)(=O)c1ccc(N2CCc3nc(-c4ccccn4)ncc3C2)cc1]

A mixture of N-methyl-4-[2-(2-pyridyl)-7,8-dihydro-5H-pyrido[4,3-d]pyrimidin-6-yl]benzenesulfonamide (44 mg, 0.12 mmol), sodium hydride (6 mg, 0.24 mmol) and methyl iodide (34 mg, 0.24 mmol) in anhydrous DMF (5 mL) was stirred at rt for 2 hrs under N₂ atmosphere. Then the reaction was quenched with water. The resulting mixture was extracted with EA (30 mL). The organic layer was washed with brine, dried over anhydrous Na₂SO₄ and concentrated in vacuo. The residue was purified by prep-HPLC to give N,N-dimethyl-4-[2-(2-pyridyl)-7,8-dihydro-5H-pyrido[4,3-d]pyrimidin-6-yl]benzenesulfonamide (3 mg). ¹H NMR (400 MHz, CDCl₃): δ 8.88 (d, 1H), 8.76 (s, 1H), 8.54 (d, 1H), 7.90 (dt, 1H), 7.73 (d, 2H), 7.44 (ddd, 1H), 7.06 (d, 2H), 4.64 (s, 2H), 3.96-3.67 (m, 2H), 3.52 (s, 3H), 3.45-3.24 (m, 2H), 2.71 (s, 3H). MS obsd. (ESI⁺) [(M+H)⁺]: 396.

Example 10: 6-(3,4-difluorophenyl)-2-(2-pyridyl)-7,8-dihydro-5H-pyrido[4,3-d]pyrimidine

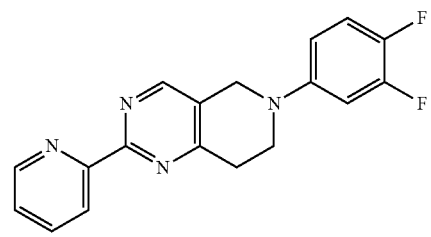 [SMILES: Fc1ccc(N2CCc3nc(-c4ccccn4)ncc3C2)cc1F]

Step 1: preparation of 8-(3,4-difluorophenyl)-1,4-dioxa-8-azaspiro[4.5]decane

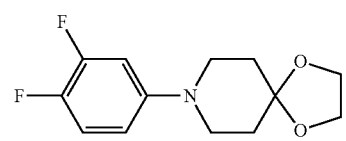 [SMILES: Fc1ccc(N2CCC3(CC2)OCCO3)cc1F]

To a flask containing a mixture of 4-bromo-1,2-difluorobenzene (580 mg, 3.0 mmol) and 1,4-dioxa-8-azaspiro[4.5]decane (515 mg, 3.6 mmol) in dioxane (20 mL) was added t-BuONa (580 mg, 6.0 mmol) followed by $Pd_2(dba)_3$ (137 mg, 0.15 mmol) and Sphos (123 mg, 0.30 mmol) successively under $N_2$. After being heated to 100° C. and stirred overnight, the resulting reaction mixture was cooled to rt, diluted with $H_2O$ (20 mL) and extracted with EA (50 mL) for three times. The combined organic layer was washed with brine (50 mL), dried over anhydrous $Na_2SO_4$ and concentrated in vacuo to afford crude 8-(3,4-difluorophenyl)-1,4-dioxa-8-azaspiro[4.5]decane (800 mg), which was used in the next step without further purification.

Step 2: preparation of 1-(3,4-difluorophenyl)piperidin-4-one

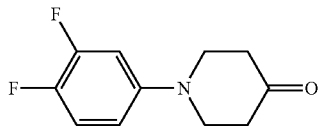

A mixture of crude 8-(3,4-difluorophenyl)-1,4-dioxa-8-azaspiro[4.5]decane (800 mg, 3.13 mmol) and 44% formic acid (10 mL) was heated with stirring at 90° C. for 8 hrs. The resulting mixture was concentrated in vacuo. The residue was diluted with sat. aqueous solution of $NaHCO_3$ (20 mL) and extracted with EA (50 mL) for three times. The combined organic layer was washed with brine (50 mL), dried over anhydrous $Na_2SO_4$ and concentrated in vacuo to give 1-(3,4-difluorophenyl)piperidin-4-one (600 mg) as brown oil, which was used in the next step without further purification.

Step 3: Preparation of 6-(3,4-difluorophenyl)-2-(2-pyridyl)-7,8-dihydro-5H-pyrido[4,3-d]pyrimidine

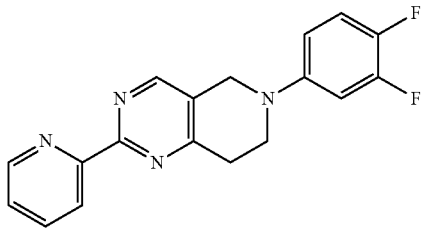 [SMILES: Fc1ccc(N2CCc3nc(-c4ccccn4)ncc3C2)cc1F]

1-(3,4-difluorophenyl)piperidin-4-one (600 mg, 2.84 mmol) was heated with DMFDMA (5 mL) at 90° C. for 3 hrs. The resulting mixture was concentrated in vacuo and the residue was dissolved in EtOH (10 mL). To the resulting solution was added pyridine-2-carboxamidine hydrochloride (450 mg, 2.84 mmol) and $K_2CO_3$ (784 mg, 5.68 mmol) successively. After being heated to 80° C. and stirred overnight, the resulting reaction mixture was cooled to rt and purified by prep-HPLC to give 6-(3,4-difluorophenyl)-2-(2-pyridyl)-7,8-dihydro-5H-pyrido[4,3-d]pyrimidine (50 mg) as yellow solid. $^1$H NMR (400 MHz, $CDCl_3$): δ 8.86 (d, 1H), 8.70 (s, 1H), 8.48-8.56 (m, 1H), 7.83-7.92 (m 1H), 7.37-7.45 (m, 1H), 7.05-7.18 (m, 1H), 6.77-6.92 (m, 1H), 6.67-6.75 (m, 1H), 4.41 (s, 2H), 3.64 (t, 2H), 3.21-3.35 (m, 2H). MS obsd. (ESI$^+$) [(M+H)$^+$]: 325.

Example 11: 6-(3-methylsulfonylphenyl)-2-(2-pyridyl)-7,8-dihydro-5H-pyrido[4,3-d]pyrimidine

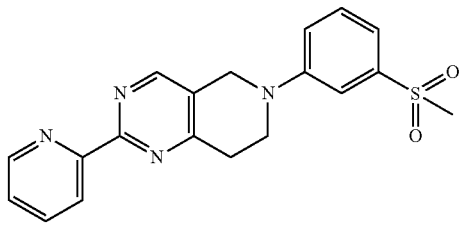 [SMILES: CS(=O)(=O)c1cccc(N2CCc3nc(-c4ccccn4)ncc3C2)c1]

Step 1: Preparation 8-(3-methylsulfonylphenyl)-1,4-dioxa-8-azaspiro[4.5]decane

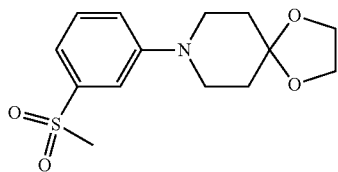 [SMILES: CS(=O)(=O)c1cccc(N2CCC3(CC2)OCCO3)c1]

To a flask containing a mixture of 1-bromo-3-methylsulfonyl-benzene (525 mg, 2.2 mmol) and 1,4-dioxa-8-azaspiro[4.5]decane (372 mg, 2.6 mmol) in dioxane (10 mL) was added t-BuONa (317 mg, 3.3 mmol), $Pd_2(dba)_3$ (37 mg, 0.04 mmol) and Sphos (33 mg, 0.08 mmol) successively under $N_2$. The resulting mixture was heated to 100° C. and stirred overnight. After being cooled to rt, the reaction mixture was diluted with $H_2O$ (20 mL) and extracted with EA (50 mL) for three times. The combined organic layer was washed with brine (50 mL), dried over anhydrous $Na_2SO_4$ and concentrated in vacuo to give crude 8-(3-methylsulfonylphenyl)-1,4-dioxa-8-azaspiro[4.5]decane (280 mg), which was used in the next step without further purification.

Step 2: Preparation of 1-(3-methylsulfonylphenyl)piperidin-4-one

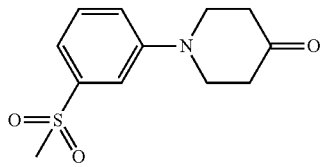 [SMILES: CS(=O)(=O)c1cccc(N2CCC(=O)CC2)c1]

Crude 8-(3-methylsulfonylphenyl)-1,4-dioxa-8-azaspiro[4.5]decane (280 mg, 0.94 mmol) was heated with 44% formic acid (10 mL) at 90° C. for 8 hrs. The mixture was concentrated in vacuo and the residue was diluted with sat. aqueous solution of $NaHCO_3$ (20 mL). The resulting mixture was extracted with EA (30 mL) three times. The combined organic layer was washed with brine (30 mL), dried over anhydrous $Na_2SO_4$ and concentrated in vacuo to give 1-(3-methylsulfonylphenyl)piperidin-4-one (220 mg) as brown oil, which was used in the next step without further purification.

Step 3: Preparation of 6-(3-methylsulfonylphenyl)-2-(2-pyridyl)-7,8-dihydro-5H-pyrido[4,3-d]pyrimidine

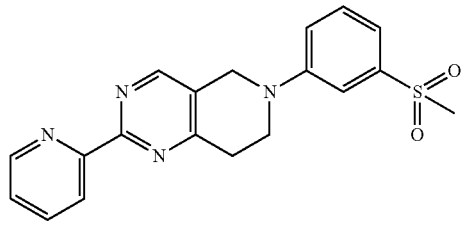 [SMILES: CS(=O)(=O)c1cccc(N2CCc3nc(-c4ccccn4)ncc3C2)c1]

Crude 1-(3-methylsulfonylphenyl)piperidin-4-one (220 mg, 0.87 mmol) was heated with DMFDMA (5 mL) at 90° C. for 3 hrs. The resulting mixture was concentrated in vacuo and the residue was dissolved in EtOH (10 mL). To the solution was added pyridine-2-carboxamidine hydrochloride (137 mg, 0.87 mmol) and $K_2CO_3$ (240 mg, 1.74 mmol) successively. After being heated to 80° C. and stirred overnight, the reaction mixture was cooled to rt and purified by prep-HPLC to give 6-(3-methylsulfonylphenyl)-2-(2-pyridyl)-7,8-dihydro-5H-pyrido[4,3-d]pyrimidine (20 mg) as pale yellow solid. $^1$H NMR (400 MHz, CDCl$_3$): δ 8.83-8.90 (m, 1H), 8.75 (s, 1H), 8.53 (d, 1H), 7.89 (td, 1H), 7.48-7.57 (m, 2H), 7.39-7.46 (m, 2H), 7.23-7.28 (m, 1H), 4.50-4.62 (m, 2H), 3.76-3.86 (m, 2H), 3.28-3.38 (m, 2H), 3.09 (s, 3H). MS obsd. (ESI$^+$) [(M+H)$^+$]: 367.

Example 12:2-(2-pyridyl)-6-[4-(trifluoromethylsulfonyl)phenyl]-7,8-dihydro-5H-pyrido[4,3-d]pyrimidine

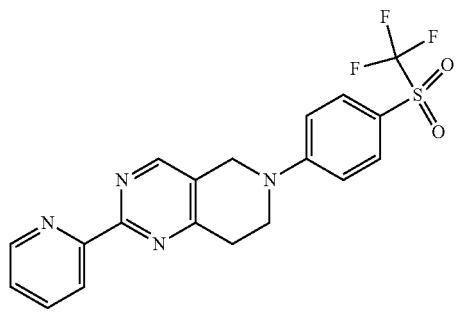 [SMILES: O=S(=O)(c1ccc(N2CCc3nc(-c4ccccn4)ncc3C2)cc1)C(F)(F)F]

Step 1: Preparation of 8-[4-(trifluoromethylsulfonyl)phenyl]-1,4-dioxa-8-azaspiro[4.5]decane

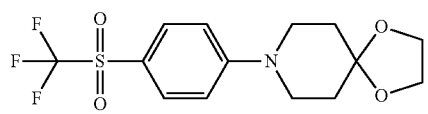 [SMILES: O=S(=O)(c1ccc(N2CCC3(CC2)OCCO3)cc1)C(F)(F)F]

To a flask containing a mixture of 1-bromo-4-(trifluoromethyl-sulfonyl)benzene (600 mg, 2.08 mmol) and 1,4-dioxa-8-azaspiro[4.5]decane (358 mg, 2.5 mmol) in dioxane (20 mL) was added $Cs_2CO_3$ (1350 mg, 4.16 mmol), Pd$_2$(dba)$_3$ (37 mg, 0.04 mmol) and Sphos (33 mg, 0.08 mmol) successively under $N_2$. The resulting mixture was heated to 100° C. and stirred overnight. After being cooled to rt, the reaction mixture was diluted with $H_2O$ (20 mL) and extracted with EA (50 mL) for three times. The combined organic layer was washed with brine (50 mL), dried over anhydrous $Na_2SO_4$ and concentrated in vacuo to give crude 8-[4-(trifluoromethylsulfonyl)phenyl]-1,4-dioxa-8-azaspiro[4.5]decane (200 mg), which was used in the next step without further purification.

Step 2: Preparation of 1-[4-(trifluoromethylsulfonyl)phenyl]piperidin-4-one

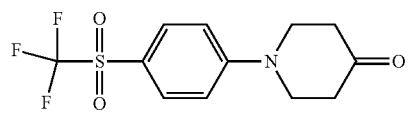

To a flask containing crude 8-[4-(trifluoromethylsulfonyl)phenyl]-1,4-dioxa-8-azaspiro[4.5]decane (200 mg, 0.57 mmol) was added 44% formic acid (10 mL). After being heated with stirring at 90° C. for 8 hrs, the resulting mixture was concentrated in vacuo, diluted with sat. aqueous solution of NaHCO$_3$ (20 mL) and extracted with EA (30 mL) for three times. The combined organic layer was washed with brine (30 mL), dried over anhydrous $Na_2SO_4$ and concentrated in vacuo to give 1-[4-(trifluoromethyl-sulfonyl)phenyl]piperidin-4-one (160 mg) as brown oil, which was used in the next step without further purification.

Step 3: Preparation of 2-(2-pyridyl)-6-[4-(trifluoromethylsulfonyl)phenyl]-7,8-dihydro-5H-pyrido[4,3-d]pyrimidine

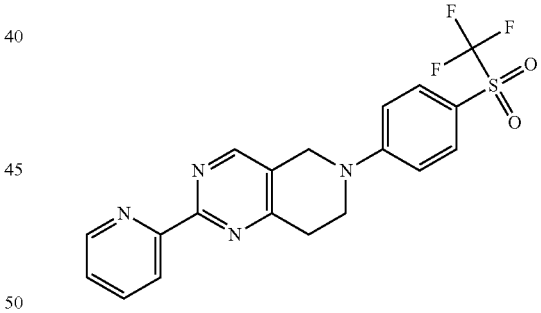

Crude 1-[4-(trifluoromethylsulfonyl)phenyl]piperidin-4-one (160 mg, 0.52 mmol) was heated with DMFDMA (5 mL) at 90° C. for 3 hrs. The mixture was concentrated in vacuo and the residue was dissolved in EtOH (10 mL). To the solution was added pyridine-2-carboxamidine hydrochloride (82 mg, 0.52 mmol) and $K_2CO_3$ (144 mg, 1.04 mmol) successively. The resulting mixture was heated to 80° C. and stirred overnight. Then the reaction mixture was cooled to rt and purified by prep-HPLC to give 2-(2-pyridyl)-6-[4-(trifluoromethylsulfonyl)phenyl]-7,8-dihydro-5H-pyrido[4,3-d]pyrimidine (5 mg). $^1$H NMR (400 MHz, MeOH-d$_4$): δ 8.73-8.80 (s, 1H), 8.45-8.53 (m, 1H), 7.99-8.07 (m, 1H), 7.93 (m, 1H), 7.83-7.89 (m, 2H), 7.64-7.71 (m, 1H), 7.10-7.17 (m, 2H), 4.72-4.78 (m, 2H), 3.90-3.99 (m, 2H), 3.26-3.31 (m, 2H). MS obsd. (ESI$^+$) [(M+H)$^+$]: 421.

Example 13: 6-(3,5-difluorophenyl)-2-(2-pyridyl)-7,8-dihydro-5H-pyrido[4,3-d]pyrimidine

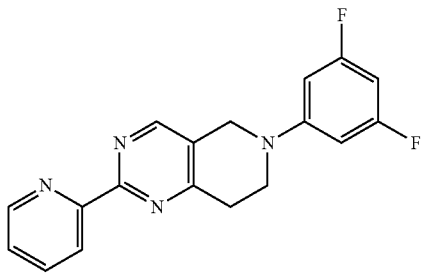 [SMILES: Fc1cc(F)cc(N2CCc3nc(-c4ccccn4)ncc3C2)c1]

Step 1: Preparation of 8-(3,5-difluorophenyl)-1,4-dioxa-8-azaspiro[4.5]decane

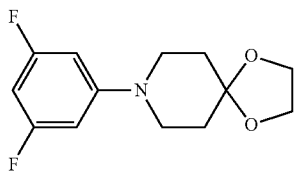

To a flask containing a mixture of 1,3-difluoro-5-iodobenzene (900 mg, 3.75 mmol) and 1,4-dioxa-8-azaspiro[4.5]decane (644 mg, 4.5 mmol) in dioxane (20 mL) was added t-BuONa (720 mg, 7.5 mmol), Pd$_2$(dba)$_3$ (174 mg, 0.19 mmol) and Sphos (156 mg, 0.38 mmol) successively under N$_2$. Then the resulting mixture was heated to 100° C. and stirred overnight. After being cooled to rt, the resulting reaction mixture was diluted with H$_2$O (20 mL) and extracted with EA (50 mL) for three times. The combined organic layer was washed with brine (50 mL), dried over anhydrous Na$_2$SO$_4$ and concentrated in vacuo to give crude 8-(3,5-difluorophenyl)-1,4-dioxa-8-azaspiro[4.5]decane (900 mg), which was used in the next step without further purification.

Step 2: Preparation of 1-(3,5-difluorophenyl)piperidin-4-one

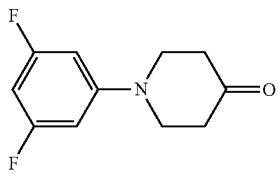

To a flask containing crude 8-(3,5-difluorophenyl)-1,4-dioxa-8-azaspiro[4.5]decane (900 mg, 3.53 mmol) was added 44% formic acid (10 mL). After being heated with stirring at 90° C. for 8 hrs, the reaction mixture was concentrated in vacuo and the residue was diluted with sat. aqueous solution of NaHCO$_3$ (20 mL) and extracted with EA (30 mL) for three times. The combined organic layer was washed with brine (30 mL), dried over anhydrous Na$_2$SO$_4$ and concentrated in vacuo to give 1-(3,5-difluorophenyl) piperidin-4-one (750 mg) as brown oil, which was used in the next step without further purification.

Step 3: 6-(3,5-difluorophenyl)-2-(2-pyridyl)-7,8-dihydro-5H-pyrido[4,3-d]pyrimidine

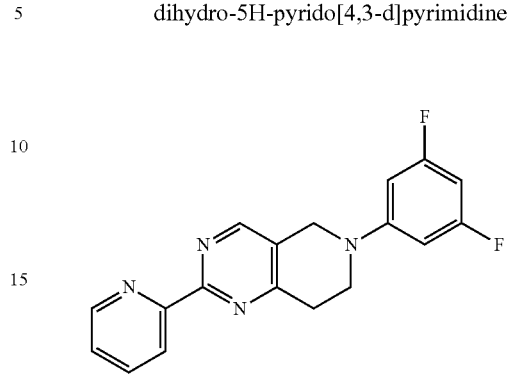

Crude 1-(3,5-difluorophenyl)piperidin-4-one (750 mg, 3.55 mmol) was heated with DMFDMA (5 mL) at 90° C. for 3 hrs. The resulting mixture was concentrated in vacuo. The residue was dissolved in EtOH (10 mL). To the solution was added pyridine-2-carboxamidine hydrochloride (560 mg, 3.55 mmol) and K$_2$CO$_3$ (980 mg, 7.1 mmol) successively. The resulting mixture was heated to 80° C. and stirred overnight. The reaction mixture was then cooled to rt and purified by prep-HPLC to give 6-(3,5-difluorophenyl)-2-(2-pyridyl)-7,8-dihydro-5H-pyrido[4,3-d]pyrimidine (50 mg). $^1$H NMR (400 MHz, CDCl$_3$): δ 8.86 (d, 1H), 8.72 (s, 1H), 8.52 (d, 1H), 7.88 (td, 1H), 7.38-7.46 (m, 1H), 6.44-6.51 (m, 2H), 6.28-6.36 (m, 1H), 4.48 (s, 2H), 3.69-3.73 (m, 2H), 3.24-3.32 (m, 2H). MS obsd. (ESI$^+$) [(M+H)$^+$]: 325.

Example 14: 6-(2,4-difluorophenyl)-2-(2-pyridyl)-7,8-dihydro-5H-pyrido[4,3-d]pyrimidine

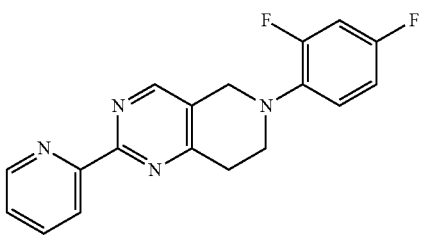 [SMILES: Fc1ccc(N2CCc3nc(-c4ccccn4)ncc3C2)c(F)c1]

Step 1: Preparation of 8-(2,4-difluorophenyl)-1,4-dioxa-8-azaspiro[4.5]decane

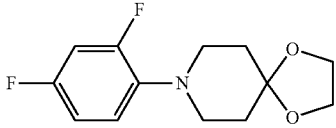 [SMILES: Fc1ccc(N2CCC3(CC2)OCCO3)c(F)c1]

To a flask containing a mixture of 2,4-difluoro-1-iodobenzene (440 mg, 1.83 mmol) and 1,4-dioxa-8-azaspiro[4.5]decane (315 mg, 2.2 mmol) in dioxane (10 mL) was added t-BuONa (350 mg, 7.5 mmol), Pd$_2$(dba)$_3$ (83 mg, 0.09 mmol) and Sphos (74 mg, 0.18 mmol) successively under N₂. The resulting mixture was heated to 100° C. and stirred overnight. After being cooled to rt, the reaction mixture was diluted with H₂O (20 mL) and extracted with EA (50 mL) for three times. The combined organic layer was washed with brine (50 mL), dried over anhydrous Na₂SO₄ and concentrated in vacuo to afford crude 8-(2,4-difluorophenyl)-1,4-dioxa-8-azaspiro[4.5]decane (450 mg), which was used in the next step without further purification.

Step 2: Preparation of
1-(2,4-difluorophenyl)piperidin-4-one

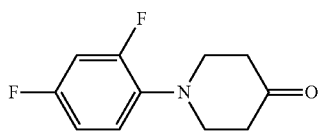

A mixture of crude 8-(2,4-difluorophenyl)-1,4-dioxa-8-azaspiro[4.5]decane (0.3 g, 1.18 mmol) H₂O (5 mL) and formic acid (5 mL) was heated with stirring at 90° C. overnight. The reaction mixture was then concentrated in vacuo, diluted with sat. aqueous solution of NaHCO₃ and extracted with EA (20 mL) for three times. The combined organic layer was washed with brine, dried over anhydrous Na₂SO₄ and concentrated in vacuo. The residue was purified by column chromatography (eluting with 2% MeOH in dichloromethane) to give 1-(2,4-difluorophenyl)piperidin-4-one (0.24 g).

Step 3: Preparation of 6-(2,4-difluorophenyl)-2-(2-pyridyl)-7,8-dihydro-5H-pyrido[4,3-d]pyrimidine

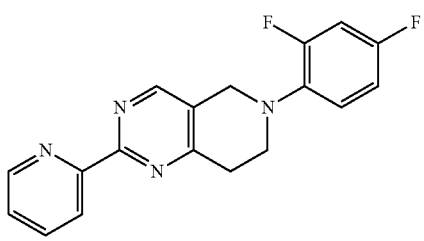 [SMILES: Fc1ccc(N2CCc3nc(-c4ccccn4)ncc3C2)c(F)c1]

A solution of 1-(2,4-difluorophenyl)piperidin-4-one (0.24 g, 1.14 mmol) and DMFDMA (0.5 mL) in acetonitrile (5 ml) was heated with stirring at 90° C. for 2 hrs. The mixture was concentrated in vacuo and the residue was dissolved in EtOH (10 mL). To the solution was added pyridine-2-carboxamidine (91 mg, 0.75 mmol) and potassium carbonate (210 mg, 1.50 mmol) successively. After being heated at 90° C. overnight, the resulting mixture was cooled to rt, diluted with water (20 mL) and extracted with EA (20 mL) for three times. The organic layers were washed with brine, dried over anhydrous Na₂SO₄ and concentrated in vacuo. The residue was purified by prep-HPLC to give 6-(2,4-difluorophenyl)-2-(2-pyridyl)-7,8-dihydro-5H-pyrido[4,3-d]pyrimidine (6 mg). ¹H NMR (400 MHz, DMSO-d₆): δ 8.77 (s, 1H), 8.74 (d, 1H), 8.36 (d, 1H), 7.97 (dt, 1H), 7.52 (ddd, 1H), 7.34-7.16 (m, 2H), 7.14-6.97 (m, 1H), 4.33 (s, 2H), 3.48 (t, 2H), 3.10 (t, 2H). MS obsd. (ESI⁺) [(M+H)⁺]: 325.

Example 15 and 16: methyl 2-fluoro-4-[2-(2-pyridyl)-7,8-dihydro-5H-pyrido[4,3-d]pyrimidin-6-yl]benzoate and methyl 5-bromo-2-[2-(2-pyridyl)-7,8-dihydro-5H-pyrido[4,3-d]pyrimidin-6-yl]benzoate Example 15

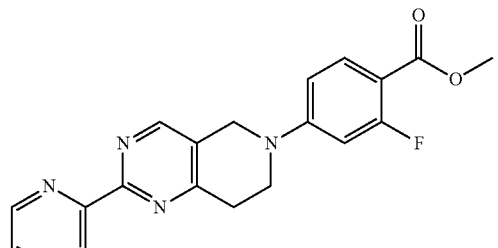

Example 16

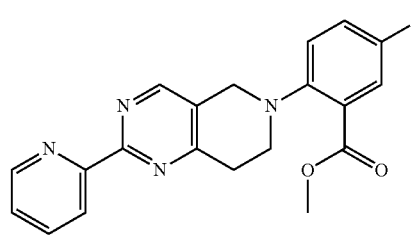

Step 1: Preparation of methyl 4-(1,4-dioxa-8-azaspiro[4.5]decan-8-yl)-2-fluoro-benzoate and methyl 5-bromo-2-(1,4-dioxa-8-azaspiro[4.5]decan-8-yl)benzoate

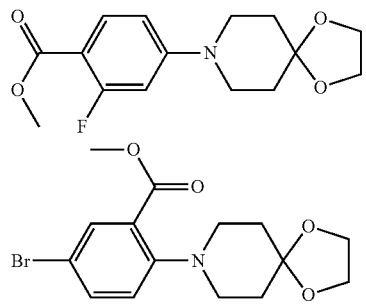

To a flask containing a mixture of methyl 4-bromo-2-fluoro-benzoate (4.0 g, 17.2 mmol) and 1,4-dioxa-8-azaspiro[4.5]decane (2.9 g, 20.6 mmol) in dioxane (50 mL) was added t-BuONa (3.3 g, 34.4 mmol), Pd₂(dba)₃ (312 mg, 0.34 mmol) and Sphos (279 mg, 0.68 mmol) successively under N₂. After being heated with stirring at 100° C. overnight, the reaction mixture was cooled to rt, diluted with H₂O (40 mL) and extracted with EA (50 mL) for three times. The combined organic layer was washed with brine (50 mL), dried over anhydrous Na₂SO₄ and concentrated in vacuo to give methyl 4-(1,4-dioxa-8-azaspiro[4.5]decan-8-yl)-2-fluoro-benzoate mixed with methyl 5-bromo-2-(1,4-dioxa-8-azaspiro[4.5]decan-8-yl)benzoate (total 4.5 g), which was used in the next step without further purification.

Step 2: Preparation of methyl 2-fluoro-4-(4-oxo-1-piperidyl)benzoate and methyl 5-bromo-2-(4-oxo-1-piperidyl)benzoate

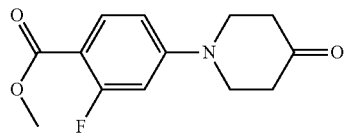

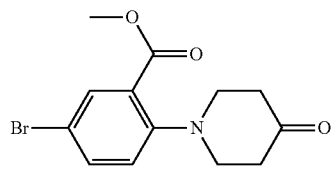

A mixture of methyl 4-(1,4-dioxa-8-azaspiro[4.5]decan-8-yl)-2-fluoro-benzoate and methyl 5-bromo-2-(1,4-dioxa-8-azaspiro[4.5]decan-8-yl)benzoate (4.5 g) was heated with 44% formic acid (20 mL) at 90° C. for 8 hrs. The reaction mixture was concentrated in vacuo. the residue was diluted with sat. aqueous solution of NaHCO$_3$ (40 mL) and extracted with EA (50 mL) for three times. The combined organic layer was washed with brine (50 mL), dried over anhydrous Na$_2$SO$_4$ and concentrated in vacuo to give a mixture of methyl 2-fluoro-4-(4-oxo-1-piperidyl)benzoate and methyl 5-bromo-2-(4-oxo-1-piperidyl)benzoate (total 3.5 g) as brown oil, which was used in the next step without further purification.

Step 3: Preparation of methyl 2-fluoro-4-[2-(2-pyridyl)-7,8-dihydro-5H-pyrido[4,3-d]pyrimidin-6-yl]benzoate and methyl 5-bromo-2-[2-(2-pyridyl)-7,8-dihydro-5H-pyrido[4,3-d]pyrimidin-6-yl]benzoate A mixture of methyl 2-fluoro-4-(4-oxo-1-piperidyl)benzoate and methyl 5-bromo-2-(4-oxo-1-piperidyl)benzoate (total 3.5 g, 13.9 mmol) was heated with DMFDMA (10 mL) at 90° C. for 3 hrs. The reaction mixture was concentrated in vacuo and the residue was dissolved in EtOH (20 mL). To the resulting solution was added pyridine-2-carboxamidine hydrochloride (2196 mg, 13.9 mmol) and K$_2$CO$_3$ (3836 mg, 27.8 mmol) successively. After being heated with stirring at 80° C. overnight, the reaction mixture was cooled to rt and purified by prep-HPLC to give methyl 2-fluoro-4-[2-(2-pyridyl)-7,8-dihydro-5H-pyrido[4,3-d]pyrimidin-6-yl]benzoate (Example 15, 5 mg) and methyl 5-bromo-2-[2-(2-pyridyl)-7,8-dihydro-5H-pyrido[4,3-d]pyrimidin-6-yl]benzoate (Example 16, 5 mg).

Example 15: methyl 2-fluoro-4-[2-(2-pyridyl)-7,8-dihydro-5H-pyrido[4,3-d]pyrimidin-6-yl]benzoate: $^1$H NMR (400 MHz, CDCl$_3$): δ 8.83-8.93 (m, 1H), 8.74 (s, 1H), 8.47-8.60 (m, 1H), 7.85-7.96 (m, 2H), 7.40-7.51 (m, 1H), 6.57-6.78 (m, 2H), 4.55-4.63 (m, 2H), 3.90 (s, 3H), 3.77-3.85 (m, 2H), 3.25-3.34 (m, 2H). MS obsd. (ESI$^+$) [(M+H)$^+$]: 365.

Example 16: methyl 5-bromo-2-[2-(2-pyridyl)-7,8-dihydro-5H-pyrido[4,3-d]pyrimidin-6-yl]benzoate: $^1$H NMR (400 MHz, CDCl$_3$): δ 8.82-8.92 (m, 1H), 8.67 (s, 1H), 8.48-8.57 (m, 1H), 7.83-7.93 (m, 1H), 7.67-7.75 (m, 1H), 7.38-7.45 (m, 1H), 7.30-7.33 (m, 1H), 7.19-7.24 (m, 1H), 4.37 (s, 2H), 3.90 (s, 3H), 3.46-3.53 (m, 2H), 3.29-3.38 (m, 2H). MS obsd. (ESI$^+$) [(M+H)$^+$]: 425.

Example 17 and 18: 6-(3,4-difluoro-5-methoxyphenyl)-2-(2-pyridyl)-7,8-dihydro-5H-pyrido[4,3-d]pyrimidine and 2,3-difluoro-5-[2-(2-pyridyl)-7,8-dihydro-5H-pyrido[4,3-d]pyrimidin-6-yl]phenol Example 15

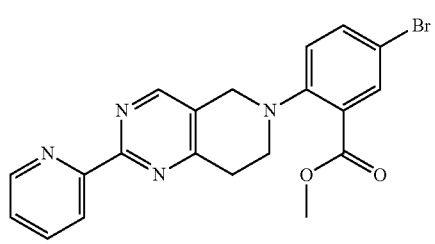

Example 16

Example 17

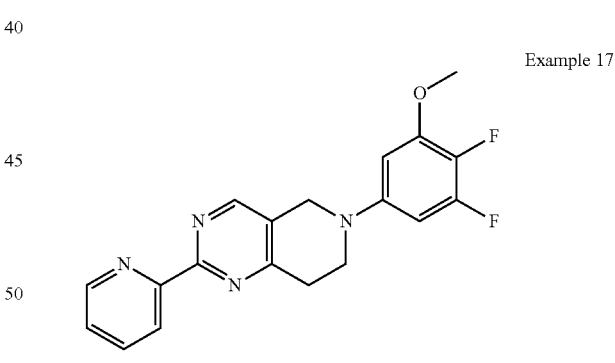

Example 18

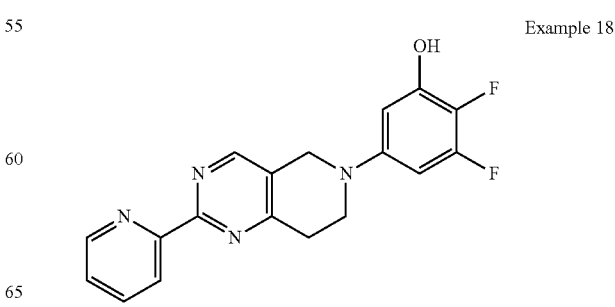

Step 1: Preparation of 5-(1,4-dioxa-8-azaspiro[4.5]decan-8-yl)-2,3-difluoro-phenol

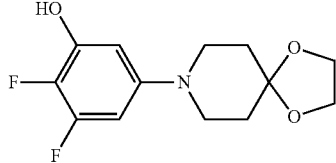 [SMILES: Oc1cc(N2CCC3(CC2)OCCO3)cc(F)c1F]

To a flask containing a mixture of 5-bromo-2,3-difluoro-phenol (2.5 g, 12 mmol) and 1,4-dioxa-8-azaspiro[4.5]decane (2.1 g, 14.4 mmol) in dioxane (40 mL) was added t-BuONa (2.3 g, 24 mmol), Pd$_2$(dba)$_3$ (220 mg, 0.24 mmol) and Sphos (197 mg, 0.48 mmol) successively under N$_2$. The resulting mixture was heated to 100° C. and stirred overnight. After being cooled to rt, the reaction mixture was diluted with H$_2$O (40 mL) and extracted with EA (50 mL) for three times. The combined organic layer was washed with brine (50 mL), dried over anhydrous Na$_2$SO$_4$ and concentrated in vacuo to afford 5-(1,4-dioxa-8-azaspiro[4.5]decan-8-yl)-2,3-difluoro-phenol (2000 mg), which was used in the next step without further purification.

Step 2: Preparation of 1-(3,4-difluoro-5-hydroxy-phenyl)piperidin-4-one

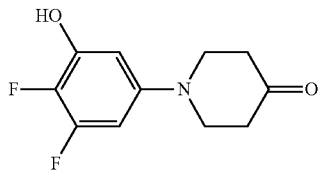

Crude 5-(1,4-dioxa-8-azaspiro[4.5]decan-8-yl)-2,3-difluoro-phenol (2.0 g, 7.38 mmol) was heated with 44% formic acid (20 mL) at 90° C. for 8 hrs. The reaction mixture was concentrated in vacuo and the residue was diluted with sat. aqueous solution of NaHCO$_3$ (20 mL). The resulting mixture was extracted with EA (30 mL) for three times. The combined organic layer was washed with brine (50 mL), dried over anhydrous Na$_2$SO$_4$ and concentrated in vacuo to give 1-(3,4-difluoro-5-hydroxy-phenyl)piperidin-4-one (1200 mg) as brown oil, which was used in the next step without further purification.

Step 3: Preparation of 6-(3,4-difluoro-5-methoxyphenyl)-2-(2-pyridyl)-7,8-dihydro-5H-pyrido[4,3-d]pyrimidine and 2,3-difluoro-5-[2-(2-pyridyl)-7,8-dihydro-5H-pyrido[4,3-d]pyrimidin-6-yl]phenol Example 17

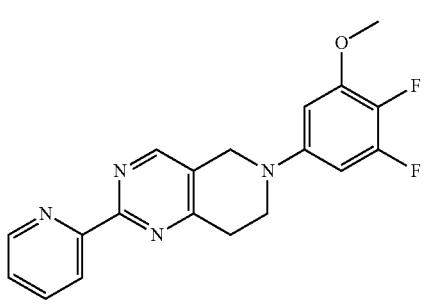

Example 18

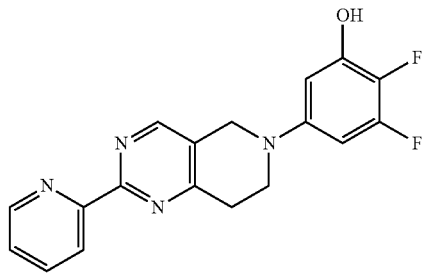

Crude 1-(3,4-difluoro-5-hydroxy-phenyl)piperidin-4-one (1200 mg, 5.29 mmol) was heated with DMFDMA (10 mL) at 90° C. for 3 hrs. The reaction mixture was concentrated in vacuo and the residue was dissolved in EtOH (20 mL). To the solution was added pyridine-2-carboxamidine hydrochloride (840 mg, 5.29 mmol) and K$_2$CO$_3$ (1460 mg, 10.58 mmol) successively. After being heated with stirring at 80° C. overnight, the reaction mixture was cooled to rt and purified by prep-HPLC to give 2,3-difluoro-5-[2-(2-pyridyl)-7,8-dihydro-5H-pyrido[4,3-d]pyrimidin-6-yl]phenol (Example 18, 5 mg) and 6-(3,4-difluoro-5-methoxyphenyl)-2-(2-pyridyl)-7,8-dihydro-5H-pyrido[4,3-d]pyrimidine (Example 17, 5 mg).

Example 17: 6-(3,4-difluoro-5-methoxy-phenyl)-2-(2-pyridyl)-7,8-dihydro-5H-pyrido[4,3-d]pyrimidine, $^1$H NMR (400 MHz, CDCl$_3$): δ 8.47-8.96 (m, 3H), 7.93 (t, 1H), 7.40-7.52 (m, 1H), 6.34-6.51 (m, 2H), 4.35-4.45 (m, 2H), 3.95 (s, 3H), 3.59-3.69 (m, 2H), 3.24-3.36 (m, 2H). MS obsd. (ESI$^+$) [(M+H)$^+$]: 354.

Example 18: 2,3-difluoro-5-[2-(2-pyridyl)-7,8-dihydro-5H-pyrido[4,3-d]pyrimidin-6-yl]phenol, $^1$H NMR (400 MHz, MeOH-d$_4$): δ 8.73-8.79 (m, 1H), 8.66-8.72 (m, 1H), 8.70 (s, 1H), 8.44-8.51 (m, 1H), 7.87-8.00 (m, 1H), 7.53-7.59 (m, 1H), 7.43-7.52 (m, 1H), 6.27-6.45 (m, 1H), 4.36-4.41 (m, 2H), 3.58-3.66 (m, 2H), 3.16-3.24 (m, 2H). MS obsd. (ESI$^+$) [(M+H)$^+$]: 340.

Example 19: 6-[3,4-difluoro-5-(3-methoxypropoxy)phenyl]-2-(2-pyridyl)-7,8-dihydro-5H-pyrido[4,3-d]pyrimidine

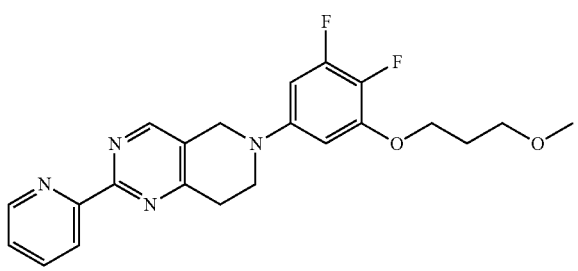 [SMILES: COCCCOc1cc(N2CCc3nc(-c4ccccn4)ncc3C2)cc(F)c1F]

To a solution of 2,3-difluoro-5-[2-(2-pyridyl)-7,8-dihydro-5H-pyrido[4,3-d]pyrimidin-6-yl]phenol (200 mg, 0.59 mmol) in DMF (5 mL) was added 1-bromo-3-methoxypropane (0.2 mL) and K$_2$CO$_3$ (160 mg, 1.18 mmol). The mixture was heated with stirring at 90° C. After the reaction finished, the reaction mixture was cooled to rt and filtered. The filtrate was purified by prep-HPLC to give 6-[3,4-difluoro-5-(3-methoxypropoxy)phenyl]-2-(2-pyridyl)-7,8-dihydro-5H-pyrido[4,3-d]pyrimidine (2 mg). $^1$H NMR (400

MHz, CDCl₃): δ 8.82-8.97 (m, 1H), 8.66-8.78 (m, 1H), 8.48-8.61 (m, 1H), 7.86-7.99 (m, 1H), 7.38-7.52 (m, 1H), 6.37-6.48 (m, 2H), 4.36-4.44 (m, 2H), 4.14-4.23 (m, 2H), 3.55-3.67 (m, 4H), 3.40 (s, 3H), 3.25-3.33 (m, 2H), 2.05-2.19 (m, 2H). MS obsd. (ESI⁺) [(M+H)⁺]: 354.

Example 20: 6-(3-benzyloxy-4,5-difluoro-phenyl)-2-(2-pyridyl)-7,8-dihydro-5H-pyrido[4,3-d]pyrimidine

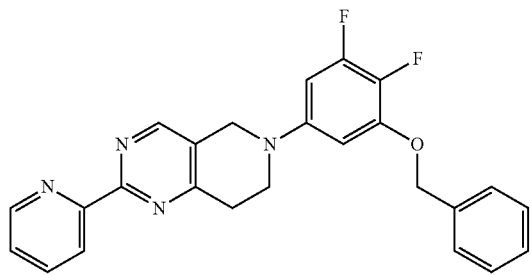 [SMILES: Fc1cc(N2CCc3nc(-c4ccccn4)ncc3C2)cc(OCc2ccccc2)c1F]

Step 1: Preparation of 1-benzyloxy-5-bromo-2,3-difluoro-benzene

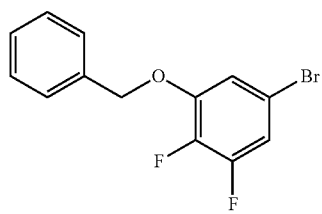 [SMILES: Fc1cc(Br)cc(OCc2ccccc2)c1F]

To a solution of 5-bromo-2,3-difluoro-phenol (3.4 g, 16.3 mmol) in acetone (40 mL) was added benzyl bromide (3.0 g, 17.9 mmol) and K₂CO₃ (4.5 g, 32.6 mmol). The reaction was heated under reflux for 5 hrs. After being cooled to rt, the resulting mixture was filtered and the filtrate was purified by flash column to give 1-benzyloxy-5-bromo-2,3-difluoro-benzene (4.9 g).

Step 2: Preparation of 8-(3-benzyloxy-4,5-difluoro-phenyl)-1,4-dioxa-8-azaspiro[4.5]decane

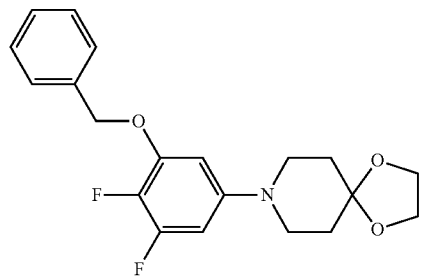 [SMILES: Fc1cc(N2CCC3(CC2)OCCO3)cc(OCc2ccccc2)c1F]

To a flask containing a mixture of 1-benzyloxy-5-bromo-2,3-difluoro-benzene (2.00 g, 6.71 mmol) and 1,4-dioxa-8-azaspiro[4.5]decane (1.06 g, 7.38 mmol) in dioxane (40 mL) was added t-BuONa (1.29 g, 13.42 mmol), Pd₂(dba)₃ (119 mg, 0.13 mmol) and Sphos (106 mg, 0.26 mmol) successively under N₂. The reaction mixture was heated to 100° C. and stirred overnight. After being cooled to rt, the resulting mixture was diluted with H₂O (40 mL) and extracted with EA (50 mL) for three times. The combined organic layer was washed with brine (50 mL), dried over anhydrous Na₂SO₄ and concentrated in vacuo to afford 8-(3-benzyloxy-4,5-difluoro-phenyl)-1,4-dioxa-8-azaspiro[4.5]decane (1.00 g), which was used in the next step without further purification.

Step 3: Preparation of 1-(3-benzyloxy-4,5-difluoro-phenyl)piperidin-4-one

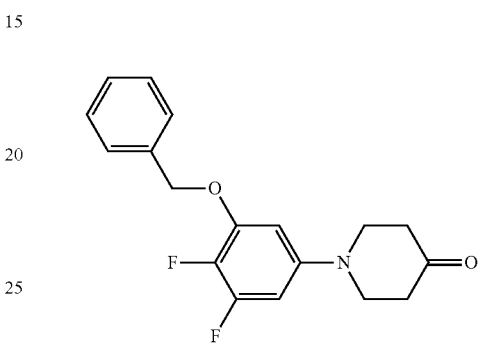

To a flask containing crude 8-(3-benzyloxy-4,5-difluoro-phenyl)-1,4-dioxa-8-azaspiro[4.5]decane (1.00 g, 2.77 mmol) was added 44% formic acid (10 mL). The resulting mixture was heated with stirring at 90° C. for 8 hrs, and then concentrated in vacuo. The residue was diluted with sat. aqueous solution of NaHCO₃ (20 mL), and extracted with EA (30 mL) for three times. The combined organic layer was washed with brine (50 mL), dried over anhydrous Na₂SO₄ and concentrated in vacuo to give 1-(3-benzyloxy-4,5-difluoro-phenyl)piperidin-4-one (800 mg) as brown oil, which was used in the next step without further purification.

Step 4: Preparation of 6-(3-benzyloxy-4,5-difluoro-phenyl)-2-(2-pyridyl)-7,8-dihydro-5H-pyrido[4,3-d]pyrimidine

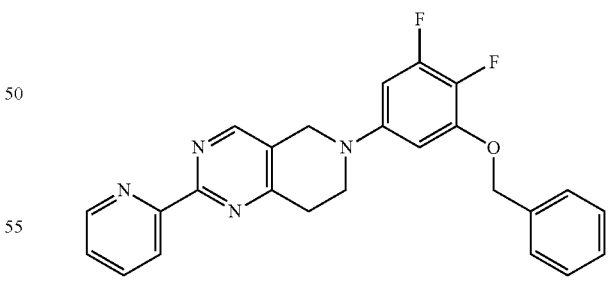

Crude 1-(3-benzyloxy-4,5-difluoro-phenyl)piperidin-4-one (800 mg, 2.52 mmol) was heated with DMFDMA (10 mL) at 90° C. for 3 hrs. The reaction mixture was concentrated in vacuo and the residue was dissolved in EtOH (20 mL). To the solution was added pyridine-2-carboxamidine hydrochloride (398 mg, 2.52 mmol) and K₂CO₃ (696 mg, 5.04 mmol) successively. After being heated with stirring at 80° C. overnight, the reaction mixture was cooled to rt and purified by prep-HPLC to give 6-(3-benzyloxy-4,5-difluorophenyl)-2-(2-pyridyl)-7,8-dihydro-5H-pyrido[4,3-d]pyrimidine (900 mg). ¹H NMR (400 MHz, CDCl₃): δ 8.91-9.08 (m, 1H), 8.67-8.77 (m, 1H), 8.55-8.66 (m, 1H), 7.97-8.11 (m, 1H), 7.51-7.64 (m, 1H), 7.34-7.50 (m, 5H), 6.38-6.49 (m, 2H), 5.17-5.24 (m, 2H), 4.32-4.39 (m, 2H), 3.54-3.65 (m, 2H), 3.23-3.35 (m, 2H). MS obsd. (ESI⁺) [(M+H)⁺]: 431.

Example 21:6-(3-ethoxy-4,5-difluoro-phenyl)-2-(2-pyridyl)-7,8-dihydro-5H-pyrido[4,3-d]pyrimidine

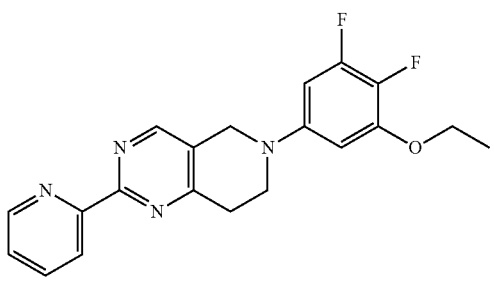 [SMILES: CCOc1cc(N2CCc3nc(-c4ccccn4)ncc3C2)cc(F)c1F]

To a solution of 2,3-difluoro-5-[2-(2-pyridyl)-7,8-dihydro-5H-pyrido[4,3-d]pyrimidin-6-yl]phenol (80 mg, 0.24 mmol) in DMF (2 mL) was added ethyliodide (112 mg, 0.72 mmol) and K₂CO₃ (66 mg, 0.48 mmol). The mixture was heated with stirring at 90° C. After the reaction finished, the reaction mixture was cooled to rt and filtered. The filtrate was purified by prep-HPLC to give 6-(3-ethoxy-4,5-difluoro-phenyl)-2-(2-pyridyl)-7,8-dihydro-5H-pyrido[4,3-d]pyrimidine (14 mg). ¹H NMR (400 MHz, CDCl₃): δ 8.84-9.01 (m, 1H), 8.65-8.80 (m, 1H), 8.51-8.63 (m, 1H), 7.90-8.00 (m, 1H), 7.43-7.56 (m, 1H), 6.36-6.48 (m, 2H), 4.40 (s, 2H), 4.16 (d, 2H), 3.63 (t, 2H), 3.30 (t, 2H), 1.49 (t, 3H). MS obsd. (ESI⁺) [(M+H)⁺]: 369.

Example 22:6-(3,4-difluoro-5-propoxy-phenyl)-2-(2-pyridyl)-7,8-dihydro-5H-pyrido[4,3-d]pyrimidine

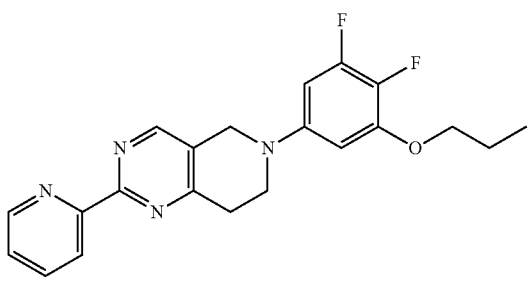 [SMILES: CCCOc1cc(N2CCc3nc(-c4ccccn4)ncc3C2)cc(F)c1F]

To a solution of 2,3-difluoro-5-[2-(2-pyridyl)-7,8-dihydro-5H-pyrido[4,3-d]pyrimidin-6-yl]phenol (80 mg, 0.24 mmol) in DMF (2 mL) was added 1-iodopropane (122 mg, 0.72 mmol) and K₂CO₃ (66 mg, 0.48 mmol). The mixture was heated with stirring at 90° C. After the reaction finished, the reaction mixture was cooled to rt and filtered. The filtrate was purified by prep-HPLC to give 6-(3,4-difluoro-5-propoxy-phenyl)-2-(2-pyridyl)-7,8-dihydro-5H-pyrido[4,3-d]pyrimidine (5 mg). ¹H NMR (400 MHz, CDCl₃): δ 8.83-8.93 (m, 1H), 8.68-8.75 (m, 1H), 8.50-8.58 (m, 1H), 7.85-7.95 (m, 1H), 7.39-7.48 (m, 1H), 6.37-6.46 (m, 2H), 4.39 (s, 2H), 4.04 (t, 2H), 3.57-3.67 (m, 2H), 3.29 (s, 2H), 1.80-1.96 (m, 2H), 1.09 (t, 3H). MS obsd. (ESI⁺) [(M+H)⁺]: 383.

Example 23: 6-[3,4-difluoro-5-(2-methoxyethoxy)phenyl]2-(2-pyridyl)-7,8-dihydro-5H-pyrido[4,3-d]pyrimidine To a solution of 2,3-difluoro-5-[2-(2-pyridyl)-7,8-dihydro-5H-pyrido[4,3-d]pyrimidin-6-yl]phenol (80 mg, 0.24 mmol) in DMF (2 mL) was added 1-bromo-2-methoxyethane (100 mg, 0.72 mmol) and K₂CO₃ (66 mg, 0.48 mmol). The mixture was heated with stirring at 90° C. After the reaction finished, the reaction mixture was cooled to rt and filtered. The filtrate was purified by prep-HPLC to give 6-[3,4-difluoro-5-(2-methoxyethoxy)phenyl]-2-(2-pyridyl)-7,8-dihydro-5H-pyrido[4,3-d]pyrimidine (5 mg). ¹H NMR (400 MHz, CDCl₃): δ 8.84-8.96 (m, 1H), 8.68-8.76 (m, 1H), 8.50-8.59 (m, 1H), 7.88-7.97 (m, 1H), 7.40-7.51 (m, 1H), 6.39-6.51 (m, 2H), 4.36-4.42 (m, 2H), 4.22-4.28 (m, 2H), 3.77-3.83 (m, 2H), 3.59-3.66 (m, 2H), 3.49 (s, 3H), 3.25-3.33 (m, 2H). MS obsd. (ESI⁺) [(M+H)⁺]: 399.

Example 24: 6-(3,4-difluoro-5-methoxy-phenyl)-2-(4-methoxy-2-pyridyl)-7,8-dihydro-5H-pyrido[4,3-d]pyrimidine

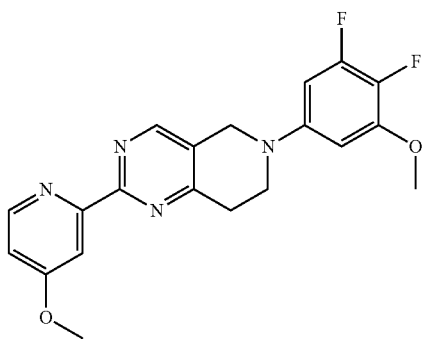 [SMILES: COc1ccnc(-c2ncc3c(n2)CCN(c2cc(F)c(F)c(OC)c2)C3)c1]

Step 1: Preparation of 4-methoxypyridine-2-carboxamidine hydrochloride

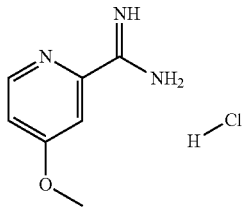

To a solution of 4-methyoxypyridine-2-carbonitrile (1.0 g, 7.46 mmol) in methanol (20 mL) was added NaOCH₃ (80 mg, 1.49 mmol). The reaction mixture was stirred at rt for 12 hrs. To the resulting mixture was added NH₄Cl (399 mg, 7.46 mmol). After being heated under reflux for 3 hrs, the reaction mixture was concentrated in vacuo. The residue was suspended in ethanol (30 mL) and the suspension was heated under reflux for 1 hr. The resulting mixture was cooled to rt and filtered. The filtrate was concentrated in vacuo to give 4-metyoxypyridine-2-carboxamidine hydrochloride (1.2 g).

Step 2: Preparation of 6-(3-benzyloxy-4,5-difluoro-phenyl)-2-(4-methoxy-2-pyridyl)-7,8-dihydro-5H-pyrido[4,3-d]pyrimidine

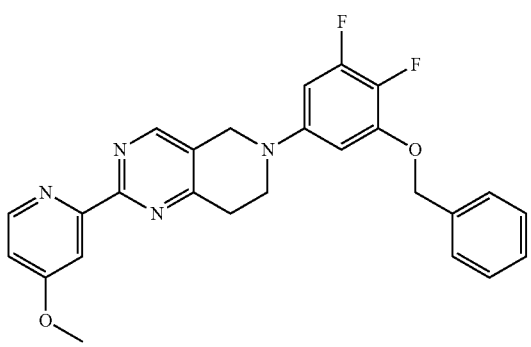 [SMILES: COc1ccnc(-c2ncc3c(n2)CCN(c2cc(F)c(F)c(OCc4ccccc4)c2)C3)c1]

A solution of 1-(3-benzyloxy-4,5-difluoro-phenyl)piperidin-4-one (314 mg, 0.99 mmol) and DMFDMA (1 mL) in acetonitrile (9 mL) was heated with stirring at 90° C. for 2 hrs. The reaction mixture was concentrated in vacuo and the residue was dissolved in EtOH (10 mL). To the solution was added 4-methoxypyridine-2-carboxamidine hydrochloride (185 mg, 0.99 mmol) and potassium carbonate (280 mg, 2.0 mmol) successively and the reaction was heated with stirring at 90° C. overnight. The reaction mixture was cooled to rt, diluted with water (20 mL) and extracted with EA (30 mL). The organic layer was separated and washed with brine, dried over anhydrous Na₂SO₄ and concentrated in vacuo to give 6-(3-benzyloxy-4,5-difluoro-phenyl)-2-(4-methoxy-2-pyridyl)-7,8-dihydro-5H-pyrido[4,3-d]pyrimidine (0.48 g), which was used in the next step without purification.

Step 3: Preparation of 2,3-difluoro-5-[2-(4-methoxy-2-pyridyl)-7,8-dihydro-5H-pyrido[4,3-d]pyrimidin-6-yl]phenol

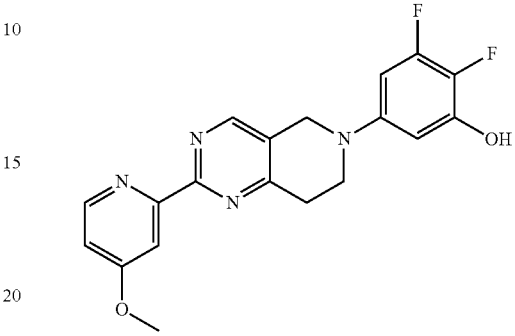

A mixture of 6-(3-benzyloxy-4,5-difluoro-phenyl)-2-(4-methoxy-2-pyridyl)-7,8-dihydro-5H-pyrido[4,3-d]pyrimidine (0.48 g, 1.04 mmol), ammonium formate (0.66 g, 10.4 mmol) and Pd(OH)₂ (25 mg, 0.18 mmol) in methanol (10 mL) was heated with stirring at 90° C. overnight. The reaction mixture was cooled to rt and filtered. The filtrate was concentrated in vacuo to give crude 2,3-difluoro-5-[2-(4-methoxy-2-pyridyl)-7,8-dihydro-5H-pyrido[4,3-d]pyrimidin-6-yl]phenol (0.9 g), which was used in the next step without purification.

Step 4: Preparation of 6-(3,4-difluoro-5-methoxy-phenyl)-2-(4-methoxy-2-pyridyl)-7,8-dihydro-5H-pyrido[4,3-d]pyrimidine

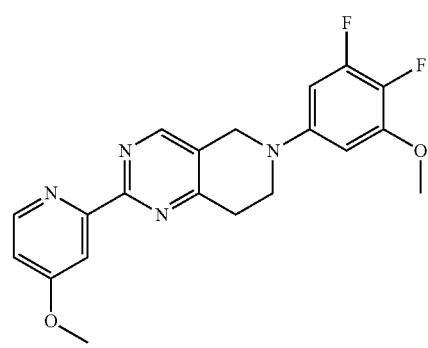 [SMILES: COc1ccnc(-c2ncc3c(n2)CCN(c2cc(F)c(F)c(OC)c2)C3)c1]

A mixture of 2,3-difluoro-5-[2-(4-methoxy-2-pyridyl)-7,8-dihydro-5H-pyrido[4,3-d]pyrimidin-6-yl]phenol (100 mg, 0.27 mmol), methyl iodide (120 mg, 0.81 mmol) and potassium carbonate (75 mg, 0.54 mmol) in DMF (2 mL) was heated with stirring at 60° C. for 5 hrs. The reaction was cooled to rt and purified by prep-HPLC to give 6-(3,4-difluoro-5-methoxy-phenyl)-2-(4-methoxy-2-pyridyl)-7,8-dihydro-5H-pyrido[4,3-d]pyrimidine (22 mg). ¹H NMR (400 MHz, DMSO-d₆): δ 8.78 (s, 1H), 8.54 (d, 1H), 7.89 (d, 1H), 7.11 (dd, 1H), 6.70-6.61 (m, 2H), 4.51 (s, 2H), 3.92 (s, 3H), 3.90 (s, 3H), 3.71 (t, 2H), 3.09 (t, 2H). MS obsd. (ESI⁺) [(M+H)⁺]: 385.

Example 25: 6-(3,4-difluoro-5-methoxy-phenyl)-2-(6-methoxy-2-pyridyl)-7,8-dihydro-5H-pyrido[4,3-d]pyrimidine

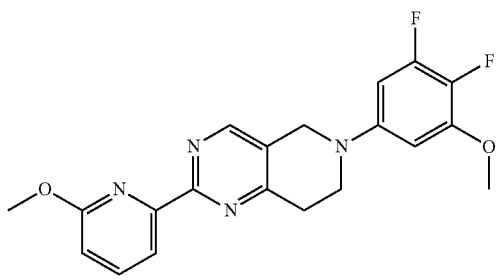

Step 1: Preparation of 6-metyoxypyridine-2-carboxamidine hydrochloride

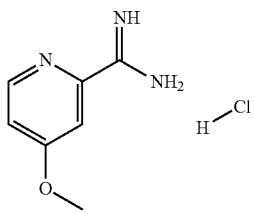

To a solution of 6-methyoxypyridine-2-carbonitrile (1.0 g, 7.46 mmol) in methanol (20 mL) was added NaOCH₃ (80 mg, 1.49 mmol). After the resulting mixture was stirred at rt for 12 hrs, to the mixture was added NH₄Cl (399 mg, 7.46 mmol). After being heated under reflux for 3 hrs, the reaction mixture was cooled to rt and concentrated in vacuo. The residue was suspended in ethanol (30 mL) and the suspension was heated under reflux for 1 hr. The mixture was filtered and the filtrate was concentrated in vacuo to give 6-metyoxypyridine-2-carboxamidine hydrochloride (1.2 g).

Step 2: Preparation of 6-(3-benzyloxy-4,5-difluoro-phenyl)-2-(6-methoxy-2-pyridyl)-7,8-dihydro-5H-pyrido[4,3-d]pyrimidine

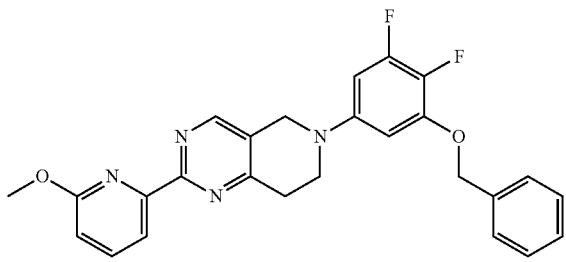 [SMILES: COc1cccc(-c2ncc3c(n2)CCN(c2cc(F)c(F)c(OCc4ccccc4)c2)C3)n1]

A solution of 1-(3-benzyloxy-4,5-difluoro-phenyl)piperidin-4-one (314 mg, 0.99 mmol) and DMFDMA (1 mL) in acetonitrile (9 mL) was heated with stirring at 90° C. for 2 hrs. The reaction mixture was concentrated in vacuo and the residue was dissolved in EtOH (10 mL). To the solution was added 6-methoxypyridine-2-carboxamidine hydrochloride (185 mg, 0.99 mmol) and potassium carbonate (280 mg, 2.0 mmol). After being heated with stirring at 90° C. overnight, the reaction mixture was cooled to rt and diluted with water (20 mL). The resulting mixture was extracted with EA (30 mL) for three times. The combined organic layer was washed with brine, dried over anhydrous Na₂SO₄ and concentrated in vacuo to give 6-(3-benzyloxy-4,5-difluoro-phenyl)-2-(6-methoxy-2-pyridyl)-7,8-dihydro-5H-pyrido[4,3-d]pyrimidine (0.52 g), which was used in the next step without purification.

Step 3: Preparation of 2,3-difluoro-5-[2-(6-methoxy-2-pyridyl)-7,8-dihydro-5H-pyrido[4,3-d]pyrimidin-6-yl]phenol

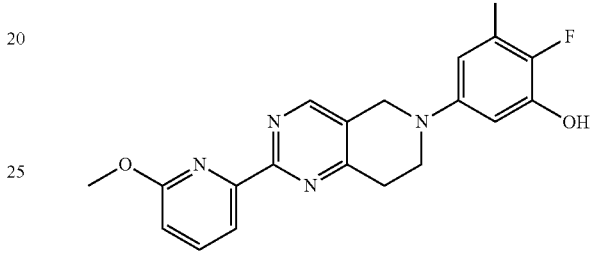

A mixture of 6-(3-benzyloxy-4,5-difluoro-phenyl)-2-(6-methoxy-2-pyridyl)-7,8-dihydro-5H-pyrido[4,3-d]pyrimidine (0.52 g, 1.13 mmol), ammonium formate (0.71 g, 11.3 mmol) and Pd(OH)₂ (25 mg, 0.18 mmol) in methanol (10 ml) was stirred at 90° C. overnight. The reaction mixture was cooled to rt and filtered. The filtrate was concentrated in vacuo to give 2,3-difluoro-5-[2-(6-methoxy-2-pyridyl)-7,8-dihydro-5H-pyrido[4,3-d]pyrimidin-6-yl]phenol (0.55 g), which was used in the next step without purification.

Step 4: Preparation of 6-(3,4-difluoro-5-methoxy-phenyl)-2-(6-methoxy-2-pyridyl)-7,8-dihydro-5H-pyrido[4,3-d]pyrimidine

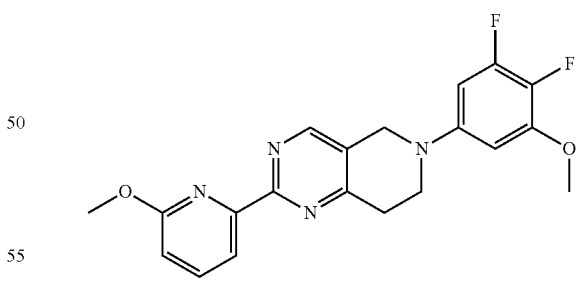

A mixture of 2,3-difluoro-5-[2-(6-methoxy-2-pyridyl)-7,8-dihydro-5H-pyrido[4,3-d]pyrimidin-6-yl]phenol (100 mg, 0.27 mmol), methyl iodide (120 mg, 0.81 mmol) and potassium carbonate (75 mg, 0.54 mmol) in DMF (2 mL) was heated with stirring at 60° C. for 5 hrs. The reaction mixture was cooled to rt and purified by prep-HPLC to give 6-(3,4-difluoro-5-methoxy-phenyl)-2-(6-methoxy-2-pyridyl)-7,8-dihydro-5H-pyrido[4,3-d]pyrimidine (40 mg). $^1$H NMR (400 MHz, DMSO-d₆): δ 8.78 (s, 1H), 7.98 (d, 1H), 7.91-7.82 (m, 1H), 6.95 (d, 1H), 6.72-6.61 (m, 2H), 4.49 (s, 2H), 3.97 (s, 3H), 3.91 (s, 3H), 3.70 (t, 2H), 3.15-3.05 (m, 2H). MS obsd. (ESI+) [(M+H)+]: 385.

Example 26: 6-(3,4-difluoro-5-methoxy-phenyl)-2-pyrimidin-2-yl-7,8-dihydro-5H-pyrido[4,3-d]pyrimidine

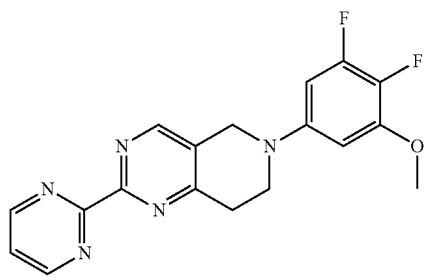 [SMILES: COc1cc(N2CCc3nc(-c4ncccn4)ncc3C2)cc(F)c1F]

Step 1: Preparation of 8-(3,4-difluoro-5-methoxy-phenyl)-1,4-dioxa-8-azaspiro[4.5]decane

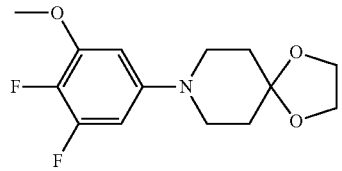 [SMILES: COc1cc(N2CCC3(CC2)OCCO3)cc(F)c1F]

To a flask containing a mixture of 5-bromo-1,2-difluoro-3-methoxy-benzene (1.1 g, 4.93 mmol) and 1,4-dioxa-8-azaspiro[4.5]decane (0.85 g, 5.92 mmol) in 1,4-dioxane (10 mL) was added t-BuONa (0.95 g, 9.86 mmol), Pd$_2$(dba)$_3$ (92 mg, 0.10 mmol) and Ru-Phos (92 mg, 0.20 mmol) under N$_2$. After being heated with stirring at 100° C. overnight, the reaction mixture was cooled to it and diluted with water (20 mL). The resulting mixture was extracted with EA (30 mL) for three times. The combined organic layer was washed with brine, dried over anhydrous Na$_2$SO$_4$ and concentrated in vacuo to give 8-(3,4-difluoro-5-methoxy-phenyl)-1,4-dioxa-8-azaspiro[4.5]decane (1.57 g), which was used in the next step without further purification.

Step 3: Preparation of 1-(3,4-difluoro-5-methoxy-phenyl)piperidin-4-one

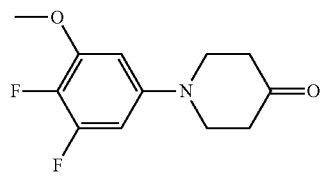

A mixture of 8-(3,4-difluoro-5-methoxy-phenyl)-1,4-dioxa-8-azaspiro[4.5]decane (1.57 g, 5.51 mmol), H$_2$O (5 mL) and formic acid (5 mL) was heated with stirring at 90° C. overnight. The reaction mixture was concentrated in vacuo, diluted with sat. aqueous solution of NaHCO$_3$ and extracted with EA (30 mL) for three times. The combined organic layer was washed with brine, dried over anhydrous Na$_2$SO$_4$ and concentrated in vacuo to give 1-(3,4-difluoro-5-methoxy-phenyl)piperidin-4-one (1.06 g), which was used in the next step without further purification.

Step 4: Preparation of 6-(3,4-difluoro-5-methoxy-phenyl)-2-pyrimidin-2-yl-7,8-dihydro-5H-pyrido[4,3-d]pyrimidine

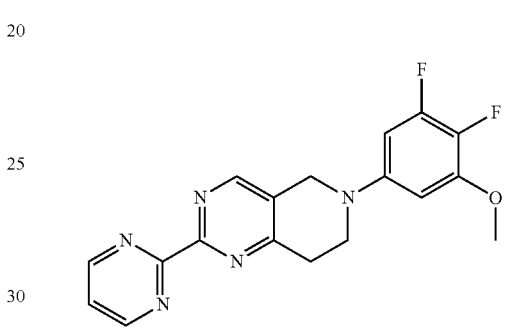

A solution of 1-(3,4-difluoro-5-methoxy-phenyl)piperidin-4-one (0.39 g, 1.64 mmol) and DMFDMA (1 mL) in acetonitrile (9 mL) was heated with stirring at 90° C. for 2 hrs. The reaction mixture was concentrated in vacuo and the residue was dissolved in EtOH (10 mL). To the solution was added pyrimidine-2-carboxamidine (200 mg, 1.64 mmol) and potassium carbonate (453 mg, 3.28 mmol) successively. After being heated with stirring at 90° C. overnight, the reaction mixture was cooled to rt and purified by prep-HPLC to give 6-(3,4-difluoro-5-methoxy-phenyl)-2-pyrimidin-2-yl-7,8-dihydro-5H-pyrido[4,3-d]pyrimidine (10 mg). $^1$H NMR (400 MHz, DMSO-d$_6$): δ 9.00 (d, J=4.8 Hz, 2H), 8.82 (s, 1H), 7.64 (t, J=4.8 Hz, 1H), 6.75-6.63 (m, 2H), 4.55 (s, 2H), 3.91 (s, 3H), 3.72 (t, J=5.9 Hz, 2H), 3.10 (t, J=5.8 Hz, 2H). MS obsd. (ESI+) [(M+H)+]: 356.

Example 27: 6-(4,5-difluoro-2-methoxy-phenyl)-2-(2-pyridyl)-7,8-dihydro-5H-pyrido[4,3-d]pyrimidine

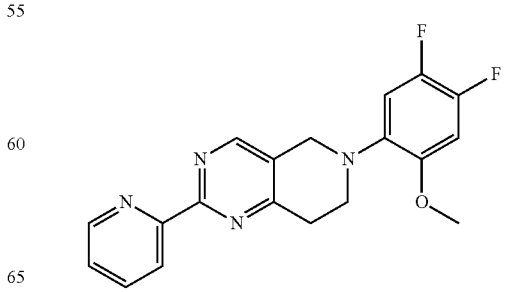

Step 1: Preparation of 1-bromo-4,5-difluoro-2-methoxy-benzene

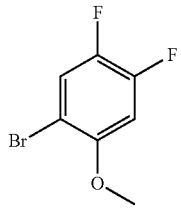

A mixture of 2-bromo-4,5-difluoro-phenol (1.0 g, 4.78 mmol), methyl iodide (1.36 g, 9.57 mmol) and potassium carbonate (1.32 g, 9.57 mmol) in DMF (5 mL) was heated with stirring at 90° C. for 4 hrs. The reaction mixture was cooled to rt, diluted with water (15 mL) and extracted with EA (30 mL) for three times. The combined organic layer was washed with brine, dried over anhydrous $Na_2SO_4$ and concentrated in vacuo to give 1-bromo-4,5-difluoro-2-methoxy-benzene (1.16 g), which was used in the next step without further purification.

Step 2: Preparation of 8-(4,5-difluoro-2-methoxy-phenyl)-1,4-dioxa-8-azaspiro[4.5]decane

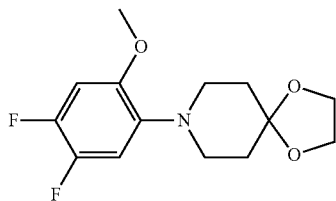 [SMILES: COc1cc(F)c(F)cc1N1CCC2(CC1)OCCO2]

To a flask containing 1-bromo-4,5-difluoro-2-methoxy-benzene (1.1 g, 4.93 mmol) and 1,4-dioxa-8-azaspiro[4.5]decane (0.78 g, 5.43 mmol) in 1,4-dioxane (10 mL) was added t-BuONa (1.18 g, 12.33 mmol), $Pd_2(dba)_3$ (92 mg, 0.10 mmol) and Ru-Phos (92 mg, 0.20 mmol) under $N_2$. After being heated with stirring at 100° C. overnight, the reaction mixture was cooled to rt, diluted with water (20 mL) and extracted with EA (30 mL) for three times. The combined organic layer was washed with brine, dried over anhydrous $Na_2SO_4$ and concentrated in vacuo to give 8-(4,5-difluoro-2-methoxy-phenyl)-1,4-dioxa-8-azaspiro[4.5]decane (1.31 g), which was used in the next step without further purification.

Step 3: Preparation of 1-(4,5-difluoro-2-methoxy-phenyl)piperidin-4-one

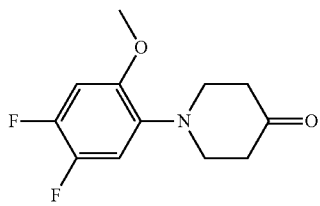 [SMILES: COc1cc(F)c(F)cc1N1CCC(=O)CC1]

A solution of 8-(4,5-difluoro-2-methoxy-phenyl)-1,4-dioxa-8-azaspiro[4.5]decane (1.31 g, 4.59 mmol) in $H_2O$ (5 mL) and formic acid (5 mL) was heated with stirring at 90° C. overnight. The reaction mixture was concentrated in vacuo. The residue was diluted with sat. aqueous solution of $NaHCO_3$ and extracted with EA (30 mL) for three times. The combined organic layer was washed with brine, dried over anhydrous $Na_2SO_4$ and concentrated in vacuo to give 1-(4,5-difluoro-2-methoxy-phenyl)piperidin-4-one (0.62 g), which was used in the next step without further purification.

Step 4: Preparation of 6-(4,5-difluoro-2-methoxy-phenyl)-2-(2-pyridyl)-7,8-dihydro-5H-pyrido[4,3-d]pyrimidine

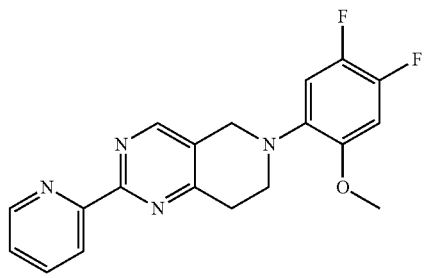 [SMILES: COc1cc(F)c(F)cc1N1CCc2nc(-c3ccccn3)ncc2C1]

A solution of 1-(4,5-difluoro-2-methoxy-phenyl)piperidin-4-one (0.62 g, 2.57 mmol) and DMFDMA (1 mL) in acetonitrile (9 mL) was heated with stirring at 90° C. for 2 hrs. The reaction mixture was concentrated in vacuo and the residue was dissolved in EtOH (10 mL). To the solution was added pyridine-2-carboxamidine (0.27 g, 2.19 mmol) and potassium carbonate (0.60 g, 4.38 mmol) successively. After being heated with stirring at 90° C. overnight, the reaction mixture was cooled to rt and purified by prep-HPLC to give 6-(4,5-difluoro-2-methoxy-phenyl)-2-(2-pyridyl)-7,8-dihydro-5H-pyrido[4,3-d]pyrimidine (30 mg). $^1$H NMR (400 MHz, DMSO-$d_6$): δ 8.76-8.71 (m, 2H), 8.36 (d, 1H), 7.97 (t, 1H), 7.52 (ddd, 1H), 7.20-7.06 (m, 2H), 4.27 (s, 2H), 3.84 (s, 3H), 3.42 (t, 2H), 3.08 (t, 2H). MS obsd. (ESI$^+$) [(M+H)$^+$]: 355.

Example 28: 6-(3,4-difluoro-5-methoxy-phenyl)-2-pyrazin-2-yl-7,8-dihydro-5H-pyrido[4,3-d]pyrimidine

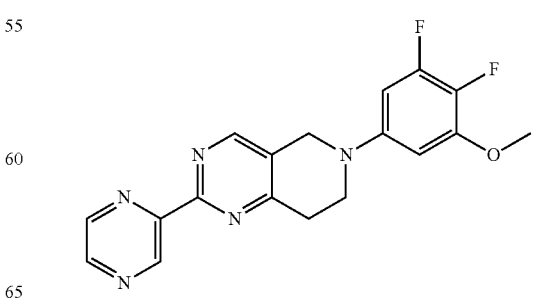

Step 1: Preparation of pyrazine-2-carboxamidine hydrochloride

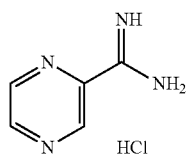

To a solution of pyrazine-2-carbonitrile (1.0 g, 9.52 mmol) in methanol (20 mL) was added NaOCH$_3$ (0.10 g, 1.90 mmol). The resulting mixture was heated with stirring at rt for 12 hrs. To the reaction mixture was added NH$_4$Cl (0.51 g, 9.52 mmol). After being heated under reflux for 3 hrs, the resulting reaction mixture was concentrated in vacuo. The residue was suspended in ethanol (30 mL). The suspension was heated under reflux for 1 hr, then cooled to rt and filtered. The filtrate was concentrated in vacuo to give pyrazine-2-carboxamidine hydrochloride (1.2 g), which was used in the next step without further purification.

Step 2: Preparation of 6-(3,4-difluoro-5-methoxy-phenyl)-2-pyrazin-2-yl-7,8-dihydro-5H-pyrido[4,3-d]pyrimidine

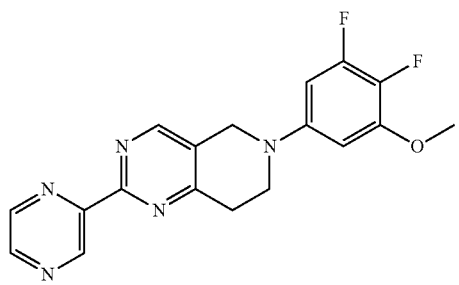 [SMILES: COc1cc(N2CCc3nc(-c4cnccn4)ncc3C2)cc(F)c1F]

A solution of 1-(4,5-difluoro-2-methoxy-phenyl)piperidin-4-one (250 mg, 1.03 mmol) and DMFDMA (1 mL) in acetonitrile (9 mL) was heated with stirring at 90° C. for 2 hrs. The reaction mixture was concentrated in vacuo and the residue was dissolved in EtOH (10 mL). To the solution was added pyrazine-2-carboxamidine hydrochloride (160 mg, 1.01 mmol) and potassium carbonate (279 mg, 2.02 mmol) After being heated with stirring at 90° C. overnight, the reaction mixture was cooled to rt and purified by prep-HPLC to give 6-(3,4-difluoro-5-methoxy-phenyl)-2-pyrazin-2-yl-7,8-dihydro-5H-pyrido[4,3-d]pyrimidine (30 mg). $^1$H NMR (400 MHz, CDCl$_3$): δ 9.75 (s, 1H), 8.81 (s, 1H), 8.78-8.70 (m, 2H), 6.50-6.38 (m, 2H), 4.42 (s, 2H), 3.95 (s, 3H), 3.65 (t, 2H), 3.31 (t, 2H). MS obsd. (ESI$^+$) [(M+H)$^+$]: 356.

Example 29: 6-(3,4-difluoro-5-methoxy-phenyl)-2-pyrimidin-4-yl-7,8-dihydro-5H-pyrido[4,3-d]pyrimidine

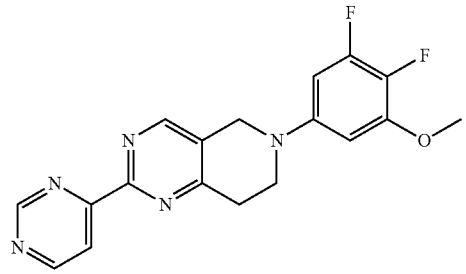 [SMILES: COc1cc(N2CCc3nc(-c4ccncn4)ncc3C2)cc(F)c1F]

Step 1: Preparation of pyrimidine-4-carboxamidine hydrochloride

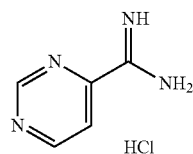

To a solution of 4-cyanopyrimidine (500 mg, 4.8 mmol) in MeOH (5 mL) was added NaOMe (30 mg, 0.48 mmol). The mixture was heated with stirring at 20° C. for 16 hrs. To the resulting mixture was added NH$_4$Cl (333 mg, 5.8 mmol). After being heated under reflux for 3 hrs, the reaction mixture was concentrated in vacuo to give crude pyrimidine-4-carboxamidine hydrochloride (680 mg), which was used directly in the next step without further purification.

Step 2: Preparation of 6-(3,4-difluoro-5-methoxy-phenyl)-2-pyrimidin-4-yl-7,8-dihydro-5H-pyrido[4,3-d]pyrimidine

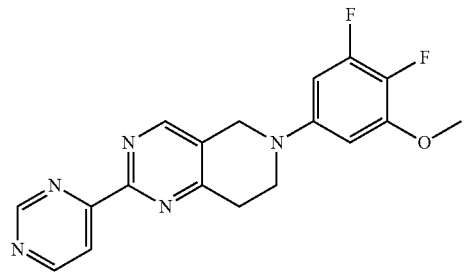 [SMILES: COc1cc(N2CCc3nc(-c4ccncn4)ncc3C2)cc(F)c1F]

A solution of 1-(4,5-difluoro-2-methoxy-phenyl)piperidin-4-one (630 mg, 2.65 mmol) and DMFDMA (2 mL) in acetonitrile (9 mL) was heated with stirring at 90° C. for 2 hrs. The reaction mixture was concentrated in vacuo and the residue was dissolved in EtOH (20 mL). To the solution was added pyrimidine-4-carboxamidine hydrochloride (420 mg, 2.65 mmol) and potassium carbonate (730 mg, 5.3 mmol). After being heated with stirring at 90° C. overnight, the reaction mixture was cooled to rt and purified by prep-HPLC to give 6-(3,4-difluoro-5-methoxy-phenyl)-2-pyrimidin-4- yl-7,8-dihydro-5H-pyrido[4,3-d]pyrimidine (6 mg). $^1$H NMR (400 MHz, CDCl$_3$): δ 9.56 (br. s., 1H), 8.46-9.10 (m, 3H), 6.44 (d, 2H), 4.45 (br. s., 2H), 3.96 (s, 3H), 3.66 (t, 2H), 3.31 (br. s., 2H). MS obsd. (ESI$^+$) [(M+H)$^+$]: 356.

Example 30: 6-(3,4-difluoro-2-methoxy-phenyl)-2-pyrimidin-2-yl-7,8-dihydro-5H-pyrido[4,3-d]pyrimidine

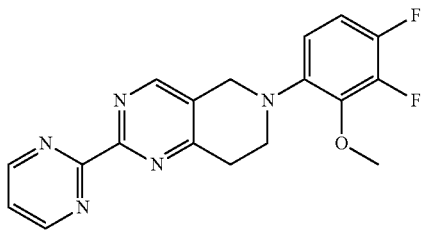 [SMILES: COc1c(N2CCc3nc(-c4ncccn4)ncc3C2)ccc(F)c1F]

Step 1: Preparation of 6-bromo-2,3-difluoro-phenol

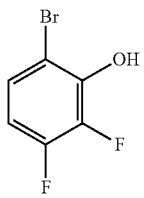

To a solution of 2,3-difluorophenol (1.0 g, 7.69 mmol) and isopropyl amine (0.45 g, 7.69 mmol) in dry DCM (20 mL) was added NBS (5.48 g, 30.76 mmol) portion-wise at −10° C. After being stirred at −10° C. for 30 minutes, the resulting mixture was allowed to warm naturally to rt, then diluted with 1.0 N HCl (40 mL) and extracted with DCM (30 mL) for three times. The combined organic layer was washed with brine, dried over anhydrous Na$_2$SO$_4$ and concentrated in vacuo to give 6-bromo-2,3-difluoro-phenol (2.6 g), which was used in the next step without purification.

Step 2: Preparation of 1-bromo-3,4-difluoro-2-methoxy-benzene

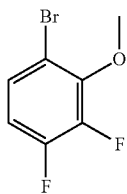

A mixture of 6-bromo-2,3-difluoro-phenol (2.6 g, 12.4 mmol), methyl iodide (1.0 mL, 15.38 mmol) and potassium carbonate (2.12 g, 15.38 mmol) in DMF (10 mL) was heated with stirring at 90° C. for 4 hrs. The reaction mixture was cooled to rt, diluted with water (15 mL) and extracted with EA (30 mL) for three times. The combined organic layer was washed with brine, dried over anhydrous Na$_2$SO$_4$ and con-centrated in vacuo to give 1-bromo-3,4-difluoro-2-methoxy-benzene (1.0 g), which was used in the next step without further purification.

Step 3: Preparation of 8-(3,4-difluoro-2-methoxy-phenyl)-1,4-dioxa-8-azaspiro[4.5]decane

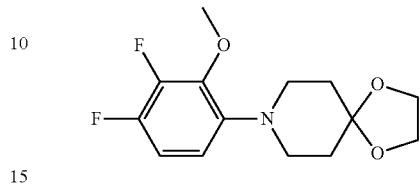

To a flask containing 1-bromo-3,4-difluoro-2-methoxy-benzene (1.0 g, 4.48 mmol) and 1,4-dioxa-8-azaspiro[4.5]decane (0.71 g, 4.93 mmol) in 1,4-dioxane (10 ml) was added t-BuONa (1.3 g, 13.44 mmol), Pd$_2$(dba)$_3$ (82 mg, 0.09 mmol) and Ru-Phos (84 mg, 0.18 mmol) under N$_2$. After being heated with stirring at 100° C. overnight, the reaction mixture was cooled to rt, diluted with water (20 mL) and extracted with EA (30 mL) for three times. The combined organic layer was washed with brine, dried over anhydrous Na$_2$SO$_4$ and concentrated in vacuo to give 8-(3,4-difluoro-2-methoxy-phenyl)-1,4-dioxa-8-azaspiro[4.5]decane (0.74 g), which was used in the next step without further purification.

Step 4: Preparation of 1-(3,4-difluoro-2-methoxy-phenyl)piperidin-4-one

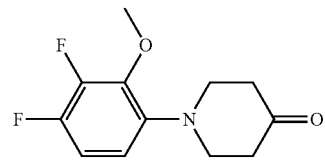 [SMILES: COc1c(N2CCC(=O)CC2)ccc(F)c1F]

A solution of 8-(3,4-difluoro-2-methoxy-phenyl)-1,4-dioxa-8-azaspiro[4.5]decane (0.74 g, 2.59 mmol) in H$_2$O (5 mL) and formic acid (5 mL) was heated with stirring at 90° C. overnight. The reaction mixture was concentrated in vacuo, diluted with sat. aqueous solution of NaHCO$_3$, and extracted with EA (30 mL) for three times. The combined organic layer was washed with brine, dried over anhydrous Na$_2$SO$_4$ and concentrated in vacuo to give 1-(3,4-difluoro-2-methoxy-phenyl)piperidin-4-one (0.65 g), which was used in the next step without further purification.

Step 5: Preparation of 6-(3,4-difluoro-2-methoxy-phenyl)-2-pyrimidin-2-yl-7,8-dihydro-5H-pyrido[4,3-d]pyrimidine

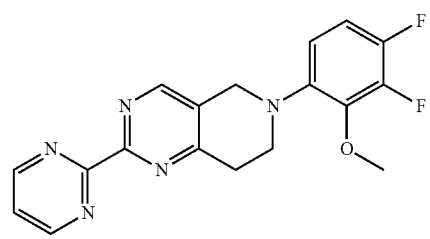 [SMILES: COc1c(N2CCc3nc(-c4ncccn4)ncc3C2)ccc(F)c1F]

A solution of 1-(3,4-difluoro-2-methoxy-phenyl)piperidin-4-one (0.40 g, 1.64 mmol) and DMFDMA (1 mL) in acetonitrile (5 mL) was heated with stirring at 90° C. for 2 hrs. The reaction mixture was concentrated in vacuo and the residue was dissolved in EtOH (10 mL). To the solution was added pyridine-2-carboxamidine hydrochloride (260 mg, 1.64 mmol) and potassium carbonate (0.45 g, 3.24 mmol) successively. After being heated with stirring at 90° C. overnight, the reaction mixture was cooled to rt and purified by prep-HPLC to give 6-(3,4-difluoro-2-methoxy-phenyl)-2-(2-pyridyl)-7,8-dihydro-5H-pyrido[4,3-d]pyrimidine (6 mg). $^1$H NMR (400 MHz, CDCl$_3$): δ 9.04 (d, 2H), 8.75 (s, 1H), 7.45 (t, 1H), 6.94-6.80 (m, 1H), 6.71 (ddd, 1H), 4.35 (s, 2H), 3.96 (d, 3H), 3.54 (t, 2H), 3.35 (t, 2H). MS obsd. (ESI$^+$) [(M+H)$^+$]: 356.

Example 31: ethyl 4-[2-(2-pyridyl)-7,8-dihydro-5H-pyrido[4,3-d]pyrimidin-6-yl]benzoate

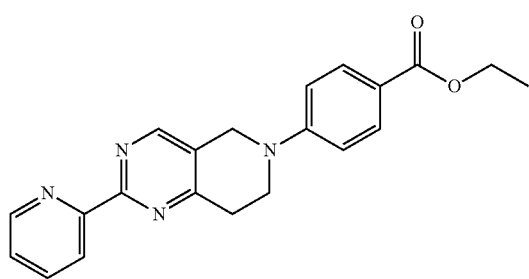 [SMILES: CCOC(=O)c1ccc(N2CCc3nc(-c4ccccn4)ncc3C2)cc1]

Step 1: tert-butyl (3Z)-3-(dimethylaminomethylene)-4-oxo-piperidine-1-carboxylate

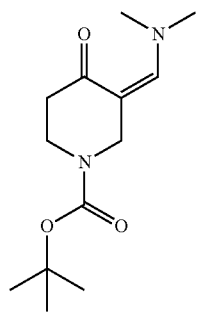 [SMILES: CN(C)/C=C1/CN(C(=O)OC(C)(C)C)CCC1=O]

A solution of tert-butyl 4-oxopiperidine-1-carboxylate (20 g, 100 mmol) and DMFDMA (13.15 g, 110.5 mmol) in DMF (150 mL) was heated with stirring at 90° C. overnight. After being cooled to rt, the reaction mixture was poured into H$_2$O (100 mL) and extracted with EA (100 mL) for three times. The combined organic layer was dried over anhydrous Na$_2$SO$_4$ and concentrated in vacuo to give tert-butyl (3Z)-3-(dimethylaminomethylene)-4-oxo-piperidine-1-carboxylate (28 g) as an oil, which was used in the next step without further purification.

Step 2: tert-butyl 2-(2-pyridyl)-7,8-dihydro-5H-pyrido[4,3-d]pyrimidine-6-carboxylate

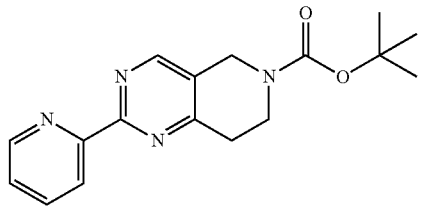 [SMILES: CC(C)(C)OC(=O)N1CCc2nc(-c3ccccn3)ncc2C1]

To a solution of tert-butyl (3Z)-3-(dimethylaminomethylene)-4-oxo-piperidine-1-carboxylate (5 g, 19.7 mmol) and pyridine-2-carboxamidine hydrochloride (2.38 g, 19.7 mmol) in EtOH (100 mL) was added NaH (3.0 g, 60% in mineral oil, 39.4 mmol). After being heated with stirring at 100° C. for 8 hrs, the reaction mixture was poured into H$_2$O (100 mL) and extracted with EA (100 mL) for three times. The combined organic layer was dried over anhydrous Na$_2$SO$_4$ and concentrated in vacuo. The residue was purified by flash column (eluting with 2% MeOH in DCM) to give tert-butyl 2-(2-pyridyl)-7,8-dihydro-5H-pyrido[4,3-d]pyrimidine-6-carboxylate (3.7 g).

Step 3: Preparation of 2-(2-pyridyl)-5,6,7,8-tetrahydropyrido[4,3-d]pyrimidine

tert-Butyl 2-(2-pyridyl)-7,8-dihydro-5H-pyrido[4,3-d]pyrimidine-6-carboxylate (3.7 g, 11.86 mmol) was heated with 1.0 N HCl in EA (50 mL) at rt. After the reaction was completed, the resulting mixture was concentrated in vacuo to give 2-(2-pyridyl)-5,6,7,8-tetrahydropyrido[4,3-d]pyrimidine, which was used in the next step without further purification.

Step 4: Preparation of ethyl 4-[2-(2-pyridyl)-7,8-dihydro-5H-pyrido[4,3-d]pyrimidin-6-yl]benzoate

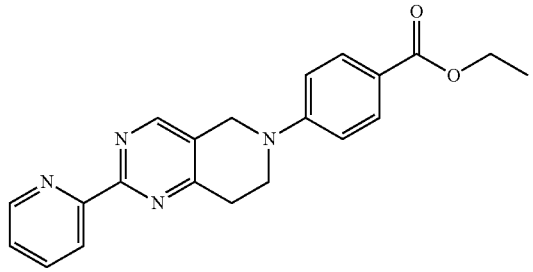 [SMILES: CCOC(=O)c1ccc(N2CCc3nc(-c4ccccn4)ncc3C2)cc1]

To a mixture of 2-(2-pyridyl)-5,6,7,8-tetrahydropyrido[4,3-d]pyrimidine (200 mg, 0.94 mmol) and ethyl 4-fluorobenzoate (316 mg, 1.88 mmol) in DMF (5 mL) was added Cs₂CO₃ (611 mg, 1.88 mmol). After being heated with stirring at 150° C. for 3 hrs, the resulting reaction mixture was purified by prep-HPLC to give ethyl 4-[2-(2-pyridyl)-7,8-dihydro-5H-pyrido[4,3-d]pyrimidin-6-yl]benzoate (4 mg). ¹H NMR (400 MHz, CDCl₃): δ 8.80-8.89 (m, 1H), 8.70-8.76 (m, 1H), 8.48-8.55 (m, 1H), 8.00 (d, 2H), 7.82-7.91 (m, 1H), 7.37-7.45 (m, 1H), 6.97 (d, 2H), 4.60 (s, 2H), 4.35 (q, 2H), 3.76-3.87 (m, 2H), 3.24-3.34 (m, 2H), 1.39 (t, 3H). MS obsd. (ESI⁺) [(M+H)⁺]: 361.

Example 32: 4-[2-(2-pyridyl)-7,8-dihydro-5H-pyrido[4,3-d]pyrimidin-6-yl]benzoic acid

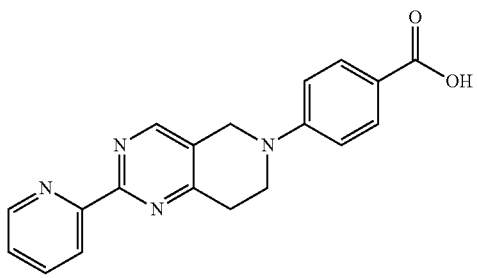 [SMILES: O=C(O)c1ccc(N2CCc3nc(-c4ccccn4)ncc3C2)cc1]

To a solution of ethyl 4-[2-(2-pyridyl)-7,8-dihydro-5H-pyrido[4,3-d]pyrimidin-6-yl]benzoate (10 mg, 0.03 mmol) in THF (2 mL) was added LiOH (1.0 M in H₂O, 1.0 mL). The resulting mixture was heated with stirring at rt. After the reaction was complete, the resulting reaction mixture was purified by prep-HPLC to give 4-[2-(2-pyridyl)-7,8-dihydro-5H-pyrido[4,3-d]pyrimidin-6-yl]benzoic acid (4 mg). ¹H NMR (400 MHz, MeOH-d₄): δ 8.84-8.89 (m, 1H), 8.74-8.84 (m, 2H), 8.31-8.41 (m, 1H), 7.93-8.01 (m, 2H), 7.79-7.88 (m, 1H), 7.04-7.13 (m, 2H), 4.66-4.73 (m, 2H), 3.86-3.95 (m, 2H), 3.25-3.30 (m, 2H). MS obsd. (ESI⁺) [(M+H)⁺]: 357.

Example 33: 6-(2-nitrophenyl)-2-(2-pyridyl)-7,8-dihydro-5H-pyrido[4,3-d]pyrimidine

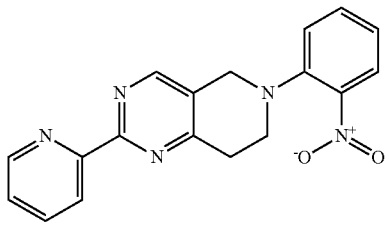

To a mixture of 2-(2-pyridyl)-5,6,7,8-tetrahydropyrido[4,3-d]pyrimidine (50 mg, 0.24 mmol) and 1-fluoro-2-nitrobenzene (68 mg, 0.48 mmol) in DMF (5 mL) was added Cs₂CO₃ (156 mg, 0.48 mmol). After being heated with stirring at 80° C. for 5 hrs, the resulting mixture was purified by prep-HPLC to give 6-(2-nitrophenyl)-2-(2-pyridyl)-7,8-dihydro-5H-pyrido[4,3-d]pyrimidine (2 mg). ¹H NMR (400 MHz, CDCl₃): δ 8.82-8.91 (m, 1H), 8.66 (s, 1H), 8.48-8.57 (m, 1H), 7.83-7.93 (m, 2H), 7.52-7.61 (m, 1H), 7.38-7.46 (m, 1H), 7.29-7.33 (m, 1H), 7.10-7.20 (m, 1H), 4.40 (s, 2H), 3.53 (s, 2H), 3.23-3.39 (m, 2H). MS obsd. (ESI⁺) [(M+H)⁺]: 334.

Example 34: 6-(2-methoxy-4-nitro-phenyl)-2-(2-pyridyl)-7,8-dihydro-5H-pyrido[4,3-d]pyrimidine

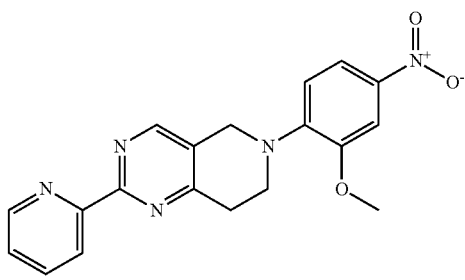 [SMILES: COc1cc([N+](=O)[O-])ccc1N1CCc2nc(-c3ccccn3)ncc2C1]

To a mixture of 2-(2-pyridyl)-5,6,7,8-tetrahydropyrido[4,3-d]pyrimidine (200 mg, 0.94 mmol) and 1-fluoro-2-methoxy-4-nitro-benzene (245 mg, 1.43 mmol) in DMSO (5 mL) was added K₂CO₃ (260 mg, 1.88 mmol). After being heated with stirring at 80° C. for 3 hrs, the reaction mixture was purified by prep-HPLC to give 6-(2-methoxy-4-nitrophenyl)-2-(2-pyridyl)-7,8-dihydro-5H-pyrido[4,3-d]pyrimidine (30 mg). ¹H NMR (400 MHz, CDCl₃): δ 8.82-8.90 (m, 1H), 8.69 (s, 1H), 8.47-8.57 (m, 1H), 7.83-7.96 (m, 2H), 7.80 (d, 1H), 7.38-7.47 (m, 1H), 7.02 (d, 1H), 4.48-4.56 (m, 2H), 4.02 (s, 3H), 3.68-3.75 (m, 2H), 3.29-3.37 (m, 2H). MS obsd. (ESI⁺) [(M+H)⁺]: 364.

Example 35: 2,6-bis(2-pyridyl)-7,8-dihydro-5H-pyrido[4,3-d]pyrimidine

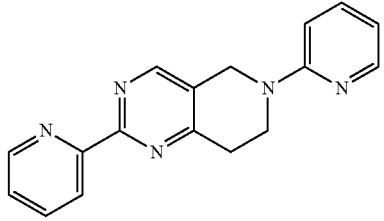 [SMILES: c1ccc(-c2ncc3c(n2)CCN(c2ccccn2)C3)nc1]

To a mixture of 2-(2-pyridyl)-5,6,7,8-tetrahydropyrido[4,3-d]pyrimidine (50 mg, 0.24 mmol) and 2-fluoropyridine (2 mL) was added K₂CO₃ (65 mg, 0.48 mmol). After being heated with stirring at 150° C. for 5 hrs in a microwave reactor, the resulting reaction mixture was purified by prep-HPLC to give 2,6-bis(2-pyridyl)-7,8-dihydro-5H-pyrido[4,3-d]pyrimidine (2 mg). ¹H NMR (400 MHz, CDCl₃): δ 8.83-8.89 (m, 1H), 8.70-8.78 (m, 1H), 8.48-8.55 (m, 1H), 8.23-8.30 (m, 1H), 7.83-7.91 (m, 1H), 7.53-7.62 (m, 1H), 7.37-7.45 (m, 1H), 6.78-6.85 (m, 1H), 6.67-6.75 (m, 1H), 4.85 (s, 2H), 3.97-4.05 (m, 2H), 3.21-3.31 (m, 2H). MS obsd. (ESI⁺) [(M+H)⁺]: 290.

Example 36: 6-(5-chloro-2-pyridyl)-2-(2-pyridyl)-7,8-dihydro-5H-pyrido[4,3-d]pyrimidine

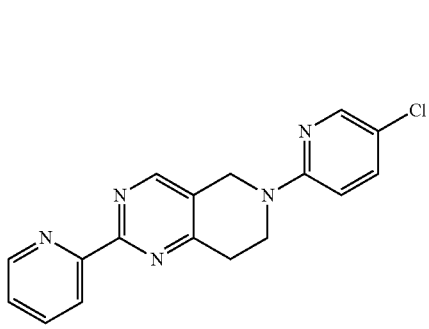

A mixture of 2-(2-pyridyl)-5,6,7,8-tetrahydropyrido[4,3-d]pyrimidine hydrogen chloride (200 mg, 0.806 mmol), 5-chloro-2-fluoro-pyridine (1.06 g, 8.06 mmol) and Et$_3$N (1.63 g, 16.13 mmol) in DMF (0.2 mL) was heated with stirring at 150° C. for 20 minutes. Then the mixture was concentrated in vacuo and the residue was purified by Prep-HPLC to give 6-(5-chloro-2-pyridyl)-2-(2-pyridyl)-7,8-dihydro-5H-pyrido[4,3-d]pyrimidine (8 mg). $^1$H NMR (400 MHz, CDCl$_3$): δ 8.86 (dd, 1H), 8.74 (s, 1H), 8.52 (d, 1H), 8.19 (d, 1H), 7.88 (dt, 1H), 7.52 (dd, 1H), 7.42 (ddd, 1H), 6.74 (d, 1H), 4.81 (s, 2H), 3.98 (t, 2H), 3.27 (t, 2H). MS obsd. (ESI$^+$) [(M+H)$^+$]: 324.

Example 37: 2-(2-pyridyl)-6-pyrimidin-2-yl-7,8-dihydro-5H-pyrido[4,3-d]pyrimidine

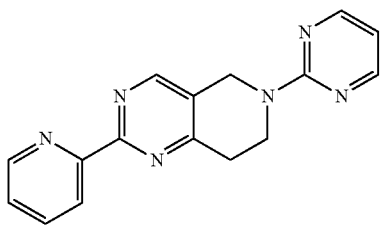 [SMILES: c1ccc(-c2ncc3c(n2)CCN(c2ncccn2)C3)nc1]

A mixture of 2-(2-pyridyl)-5,6,7,8-tetrahydropyrido[4,3-d]pyrimidine trifluoroacetic acid (500 mg, 1.53 mmol), 2-chloropyrimidine (350 mg, 3.07 mmol) and sodium t-butoxide (442 mg, 4.6 mmol) in DMF (10 mL) was heated with stirring at 140° C. for 1 hr. The resulting reaction mixture was diluted with water (20 mL) and extracted with DCM (30 mL) for three times. The combined organic layer was dried and concentrated in vacuo. The residue was purified by prep-HPLC to give 2-(2-pyridyl)-6-pyrimidin-2-yl-7,8-dihydro-5H-pyrido[4,3-d]pyrimidine as a light yellow solid (107 mg). $^1$H NMR (400 MHz, CDCl$_3$): δ 8.86 (d, 1H), 8.74 (s, 1H), 8.52 (d, 1H), 8.40 (d, 2H), 7.88 (dt, 1H), 7.36-7.46 (m, 1H), 6.60 (s, 1H), 5.05 (s, 2H), 4.18-4.31 (m, 2H), 3.24 (s, 2H). MS obsd. (ESI$^+$) [(M+H)$^+$]: 291.

Example 38: 6-(2-benzyloxy-4-fluoro-phenyl)-2-(2-pyridyl)-7,8-dihydro-5H-pyrido[4,3-d]pyrimidine

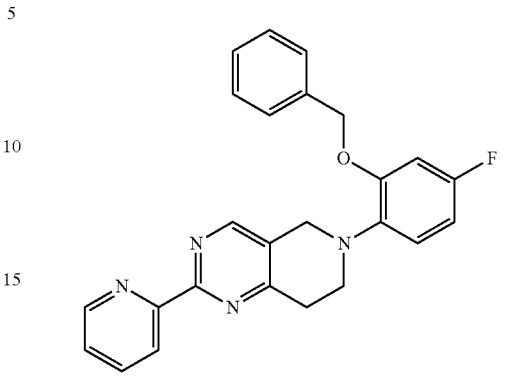

Step 1: Preparation of 2-(1,4-dioxa-8-azaspiro[4.5]decan-8-yl)-5-fluoro-phenol

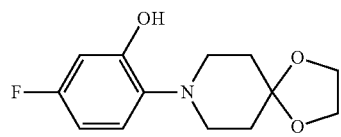 [SMILES: Oc1cc(F)ccc1N1CCC2(CC1)OCCO2]

A mixture of 1,4-dioxa-8-azaspiro[4.5]decane hydrochloride (9.02 g, 0.05 mol), 2-bromo-5-fluoro-phenol (8 g, 0.042 mol), CuI (1.6 g, 0.0084 mol), L-proline (4.8 g, 0.042 mmol) and K$_2$CO$_3$ (23.12 g, 0.168 mmol) in DMSO (100 mL) was heated with stirring at 110° C. overnight. The resulting reaction mixture was diluted with water (50 mL), acidified to pH=5-6 with 2 N hydrochloric acid and extracted with EA (30 mL) for three times. The combined organic layer was dried over anhydrous Na$_2$SO$_4$ and concentrated in vacuo. The residue was purified by flash column to give 2-(1,4-dioxa-8-azaspiro[4.5]decan-8-yl)-5-fluoro-phenol as a yellow oil (1.2 g).

Step 2: Preparation of 8-(2-benzyloxy-4-fluoro-phenyl)-1,4-dioxa-8-azaspiro[4.5]decan

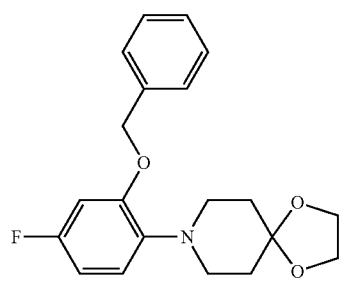 [SMILES: Fc1ccc(N2CCC3(CC2)OCCO3)c(OCc2ccccc2)c1]

A mixture of 2-(1,4-dioxa-8-azaspiro[4.5]decan-8-yl)-5-fluoro-phenol (460 mg, 1.818 mmol), bromomethylbenzene (311 mg, 1.818 mmol) and K$_2$CO$_3$ (502 mg, 3.64 mmol) in DMF (5 mL) was heated with stirring at rt overnight. The resulting reaction mixture was diluted with water (5 mL) and extracted with EA (30 mL) for three times. The combined organic layer was dried over anhydrous Na₂SO₄ and concentrated in vacuo. The residue was purified by flash column to give 8-(2-benzyloxy-4-fluoro-phenyl)-1,4-dioxa-8-azaspiro[4.5]decane as an oil (440 mg).

Step 3: preparation of 1-(2-benzyloxy-4-fluoro-phenyl)piperidin-4-one

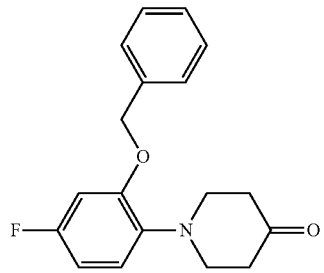 [SMILES: O=C1CCN(c2ccc(F)cc2OCc2ccccc2)CC1]

A mixture of 8-(2-benzyloxy-4-fluoro-phenyl)-1,4-dioxa-8-azaspiro[4.5]decane (400 mg, 1.17 mmol), formic acid (3 mL) and H₂O (3 mL) was heated with stirring at 90° C. overnight. The resulting reaction mixture was concentrated in vacuo. The residue was diluted with sat. aqueous solution of NaHCO₃ and extracted with EA (30 mL) for three times. The combined organic layer was washed with brine, dried over anhydrous Na₂SO₄ and concentrated in vacuo. The residue was purified by flash column to give 1-(2-benzyloxy-4-fluoro-phenyl)piperidin-4-one as an oil (130 mg).

Step 4: 6-(2-benzyloxy-4-fluoro-phenyl)-2-(2-pyridyl)-7,8-dihydro-5H-pyrido[4,3-d]pyrimidine

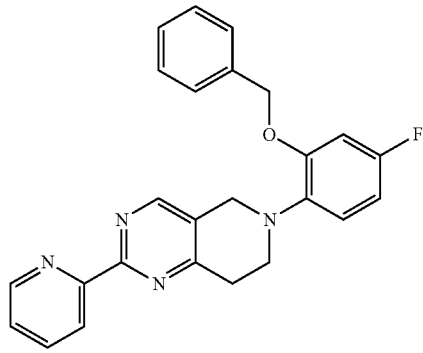 [SMILES: Fc1ccc(N2CCc3nc(-c4ccccn4)ncc3C2)c(OCc2ccccc2)c1]

A mixture of 1-(2-benzyloxy-4-fluoro-phenyl)piperidin-4-one (130 mg, 0.44 mmol) and DMFDMA (5 mL) was heated with stirring at 90° C. overnight. The resulting reaction mixture was concentrated in vacuo and the residue was dissolved in EtOH (5 mL). To the solution was added pyridine-2-carboxamidine hydrochloride (68 mg, 0.44 mmol) and CH₃ONa (47 mg, 0.87 mmol). After being heated with stirring at 90° C. overnight, the resulting reaction mixture was concentrated in vacuo. The residue was purified by prep-HPLC to give 6-(2-benzyloxy-4-fluoro-phenyl)-2-(2-pyridyl)-7,8-dihydro-5H-pyrido[4,3-d]pyrimidine (2 mg). ¹H NMR (400 MHz, CDCl₃): δ 8.83-8.91 (m, 1H), 8.60 (s, 1H), 8.52 (d, 1H), 7.84-7.91 (m, 1H), 7.33-7.50 (m, 6H), 7.01 (dd, 1H), 6.79 (dd, 1H), 6.70 (dt, 1H), 5.13 (s, 2H), 4.33 (s, 2H), 3.51 (t, 2H), 3.23 (t, 2H). MS obsd. (ESI⁺) [(M+H)⁺]: 413.

Example 39: 2-(2-pyridyl)-6-(3-pyridyl)-7,8-dihydro-5H-pyrido[4,3-d]pyrimidine

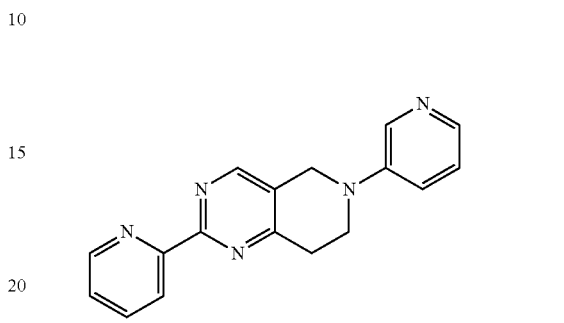

Step 1: Preparation of 8-(3-pyridyl)-1,4-dioxa-8-azaspiro[4.5]decane

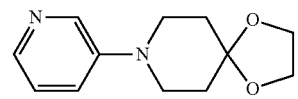 [SMILES: c1cncc(N2CCC3(CC2)OCCO3)c1]

A mixture of 1,4-dioxa-8-azaspiro[4.5]decane hydrochloride (3 g, 16.7 mmol), 3-bromopyridine (2.9 g, 18.4 mmol), Pd(OAc)₂ (0.187 g, 0.83 mmol), Xphos (0.398 g, 0.83 mmol) and sodium tert-butoxide (3.2 g, 33.4 mmol) in a mixed solution of toluene (50 mL) and tert-butyl alcohol (10 mL) was heated with stirring at 120° C. overnight. The reaction mixture was diluted with water (50 mL) and extracted with EA (30 mL) for three times. The combined organic layer was dried over anhydrous Na₂SO₄ and concentrated in vacuo. The residue was purified by flash column to give 8-(3-pyridyl)-1,4-dioxa-8-azaspiro[4.5]decane (590 mg).

Step 2: Preparation of 1-(3-pyridyl)piperidin-4-one

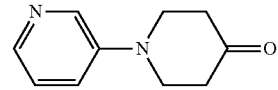 [SMILES: O=C1CCN(c2cccnc2)CC1]

A mixture of 8-(3-pyridyl)-1,4-dioxa-8-azaspiro[4.5]decane (590 mg, 1.17 mmol), formic acid (5 mL) and H₂O (5 mL) was heated with stirring at 90° C. overnight. The reaction mixture was concentrated in vacuo, diluted with sat. aqueous solution of NaHCO₃ and extracted with EA (30 mL) for three times. The combined organic layer was dried over anhydrous Na₂SO₄ and concentrated in vacuo to give crude 1-(3-pyridyl)piperidin-4-one, which was used for next step without further purification.

Step 3: Preparation of 2-(2-pyridyl)-6-(3-pyridyl)-7,8-dihydro-5H-pyrido[4,3-d]pyrimidine

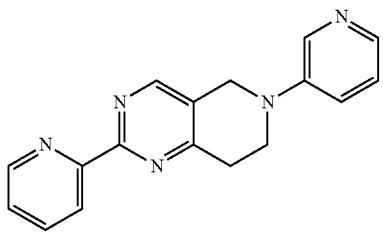 [SMILES: c1ccc(-c2ncc3c(n2)CCN(c2cccnc2)C3)nc1]

A mixture of 1-(3-pyridyl)piperidin-4-one (470 mg, 2.67 mmol) and DMFDMA (1.14 g, 9.6 mmol) in DMF (5 mL) was heated with stirring at 90° C. for 2 hrs. The reaction mixture was concentrated in vacuo and the residue was dissolved in EtOH (20 mL). To the solution was added pyridine-2-carboxamidine (262 mg, 2.16 mmol) and CH₃ONa (234 mg, 4.33 mmol). After being heated with stirring at 90° C. overnight, the resulting mixture was concentrated in vacuo and the residue was dissolved in EA (50 mL). The organic phase was washed with water, dried over anhydrous Na₂SO₄ and concentrated in vacuo. The residue was purified by prep-HPLC to give 2-(2-pyridyl)-6-(3-pyridyl)-7,8-dihydro-5H-pyrido[4,3-d]pyrimidine (25 mg). $^1$H NMR (400 MHz, CDCl₃): δ 8.87 (dd, 1H), 8.74 (s, 1H), 8.53 (d, 1H), 8.46 (d, 1H), 8.18 (dd, 1H), 7.89 (dt, 1H), 7.43 (ddd, 1H), 7.31-7.37 (m, 1H), 7.25-7.28 (m, 1H), 4.53 (s, 2H), 3.76 (t, 2H), 3.28-3.36 (m, 2H). MS obsd. (ESI⁺) [(M+H)⁺]: 290.

Example 40: 6-(3-fluoro-5-methyl-phenyl)-2-(2-pyridyl)-7,8-dihydro-5H-pyrido[4,3-d]pyrimidine

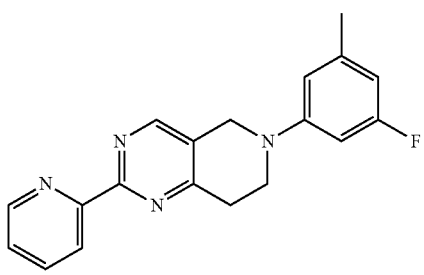 [SMILES: Cc1cc(F)cc(N2CCc3nc(-c4ccccn4)ncc3C2)c1]

Step 1: Preparation of 8-(3-fluoro-5-methyl-phenyl)-1,4-dioxa-8-azaspiro[4.5]decane

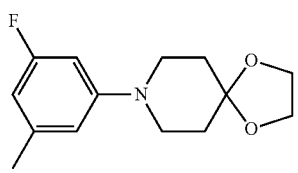 [SMILES: Cc1cc(F)cc(N2CCC3(CC2)OCCO3)c1]

A mixture of 1,4-dioxa-8-azaspiro[4.5]decane hydrochloride (2.85 g, 15.86 mmol), 1-bromo-3-fluoro-5-methyl-benzene (6 g, 31.7 mmol), Pd₂(dba)₃ (0.29 g, 3.17 mmol), Ruphos (0.296 g, 6.3 mmol) and Cs₂CO₃ (20.6 g, 63.4 mmol) in toluene (50 mL) was heated with stirring at 120° C. overnight. The resulting reaction mixture was filtered. The filtrate was concentrated in vacuo to give crude 8-(3-fluoro-5-methyl-phenyl)-1,4-dioxa-8-azaspiro[4.5]decane (3.5 g), which was used in the next step without further purification.

Step 2: Preparation of 1-(3-fluoro-5-methyl-phenyl)piperidin-4-one

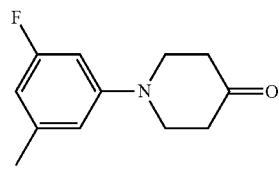

A mixture of 8-(3-fluoro-5-methyl-phenyl)-1,4-dioxa-8-azaspiro[4.5]decane (3.5 g, 13.94 mmol), formic acid (24 mL) and H₂O (24 mL) was heated with stirring at 90° C. overnight. The resulting reaction mixture was concentrated in vacuo, diluted with sat. aqueous solution of NaHCO₃ and extracted with EA (30 ml) for three times. The combined organic layer was dried over anhydrous Na₂SO₄ and concentrated in vacuo to give crude 1-(3-fluoro-5-methyl-phenyl)piperidin-4-one as a black oil (2.8 g), which was used in the next step without further purification.

Step 3: Preparation of 1-(3-fluoro-5-methyl-phenyl)-2-pyridyl)-7,8-dihydro-5H-pyrido[4,3-d]pyrimidine

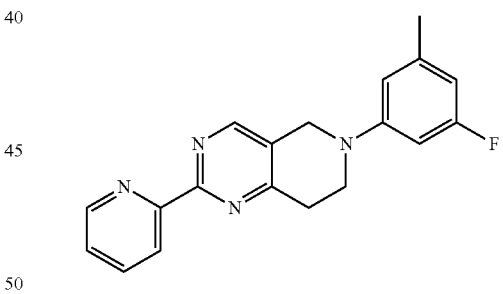

A mixture of 1-(3-fluoro-5-methyl-phenyl)piperidin-4-one (2.8 g, 13.5 mmol) and DMFDMA (1.93 g, 16.23 mmol) in DMF (20 mL) was heated with stirring at 90° C. overnight. The reaction mixture was concentrated in vacuo and the residue was dissolved in EtOH (20 mL). To the solution was added pyridine-2-carboxamidine hydrochloride (2.89 g, 18.3 mmol) and CH₃ONa (1.32 g, 24.4 mmol). After being heated with stirring at 90° C. overnight, the resulting reaction mixture was concentrated in vacuo and the residue was purified by Prep-HPLC to give 6-(3-fluoro-5-methyl-phenyl)-2-(2-pyridyl)-7,8-dihydro-5H-pyrido[4,3-d]pyrimidine (155 mg). $^1$H NMR (400 MHz, CDCl₃): δ 8.83-8.90 (m, 1H), 8.72 (s, 1H), 8.52 (d, 1H), 7.88 (d, 1H), 7.42 (s, 1H), 6.61 (s, 1H), 6.53 (d, 1H), 6.44 (d, 1H), 4.46 (s, 2H), 3.70 (t, 2H), 3.28 (t, 2H), 2.35 (s, 3H). MS obsd. (ESI⁺) [(M+H)⁺]: 321.

Example 41: 6-(3-bromo-5-fluoro-phenyl)-2-pyrimidin-2-yl-7,8-dihydro-5H-pyrido[4,3-d]pyrimidine

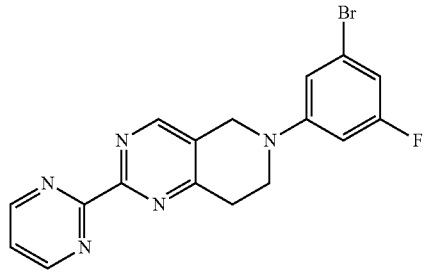 [SMILES: Fc1cc(Br)cc(N2CCc3nc(-c4ncccn4)ncc3C2)c1]

Step 1: Preparation of 8-(3-bromo-5-fluoro-phenyl)-1,4-dioxa-8-azaspiro[4.5]decane

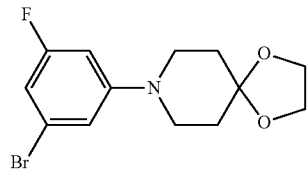 [SMILES: Fc1cc(Br)cc(N2CCC3(CC2)OCCO3)c1]

A mixture of 1,4-dioxa-8-azaspiro[4.5]decane hydrochloride (2.0 g, 11.1 mmol), 1,3-dibromo-5-fluoro-benzene (3.39 g, 13.4 mmol), CuI (0.423 g, 2.23 mmol), L-proline (1.28 g, 11.1 mmol) and $K_2CO_3$ (4.61 g, 33.4 mmol) in DMF (20 mL) was heated with stirring at 90° C. overnight. The resulting reaction mixture was diluted with water (20 mL) and extracted with EA (30 mL) for three times. The combined organic layer was dried over anhydrous $Na_2SO_4$ and concentrated in vacuo. The residue was purified by flash column to give 8-(3-bromo-5-fluoro-phenyl)-1,4-dioxa-8-azaspiro[4.5]decane as an oil (1.79 g).

Step 2: Preparation of 1-(3-bromo-5-fluoro-phenyl)piperidin-4-one

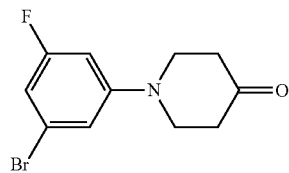

A mixture of 8-(3-bromo-5-fluoro-phenyl)-1,4-dioxa-8-azaspiro[4.5]decane (1.7 g, 5.4 mmol), formic acid (20 mL) and $H_2O$ (20 mL) was heated with stirring 90° C. for 6 hrs. The reaction mixture was concentrated in vacuo, diluted with sat. aqueous solution of $NaHCO_3$ and extracted with EA (30 mL) for three times. The combined organic layer was washed with brine, dried over anhydrous $Na_2SO_4$ and concentrated in vacuo to give 1-(3-bromo-5-fluoro-phenyl)piperidin-4-one as an oil (1.4 g), which was used in the next step without further purification.

Step 3: Preparation of 6-(3-bromo-5-fluoro-phenyl)-2-pyrimidin-2-yl-7,8-dihydro-5H-pyrido[4,3-d]pyrimidine

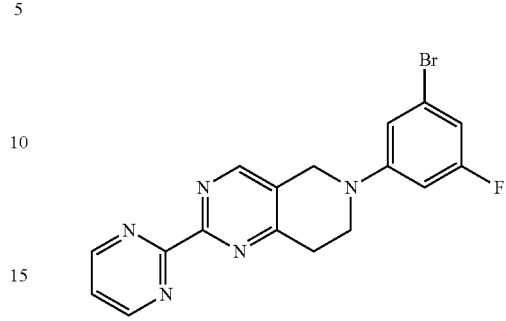

A mixture of 1-(3-bromo-5-fluoro-phenyl)piperidin-4-one (1.4 g, 5.17 mmol) and DMFDMA (0.74 g, 6.2 mmol) in DMF (10 mL) was heated with stirring at 90° C. for 3 hrs. The reaction mixture was concentrated in vacuo and the residue was dissolved in EtOH (20 mL). To the solution was added pyrimidine-2-carboxamidine hydrochloride (1.23 g, 7.75 mmol) and $CH_3ONa$ (0.56 g, 10.34 mmol). After being heated with stirring at 80° C. overnight, the resulting reaction mixture was concentrated in vacuo and the residue was purified by Prep-HPLC to give 6-(3-bromo-5-fluoro-phenyl)-2-pyrimidin-2-yl-7,8-dihydro-5H-pyrido[4,3-d]pyrimidine (20 mg). $^1$H NMR (400 MHz, $CDCl_3$): δ 9.06 (d, 2H), 8.85 (s, 1H), 7.47 (t, 1H), 6.90-6.96 (m, 1H), 6.77 (td, 1H), 6.64 (td, 1H), 4.45-4.60 (m, 2H), 3.68-3.83 (m, 2H), 3.30-3.44 (m, 2H). MS obsd. (ESI$^+$) [(M+H)$^+$]: 386.

Example 42: 6-(3-cyclopropyl-5-fluoro-phenyl)-2-pyrimidin-2-yl-7,8-dihydro-5H-pyrido[4,3-d]pyrimidine

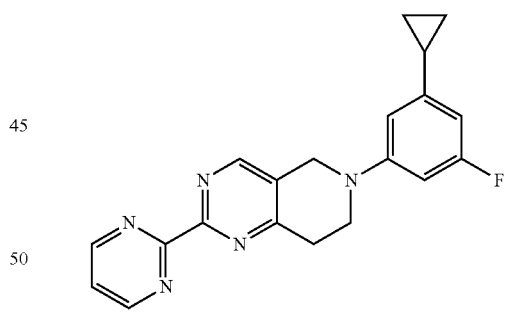

A mixture of 6-(3-bromo-5-fluoro-phenyl)-2-pyrimidin-2-yl-7,8-dihydro-5H-pyrido[4,3-d]pyrimidine (150 mg, 0.39 mmol), potassium cyclopropyltrifluoroborate (86 mg, 0.58 mmol), $PdCl_2(dppf)_2 \cdot CH_2Cl_2$ (6.35 mg, 0.01 mmol) and $K_2CO_3$ (161 mg, 1.17 mmol) in toluene (3 mL) and $H_2O$ (1 mL) was heated with stirring at 90° C. for 2 days. The resulting mixture was concentrated in vacuo and the residue was purified by Prep-HPLC to give 6-(3-cyclopropyl-5-fluoro-phenyl)-2-pyrimidin-2-yl-7,8-dihydro-5H-pyrido[4,3-d]pyrimidine (12 mg). $^1$H NMR (400 MHz, $CDCl_3$) δ 9.05 (d, 2H), 8.83 (s, 1H), 7.43-7.49 (m, 1H), 6.59 (s, 1H), 6.52 (d, 1H), 6.24-6.33 (m, 1H), 4.51 (s, 2H), 3.72 (t, 2H), 3.35 (t, 2H), 1.83-1.94 (m, 1H), 0.93-1.03 (m, 2H), 0.63-0.77 (m, 2H). MS obsd. (ESI$^+$) [(M+H)$^+$]: 348.

Example 43: 2-pyrimidin-2-yl-6-[3-trifluoromethoxy)phenyl]-7,8-dihydro-5H-pyrido[4,3-d]pyrimidine

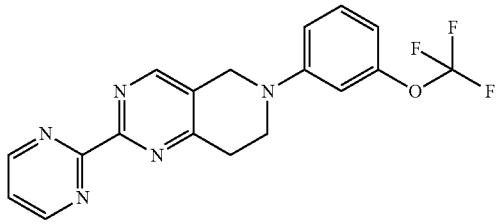 [SMILES: FC(F)(F)Oc1cccc(N2CCc3nc(-c4ncccn4)ncc3C2)c1]

Step 1: Preparation of 8-[3-(trifluoromethoxy)phenyl]-1,4-dioxa-8-azaspiro[4.5]decane

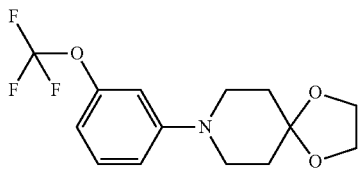 [SMILES: FC(F)(F)Oc1cccc(N2CCC3(CC2)OCCO3)c1]

A mixture of 1,4-dioxa-8-azaspiro[4.5]decane hydrochloride (2.0 g, 11.1 mmol), 1-bromo-3-(trifluoromethoxy)benzene (5.72 g, 22.3 mmol), Pd$_2$(dba)$_3$ (0.204 g, 0.223 mmol), Ruphos (0.21 g, 0.445 mmol) and Cs$_2$CO$_3$ (14.5 g, 44.5 mmol) in toluene (50 mL) was heated with stirring at 120° C. overnight. The resulting reaction mixture cooled to rt and filtered. The filtrate was concentrated in vacuo and the residue was purified by flash column to give 8-[3-(trifluoromethoxy)-phenyl]-1,4-dioxa-8-azaspiro[4.5]decane as an oil (3.0 g).

Step 2: Preparation of 1-[3-(trifluoromethoxy)phenyl]piperidin-4-one

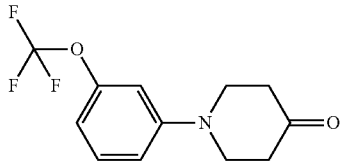 [SMILES: O=C1CCN(c2cccc(OC(F)(F)F)c2)CC1]

A mixture of 8-[3-(trifluoromethoxy)phenyl]-1,4-dioxa-8-azaspiro[4.5]decane (1.5 g, 4.95 mmol), formic acid (20 mL) and H$_2$O (20 mL) was heated with stirring at 90° C. overnight. The resulting mixture was concentrated in vacuo, diluted with sat. aqueous solution of NaHCO$_3$, and extracted with EA (30 mL) for three times. The combined organic layer was dried over anhydrous Na$_2$SO$_4$ and concentrated in vacuo to give 1-[3-(trifluoromethoxy)phenyl]piperidin-4-one as an oil (1.2 g), which was used in the next step without further purification.

Step 4: Preparation of 2-pyrimidin-2-yl-6-[3-(trifluoromethoxy)phenyl]-7,8-dihydro-5H-pyrido[4,3-d]pyrimidine

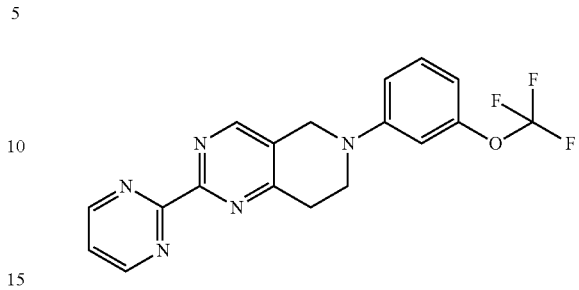

A mixture of 1-[3-(trifluoromethoxy)phenyl]piperidin-4-one (0.685 g, 2.64 mmol) and DMFDMA (1.26 g, 10.6 mmol) in DMF (10 mL) was heated with stirring at 90° C. for 3 hrs. The resulting reaction mixture was concentrated in vacuo and the residue was dissolved in EtOH (20 mL). To this solution was added pyrimidine-2-carboxamidine hydrochloride (0.63 g, 3.97 mmol) and CH$_3$ONa (0.29 g, 5.285 mmol). After being heated with stirring at 90° C. overnight, the reaction mixture was filtered. The filtrate was concentrated in vacuo and the residue was dissolved in EA (50 mL). The solution was washed with water, dried over anhydrous Na$_2$SO$_4$ and concentrated in vacuo. The residue was purified by prep-HPLC to give 2-pyrimidin-2-yl-6-[3-(trifluoromethoxy)-phenyl]-7,8-dihydro-5H-pyrido[4,3-d]pyrimidine (4 mg). $^1$H NMR (400 MHz, CDCl$_3$): δ 9.06 (d, 2H), 8.85 (s, 1H), 7.46 (t, 1H), 7.31-7.36 (m, 1H), 6.93-6.98 (m, 1H), 6.86 (s, 1H), 6.79 (s, 1H), 4.54 (s, 2H), 3.76 (s, 2H), 3.38 (s, 2H). MS obsd. (ESI$^+$) [(M+H)$^+$]: 348.

Example 44: 6-[3-methoxy-4-(3-methoxypropoxy)phenyl]-2-(2-pyridyl)-7,8-dihydro-5H-pyrido[4,3-d]pyrimidine

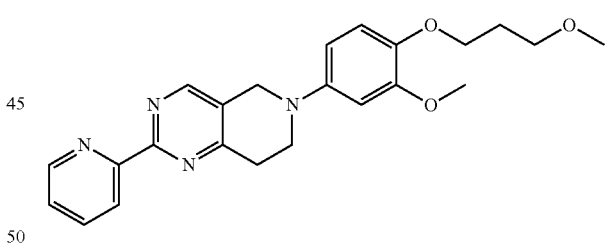

Step 1: Preparation of 4-bromo-2-methoxy-1-(3-methoxypropoxy)benzene

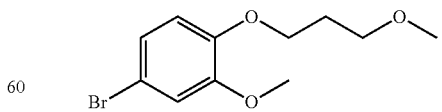

A mixture of 4-bromo-2-methoxy-phenol (3.00 g, 14.78 mmol), 1-bromo-3-methoxy-propane (2.71 g, 17.73 mmol) and K$_2$CO$_3$ (6.12 g, 44.33 mmol) in DMF (30 mL) was stirred at rt for 3 hrs. The mixture was concentrated in vacuo, diluted with water (30 mL) and extracted with DCM (30 mL) for three times. The combined organic layer was dried over anhydrous Na$_2$SO$_4$ and concentrated in vacuo to give 4-bromo-2-methoxy-1-(3-methoxypropoxy)benzene (3.00 g), which was used in the next step without further purification.

Step 2: Preparation of 8-[3-methoxy-4-(3-methoxypropoxy)phenyl]-1,4-dioxa-8-azaspiro[4.5]decane

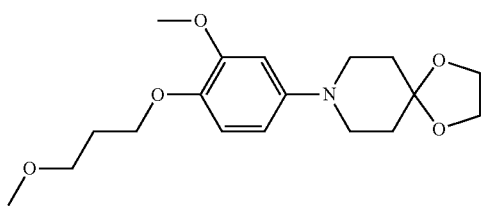 [SMILES: COCCCOc1ccc(N2CCC3(CC2)OCCO3)cc1OC]

A mixture of 1,4-dioxa-8-azaspiro[4.5]decane hydrochloride (2.00 g, 11.1 mmol), 4-bromo-2-methoxy-1-(3-methoxypropoxy)benzene (4.58 g, 16.65 mmol), CuI (0.423 g, 2.23 mmol), L-proline (1.28 g, 11.1 mmol) and K$_2$CO$_3$ (4.61 g, 33.4 mmol) in DMF (20 mL) was heated with stirring at 90° C. overnight. The resulting mixture was diluted with water (30 mL) and extracted with EA (50 mL) for three times. The combined organic layer was dried over anhydrous Na$_2$SO$_4$ and concentrated in vacuo. The residue was purified by flash column to give 8-[3-methoxy-4-(3-methoxypropoxy)phenyl]-1,4-dioxa-8-azaspiro[4.5]decane (1.5 g).

Step 3: Preparation of 1-[3-methoxy-4-(3-methoxypropoxy)phenyl]piperidin-4-one

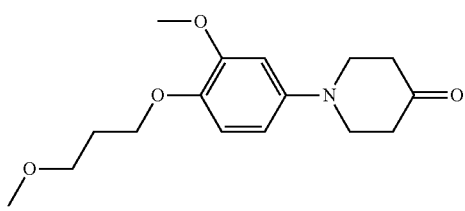 [SMILES: COCCCOc1ccc(N2CCC(=O)CC2)cc1OC]

A mixture of 8-[3-methoxy-4-(3-methoxypropoxy)phenyl]-1,4-dioxa-8-azaspiro[4.5]decane (1.5 g, 8.89 mmol), formic acid (10 mL) and H$_2$O (10 mL) was heated with stirring at 90° C. for 6 hrs. The resulting reaction mixture was concentrated in vacuo, diluted with sat. aqueous solution of NaHCO$_3$ and extracted with EA (30 mL) for three times. The combined organic layer was washed with water, dried over anhydrous Na$_2$SO$_4$ and concentrated in vacuo to give 1-[3-methoxy-4-(3-methoxypropoxy)phenyl]piperidin-4-one (1 g), which was used in the next step without further purification.

Step 4: Preparation of 6-[3-methoxy-4-(3-methoxypropoxy)phenyl]-2-(2-pyridyl)-7,8-dihydro-5H-pyrido[4,3-d]pyrimidine

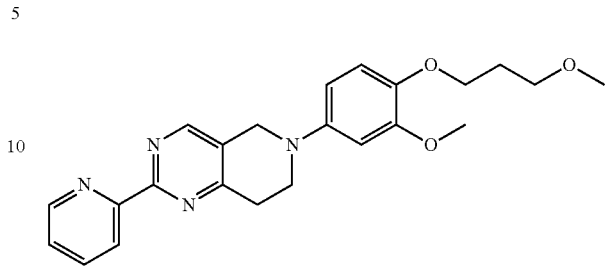

A mixture of 1-[3-methoxy-4-(3-methoxypropoxy)phenyl]piperidin-4-one (1.0 g, 3.41 mmol) and 1,1-dimethoxy-N,N-dimethyl-methanamine (0.49 g, 4.1 mmol) in DMF (10 mL) was heated with stirring at 90° C. overnight. The reaction mixture was concentrated in vacuo and the residue was dissolved in EtOH (20 mL). To this solution was added pyridine-2-carboxamidine hydrochloride (0.577 g, 3.66 mmol) and CH$_3$ONa (0.395 g, 9.32 mmol). After being heated with stirring at 80° C. overnight, the resulting mixture was concentrated in vacuo and the residue was purified by Prep-HPLC to give 6-[3-methoxy-4-(3-methoxypropoxy)phenyl]-2-(2-pyridyl)-7,8-dihydro-5H-pyrido[4,3-d]pyrimidine (20 mg). $^1$H NMR (400 MHz, MeOH-d$_4$): δ 8.69-8.78 (m, 2H), 8.50 (d, 1H), 8.43-8.55 (m, 1H), 8.00 (d, 1H), 7.55 (ddd, 1H), 6.91 (d, 1H), 6.82 (d, 1H), 6.64 (dd, 1H), 4.38 (s, 2H), 4.03 (s, 2H), 3.53-3.65 (m, 4H), 3.37 (s, 3H), 3.33 (t, 3H), 3.20 (t, 2H), 1.95-2.06 (m, 2H). MS obsd. (ESI$^+$) [(M+H)$^+$]: 374.

Example 45: 6-(4-chlorophenyl)-2-(2-pyridyl)-7,8-dihydro-5H-pyrido[4,3-d]pyrimidine

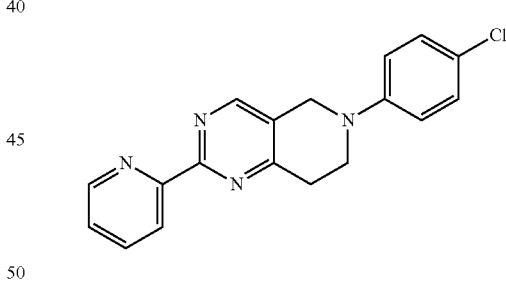

Step 1: Preparation of 8-(4-chlorophenyl)-1,4-dioxa-8-azaspiro[4.5]decane

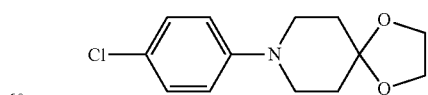

To a flask containing 1-chloro-4-iodo-benzene (1170 mg, 4.92 mmol) and 1,4-dioxa-8-azaspiro[4.5]decane (774 mg, 5.41 mmol) in dioxane (20 mL) was added t-BuONa (945 mg, 9.84 mmol), Pd$_2$(dba)$_3$ (229 mg, 0.25 mmol) and Sphos (201 mg, 0.49 mmol) under N$_2$. After being heated with stirring at 100° C. overnight, the resulting mixture was cooled to rt, diluted with H₂O (40 mL) and extracted with EA (50 mL) for three times. The combined organic layer was washed with brine (50 mL), dried over anhydrous Na₂SO₄ and concentrated in vacuo to give 8-(4-chlorophenyl)-1,4-dioxa-8-azaspiro[4.5]decane (1100 mg), which was used in the next step without further purification.

Step 2: Preparation of
1-(4-chlorophenyl)piperidin-4-one

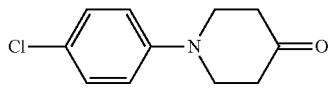

A mixture of crude 8-(4-chlorophenyl)-1,4-dioxa-8-azaspiro[4.5]decane (1100 mg, 4.34 mmol) and 44% formic acid (10 mL) was heated with stirring at 90° C. for 8 hrs. The resulting reaction mixture was concentrated in vacuo, diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 1-(4-chlorophenyl)piperidin-4-one (820 mg) as brown oil, which was used in the next step without further purification.

Step 3: Preparation of 6-(4-chlorophenyl)-2-(2-pyridyl)-7,8-dihydro-5H-pyrido[4,3-d]pyrimidine

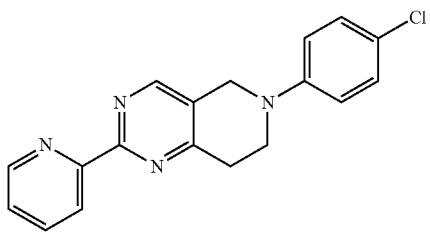 [SMILES: Clc1ccc(N2CCc3nc(-c4ccccn4)ncc3C2)cc1]

A mixture of 1-(4-chlorophenyl)piperidin-4-one (820 mg, 3.91 mmol) and DMFDMA (10 mL) was heated with stirring at 90° C. for 3 hrs. The resulting reaction mixture was concentrated in vacuo and the residue was dissolved in EtOH (20 mL). To this solution was added pyridine-2-carboxamidine hydrochloride (618 mg, 3.91 mmol) and K₂CO₃ (1079 mg, 7.82 mmol) successively. After being heated with stirring at 80° C. overnight, the resulting reaction mixture was cooled to rt and purified by prep-HPLC to give 6-(4-chlorophenyl)-2-(2-pyridyl)-7,8-dihydro-5H-pyrido[4,3-d]pyrimidine (20 mg). ¹H NMR (400 MHz, CDCl₃): δ 8.82-8.90 (m, 1H), 8.71 (s, 1H), 8.52 (d, 1H), 7.88 (d, 1H), 7.40-7.45 (m, 1H), 7.26-7.32 (m, 3H), 6.91-7.01 (m, 2H), 4.45 (s, 2H), 3.69 (s, 2H), 3.29 (s, 2H). MS obsd. (ESI⁺) [(M+H)⁺]: 323.

Example 46: 6-(4-benzyloxyphenyl)-2-(2-pyridyl)-7,8-dihydro-5H-pyrido[4,3-d]pyrimidine

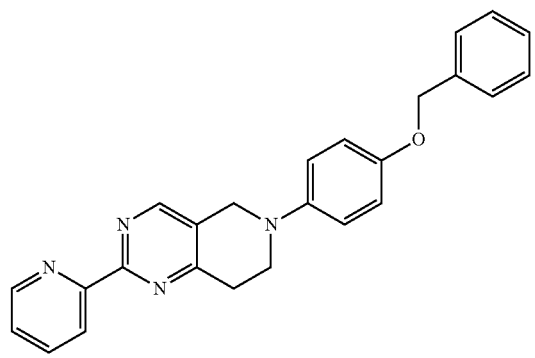 [SMILES: c1ccc(COc2ccc(N3CCc4nc(-c5ccccn5)ncc4C3)cc2)cc1]

Step 1: Preparation of 8-(4-benzyloxyphenyl)-1,4-dioxa-8-azaspiro[4.5]decane

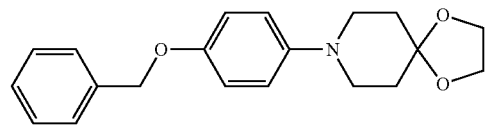 [SMILES: c1ccc(COc2ccc(N3CCC4(CC3)OCCO4)cc2)cc1]

To a flask containing 1-benzyloxy-4-iodo-benzene (5000 mg, 16.1 mmol) and 1,4-dioxa-8-azaspiro[4.5]decane (2500 mg, 17.7 mmol) in dioxane (20 mL) was added t-BuONa (12700 mg, 32.2 mmol), Pd₂(dba)₃ (732 mg, 0.8 mmol) and Sphos (656 mg, 1.6 mmol) under N₂. After being heated with stirring at 100° C. overnight, the resulting mixture was cooled to rt, diluted with H₂O (50 mL) and extracted with EA (50 mL) for three times. The combined organic layer was washed with brine (50 mL) and dried over anhydrous Na₂SO₄ and concentrate in vacuo to give 8-(4-benzyloxyphenyl)-1,4-dioxa-8-azaspiro[4.5]decane (5700 mg), which was used in the next step without further purification.

Step 2: Preparation of
1-(4-benzyloxyphenyl)piperidin-4-one

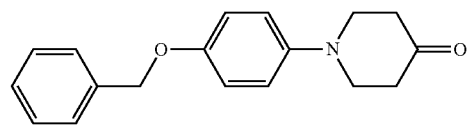 [SMILES: O=C1CCN(c2ccc(OCc3ccccc3)cc2)CC1]

A mixture of crude 8-(4-benzyloxyphenyl)-1,4-dioxa-8-azaspiro[4.5]decane (3200 mg, 9.85 mmol) in 44% formic acid (10 mL) was heated with stirring at 90° C. for 8 hrs. The resulting reaction mixture was concentrated in vacuo, diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 1-(4-benzyloxyphenyl)piperidin-4-one (2500 mg) as brown oil, which was used in the next step without further purification.

Step 3: Preparation of 6-(4-benzyloxyphenyl)-2-(2-pyridyl)-7,8-dihydro-5H-pyrido[4,3-d]pyrimidine

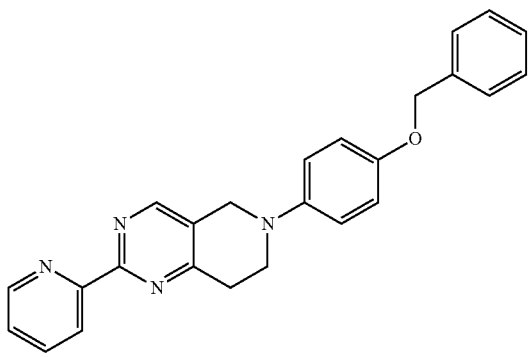 [SMILES: c1ccc(COc2ccc(N3CCc4nc(-c5ccccn5)ncc4C3)cc2)cc1]

A mixture of 1-(4-benzyloxyphenyl)piperidin-4-one (700 mg, 2.49 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (393 mg, 2.49 mmol) and K$_2$CO$_3$ (677 mg, 4.98 mmol) successively. After being heated with stirring at 80° C. overnight, the resulting reaction mixture was cooled to rt and purified by prep-HPLC to give 6-(4-benzyloxyphenyl)-2-(2-pyridyl)-7,8-dihydro-5H-pyrido[4,3-d]pyrimidine (850 mg). $^1$H NMR (400 MHz, CDCl$_3$): δ 8.80-8.91 (m, 1H), 8.64-8.71 (m, 1H), 8.49-8.57 (m, 1H), 7.81-7.93 (m, 1H), 7.30-7.51 (m, 6H), 6.93-7.09 (m, 4H), 5.06 (s, 2H), 4.36 (s, 2H), 3.59 (s, 2H), 3.24-3.32 (m, 2H). MS obsd. (ESI$^+$) [(M+H)$^+$]: 395.

Example 47: 6-(p-tolyl)-2-(2-pyridyl)-7,8-dihydro-5H-pyrido[4,3-d]pyrimidine

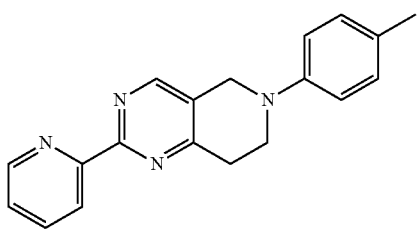 [SMILES: Cc1ccc(N2CCc3nc(-c4ccccn4)ncc3C2)cc1]

Step 1: Preparation of 8-(p-tolyl)-1,4-dioxa-8-azaspiro[4.5]decane

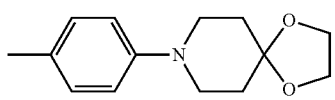

To a flask containing 1-iodo-4-methyl-benzene (1500 mg, 6.88 mmol) and 1,4-dioxa-8-azaspiro[4.5]decane (1080 mg, 7.57 mmol) in dioxane (20 mL) was added t-BuONa (1320 mg, 13.76 mmol), Pd$_2$(dba)$_3$ (311 mg, 0.34 mmol) and Sphos (283 mg, 0.68 mmol) under N$_2$. After being heated with stirring at 100° C. overnight, the resulting reaction mixture was cooled to rt, diluted with H$_2$O (50 mL) and extracted with EA (50 mL) for three times. The combined organic layer was washed with brine (50 mL) and dried over anhydrous Na$_2$SO$_4$ and concentrated in vacuo to give 8-(p-tolyl)-1,4-dioxa-8-azaspiro[4.5]decane (1450 mg), which was used in the next step without further purification.

Step 2: Preparation of 1-(p-tolyl)piperidin-4-one

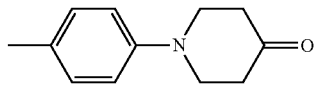

To a flask containing crude 8-(p-tolyl)-1,4-dioxa-8-azaspiro[4.5]decane (1.45 g, 6.22 mmol) was added 44% formic acid (10 mL). After being heated with stirring at 90° C. for 8 hrs, the resulting reaction mixture was concentrated in vacuo, diluted with sat. aqueous solution of NaHCO$_3$ (20 mL) and extracted with EA (30 mL) for three times. The combined organic layer was washed with brine (50 mL), dried over anhydrous Na$_2$SO$_4$ and concentrated in vacuo to give 1-(p-tolyl)piperidin-4-one (1.0 g) as brown oil, which was used in the next step without further purification.

Step 3: Preparation of 6-(p-tolyl)-2-(2-pyridyl)-7,8-dihydro-5H-pyrido[4,3-d]pyrimidine A mixture of 1-(p-tolyl)piperidin-4-one (500 mg, 2.65 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (418 mg, 2.65 mmol) and K$_2$CO$_3$ (731 mg, 5.3 mmol) successively. After being heated with stirring at 80° C. overnight, the resulting reaction mixture was cooled to rt and purified by prep-HPLC to give 6-(p-tolyl)-2-(2-pyridyl)-7,8-dihydro-5H-pyrido[4,3-d]pyrimidine (15 mg). $^1$H NMR (400 MHz, CDCl$_3$): δ 8.83-8.90 (m, 1H), 8.70 (s, 1H), 8.49-8.56 (m, 1H), 7.83-7.92 (m, 1H), 7.37-7.46 (m, 1H), 7.11-7.20 (m, 2H), 6.95-7.02 (m, 2H), 4.42 (s, 2H), 3.66 (t, 2H), 3.29 (t, 2H), 2.32 (s, 3H). MS obsd. (ESI$^+$) [(M+H)$^+$]: 303.

Example 48: 8-methyl-6-(4-nitrophenyl)-2-(2-pyridyl)-7,8-dihydro-5H-pyrido[4,3-d]pyrimidine

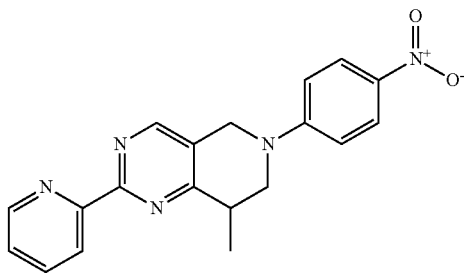 [SMILES: CC1CN(c2ccc([N+](=O)[O-])cc2)Cc2cnc(-c3ccccn3)nc21]

Step 1: Preparation of
1-benzyl-3-methyl-piperidin-4-one

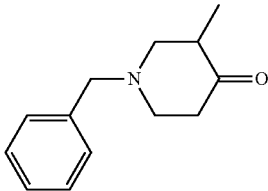

To a solution of 1-benzylpiperidin-4-one (5.50 g, 29.1 mmol) in THF (100 mL) was added NaH (1700 mg, 60% in mineral oil, 43.7 mmol) at 0° C. The resulting mixture was stirred at 0° C. for 30 minutes. To the resulting mixture was added MeI (6200 mg, 43.7 mmol) at 0° C. After being heated with stirring at 60° C. overnight, the resulting reaction mixture was cooled to rt, diluted with sat. aqueous solution of NH$_4$Cl (50 mL) and extracted with EA (50 mL) for three times. The combined organic layer was dried over anhydrous Na$_2$SO$_4$ and concentrated in vacuo. The residue was purified by flash column (eluting with 1% MeOH in DCM) to give 1-benzyl-3-methyl-piperidin-4-one (2.50 g).

Step 2: Preparation of 6-benzyl-8-methyl-2-(2-pyridyl)-7,8-dihydro-5H-pyrido[4,3-d]pyrimidine

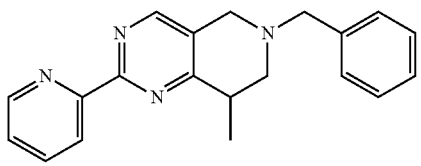 [SMILES: CC1CN(Cc2ccccc2)Cc2cnc(-c3ccccn3)nc21]

A mixture of 1-benzyl-3-methyl-piperidin-4-one (2.50 g, 12.32 mmol) and DMFDMA (10 mL) was heated with stirring at 120° C. for 8 hrs. The resulting reaction mixture was concentrated in vacuo and the residue was dissolved in EtOH (20 mL). To the solution was added pyridine-2-carboxamidine hydrochloride (1.95 g, 12.32 mmol) and K$_2$CO$_3$ (3.4 g, 24.64 mmol) successively. After being heated with stirring at 80° C. overnight, the resulting reaction mixture was cooled to rt, diluted with H$_2$O (40 mL) and extracted with EA (50 mL) for three times. The combined organic layer was dried over anhydrous Na$_2$SO$_4$ and concentrated in vacuo. The residue was purified by flash column to give 6-benzyl-8-methyl-2-(2-pyridyl)-7,8-dihydro-5H-pyrido[4,3-d]pyrimidine (500 mg).

Step 3: Preparation of 8-methyl-2-(2-pyridyl)-5,6,7,8-tetrahydropyrido[4,3-d]pyrimidine

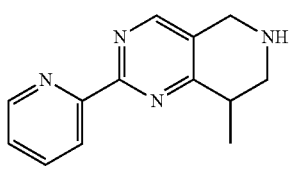 [SMILES: CC1CNCc2cnc(-c3ccccn3)nc21]

To a solution of 6-benzyl-8-methyl-2-(2-pyridyl)-7,8-dihydro-5H-pyrido[4,3-d]pyrimidine (500 mg, 1.58 mmol) in MeOH (15 mL) was added ammonium formate (995 mg, 15.8 mmol) and 5% Pd on charcoal (100 mg). After being degassed and heated with stirring at 80° C. overnight, the reaction was cooled to rt and filtered. The filtrate was concentrated in vacuo to give 8-methyl-2-(2-pyridyl)-5,6,7,8-tetrahydropyrido[4,3-d]pyrimidine (200 mg), which was used directly in the next step without further purification.

Step 4: Preparation of 8-methyl-6-(4-nitrophenyl)-2-(2-pyridyl)-7,8-dihydro-5H-pyrido[4,3-d]pyrimidine

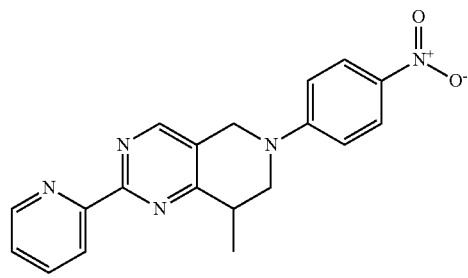 [SMILES: CC1CN(c2ccc([N+](=O)[O-])cc2)Cc2cnc(-c3ccccn3)nc21]

To a mixture of 8-methyl-2-(2-pyridyl)-5,6,7,8-tetrahydropyrido[4,3-d]pyrimidine (100 mg, 0.44 mmol) and 1-fluoro-4-nitro-benzene (186 mg, 1.32 mmol) in DMSO (5 mL) was added K$_2$CO$_3$ (120 mg, 0.88 mmol). After being heated with stirring at 80° C. for 3 hrs, The resulting reaction mixture was purified by prep-HPLC to give 8-methyl-6-(4-nitrophenyl)-2-(2-pyridyl)-7,8-dihydro-5H-pyrido[4,3-d]pyrimidine (10 mg). $^1$H NMR (400 MHz, CDCl$_3$): δ 8.84-8.91 (m, 1H), 8.79 (s, 1H), 8.51-8.60 (m, 1H), 8.19-8.27 (m, 2H), 7.85-7.94 (m, 1H), 7.41-7.47 (m, 1H), 6.93-6.99 (m, 2H), 4.61-4.78 (m, 2H), 3.84-3.96 (m, 1H), 3.63-3.74 (m, 1H), 3.37-3.50 (m, 1H), 1.58 (s, 3H). MS obsd. (ESI$^+$) [(M+H)$^+$]: 348.

Example 49: 6-(3,4-dichlorophenyl)-2-(2-pyridyl)-7,8-dihydro-5H-pyrido[4,3-d]pyrimidine

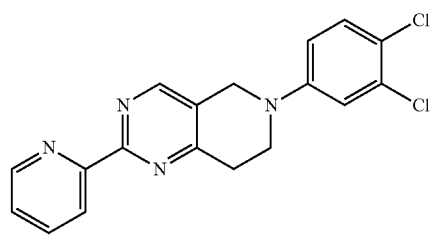 [SMILES: Clc1ccc(N2CCc3nc(-c4ccccn4)ncc3C2)cc1Cl]

Step 1: Preparation of 8-(3,4-dichlorophenyl)-1,4-dioxa-8-azaspiro[4.5]decane

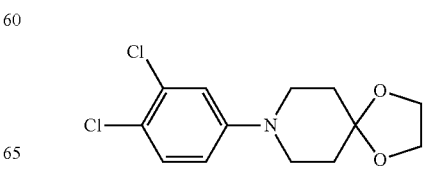

To a flask containing 1,2-dichloro-4-iodo-benzene (1700 mg, 6.23 mmol) and 1,4-dioxa-8-azaspiro[4.5]decane (1070 mg, 7.48 mmol) in dioxane (20 mL) was added t-BuONa (1200 mg, 12.46 mmol), Pd$_2$(dba)$_3$ (284 mg, 0.31 mmol) and Sphos (254 mg, 0.62 mmol) under N$_2$. After being heated with stirring at 100° C. overnight, the resulting mixture was cooled to rt, diluted with H$_2$O (50 mL) and extracted with EA (50 mL) for three times. The combined organic layer was washed with brine (50 mL), dried over anhydrous Na$_2$SO$_4$ and concentrated in vacuo to give 8-(3,4-dichlorophenyl)-1,4-dioxa-8-azaspiro[4.5]decane (700 mg), which was used in the next step without further purification.

Step 2: Preparation of 1-(3,4-dichlorophenyl)piperidin-4-one

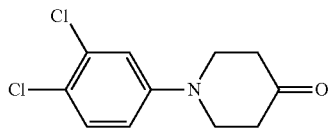

A mixture of 8-(3,4-dichlorophenyl)-1,4-dioxa-8-azaspiro[4.5]decane (700 mg, 2.43 mmol) and 44% formic acid (10 mL) was heated with stirring at 90° C. for 8 hrs. The reaction mixture was concentrated in vacuo and the residue was diluted with sat. aqueous solution of NaHCO$_3$ (20 mL). The resulting mixture was extracted with EA (30 mL) for three times. The combined organic layer was washed with brine (50 mL), dried over anhydrous Na$_2$SO$_4$ and concentrated in vacuo to give 1-(3,4-dichlorophenyl)piperidin-4-one (590 mg) as brown oil, which was used in the next step without further purification.

Step 3: Preparation of 6-(3,4-dichlorophenyl)-2-(2-pyridyl)-7,8-dihydro-5H-pyrido[4,3-d]pyrimidine

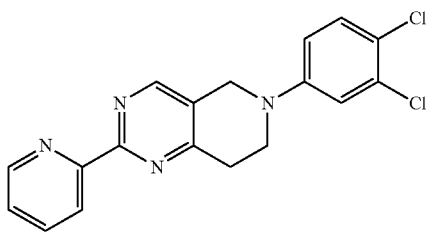 [SMILES: Clc1ccc(N2CCc3nc(-c4ccccn4)ncc3C2)cc1Cl]

A mixture of 1-(3,4-dichlorophenyl)piperidin-4-one (590 mg, 2.42 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (382 mg, 2.42 mmol) and K$_2$CO$_3$ (668 mg, 4.84 mmol) successively. After being heated with stirring at 80° C. overnight, the resulting reaction mixture was cooled to rt and purified by prep-HPLC to give 6-(3,4-dichlorophenyl)-2-(2-pyridyl)-7,8-dihydro-5H-pyrido[4,3-d]pyrimidine (15 mg). $^1$H NMR (400 MHz, CDCl$_3$): δ 8.83-8.91 (m, 1H), 8.69-8.77 (m, 1H), 8.50-8.56 (m, 1H), 7.85-7.93 (m, 1H), 7.40-7.46 (m, 1H), 7.34-7.38 (m, 1H), 7.08-7.11 (m, 1H), 6.85-6.90 (m, 1H), 4.43-4.51 (m, 2H), 3.66-3.74 (m, 2H), 3.24-3.34 (m, 2H). MS obsd. (ESI$^+$) [(M+H)$^+$]: 357.

Example 50: 6-(4-methoxyphenyl)-2-(2-pyridyl)-7,8-dihydro-5H-pyrido[4,3-d]pyrimidine

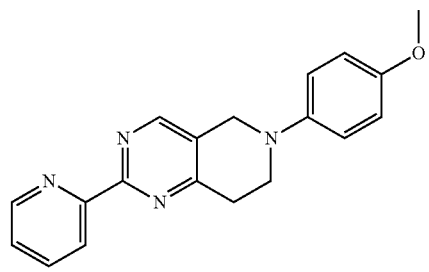 [SMILES: COc1ccc(N2CCc3nc(-c4ccccn4)ncc3C2)cc1]

Step 1: Preparation of 8-(4-methoxyphenyl)-1,4-dioxa-8-azaspiro[4.5]decane

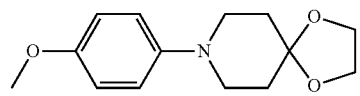

To a flask containing 1-iodo-4-methoxy-benzene (2.0 g, 8.5 mmol) and 1,4-dioxa-8-azaspiro[4.5]decane (1.5 g, 10.2 mmol) in dioxane (30 mL) was added t-BuONa (1.60 g, 17 mmol), Pd$_2$(dba)$_3$ (366 mg, 0.4 mmol) and Sphos (328 mg, 0.8 mmol) under N$_2$. After being heated with stirring at 100° C. overnight, the resulting mixture was cooled to rt, diluted with H$_2$O (50 mL) and extracted with EA (50 mL) for three times. The combined organic layer was washed with brine (50 mL) and dried over anhydrous Na$_2$SO$_4$ and concentrated in vacuo to give 8-(4-methoxyphenyl)-1,4-dioxa-8-azaspiro[4.5]decane (1.5 g), which was used in the next step without further purification.

Step 2: Preparation of 1-(4-methoxyphenyl)piperidin-4-one

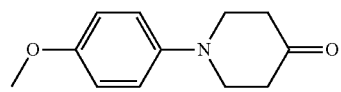

A mixture of 8-(4-methoxyphenyl)-1,4-dioxa-8-azaspiro[4.5]decane (1.5 g, 6.02 mmol) and 44% formic acid (10 mL) was heated with stirring at 90° C. for 8 hrs. The resulting reaction mixture was concentrated in vacuo, diluted with sat. aqueous solution of NaHCO$_3$ (20 mL) and extracted with EA (30 mL) for three times. The combined organic layer was washed with brine (50 mL), dried over anhydrous Na$_2$SO$_4$ and concentrated in vacuo to give 1-(4-methoxyphenyl)piperidin-4-one (1.2 g) as brown oil, which was used in the next step without further purification.

Step 3: Preparation of 6-(4-methoxyphenyl)-2-(2-pyridyl)-7,8-dihydro-5H-pyrido[4,3-d]pyrimidine

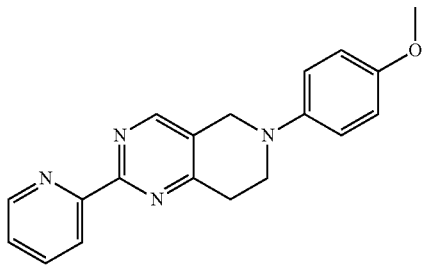 [SMILES: COc1ccc(N2CCc3nc(-c4ccccn4)ncc3C2)cc1]

A mixture of 1-(4-methoxyphenyl)piperidin-4-one (1.2 g, 5.85 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (924 mg, 5.85 mmol) and $K_2CO_3$ (1615 mg, 11.7 mmol) successively. After being heated with stirring at 80° C. overnight, the reaction mixture was cooled to rt and purified by prep-HPLC to give 6-(4-methoxyphenyl)-2-(2-pyridyl)-7,8-dihydro-5H-pyrido[4,3-d]pyrimidine (10 mg). $^1$H NMR (400 MHz, MeOH-$d_4$): δ 8.69-8.77 (m, 1H), 8.62-8.68 (m, 1H), 8.45-8.54 (m, 1H), 7.88-7.99 (m, 1H), 7.44-7.51 (m, 1H), 7.00-7.07 (m, 2H), 6.84-6.92 (m, 2H), 4.31-4.37 (m, 2H), 3.78 (s, 3H), 3.52-3.61 (m, 2H), 3.19-3.28 (m, 2H). MS obsd. (ESI$^+$) [(M+H)$^+$]: 319.

Example 51: 6-(3-bromo-4-fluoro-phenyl)-2-(2-pyridyl)-7,8-dihydro-5H-pyrido[4,3-d]pyrimidine

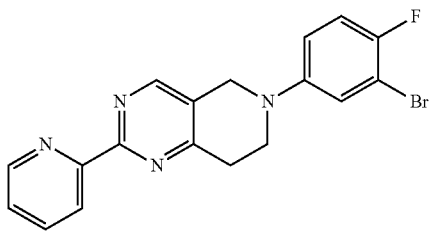 [SMILES: Fc1ccc(N2CCc3nc(-c4ccccn4)ncc3C2)cc1Br]

Step 1: Preparation of 8-(3-bromo-4-fluoro-phenyl)-1,4-dioxa-8-azaspiro[4.5]decane

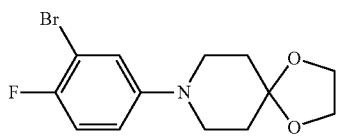

To a flask containing 2-bromo-1-fluoro-4-iodo-benzene (4.0 g, 13.3 mmol) and 1,4-dioxa-8-azaspiro[4.5]decane (2.09 g, 14.6 mmol) in N-methyl-2-pyrrolidone (50 mL) was added $K_2CO_3$ (3.67 g, 26.6 mmol), CuI (128 mg, 0.67 mmol) and L-proline (77 mg, 0.67 mmol) under $N_2$. After being heated with stirring at 120° C. overnight, the resulting mixture was cooled to rt, diluted with $H_2O$ (50 mL) and extracted with EA (50 mL) for three times. The combined organic layer was washed with brine (50 mL), dried over anhydrous $Na_2SO_4$ and concentrated in vacuo. The residue was purified by flash chromatography to give 8-(3-bromo-4-fluoro-phenyl)-1,4-dioxa-8-azaspiro[4.5]decane (1.4 g).

Step 2: Preparation of 1-(3-bromo-4-fluoro-phenyl)piperidin-4-one

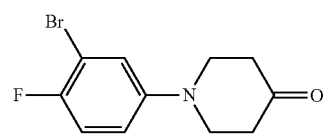 [SMILES: O=C1CCN(c2ccc(F)c(Br)c2)CC1]

A mixture of 8-(3-bromo-4-fluoro-phenyl)-1,4-dioxa-8-azaspiro[4.5]decane (1.4 g, 4.43 mmol) and 44% formic acid (10 mL) was heated with stirring at 90° C. for 8 hrs. The resulting reaction mixture was concentrated in vacuo, diluted with sat. $NaHCO_3$ (20 mL) and extracted with EA (30 mL) for three times. The combined organic layer was washed with brine (50 mL), dried over anhydrous $Na_2SO_4$ and concentrated in vacuo to give 1-(3-bromo-4-fluoro-phenyl)piperidin-4-one (1.2 mg) as brown oil, which was used in the next step without further purification.

Step 3: Preparation of 6-(3-bromo-4-fluoro-phenyl)-2-(2-pyridyl)-7,8-dihydro-5H-pyrido[4,3-d]pyrimidine

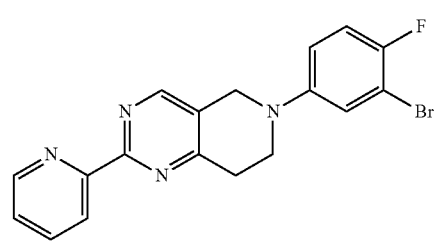 [SMILES: Fc1ccc(N2CCc3nc(-c4ccccn4)ncc3C2)cc1Br]

A mixture of 1-(3-bromo-4-fluoro-phenyl)piperidin-4-one (1.2 mg, 4.43 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (700 mg, 4.43 mmol) and $K_2CO_3$ (1220 mg, 8.86 mmol) successively. After being heated with stirring at 80° C. overnight, the resulting reaction mixture was cooled to rt and purified by prep-HPLC to give 6-(3-bromo-4-fluoro-phenyl)-2-(2-pyridyl)-7,8-dihydro-5H-pyrido[4,3-d]pyrimidine (600 mg). $^1$H NMR (400 MHz, CDCl$_3$): δ 8.90-9.00 (m, 1H), 8.73 (s, 1H), 8.54-8.65 (m, 1H), 7.90-8.04 (m, 1H), 7.44-7.57 (m, 1H), 7.19-7.23 (m, 1H), 7.06-7.15 (m, 1H), 6.92-7.00 (m, 1H), 4.42 (s, 2H), 3.62-3.70 (m, 2H), 3.26-3.36 (m, 2H). MS obsd. (ESI$^+$) [(M+H)$^+$]: 385.

Example 52: 6-(4-bromo-3-fluoro-phenyl)-2-(2-pyridyl)-7,8-dihydro-5H-pyrido[4,3-d]pyrimidine

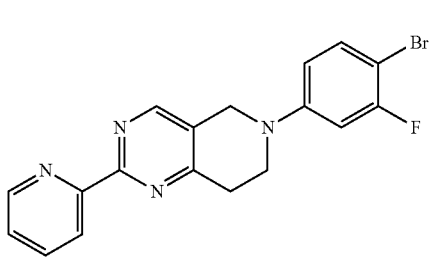 [SMILES: Fc1cc(N2CCc3nc(-c4ccccn4)ncc3C2)ccc1Br]

Step 1: Preparation of 8-(4-bromo-3-fluoro-phenyl)-1,4-dioxa-8-azaspiro[4.5]decane

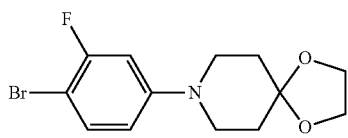 [SMILES: Fc1cc(N2CCC3(CC2)OCCO3)ccc1Br]

A mixture of 1-bromo-2-fluoro-4-iodo-benzene (100 mg, 0.33 mmol), 1,4-dioxa-8-azaspiro[4.5]decane (53 mg, 0.37 mmol), K$_2$CO$_3$ (91 mg, 0.66 mmol), CuI (4 mg, 0.02 mmol) and L-Proline (2 mg, 0.02 mmol) in DMSO (1 mL) was heated with stirring under N$_2$ atmosphere at 120° C. overnight. The resulting reaction mixture was cooled to rt, diluted with water (5 ml) and extracted with EA (50 mL) The organic layer was washed with brine, dried over anhydrous Na$_2$SO$_4$ and concentrated in vacuo. The residue was purified by column chromatography (eluting with 2.5% EA in PE) to give 8-(4-bromo-3-fluoro-phenyl)-1,4-dioxa-8-azaspiro[4.5]decane (50 mg).

Step 2: Preparation of 1-(4-bromo-3-fluoro-phenyl)piperidin-4-one

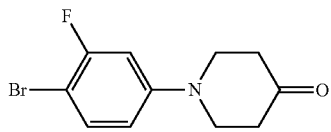

A mixture of 8-(4-bromo-3-fluoro-phenyl)-1,4-dioxa-8-azaspiro[4.5]decane (2.6 g, 8.2 mmol), H$_2$O (15 mL) and formic acid (15 mL) was heated with stirring at 90° C. overnight. The resulting reaction mixture was concentrated in vacuo, diluted with sat. aqueous solution of NaHCO$_3$ and extracted with EA (30 mL) for three times. The combined organic layer was washed with brine, dried over anhydrous Na$_2$SO$_4$ and concentrated in vacuo. The residue was purified by column chromatography (eluting with 2.5% MeOH in DCM) to give 1-(4-bromo-3-fluoro-phenyl)piperidin-4-one (1.9 g).

Step 3: Preparation of 6-(4-bromo-3-fluoro-phenyl)-2-(2-pyridyl)-7,8-dihydro-5H-pyrido[4,3-d]pyrimidine

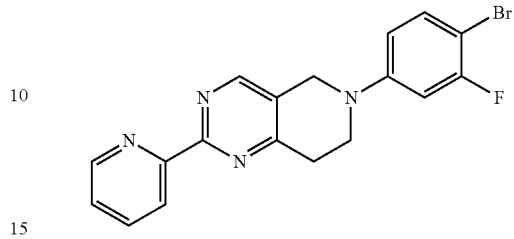

A mixture of 1-(4-bromo-3-fluoro-phenyl)piperidin-4-one (0.35 g, 1.29 mmol) and DMFDMA (2 mL) in acetonitrile (8 mL) was heated with stirring at 90° C. for 2 hrs. The resulting reaction mixture was concentrated in vacuo and the residue was dissolved in EtOH (20 mL). To the solution was added pyridine-2-carboxamidine hydrochloride (0.21 g, 1.35 mmol) and potassium carbonate (0.37 g, 2.70 mmol) successively. After being heated with stirring at 90° C. overnight, the reaction mixture was cooled to rt, diluted with water (20 ml) and extracted with EA (20 mL) for three times. The combined organic layer was washed with brine, dried over anhydrous Na$_2$SO$_4$ and concentrated in vacuo. The residue was purified by prep-HPLC to give 6-(4-bromo-3-fluoro-phenyl)-2-(2-pyridyl)-7,8-dihydro-5H-pyrido[4,3-d]pyrimidine (10 mg). $^1$H NMR (400 MHz, CDCl$_3$): δ 8.96-8.81 (m, 1H), 8.73 (s, 1H), 8.53 (d, 1H), 7.90 (dt, 1H), 7.51-7.41 (m, 2H), 6.79 (d, 1H), 6.71 (d, 1H), 4.47 (s, 2H), 3.71 (t, 2H), 3.29 (t, J=5.8 Hz, 2H). MS obsd. (ESI$^+$) [(M+H)$^+$]: 385.

Example 53: 6-(4-benzyloxy-3-fluoro-phenyl)-2-(2-pyridyl)-7,8-dihydro-5H-pyrido[4,3-d]pyrimidine

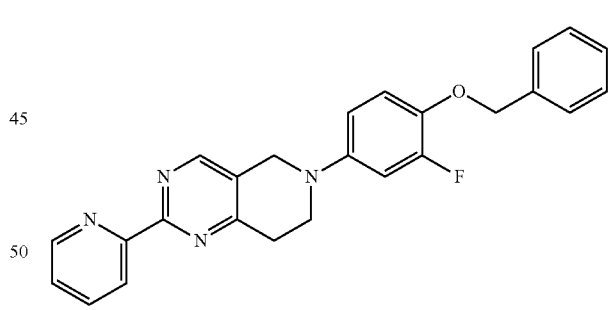

Step 1: Preparation of 1-benzyloxy-4-bromo-2-fluoro-benzene

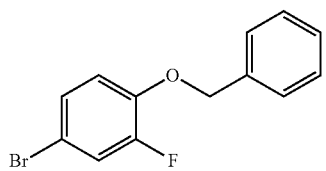 [SMILES: Fc1cc(Br)ccc1OCc1ccccc1]

A mixture of 4-bromo-2-fluoro-phenol (3.0 g, 15.7 mmol), bromomethylbenzene (4.0 g, 23.6 mmol) and potassium carbonate (4.3 g, 31.4 mmol) in acetonitrile (30 mL) was heated with stirring at 100° C. overnight. The resulting reaction mixture was cooled to rt, diluted with water (50 mL) and extracted with EA (30 mL) for three times. The combined organic layer was washed with brine, dried over anhydrous Na$_2$SO$_4$ and concentrated in vacuo. The residue was purified by column chromatography (eluting with 2% EA in PE) to give 1-benzyloxy-4-bromo-2-fluoro-benzene (3.89 g).

Step 2: Preparation of 8-(4-benzyloxy-3-fluoro-phenyl)-1,4-dioxa-8-azaspiro[4.5]decane

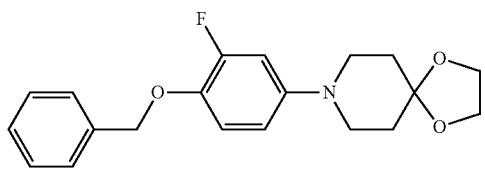 [SMILES: Fc1cc(N2CCC3(CC2)OCCO3)ccc1OCc1ccccc1]

To a flask containing 1-benzyloxy-4-bromo-2-fluoro-benzene (5.85 g, 20.82 mmol), 1,4-dioxa-8-azaspiro[4.5]decane (3.58 g, 24.98 mmol) in 1,4-dioxane (50 mL) was added t-BuONa (4.0 g, 41.64 mmol) under N$_2$. After being heated with stirring at 100° C. overnight, the reaction mixture was cooled to rt, diluted with water (60 mL) and extracted with EA (50 mL) for three times. The combined organic layer was washed with brine, dried over anhydrous Na$_2$SO$_4$ and concentrated in vacuo to give 8-(4-benzyloxy-3-fluoro-phenyl)-1,4-dioxa-8-azaspiro[4.5]decane (7.85 g), which was used in the next step without purification.

Step 3: Preparation of 1-(4-benzyloxy-3-fluoro-phenyl)piperidin-4-one

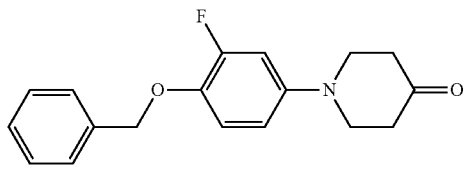 [SMILES: O=C1CCN(c2ccc(OCc3ccccc3)c(F)c2)CC1]

A mixture of 8-(4-benzyloxy-3-fluoro-phenyl)-1,4-dioxa-8-azaspiro[4.5]decane (7.85 g, 22.87 mmol), H$_2$O (15 mL) and formic acid (15 mL) was heated with stirring at 90° C. overnight. The resulting reaction mixture was concentrated in vacuo, diluted with sat. aqueous solution of NaHCO$_3$ and extracted with EA (50 mL) for three times. The combined organic layer was washed with brine, dried over anhydrous Na$_2$SO$_4$ and concentrated in vacuo. The residue was purified by column chromatography (eluting with 2.5% MeOH in DCM) to give 1-(4-benzyloxy-3-fluoro-phenyl)piperidin-4-one (4.17 g).

Step 4: Preparation of 6-(4-benzyloxy-3-fluoro-phenyl)-2-(2-pyridyl)-7,8-dihydro-5H-pyrido[4,3-d]pyrimidine

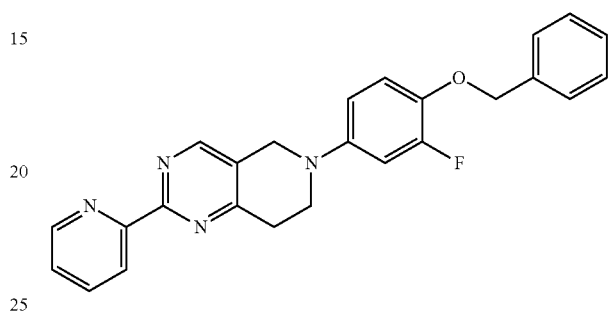

A mixture of 1-(4-benzyloxy-3-fluoro-phenyl)piperidin-4-one (4.17 g, 13.94 mmol) and DMFDMA (20 mL) in acetonitrile (10 mL) was heated with stirring at 90° C. for 2 hrs. The resulting reaction mixture was concentrated in vacuo and the residue was dissolved in EtOH (40 mL). To the solution was added pyridine-2-carboxamidine (1.8 g, 14.96 mmol) and potassium carbonate (4.1 g, 29.92 mmol) successively. After being heated with stirring at 90° C. overnight, the resulting reaction mixture was cooled to rt, diluted with water (60 mL) and extracted with EA (30 mL) for three times. The combined organic layer was washed with brine, dried over anhydrous Na$_2$SO$_4$ and concentrated in vacuo. The residue was purified by column chromatography (eluting with 5% MeOH in DCM) to give 6-(4-benzyloxy-3-fluoro-phenyl)-2-(2-pyridyl)-7,8-dihydro-5H-pyrido[4,3-d]pyrimidine (2.33 g). $^1$H NMR (400 MHz, CDCl$_3$): δ 8.96-8.85 (m, 1H), 8.69 (s, 1H), 8.53 (d, 1H), 7.89 (t, 1H), 7.52-7.32 (m, 6H), 6.98 (t, 1H), 6.85 (dd, 1H), 6.77-6.63 (m, 1H), 5.12 (s, 2H), 4.38 (s, 2H), 3.61 (t, 2H), 3.28 (t, 2H). MS obsd. (ESI$^+$) [(M+H)$^+$]: 413.

Example 54: 6-(4-ethoxy-3-fluoro-phenyl)-2-(2-pyridyl)-7,8-dihydro-5H-pyrido[4,3-d]pyrimidine

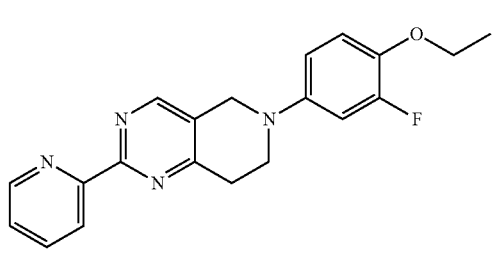 [SMILES: CCOc1ccc(N2CCc3nc(-c4ccccn4)ncc3C2)cc1F]

Step 1: Preparation of 2-fluoro-4-[2-(2-pyridyl)-7,8-dihydro-5H-pyrido[4,3-d]pyrimidin-6-yl]phenol

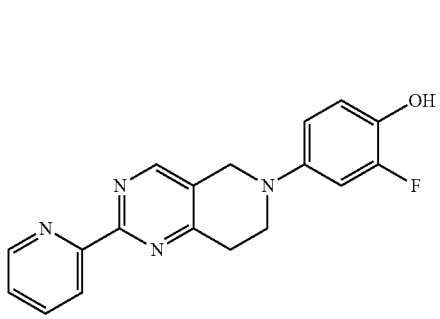 [SMILES: Oc1ccc(N2CCc3nc(-c4ccccn4)ncc3C2)cc1F]

A mixture of 6-(4-benzyloxy-3-fluoro-phenyl)-2-(2-pyridyl)-7,8-dihydro-5H-pyrido[4,3-d]pyrimidine (2.33 g, 5.65 mmol), ammonium formate (3.56 g, 56.5 mmol) and Pd(OH)$_2$ (50 mg, 0.36 mmol) in methanol (30 mL) was heated with stirring at 90° C. overnight. The resulting reaction mixture was cooled to rt and filtered. The filtrate was concentrated in vacuo to give 2-fluoro-4-[2-(2-pyridyl)-7,8-dihydro-5H-pyrido[4,3-d]pyrimidin-6-yl]phenol (4.0 g), which was used in the next step without further purification.

Step 2: Preparation of 6-(4-ethoxy-3-fluoro-phenyl)-2-(2-pyridyl)-7,8-dihydro-5H-pyrido[4,3-d]pyrimidine

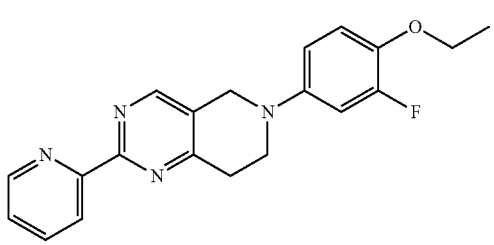 [SMILES: CCOc1ccc(N2CCc3nc(-c4ccccn4)ncc3C2)cc1F]

A mixture of 2-fluoro-4-[2-(2-pyridyl)-7,8-dihydro-5H-pyrido[4,3-d]pyrimidin-6-yl]phenol (50 mg, 0.16 mmol), ethyl iodide (50 mg, 0.32 mmol) and potassium carbonate (44 mg 0.32 mmol) in acetone (5 mL) was heated with stirring at 85° C. for 5 hrs. The resulting reaction mixture was cooled to rt, diluted with water (10 mL) and extracted with EA (20 mL) for three times. The combined organic layer was washed with brine, dried over anhydrous Na$_2$SO$_4$ and concentrated in vacuo. The residue was purified by prep-HPLC to give 6-(4-ethoxy-3-fluoro-phenyl)-2-(2-pyridyl)-7,8-dihydro-5H-pyrido[4,3-d]pyrimidine (10 mg). $^1$H NMR (400 MHz, CDCl$_3$) δ: 8.87 (d, 1H), 8.69 (s, 1H), 8.52 (d, 1H), 7.88 (dt, 1H), 7.42 (ddd, 1H), 6.96 (t, 1H), 6.85 (dd, 1H), 6.79-6.65 (m, 1H), 4.38 (s, 2H), 4.09 (q, 2H), 3.61 (t, 2H), 3.28 (t, 2H), 1.44 (t, 3H). MS obsd. (ESI$^+$) [(M+H)$^+$]: 351.

Example 55: 6-(3-fluoro-4-propoxy-phenyl)-2-(2-pyridyl)-7,8-dihydro-5H-pyrido[4,3-d]pyrimidine

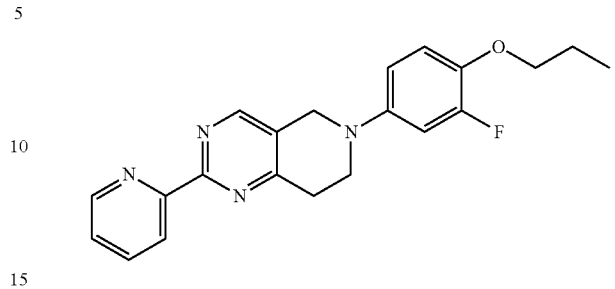

A mixture of 2-fluoro-4-[2-(2-pyridyl)-7,8-dihydro-5H-pyrido[4,3-d]pyrimidin-6-yl]phenol (200 mg, 0.62 mmol), iodopropane (320 mg, 1.86 mmol) and potassium carbonate (171 mg, 1.24 mmol) in acetone (5 mL) was heated with stirring at 85° C. for 5 hrs. The reaction mixture was cooled to rt, diluted with water (10 mL) and extracted with EA (30 mL) for three times. The combined organic layer was washed with brine, dried over anhydrous Na$_2$SO$_4$ and concentrated in vacuo. The residue was purified by prep-HPLC to give 6-(3-fluoro-4-propoxy-phenyl)-2-(2-pyridyl)-7,8-dihydro-5H-pyrido[4,3-d]pyrimidine (6 mg). $^1$H NMR (400 MHz, CDCl$_3$): δ 8.87 (d, 1H), 8.70 (s, 1H), 8.52 (d, 1H), 7.88 (dt, 1H), 7.42 (t, 1H), 6.96 (t, 1H), 6.85 (dd, 1H), 6.73 (ddd, 1H), 4.37 (s, 2H), 3.98 (t, 2H), 3.61 (t, 2H), 3.28 (t, 2H), 1.84 (sxt, 2H), 1.06 (t, 3H). MS obsd. (ESI$^+$) [(M+H)$^+$]: 365.

Example 56: 6-[3-fluoro-4-(3-methoxypropoxy)phenyl]-2-(2-pyridyl)-7,8-dihydro-5H-pyrido[4,3-d]pyrimidine

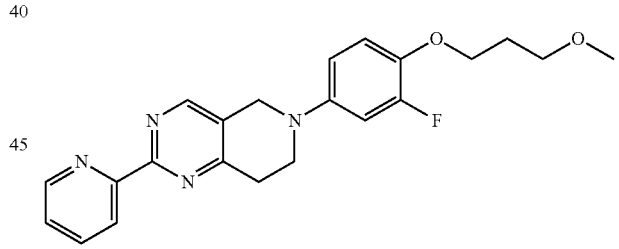

A mixture of 2-fluoro-4-[2-(2-pyridyl)-7,8-dihydro-5H-pyrido[4,3-d]pyrimidin-6-yl]phenol (200 mg, 0.62 mmol), 1-bromo-3-methoxy-propane (280 mg, 1.86 mmol) and potassium carbonate (257 mg, 1.86 mmol) in acetone (5 mL) was heated with stirring at 85° C. for 5 hrs. The resulting reaction mixture was cooled to rt, diluted with water (10 mL) and extracted with EA (30 mL) for three times. The combined organic layer was washed with brine, dried over anhydrous Na$_2$SO$_4$ and concentrated in vacuo. The residue was purified by prep-HPLC to give 6-[3-fluoro-4-(3-methoxypropoxy)phenyl]-2-(2-pyridyl)-7,8-dihydro-5H-pyrido[4,3-d]pyrimidine (6 mg). $^1$H NMR (400 MHz, CDCl$_3$): δ 8.87 (d, 1H), 8.70 (s, 1H), 8.53 (d, 1H), 7.88 (dt, 1H), 7.42 (ddd, 1H), 6.98 (t, 1H), 6.85 (dd, 1H), 6.79-6.51 (m, 1H), 4.38 (s, 2H), 4.12 (t, 2H), 3.60 (q, 4H), 3.38 (s, 3H), 3.29 (t, 2H), 2.08 (q, 2H). MS obsd. (ESI$^+$) [(M+H)$^+$]: 395.

Example 57: 6-[3-methoxy-4-(2-methoxyethoxy)phenyl]-2-(2-pyridyl)-7,8-dihydro-5H-pyrido[4,3-d]pyrimidine

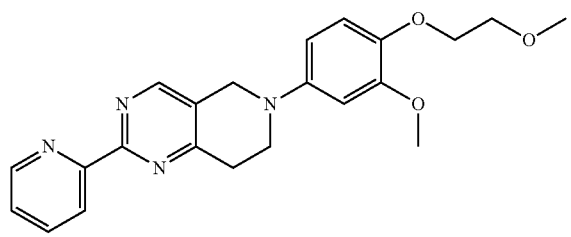 [SMILES: COCCOc1ccc(N2CCc3nc(-c4ccccn4)ncc3C2)cc1OC]

Step 1: Preparation of 4-bromo-2-methoxy-1-(2-methoxyethoxy)benzene

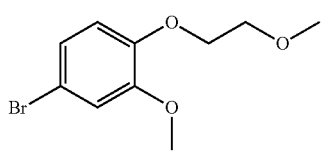

A mixture of 4-bromo-2-methoxy-phenol (1.0 g, 4.93 mmol), 1-bromo-2-methoxy-ethane (1.4 mL, 14.78 mmol) and potassium carbonate (2.0 g, 14.78 mmol) in DMF (15 mL) was heated with stirring at 120° C. for 4 hrs. The resulting reaction mixture was cooled to rt, diluted with water (30 mL) and extracted with EA (20 mL) for three times. The combined organic layer was washed with brine, dried over anhydrous Na₂SO₄ and concentrated in vacuo to give 4-bromo-2-methoxy-1-(2-methoxyethoxy)benzene (1.3 g), which was used in the next step without purification.

Step 2: Preparation of 8-[3-methoxy-4-(2-methoxyethoxy)phenyl]-1,4-dioxa-8-azaspiro[4.5]decane

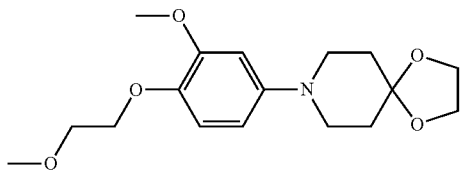 [SMILES: COCCOc1ccc(N2CCC3(CC2)OCCO3)cc1OC]

To a flask containing 4-bromo-2-methoxy-1-(2-methoxyethoxy)benzene (1.30 g, 4.98 mmol) and 1,4-dioxa-8-azaspiro[4.5]decane (0.86 g, 5.98 mmol) in 1,4-dioxane (15 ml) was added t-BuONa (0.96 g, 9.96 mmol), Pd₂(dba)₃ (92 mg, 0.10 mmol) and Ru-Phos (93 mg, 0.20 mmol) under N₂. After being heated with stirring at 100° C. overnight, the resulting reaction mixture was cooled to rt, diluted with water (20 mL) and extracted with EA (20 mL) for three times. The combined organic layer was washed with brine, dried over anhydrous Na₂SO₄ and concentrated in vacuo to give 8-[3-methoxy-4-(2-methoxyethoxy)phenyl]-1,4-dioxa-8-azaspiro[4.5]decane (2.1 g), which was used in the next step without purification.

Step 3: Preparation of 1-[3-methoxy-4-(2-methoxyethoxy)phenyl]piperidin-4-one

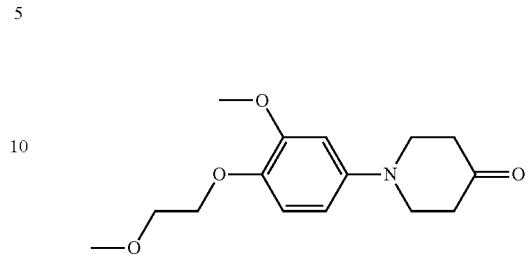

To a flask containing 8-[3-methoxy-4-(2-methoxyethoxy)phenyl]-1,4-dioxa-8-azaspiro[4.5]decane (2.10 g, 6.50 mmol) was added H₂O (15 mL) and formic acid (15 mL). After being heated with stirring at 90° C. overnight, the resulting reaction mixture was concentrated in vacuo, diluted with sat. aqueous solution of NaHCO₃ and extracted with EA (30 mL) for three times. The combined organic layer was washed with brine, dried over anhydrous Na₂SO₄ and concentrated in vacuo to give 1-[3-methoxy-4-(2-methoxyethoxy)phenyl]piperidin-4-one (1.0 g), which was used in the next step without purification.

Step 4: Preparation of 6-[3-methoxy-4-(2-methoxyethoxy)phenyl]-2-(2-pyridyl)-7,8-dihydro-5H-pyrido[4,3-d]pyrimidine

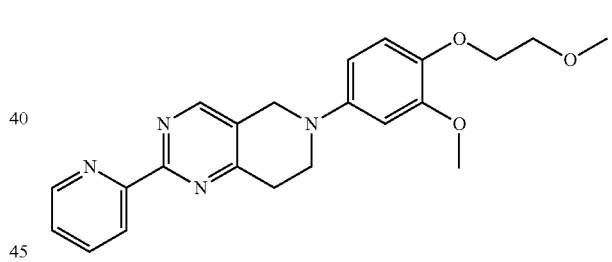

A mixture of 1-[3-methoxy-4-(2-methoxyethoxy)phenyl]piperidin-4-one (1.0 g, 3.58 mmol) and DMFDMA (2 mL) in acetonitrile (8 mL) was heated with stirring at 90° C. for 2 hrs. The resulting reaction mixture was concentrated in vacuo and the residue was dissolved in EtOH (20 mL). To the solution was added pyridine-2-carboxamidine hydrochloride (0.56 g, 3.57 mmol) and potassium carbonate (0.98 g, 7.13 mmol) successively. After being heated with stirring at 90° C. overnight, the resulting reaction mixture was cooled to rt, diluted with water (20 mL) and extracted with EA (30 mL) for three times. The combined organic layer was washed with brine, dried over anhydrous Na₂SO₄ and concentrated in vacuo. The residue was purified by prep-HPLC to give 6-[3-methoxy-4-(2-methoxyethoxy)phenyl]-2-(2-pyridyl)-7,8-dihydro-5H-pyrido[4,3-d]pyrimidine. $^1$H NMR (400 MHz, CDCl₃): δ 8.87 (d, 1H), 8.69 (s, 1H), 8.53 (d, J=8.0 Hz, 1H), 7.88 (dt, 1H), 7.42 (t, 1H), 6.92 (d, 1H), 6.69 (d, 1H), 6.56 (dd, 1H), 4.38 (s, 2H), 4.16 (dd, 2H), 3.91 (s, 3H), 3.78 (dd, 2H), 3.61 (t, 2H), 3.47 (s, 3H), 3.30 (t, 2H). MS obsd. (ESI⁺) [(M+H)⁺]: 393.

Example 58: 6-[4-methoxy-3-(2-methoxyethoxy)phenyl]-2-(2-pyridyl)-7,8-dihydro-5H-pyrido[4,3-d]pyrimidine

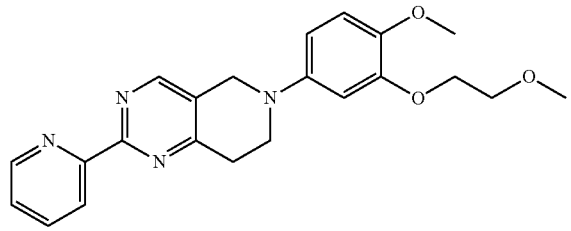 [SMILES: COCCOc1cc(N2CCc3nc(-c4ccccn4)ncc3C2)ccc1OC]

Step 1: Preparation of 4-bromo-1-methoxy-2-(2-methoxyethoxy)benzene

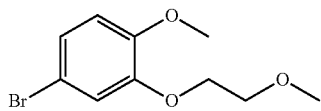

A mixture of 5-bromo-2-methoxy-phenol (0.50 g, 2.46 mmol), 1-bromo-3-methoxy-propane (1.03 g, 7.39 mmol) and potassium carbonate (1.02 g, 7.39 mmol) in DMF (5 mL) was heated with stirring at 120° C. for 4 hrs. The resulting reaction mixture was cooled to rt, diluted with water (15 mL) and extracted with EA (20 mL) for three times. The combined organic layer was washed with brine, dried over anhydrous $Na_2SO_4$ and concentrated in vacuo to give 4-bromo-1-methoxy-2-(2-methoxyethoxy)benzene (0.65 g), which was used in the next step without further purification.

Step 2: Preparation of 8-[4-methoxy-3-(2-methoxyethoxy)phenyl]-1,4-dioxa-8-azaspiro[4.5]decane

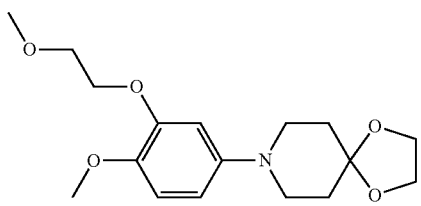 [SMILES: COCCOc1cc(N2CCC3(CC2)OCCO3)ccc1OC]

To a flask containing 4-bromo-1-methoxy-2-(2-methoxyethoxy)benzene (0.65 g, 2.48 mmol) and 1,4-dioxa-8-azaspiro[4.5]decane (0.43 g, 2.98 mmol) in 1,4-dioxane (10 ml) was added t-BuONa (0.48 g, 4.96 mmol), $Pd_2(dba)_3$ (46 mg, 0.05 mmol) and Ru-Phos (46 mg, 0.10 mmol) under $N_2$. After being heated with stirring at 100° C. overnight, the resulting reaction mixture was cooled to rt, diluted with water (20 mL) and extracted with EA (30 mL) for three times. The combined organic layer was washed with brine, dried over anhydrous $Na_2SO_4$ and concentrated in vacuo to give 8-[4-methoxy-3-(2-methoxyethoxy)phenyl]-1,4-dioxa-8-azaspiro[4.5]decane (0.78 g), which was used in the next step without further purification.

Step 3: Preparation of 1-[4-methoxy-3-(2-methoxyethoxy)phenyl]piperidin-4-one

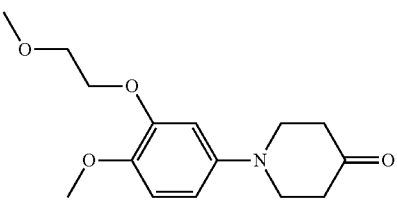 [SMILES: COCCOc1cc(N2CCC(=O)CC2)ccc1OC]

To a flask containing 8-[4-methoxy-3-(2-methoxyethoxy)phenyl]-1,4-dioxa-8-azaspiro[4.5]decane (0.78 g, 2.41 mmol) was added $H_2O$ (2 mL) and formic acid (2 mL). After being heated with stirring at 90° C. overnight, the resulting reaction mixture was concentrated in vacuo, diluted with sat. aqueous solution of $NaHCO_3$ and extracted with EA (30 mL) for three times. The combined organic layer was washed with brine, dried over anhydrous $Na_2SO_4$ and concentrated in vacuo to give 1-[4-methoxy-3-(2-methoxyethoxy)phenyl]piperidin-4-one (0.7 g), which was used in the next step without further purification.

Step 4: Preparation of 6-[4-methoxy-3-(2-methoxyethoxy)phenyl]-2-(2-pyridyl)-7,8-dihydro-5H-pyrido[4,3-d]pyrimidine

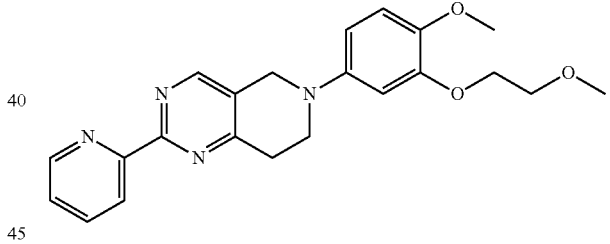

A mixture of 1-[4-methoxy-3-(2-methoxyethoxy)phenyl]piperidin-4-one (0.7 g, 2.50 mmol) and DMFDMA (2 mL) in acetonitrile (8 mL) was heated with stirring at 90° C. for 2 hrs. The resulting reaction mixture was concentrated in vacuo and the residue was dissolved in EtOH (10 mL). To the solution was added pyridine-2-carboxamidine hydrochloride (0.34 g, 2.15 mmol) and potassium carbonate (0.59 g, 4.30 mmol) successively. After being heated with stirring at 90° C. overnight, the reaction mixture was cooled to rt, diluted with water (20 mL) and extracted with EA (30 mL) for three times. The combined organic layer was washed with brine, dried over anhydrous $Na_2SO_4$ and concentrated in vacuo. The residue was purified by prep-HPLC to give 6-[4-methoxy-3-(2-methoxyethoxy)phenyl]-2-(2-pyridyl)-7,8-dihydro-5H-pyrido[4,3-d]pyrimidine (44 mg). $^1$H NMR (400 MHz, DMSO-$d_6$): δ 8.79 (s, 1H), 8.74 (td, 1H), 8.36 (d, 1H), 7.96 (dt, 1H), 7.52 (ddd, 1H), 6.87 (d, 1H), 6.80 (d, 1H), 6.57 (dd, 1H), 4.38 (s, 2H), 4.12 (dd, 2H), 3.71-3.64 (m, 5H), 3.59 (t, 2H), 3.33 (s, 3H), 3.09 (t, 2H). MS obsd. (ESI$^+$) [(M+H)$^+$]: 393.

Example 59: 6-(3,4-dimethoxyphenyl)-2-(2-pyridyl)-7,8-dihydro-5H-pyrido[4,3-d]pyrimidine

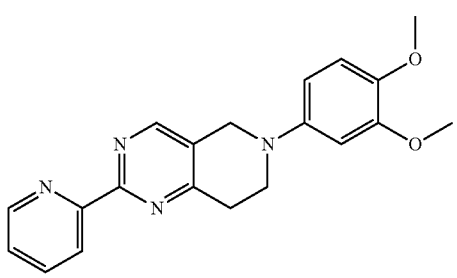 [SMILES: COc1ccc(N2CCc3nc(-c4ccccn4)ncc3C2)cc1OC]

Step 1: Preparation of 8-(3,4-dimethoxyphenyl)-1,4-dioxa-8-azaspiro[4.5]decane

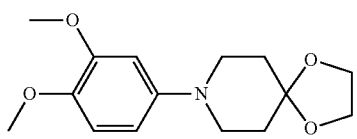 [SMILES: COc1ccc(N2CCC3(CC2)OCCO3)cc1OC]

To a flask containing 4-bromo-1,2-dimethoxy-benzene (1.1 g, 5.1 mmol) and 1,4-dioxa-8-azaspiro[4.5]decane (800 mg, 5.6 mmol) in dioxane (20 mL) was added t-BuONa (980 mg, 10.2 mmol), $Pd_2(dba)_3$ (239 mg, 0.26 mmol) and Sphos (209 mg, 0.51 mmol) under $N_2$. After being heated with stirring at 100° C. overnight, the resulting mixture was cooled to rt, diluted with $H_2O$ (50 mL) and extracted with EA (30 mL) for three times. The combined organic layer was washed with brine (50 mL), dried over anhydrous $Na_2SO_4$ and concentrated in vacuo to give 8-(3,4-dimethoxyphenyl)-1,4-dioxa-8-azaspiro[4.5]decane (1.3 g), which was used in the next step without further purification.

Step 2: Preparation of 1-(3,4-dimethoxyphenyl)piperidin-4-one

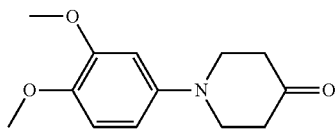 [SMILES: COc1ccc(N2CCC(=O)CC2)cc1OC]

A mixture of 8-(3,4-dimethoxyphenyl)-1,4-dioxa-8-azaspiro[4.5]decane (1.3 g, 4.66 mmol) and 44% formic acid (10 mL) was heated with stirring at 90° C. for 8 hrs. The resulting reaction mixture was concentrated in vacuo, diluted with sat. aqueous solution of $NaHCO_3$ (20 mL) and extracted with EA (30 mL) for three times. The combined organic layer was washed with brine (50 mL), dried over anhydrous $Na_2SO_4$ and concentrated in vacuo to give 1-(3,4-dimethoxyphenyl)piperidin-4-one (1.1 g) as brown oil, which was used in the next step without further purification.

Step 3: Preparation of 6-(3,4-dimethoxyphenyl)-2-(2-pyridyl)-7,8-dihydro-5H-pyrido[4,3-d]pyrimidine

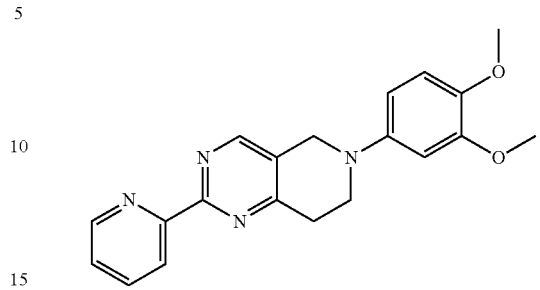

A mixture of 1-(3,4-dimethoxyphenyl)piperidin-4-one (1.1 g, 4.68 mmol) and DMFDMA (10 mL) was heated with stirring at 90° C. for 3 hrs. The reaction mixture was concentrated in vacuo and the residue was dissolved in EtOH (20 mL). To the solution was added pyridine-2-carboxamidine hydrochloride (739 mg, 4.68 mmol) and $K_2CO_3$ (1.29 g, 9.36 mmol) successively. After being heated with stirring at 80° C. overnight, the resulting reaction mixture was cooled to rt and purified by prep-HPLC to give 6-(3,4-dimethoxyphenyl)-2-(2-pyridyl)-7,8-dihydro-5H-pyrido[4,3-d]pyrimidine (800 mg). $^1$H NMR (400 MHz, $CDCl_3$) δ: 8.81-8.89 (m, 1H), 8.68 (s, 1H), 8.48-8.55 (m, 1H), 7.82-7.91 (m, 1H), 7.36-7.44 (m, 1H), 6.81-6.88 (m, 1H), 6.67-6.72 (m, 1H), 6.54-6.62 (m, 1H), 4.36 (s, 2H), 3.80-3.98 (m, 6H), 3.54-3.62 (m, 2H), 3.25-3.32 (m, 2H). MS obsd. (ESI$^+$) [(M+H)$^+$]: 349.

Example 60: 2-methoxy-4-[2-(2-pyridyl)-7,8-dihydro-5H-pyrido[4,3-d]pyrimidin-6-yl]benzonitrile

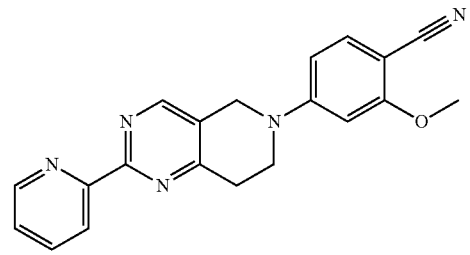 [SMILES: COc1cc(N2CCc3nc(-c4ccccn4)ncc3C2)ccc1C#N]

Step 1: Preparation of 4-(1,4-dioxa-8-azaspiro[4.5]decan-8-yl)-2-methoxy-benzonitrile

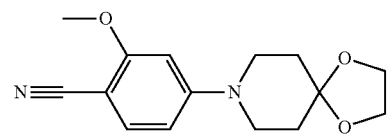

To a flask containing 4-bromo-2-methoxy-benzonitrile (500 mg, 2.37 mmol) and 1,4-dioxa-8-azaspiro[4.5]decane (374 mg, 2.61 mmol) in dioxane (10 mL) was added t-BuONa (455 mg, 4.74 mmol), $Pd_2(dba)_3$ (174 mg, 0.19 mmol) and Sphos (156 mg, 0.38 mmol) under $N_2$. After being heated with stirring at 100° C. overnight, the resulting reaction mixture was cooled to rt, diluted with H₂O (50 mL) and extracted with EA (50 mL) for three times. The combined organic layer was washed with brine (50 mL), dried over anhydrous Na₂SO₄ and concentrated in vacuo to give 4-(1,4-dioxa-8-azaspiro[4.5]decan-8-yl)-2-methoxy-benzonitrile (650 mg), which was used in the next step without further purification.

Step 2: Preparation of 2-methoxy-4-(4-oxo-1-piperidyl)benzonitrile

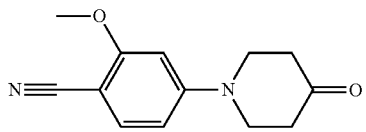 [SMILES: COc1cc(N2CCC(=O)CC2)ccc1C#N]

A mixture of 4-(1,4-dioxa-8-azaspiro[4.5]decan-8-yl)-2-methoxy-benzonitrile (650 mg, 2.37 mmol) and 44% formic acid (10 mL) was heated with stirring at 90° C. for 8 hrs. The resulting reaction mixture was concentrated in vacuo, diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 2-methoxy-4-(4-oxo-1-piperidyl)benzonitrile (540 mg) as brown oil, which was used in the next step without further purification.

Step 3: Preparation of 2-methoxy-4-[2-(2-pyridyl)-7,8-dihydro-5H-pyrido[4,3-d]pyrimidin-6-yl]benzonitrile

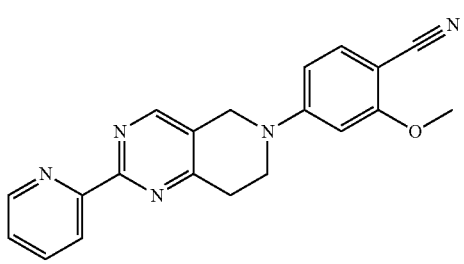 [SMILES: COc1cc(N2CCc3nc(-c4ccccn4)ncc3C2)ccc1C#N]

A mixture of 2-methoxy-4-(4-oxo-1-piperidyl)benzonitrile (540 mg, 2.37 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (374 mg, 2.37 mmol) and K₂CO₃ (654 mg, 4.74 mmol) successively. After being heated with stirring at 80° C. overnight, the resulting reaction mixture was cooled to rt and purified by prep-HPLC to give 2-methoxy-4-[2-(2-pyridyl)-7,8-dihydro-5H-pyrido[4,3-d]pyrimidin-6-yl]benzonitrile (160 mg). ¹H NMR (400 MHz, CDCl₃): δ 8.86-8.97 (m, 1H), 8.73-8.82 (m, 1H), 8.52-8.61 (m, 1H), 7.88-7.99 (m, 1H), 7.42-7.54 (m, 2H), 6.52-6.61 (m, 1H), 6.40-6.47 (m, 1H), 4.62 (s, 2H), 3.98 (s, 3H), 3.80-3.87 (m, 2H), 3.29-3.37 (m, 2H). MS obsd. (ESI⁺) [(M+H)⁺]: 344.

Example 61: 6-(2,3-difluoro-4-methoxy-phenyl)-2-(2-pyridyl)-7,8-dihydro-5H-pyrido[4,3-d]pyrimidine

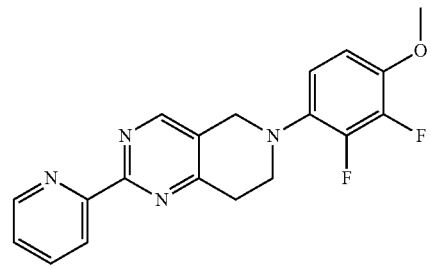 [SMILES: COc1ccc(N2CCc3nc(-c4ccccn4)ncc3C2)c(F)c1F]

Step 1: Preparation of 8-(2,3-difluoro-4-methoxy-phenyl)-1,4-dioxa-8-azaspiro[4.5]decane

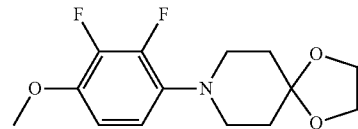 [SMILES: COc1ccc(N2CCC3(CC2)OCCO3)c(F)c1F]

To a flask containing 1-bromo-2,3-difluoro-4-methoxy-benzene (500 mg, 2.25 mmol) and 1,4-dioxa-8-azaspiro[4.5]decane (355 mg, 2.48 mmol) in dioxane (10 mL) was added t-BuONa (432 mg, 4.5 mmol) under N₂. After being heated with stirring at 100° C. overnight, the resulting reaction mixture was cooled to rt, diluted with H₂O (30 mL) and extracted with EA (30 mL) for three times. The combined organic layer was washed with brine (30 mL), dried over anhydrous Na₂SO₄ and concentrated in vacuo to afford 8-(2,3-difluoro-4-methoxy-phenyl)-1,4-dioxa-8-azaspiro[4.5]decane (600 mg), which was used in the next step without further purification.

Step 2: Preparation of 1-(2,3-difluoro-4-methoxy-phenyl)piperidin-4-one

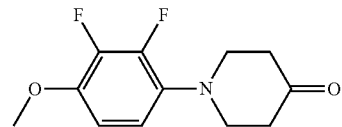 [SMILES: COc1ccc(N2CCC(=O)CC2)c(F)c1F]

A mixture of 8-(2,3-difluoro-4-methoxy-phenyl)-1,4-dioxa-8-azaspiro[4.5]decane (600 mg, 2.1 mmol) and 44% formic acid (10 mL) was heated with stirring at 90° C. for 8 hrs. The reaction mixture was concentrated in vacuo, diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 1-(2,3-difluoro-4-methoxy-phenyl)piperidin-4-one (500 mg) as brown oil, which was used in the next step without further purification.

Step 3: Preparation of 6-(2,3-difluoro-4-methoxy-phenyl)-2-(2-pyridyl)-7,8-dihydro-5H-pyrido[4,3-d]pyrimidine

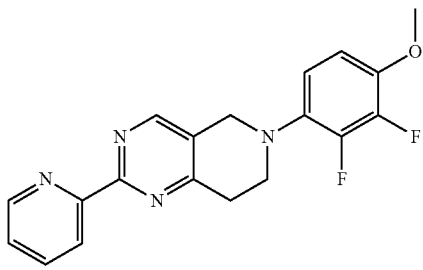 [SMILES: COc1ccc(N2CCc3nc(-c4ccccn4)ncc3C2)c(F)c1F]

A mixture of 1-(2,3-difluoro-4-methoxy-phenyl)piperidin-4-one (500 mg, 2.1 mmol) and DMFDMA (10 mL) was heated with stirring at 90° C. for 3 hrs. The resulting reaction mixture was concentrated in vacuo and the residue was dissolved in EtOH (10 mL). To the solution was added pyridine-2-carboxamidine hydrochloride (330 mg, 2.1 mmol) and K$_2$CO$_3$ (580 mg, 4.2 mmol) successively. After being heated with stirring at 80° C. overnight, the reaction mixture was cooled to rt and purified by prep-HPLC to give 6-(2,3-difluoro-4-methoxy-phenyl)-2-(2-pyridyl)-7,8-dihydro-5H-pyrido[4,3-d]pyrimidine (30 mg). $^1$H NMR (400 MHz, CDCl$_3$): δ 8.80-8.93 (m, 1H), 8.62-8.70 (m, 1H), 8.47-8.57 (m, 1H), 7.83-7.93 (m, 1H), 7.37-7.47 (m, 1H), 6.62-6.82 (m, 2H), 4.31 (s, 2H), 3.90 (s, 3H), 3.46-3.57 (m, 2H), 3.24-3.34 (m, 2H). MS obsd. (ESI$^+$) [(M+H)$^+$]: 356.

Example 62: 6-(4-chloro-3-methoxy-phenyl)-2-(2-pyridyl)-7,8-dihydro-5H-pyrido[4,3-d]pyrimidine

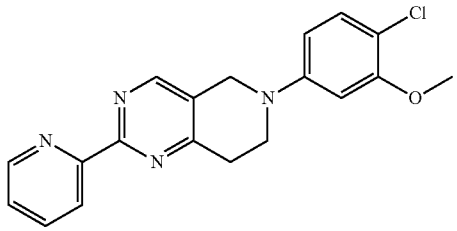 [SMILES: COc1cc(N2CCc3nc(-c4ccccn4)ncc3C2)ccc1Cl]

Step 1: Preparation of 8-(4-chloro-3-methoxy-phenyl)-1,4-dioxa-8-azaspiro[4.5]decane

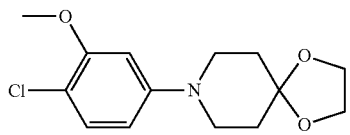 [SMILES: COc1cc(N2CCC3(CC2)OCCO3)ccc1Cl]

To a flask containing 4-bromo-1-chloro-2-methoxy-benzene (550 mg, 2.5 mmol) and 1,4-dioxa-8-azaspiro[4.5]decane (393 mg, 2.75 mmol) in dioxane (10 mL) was added t-BuONa (720 mg, 7.5 mmol), Pd$_2$(dba)$_3$ (119 mg, 0.13 mmol) and Sphos (103 mg, 0.26 mmol) under N$_2$. After being heated with stirring at 100° C. overnight, the resulting reaction mixture was cooled to rt, diluted with H$_2$O (30 mL) and extracted with EA (30 mL) for three times. The combined organic layer was washed with brine (30 mL), dried over anhydrous Na$_2$SO$_4$ and concentrated in vacuo to give 8-(4-chloro-3-methoxy-phenyl)-1,4-dioxa-8-azaspiro[4.5]decane (710 mg), which was used in the next step without further purification.

Step 2: Preparation of 1-(4-chloro-3-methoxy-phenyl)piperidin-4-one

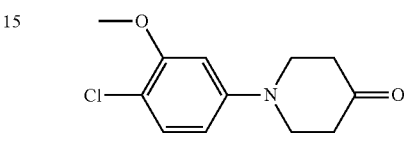

A mixture of 8-(4-chloro-3-methoxy-phenyl)-1,4-dioxa-8-azaspiro[4.5]decane (710 mg, 2.5 mmol) and 44% formic acid (10 mL) was heated with stirring at 90° C. for 8 hrs. The resulting reaction mixture was concentrated in vacuo, diluted with sat. aqueous solution of NaHCO$_3$ (20 mL) and extracted with EA (30 mL) for three times. The combined organic layer was washed with brine (50 mL), dried over anhydrous Na$_2$SO$_4$ and concentrated in vacuo to give 1-(4-chloro-3-methoxy-phenyl)piperidin-4-one (600 mg) as brown oil, which was used in the next step without further purification.

Step 3: Preparation of 6-(4-chloro-3-methoxy-phenyl)-2-(2-pyridyl)-7,8-dihydro-5H-pyrido[4,3-d]pyrimidine

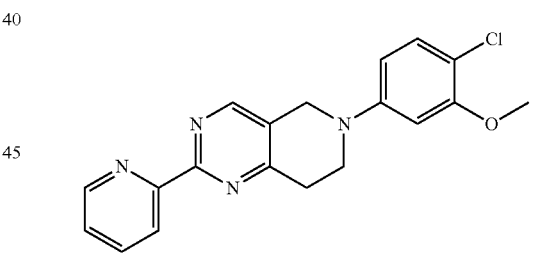

A mixture of 1-(4-chloro-3-methoxy-phenyl)piperidin-4-one (600 mg, 2.5 mmol) and DMFDMA (10 mL) was heated with stirring at 90° C. for 3 hrs. The resulting reaction mixture was concentrated in vacuo and the residue was dissolved in EtOH (10 mL). To the solution was added pyridine-2-carboxamidine hydrochloride (395 mg, 2.5 mmol) and K$_2$CO$_3$ (690 mg, 5.0 mmol) successively. After being heated with stirring at 80° C. overnight, the resulting reaction mixture was cooled to rt and purified by prep-HPLC to give 6-(4-chloro-3-methoxy-phenyl)-2-(2-pyridyl)-7,8-dihydro-5H-pyrido[4,3-d]pyrimidine (15 mg). $^1$H NMR (400 MHz, CDCl$_3$): δ 8.84-8.92 (m, 1H), 8.72 (s, 1H), 8.48-8.59 (m, 1H), 7.84-7.94 (m, 1H), 7.39-7.48 (m, 1H), 7.24-7.32 (m, 1H), 6.52-6.66 (m, 2H), 4.45 (s, 2H), 3.95 (s, 3H), 3.64-3.75 (m, 2H), 3.23-3.35 (m, 2H). MS obsd. (ESI$^+$) [(M+H)$^+$]: 353.

Example 63: 6-[3-(difluoromethoxy)phenyl]-2-pyrimidin-2-yl-7,8-dihydro-5H-pyrido[4,3-d]pyrimidine

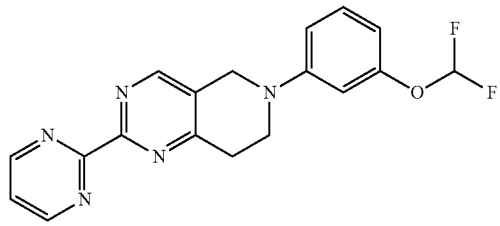 [SMILES: FC(F)Oc1cccc(N2CCc3nc(-c4ncccn4)ncc3C2)c1]

Step 1: Preparation of 8-[3-(difluoromethoxy)phenyl]-1,4-dioxa-8-azaspiro[4.5]decane

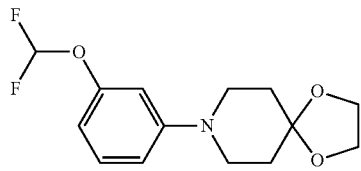 [SMILES: FC(F)Oc1cccc(N2CCC3(CC2)OCCO3)c1]

To a flask containing 1-bromo-3-(difluoromethoxy)benzene (350 mg, 1.58 mmol) and 1,4-dioxa-8-azaspiro[4.5]decane (249 mg, 1.74 mmol) in dioxane (10 mL) was added t-BuONa (303 mg, 3.16 mmol), under $N_2$. After being heated with stirring at 100° C. overnight, the resulting reaction mixture was cooled to rt, diluted with $H_2O$ (30 mL) and extracted with EA (30 mL) for three times. The combined organic layer was washed with brine (30 mL), dried over anhydrous $Na_2SO_4$ and concentrated in vacuo to give 8-[3-(difluoromethoxy)phenyl]-1,4-dioxa-8-azaspiro[4.5]decane (450 mg), which was used in the next step without further purification.

Step 2: Preparation of 1-[3-(difluoromethoxy)phenyl]piperidin-4-one

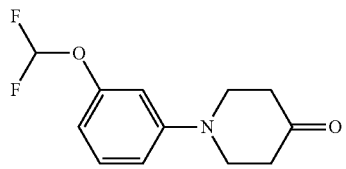

A mixture of 8-[3-(difluoromethoxy)phenyl]-1,4-dioxa-8-azaspiro[4.5]decane (450 mg, 1.58 mmol) and 44% formic acid (10 mL) was heated with stirring at 90° C. for 8 hrs. The resulting reaction mixture was concentrated in vacuo, diluted with sat. aqueous solution of $NaHCO_3$ (20 mL) and extracted with EA (30 mL) for three times. The combined organic layer was washed with brine (50 mL), dried over anhydrous $Na_2SO_4$ and concentrated in vacuo to give 1-[3-(difluoromethoxy)phenyl]piperidin-4-one (380 mg) as brown oil, which was used in the next step without further purification.

Step 3: Preparation of 6-[3-(difluoromethoxy)phenyl]-2-(2-pyridyl)-7,8-dihydro-5H-pyrido[4,3-d]pyrimidine

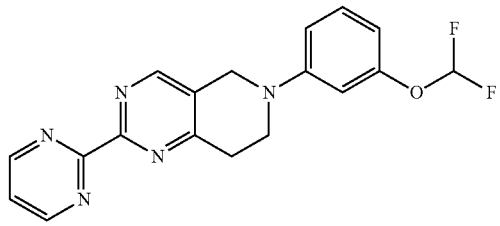 [SMILES: FC(F)Oc1cccc(N2CCc3nc(-c4ncccn4)ncc3C2)c1]

A mixture of 1-[3-(difluoromethoxy)phenyl]piperidin-4-one (380 mg, 1.58 mmol) and DMFDMA (10 mL) was heated with stirring at 90° C. for 3 hrs. The resulting reaction mixture was concentrated in vacuo and the residue was dissolved in EtOH (10 mL). To the solution was added pyrimidine-2-carboxamidine hydrochloride (250 mg, 1.58 mmol) and $K_2CO_3$ (436 mg, 3.16 mmol) successively. After being heated with stirring at 80° C. overnight, the resulting reaction mixture was cooled to rt and purified by prep-HPLC to give 6-[3-(difluoromethoxy)phenyl]-2-pyrimidin-2-yl-7,8-dihydro-5H-pyrido[4,3-d]pyrimidine (20 mg). $^1H$ NMR (400 MHz, DMSO-$d_6$): δ 3.09 (t, 2H), 3.76 (s, 2H), 4.58 (s, 2H), 6.59 (dd, 1H), 6.80-6.88 (m, 1H), 6.92-7.00 (m, 1H), 7.21-7.34 (m, 2H), 7.64 (t, 1H), 8.85 (s, 1H), 9.00 (d, 2H). MS obsd. (ESI$^+$) [(M+H)$^+$]: 356.

Example 64: 6-(4-benzyloxy-3,5-difluoro-phenyl)-2-(2-pyridyl)-7,8-dihydro-5H-pyrido[4,3-d]pyrimidine

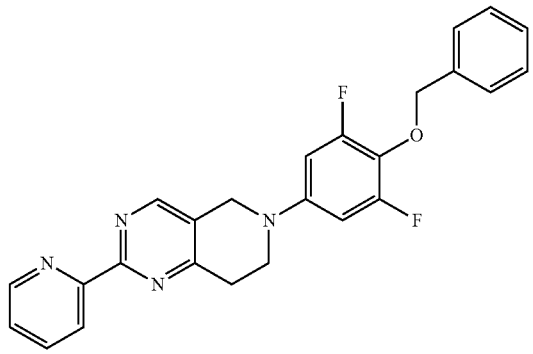 [SMILES: Fc1cc(N2CCc3nc(-c4ccccn4)ncc3C2)cc(F)c1OCc1ccccc1]

Step 1: Preparation of 8-(4-benzyloxy-3,5-difluoro-phenyl)-1,4-dioxa-8-azaspiro[4.5]decane

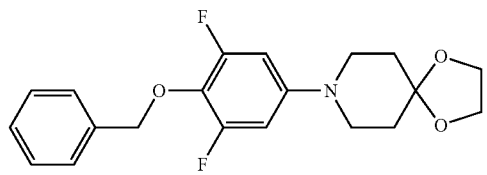 [SMILES: Fc1cc(N2CCC3(CC2)OCCO3)cc(F)c1OCc1ccccc1]

To a flask containing 2-benzyloxy-5-bromo-1,3-difluorobenzene (500 mg, 1.67 mmol) and 1,4-dioxa-8-azaspiro[4.5]decane (263 mg, 1.84 mmol) in dioxane (10 mL) was added t-BuONa (320 mg, 3.34 mmol), Pd$_2$(dba)$_3$ (73 mg, 0.08 mmol) and Ruphos (74 mg, 0.16 mmol) under N$_2$. After being heated with stirring at 100° C. overnight, the resulting reaction mixture was cooled to rt, diluted with H$_2$O (30 mL) and extracted with EA (30 mL) for three times. The combined organic layer was washed with brine (30 mL), dried over anhydrous Na$_2$SO$_4$ and concentrated in vacuo to give 5-difluoro-phenyl)-1,4-dioxa-8-azaspiro[4.5]decane (600 mg), which was used in the next step without further purification.

Step 2: Preparation of 1-(4-benzyloxy-3,5-difluoro-phenyl)piperidin-4-one

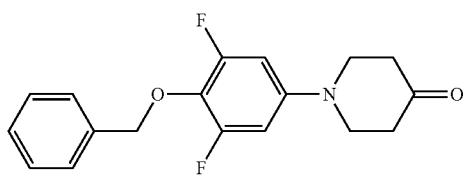 [SMILES: O=C1CCN(c2cc(F)c(OCc3ccccc3)c(F)c2)CC1]

A mixture of 8-(4-benzyloxy-3,5-difluoro-phenyl)-1,4-dioxa-8-azaspiro[4.5]decane (600 mg, 1.67 mmol) and 44% formic acid (10 mL) was heated with stirring at 90° C. for 8 hrs. The resulting reaction mixture was concentrated in vacuo, diluted with sat. aqueous solution of NaHCO$_3$ (20 mL) and extracted with EA (30 mL) for three times. The combined organic layer was washed with brine (50 mL), dried over anhydrous Na$_2$SO$_4$ and concentrated in vacuo to give 1-(4-benzyloxy-3,5-difluoro-phenyl)piperidin-4-one (530 mg) as brown oil, which was used in the next step without further purification.

Step 3: Preparation of 6-(4-benzyloxy-3,5-difluoro-phenyl)-2-(2-pyridyl)-7,8-dihydro-5H-pyrido[4,3-d]pyrimidine

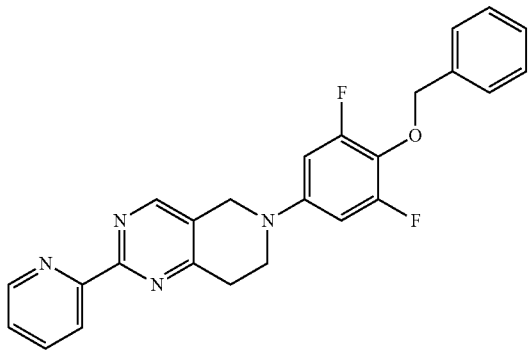 [SMILES: Fc1cc(N2CCc3nc(-c4ccccn4)ncc3C2)cc(F)c1OCc1ccccc1]

A mixture of 1-(4-benzyloxy-3,5-difluoro-phenyl)piperidin-4-one (530 mg, 1.67 mmol) and DMFDMA (10 mL) was heated with stirring at 90° C. for 3 hrs. The resulting reaction mixture was concentrated in vacuo and the residue was dissolved in EtOH (10 mL). To the solution was added pyridine-2-carboxamidine hydrochloride (250 mg, 1.67 mmol) and K$_2$CO$_3$ (460 mg, 3.34 mmol) successively. After being heated with stirring at 80° C. overnight, the resulting reaction mixture was cooled to rt and purified by prep-HPLC to give 6-(4-benzyloxy-3,5-difluoro-phenyl)-2-(2-pyridyl)-7,8-dihydro-5H-pyrido[4,3-d]pyrimidine (50 mg). $^1$H NMR (400 MHz, MeOH-d$_4$): δ 8.72-8.80 (m, 2H), 8.48-8.58 (m, 1H), 7.97-8.05 (m, 1H), 7.51-7.60 (m, 1H), 7.39-7.46 (m, 2H), 7.29-7.39 (m, 3H), 6.67-6.78 (m, 2H), 5.05 (s, 2H), 4.46 (s, 2H), 3.63-3.75 (m, 2H), 3.16-3.25 (m, 2H). MS obsd. (ESI$^+$) [(M+H)$^+$]: 431.

Example 65: 2-methoxy-4-[2-(2-pyridyl)-7,8-dihydro-5H-pyrido[4,3-d]pyrimidin-6-yl]benzoic acid

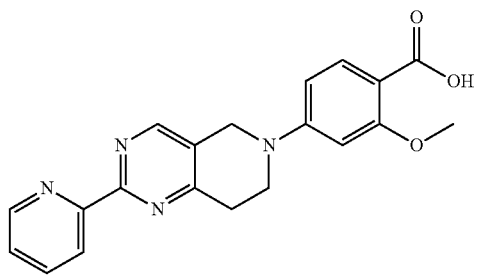 [SMILES: COc1cc(N2CCc3nc(-c4ccccn4)ncc3C2)ccc1C(=O)O]

Step 1: Preparation of methyl 4-(1,4-dioxa-8-azaspiro[4.5]decan-8-yl)-2-methoxy-benzoate

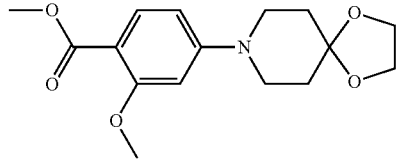

To a flask containing methyl 4-bromo-2-methoxy-benzoate (500 mg, 2.0 mmol) and 1,4-dioxa-8-azaspiro[4.5]decane (340 mg, 2.4 mmol) in dioxane (10 mL) was added t-BuONa (384 mg, 4.0 mmol), Pd$_2$(dba)$_3$ (37 mg, 0.04 mmol) and Sphos (33 mg, 0.08 mmol) under N$_2$. After being heated with stirring at 100° C. overnight, the resulting reaction mixture was cooled to rt, diluted with H$_2$O (30 mL) and extracted with EA (30 mL) for three times. The combined organic layer was washed with brine (30 mL) and dried over anhydrous Na$_2$SO$_4$ and concentrated in vacuo to give methyl 4-(1,4-dioxa-8-azaspiro[4.5]decan-8-yl)-2-methoxy-benzoate (600 mg), which was used in the next step without further purification.

Step 2: Preparation of methyl 2-methoxy-4-(4-oxo-1-piperidyl)benzoate

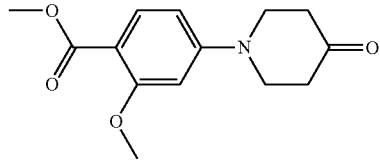 [SMILES: COC(=O)c1ccc(N2CCC(=O)CC2)cc1OC]

A mixture of methyl 4-(1,4-dioxa-8-azaspiro[4.5]decan-8-yl)-2-methoxy-benzoate (600 mg, 2.0 mmol) and 44% formic acid (10 mL) was heated with stirring at 90° C. for 8 hrs. The resulting reaction mixture was concentrated in vacuo, diluted with sat. NaHCO₃ (20 mL) and extracted with EA (30 mL) for three times. The combined organic layer was washed with brine (50 mL), dried over anhydrous Na₂SO₄ and concentrated in vacuo to give methyl 2-methoxy-4-(4-oxo-1-piperidyl)benzoate (530 mg) as brown oil, which was used in the next step without further purification.

Step 3: Preparation of 2-methoxy-4-[2-(2-pyridyl)-7,8-dihydro-5H-pyrido[4,3-d]pyrimidin-6-yl]benzoic acid

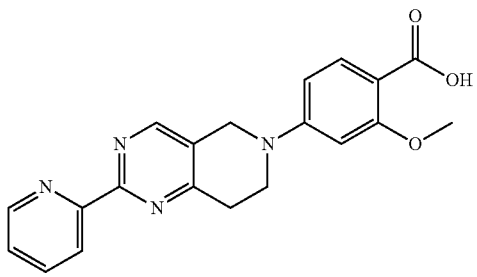 [SMILES: COc1cc(N2CCc3nc(-c4ccccn4)ncc3C2)ccc1C(=O)O]

A mixture of methyl 2-methoxy-4-(4-oxo-1-piperidyl)benzoate (530 mg, 2.0 mmol) and DMFDMA (10 mL) was heated with stirring at 90° C. for 3 hrs. The resulting reaction mixture was concentrated in vacuo and the residue was dissolved in EtOH (10 mL). To the solution was added pyridine-2-carboxamidine hydrochloride (320 mg, 2.0 mmol) and K₂CO₃ (552 mg, 4.0 mmol) successively. After being heated with stirring at 80° C. overnight, the resulting reaction mixture was cooled to rt and purified by prep-HPLC to give 2-methoxy-4-[2-(2-pyridyl)-7,8-dihydro-5H-pyrido[4,3-d]pyrimidin-6-yl]benzoic acid (10 mg). ¹H NMR (400 MHz, MeOH-d₄): δ 8.82 (s, 1H), 8.71-8.78 (m, 1H), 8.51-8.58 (m, 1H), 7.97-8.06 (m, 1H), 7.83-7.90 (m, 1H), 7.51-7.59 (m, 1H), 6.65-6.79 (m, 2H), 4.71 (s, 2H), 3.98-4.05 (m, 3H), 3.87-3.95 (m, 2H), 3.20-3.28 (m, 2H). MS obsd. (ESI⁺) [(M+H)⁺]: 363.

Example 66: 2-ethoxy-4-[2-(2-pyridyl)-7,8-dihydro-5H-pyrido[4,3-d]pyrimidin-6-yl]benzoic acid

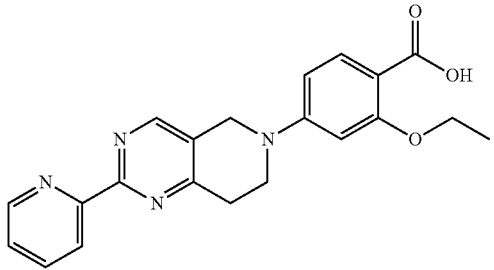 [SMILES: CCOc1cc(N2CCc3nc(-c4ccccn4)ncc3C2)ccc1C(=O)O]

Step 1: Preparation of methyl 4-(1,4-dioxa-8-azaspiro[4.5]decan-8-yl)-2-hydroxy-benzoate

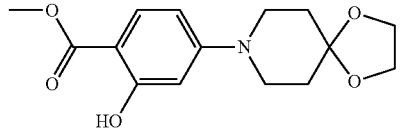 [SMILES: COC(=O)c1ccc(N2CCC3(CC2)OCCO3)cc1O]

A mixture of methyl 4-bromo-2-hydroxy-benzoate (100 mg, 0.43 mmol), 1,4-dioxa-8-azaspiro[4.5]decane (74 mg, 0.52 mmol), Cs₂CO₃ (280 mg, 0.86 mmol), Pd₂(dba)₃ (8 mg, 0.009 mmol) and Ru-Phos (8 mg, 0.018 mmol) in toluene (10 mL) was heated with stirring at 100° C. overnight. The reaction mixture was cooled to rt, diluted with water (20 mL) and extracted with EA (20 mL) for three times. The combined organic layer was washed with brine, dried over anhydrous Na₂SO₄ and concentrated in vacuo to give methyl 4-(1,4-dioxa-8-azaspiro[4.5]decan-8-yl)-2-hydroxy-benzoate (95 mg), which was used in the next step directly without further purification.

Step 2: Preparation of methyl 2-hydroxy-4-(4-oxo-1-piperidyl)benzoate

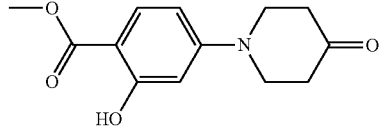 [SMILES: COC(=O)c1ccc(N2CCC(=O)CC2)cc1O]

To a flask containing methyl 4-(1,4-dioxa-8-azaspiro[4.5]decan-8-yl)-2-hydroxy-benzoate (5.0 g, 17.0 mmol) was added to H₂O (20 mL) and formic acid (20 mL). After being heated with stirring at 90° C. overnight, the resulting reaction mixture was concentrated in vacuo, diluted with sat. aqueous solution of NaHCO₃ and extracted with EA (40 mL) for three times. The combined organic layer was washed with brine, dried over anhydrous Na₂SO₄ and concentrated in vacuo. The residue was purified by column chromatography (eluting with 2.5% MeOH in DCM) to give methyl 2-hydroxy-4-(4-oxo-1-piperidyl)benzoate (1.9 g).

Step 3: Preparation of ethyl 2-hydroxy-4-[2-(2-pyridyl)-7,8-dihydro-5H-pyrido[4,3-d]pyrimidin-6-yl]benzoate

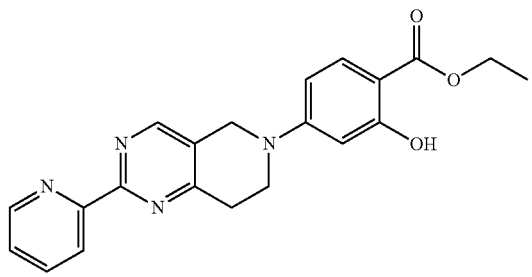 [SMILES: CCOC(=O)c1ccc(N2CCc3nc(-c4ccccn4)ncc3C2)cc1O]

A solution of methyl 2-hydroxy-4-(4-oxo-1-piperidyl)benzoate (1.9 g, 7.6 mmol) and DMFDMA (10 mL) in acetonitrile (10 mL) was heated with stirring at 90° C. for 2 hrs. The reaction mixture was concentrated in vacuo and the residue was dissolved in EtOH (10 mL). To the solution was added pyridine-2-carboxamidine hydrochloride (1.24 g, 7.86 mmol) and potassium carbonate (2.2 g, 15.72 mmol) successively. After being heated with stirring at 90° C. overnight, the resulting reaction mixture was cooled to rt, diluted with water (30 mL) and extracted with EA (20 mL) for three times. The combined organic layer was washed with brine, dried over anhydrous Na$_2$SO$_4$ and concentrated in vacuo. The residue was purified by column chromatography (eluting with 2.5% MeOH in DCM) to give ethyl 2-hydroxy-4-[2-(2-pyridyl)-7,8-dihydro-5H-pyrido[4,3-d]pyrimidin-6-yl]benzoate (1.2 g).

Step 4: Preparation of 2-hydroxy-4-[2-(2-pyridyl)-7,8-dihydro-5H-pyrido[4,3-d]pyrimidin-6-yl]benzoic acid

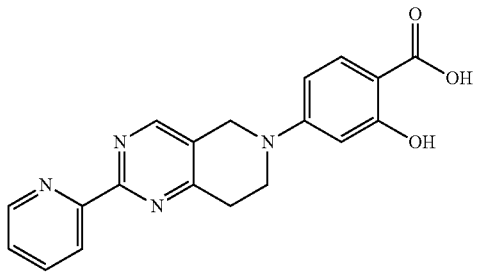 [SMILES: O=C(O)c1ccc(N2CCc3nc(-c4ccccn4)ncc3C2)cc1O]

A mixture of ethyl 2-hydroxy-4-[2-(2-pyridyl)-7,8-dihydro-5H-pyrido[4,3-d]pyrimidin-6-yl]benzoate (100 mg, 0.27 mmol) and LiOH (62 mg, 2.7 mmol) in a mixed solvent of THF (5 mL) and H$_2$O (5 mL) was heated with stirring at 90° C. for 3 hrs. The resulting reaction mixture was cooled to rt, diluted with 1.0 N HCl solution and extracted with EA (30 mL) for three times. The combined organic layer was washed with brine, dried over anhydrous Na$_2$SO$_4$ and concentrated in vacuo to give crude 2-hydroxy-4-[2-(2-pyridyl)-7,8-dihydro-5H-pyrido[4,3-d]pyrimidin-6-yl]benzoic acid (100 mg), which was used in the next step without further purification.

Step 5: Preparation of ethyl 2-ethoxy-4-[2-(2-pyridyl)-7,8-dihydro-5H-pyrido[4,3-d]pyrimidin-6-yl]benzoate

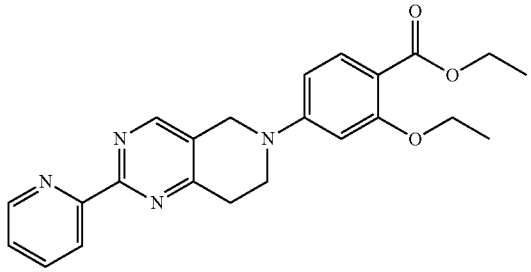 [SMILES: CCOC(=O)c1ccc(N2CCc3nc(-c4ccccn4)ncc3C2)cc1OCC]

A mixture of ethyl 2-hydroxy-4-[2-(2-pyridyl)-7,8-dihydro-5H-pyrido[4,3-d]pyrimidin-6-yl]benzoate (100 mg, 0.26 mmol), ethyl bromide (142 mg, 1.30 mmol) and potassium carbonate (72 mg, 0.52 mmol) in DMF (3 mL) was heated with stirring at 90° C. for 3 hrs. The resulting reaction mixture was cooled to rt, diluted with water (10 mL) and extracted with EA (20 mL) for three times. The combined organic layer was washed with brine, dried over anhydrous Na$_2$SO$_4$ and concentrated in vacuo to give ethyl 2-ethoxy-4-[2-(2-pyridyl)-7,8-dihydro-5H-pyrido[4,3-d]pyrimidin-6-yl]benzoate (100 mg), which was used in the next step without further purification.

Step 6: Preparation of 2-ethoxy-4-[2-(2-pyridyl)-7,8-dihydro-5H-pyrido[4,3-d]pyrimidin-6-yl]benzoic acid

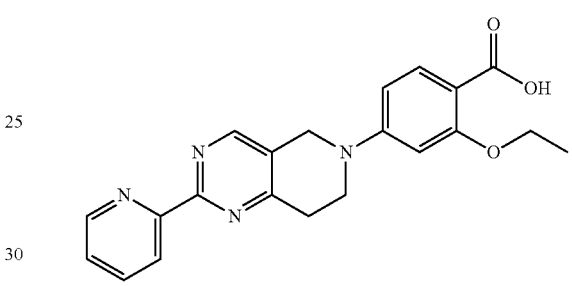

A mixture of ethyl 2-ethoxy-4-[2-(2-pyridyl)-7,8-dihydro-5H-pyrido[4,3-d]pyrimidin-6-yl]benzoate (100 mg, 0.25 mmol) and LiOH (119 mg, 4.94 mmol) in a mixed solvent of THF (5 mL) and H$_2$O (5 mL) was heated with stirring at 90° C. for 3 hrs. The resulting reaction mixture was cooled to rt, diluted with 1.0 N HCl solution and extracted with EA (20 mL) for three times. The combined organic layer was washed with brine, dried over anhydrous Na$_2$SO$_4$ and concentrated in vacuo. The residue was purified by prep-HPLC to give 2-ethoxy-4-[2-(2-pyridyl)-7,8-dihydro-5H-pyrido[4,3-d]pyrimidin-6-yl]benzoic acid (13 mg). $^1$H NMR (400 MHz, CDCl$_3$): δ 8.88 (d, 1H), 8.77 (s, 1H), 8.55 (d, 1H), 8.12 (d, 1H), 7.91 (dt, 1H), 7.45 (ddd, 1H), 6.72 (dd, 1H), 6.47 (d, 1H), 4.64 (s, 2H), 4.38 (q, 2H), 3.85 (t, 2H), 3.33 (t, 2H). MS obsd. (ESI$^+$) [(M+H)$^+$]: 377.

Example 67: 2-butoxy-4-[2-(2-pyridyl)-7,8-dihydro-5H-pyrido[4,3-d]pyrimidin-6-yl]benzoic acid

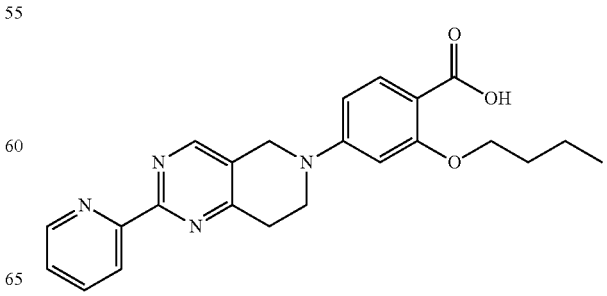

115

Step 1: Preparation of ethyl 2-butoxy-4-[2-(2-pyridyl)-7,8-dihydro-5H-pyrido[4,3-d]pyrimidin-6-yl]benzoate

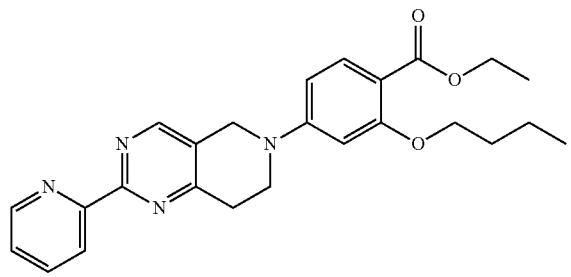 [SMILES: CCCCOc1cc(N2CCc3nc(-c4ccccn4)ncc3C2)ccc1C(=O)OCC]

A mixture of ethyl 2-hydroxy-4-[2-(2-pyridyl)-7,8-dihydro-5H-pyrido[4,3-d]pyrimidin-6-yl]benzoate (100 mg, 0.26 mmol), butyl bromide (190 mg, 1.30 mmol) and potassium carbonate (72 mg, 0.52 mmol) in DMF (3 mL) was heated with stirring at 90° C. for 3 hrs. The resulting reaction mixture was cooled to rt, diluted with water (10 mL) and extracted with EA (20 mL) for three times. The combined organic layer was washed with brine, dried over anhydrous $Na_2SO_4$ and concentrated in vacuo to give ethyl 2-butoxy-4-[2-(2-pyridyl)-7,8-dihydro-5H-pyrido[4,3-d]pyrimidin-6-yl]benzoate (95 mg), which was used in the next step without further purification.

Step 2: Preparation of 2-butoxy-4-[2-(2-pyridyl)-7,8-dihydro-5H-pyrido[4,3-d]pyrimidin-6-yl]benzoic acid

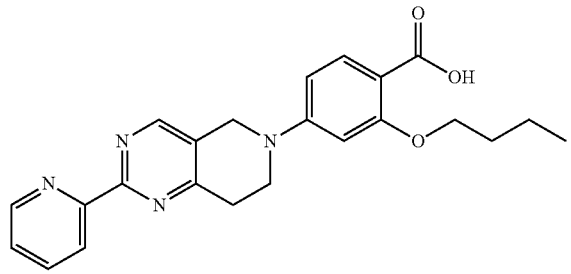 [SMILES: CCCCOc1cc(N2CCc3nc(-c4ccccn4)ncc3C2)ccc1C(=O)O]

A mixture of ethyl 2-butoxy-4-[2-(2-pyridyl)-7,8-dihydro-5H-pyrido[4,3-d]pyrimidin-6-yl]benzoate (110 mg, 0.25 mmol) and LiOH (119 mg, 4.94 mmol) in a mixed solvent of THF (5 mL) and $H_2O$ (5 mL) was heated with stirring at 90° C. for 3 hrs. The resulting reaction mixture was cooled to rt, diluted with 1.0 N HCl solution and extracted with EA (20 mL) for three times. The combined organic layer was washed with brine, dried over anhydrous $Na_2SO_4$ and concentrated in vacuo. The residue was purified by prep-HPLC to give 2-butoxy-4-[2-(2-pyridyl)-7,8-dihydro-5H-pyrido[4,3-d]pyrimidin-6-yl]benzoic acid (8 mg). $^1$H NMR (400 MHz, $CDCl_3$): δ 8.93 (d, 1H), 8.78 (s, 1H), 8.60 (d, 1H), 8.13 (d, 1H), 8.00 (d, 1H), 7.53 (dd, 1H), 6.71 (dd, 1H), 6.48 (d, 1H), 4.65 (s, 2H), 4.30 (t, 2H), 3.86 (t, 2H), 3.33 (t, 2H), 1.93 (m, 2H), 1.59 (m, 2H), 1.06 (t, 3H). MS obsd. ($ESI^+$) [$(M+H)^+$]: 405.

116

Example 68 and 69: 6-(5-chloro-4-methoxy-pyrimidin-2-yl)-2-(2-pyridyl)-7,8-dihydro-5H-pyrido[4,3-d]pyrimidine and 6-(5-chloro-2-methoxy-pyrimidin-4-yl)-2-(2-pyridyl)-7,8-dihydro-5H-pyrido[4,3-d]pyrimidine Example 68

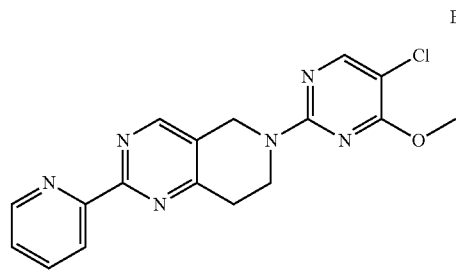

Example 69

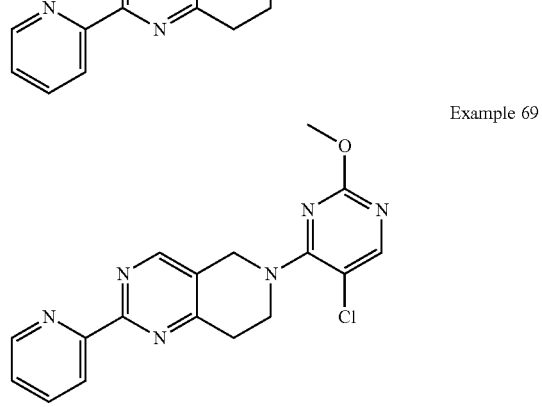

Step 1: Preparation of 2,5-dichloro-4-methoxy-pyrimidine and 4,5-dichloro-2-methoxy-pyrimidine

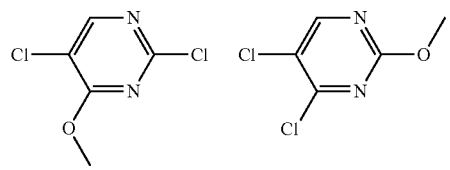

To a solution of 2,4,5-trichloropyrimidine (5.0 g, 27.26 mmol) in MeOH (30 mL) was added MeONa (1.47 g, 27.26 mmol). The resulting mixture was stirred at rt overnight. The resulting reaction mixture was purified by flash column to give a mixture of 2,5-dichloro-4-methoxy-pyrimidine and 4,5-dichloro-2-methoxy-pyrimidine (total 3.1 g).

Step 2: Preparation of 8-(5-chloro-4-methoxy-pyrimidin-2-yl)-1,4-dioxa-8-azaspiro[4.5]decane and 8-(5-chloro-2-methoxy-pyrimidin-4-yl)-1,4-dioxa-8-azaspiro[4.5]decane

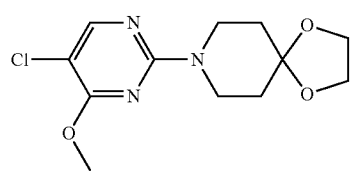

-continued

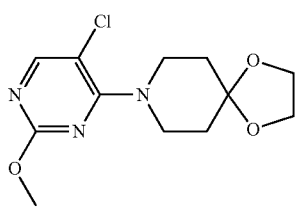

To a solution of a mixture of 2,5-dichloro-4-methoxy-pyrimidine and 4,5-dichloro-2-methoxy-pyrimidine (total 1.2 g, 6.74 mmol), and 1,4-dioxa-8-azaspiro[4.5]decane (1.06 g, 7.41 mmol) in dioxane (40 mL) was added $Cs_2CO_3$ (4.38 g, 13.48 mmol) under $N_2$. After being heated with stirring at 100° C. overnight, the resulting reaction mixture was cooled to rt, diluted with $H_2O$ (30 mL) and extracted with EA (30 mL) for three times. The combined organic layer was washed with brine (30 mL), dried over anhydrous $Na_2SO_4$ and concentrated in vacuo to give a mixture of 8-(5-chloro-4-methoxy-pyrimidin-2-yl)-1,4-dioxa-8-azaspiro[4.5]decane and 8-(5-chloro-2-methoxy-pyrimidin-4-yl)-1,4-dioxa-8-azaspiro[4.5]decane (total 1.4 g), which was used in the next step without further purification.

Step 3: Preparation of 1-(5-chloro-4-methoxy-pyrimidin-2-yl)piperidin-4-one and 1-(5-chloro-2-methoxy-pyrimidin-4-yl)piperidin-4-one

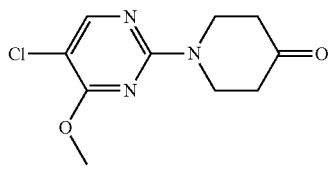

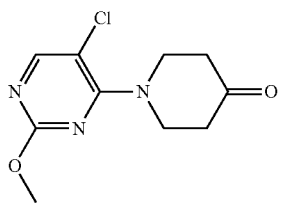

A mixture of 8-(5-chloro-4-methoxy-pyrimidin-2-yl)-1,4-dioxa-8-azaspiro[4.5]decane and 8-(5-chloro-2-methoxy-pyrimidin-4-yl)-1,4-dioxa-8-azaspiro[4.5]decane (total 1.4 g, 4.9 mmol) and 44% formic acid (10 mL) was heated with stirring at 90° C. for 8 hrs. The resulting reaction mixture was cooled to rt, diluted with sat. aqueous solution of $NaHCO_3$ (20 mL) and extracted with EA (30 mL) for three times. The combined organic layer was washed with brine (50 mL), dried over anhydrous $Na_2SO_4$ and concentrated in vacuo to give a mixture of 1-(5-chloro-4-methoxy-pyrimidin-2-yl)piperidin-4-one and 1-(5-chloro-2-methoxy-pyrimidin-4-yl)piperidin-4-one (total 1.2 g) as brown oil, which was used in the next step without further purification.

Step 4: Preparation of 6-(5-chloro-4-methoxy-pyrimidin-2-yl)-2-(2-pyridyl)-7,8-dihydro-5H-pyrido[4,3-d]pyrimidine and 6-(5-chloro-2-methoxy-pyrimidin-4-yl)-2-(2-pyridyl)-7,8-dihydro-5H-pyrido[4,3-d]pyrimidine Example 68

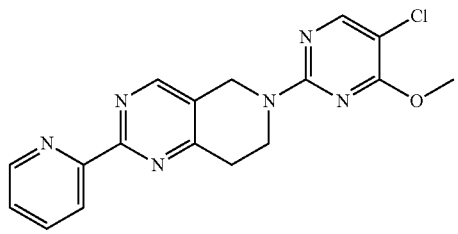

Example 69

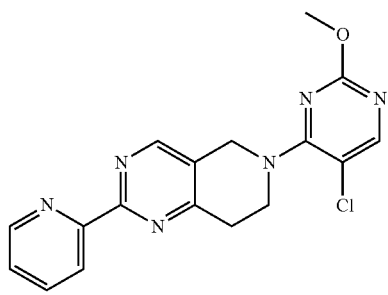

A mixture of 1-(5-chloro-4-methoxy-pyrimidin-2-yl)piperidin-4-one and 1-(5-chloro-2-methoxy-pyrimidin-4-yl)piperidin-4-one (total 1.2 g, 4.9 mmol) and DMFDMA (20 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (774 mg, 4.9 mmol) and $K_2CO_3$ (1350 mg, 9.8 mmol) successively. After being heated with stirring at 80° C. overnight, the resulting reaction mixture was cooled to rt and purified by prep-HPLC to give 6-(5-chloro-4-methoxy-pyrimidin-2-yl)-2-(2-pyridyl)-7,8-dihydro-5H-pyrido[4,3-d]pyrimidine (Example 68, 200 mg) and 6-(5-chloro-2-methoxy-pyrimidin-4-yl)-2-(2-pyridyl)-7,8-dihydro-5H-pyrido[4,3-d]pyrimidine (Example 69, 40 mg).

Example 68: 6-(5-chloro-4-methoxy-pyrimidin-2-yl)-2-(2-pyridyl)-7,8-dihydro-5H-pyrido[4,3-d]pyrimidine, $^1$H NMR (400 MHz, $CDCl_3$): δ 8.79-8.89 (m, 1H), 8.73 (s, 1H), 8.47-8.55 (m, 1H), 8.24-8.33 (m, 1H), 8.11 (s, 1H), 7.86-7.96 (m, 1H), 7.40-7.49 (m, 1H), 4.99 (s, 2H), 4.14-4.23 (m, 2H), 4.05 (s, 3H), 3.14-3.24 (m, 2H). MS obsd. (ESI$^+$) [(M+H)$^+$]: 355.

Example 69: 6-(5-chloro-2-methoxy-pyrimidin-4-yl)-2-(2-pyridyl)-7,8-dihydro-5H-pyrido[4,3-d]pyrimidine, $^1$H NMR (400 MHz, $CDCl_3$): δ 8.81-8.90 (m, 1H), 8.71 (s, 1H), 8.51 (d, 1H), 8.13-8.20 (m, 1H), 7.88 (t, 1H), 7.39-7.47 (m, 1H), 4.92 (s, 2H), 4.12 (t, 2H), 3.98 (s, 3H), 3.29-3.38 (m, 2H). MS obsd. (ESI$^+$) [(M+H)$^+$]: 355.

Example 70 and 71: 6-(5-fluoro-4-methoxy-2-pyridyl)-2-(2-pyridyl)-7,8-dihydro-5H-pyrido[4,3-d]pyrimidine and 6-(3-fluoro-4-methoxy-2-pyridyl)-2-(2-pyridyl)-7,8-dihydro-5H-pyrido[4,3-d]pyrimidine

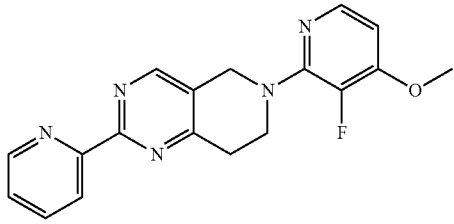

Example 70

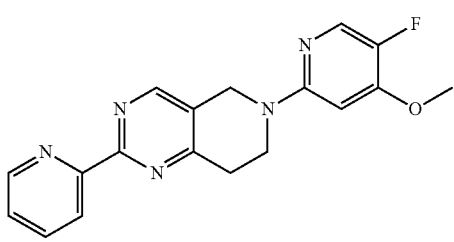

Example 71

Step 1: Preparation of 2-chloro-5-fluoro-4-methoxy-pyridine and 2-chloro-3-fluoro-4-methoxy-pyridine

A mixture of 3-fluoro-4-methoxy-pyridine (3.0 g, 23.62 mmol) and $H_2O_2$ (35 wt. % in $H_2O$, 2.0 mL, 23.6 mmol) was refluxed overnight. The resulting reaction mixture was concentrated in vacuo to give pyridine oxide. A mixture of the above pyridine oxide and $POCl_3$ (10 mL) was heated with stirring for 5 hrs. The resulting reaction mixture was concentrated in vacuo, diluted with sat. aqueous solution of $NaHCO_3$ (10 mL) and extracted with EA (50 mL) for three times. The combined organic layer was dried and concentrated in vacuo. The residue was purified by flash column to give a mixture of 2-chloro-5-fluoro-4-methoxy-pyridine and 2-chloro-3-fluoro-4-methoxy-pyridine (500 mg).

Step 2: Preparation of 8-(5-fluoro-4-methoxy-2-pyridyl)-1,4-dioxa-8-azaspiro[4.5]decane and 8-(3-fluoro-4-methoxy-2-pyridyl)-1,4-dioxa-8-azaspiro[4.5]decane

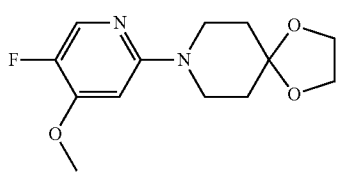

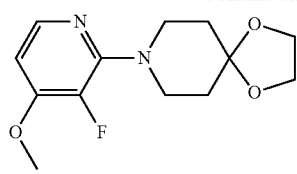

To a flask containing 2-chloro-5-fluoro-4-methoxy-pyridine and 2-chloro-3-fluoro-4-methoxy-pyridine (total 500 mg, 3.11 mmol) and 1,4-dioxa-8-azaspiro[4.5]decane (489 mg, 3.42 mmol) in dioxane (15 mL) was added t-BuONa (896 mg, 9.33 mmol), $Pd_2(dba)_3$ (147 mg, 0.16 mmol) and Ruphos (144 mg, 0.32 mmol) under $N_2$. After being heated with stirring at 100° C. overnight, the resulting reaction mixture was cooled to rt, diluted with $H_2O$ (30 mL) and extracted with EA (30 mL) for three times. The combined organic layer was washed with brine (30 mL), dried over anhydrous $Na_2SO_4$ and concentrated in vacuo to give a mixture of 8-(5-fluoro-4-methoxy-2-pyridyl)-1,4-dioxa-8-azaspiro[4.5]decane and 8-(3-fluoro-4-methoxy-2-pyridyl)-1,4-dioxa-8-azaspiro[4.5]decane (total 800 mg), which was used in the next step without further purification.

Step 3: Preparation of 1-(5-fluoro-4-methoxy-2-pyridyl)piperidin-4-one and 1-(3-fluoro-4-methoxy-2-pyridyl)piperidin-4-one

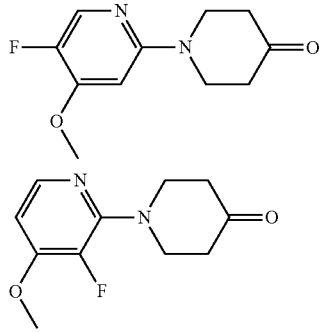

A mixture of 8-(5-fluoro-4-methoxy-2-pyridyl)-1,4-dioxa-8-azaspiro[4.5]decane and 8-(3-fluoro-4-methoxy-2-pyridyl)-1,4-dioxa-8-azaspiro[4.5]decane (total 800 mg, 3.1 mmol) and 44% formic acid (10 mL) was heated with stirring at 90° C. for 8 hrs. The resulting reaction mixture was concentrated in vacuo, diluted with sat. aqueous solution of $NaHCO_3$ (20 mL) and extracted with EA (30 mL) for three times. The combined organic layer was washed with brine (50 mL), dried over anhydrous $Na_2SO_4$ and concentrated in vacuo to give a mixture of 1-(5-fluoro-4-methoxy-2-pyridyl)piperidin-4-one and 1-(3-fluoro-4-methoxy-2-pyridyl)piperidin-4-one (total 690 mg) as brown oil, which was used in the next step without further purification.

Step 4: 6-(5-fluoro-4-methoxy-2-pyridyl)-2-(2-pyridyl)-7,8-dihydro-5H-pyrido[4,3-d]pyrimidine and 6-(3-fluoro-4-methoxy-2-pyridyl)-2-(2-pyridyl)-7,8-dihydro-5H-pyrido[4,3-d]pyrimidine Example 70

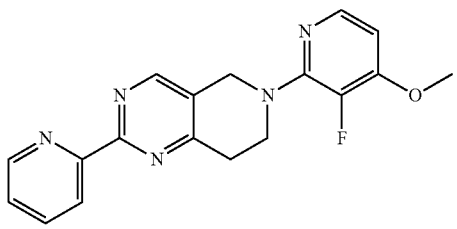

Example 71

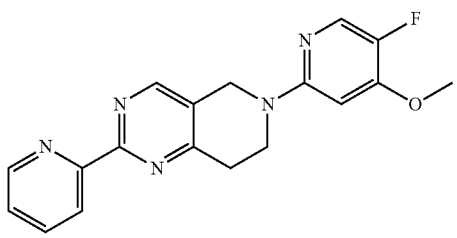

A mixture of 1-(5-fluoro-4-methoxy-2-pyridyl)piperidin-4-one and 1-(3-fluoro-4-methoxy-2-pyridyl)piperidin-4-one (total 690 mg, 3.1 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (490 mg, 3.1 mmol) and K₂CO₃ (850 mg, 6.2 mmol) successively. After being heated with stirring at 80° C. overnight, the resulting reaction mixture was cooled to rt and purified by prep-HPLC to give 6-(5-fluoro-4-methoxy-2-pyridyl)-2-(2-pyridyl)-7,8-dihydro-5H-pyrido[4,3-d]pyrimidine (Example 71, 5 mg) and 6-(3-fluoro-4-methoxy-2-pyridyl)-2-(2-pyridyl)-7,8-dihydro-5H-pyrido[4,3-d]pyrimidine (Example 70, 5 mg).

Example 71: 6-(5-fluoro-4-methoxy-2-pyridyl)-2-(2-pyridyl)-7,8-dihydro-5H-pyrido[4,3-d]pyrimidine, ¹H NMR (400 MHz, CDCl₃): δ 8.82-8.92 (m, 1H), 8.75 (s, 1H), 8.49-8.59 (m, 1H), 7.96-8.03 (m, 1H), 7.85-7.93 (m, 1H), 7.38-7.48 (m, 1H), 6.29-6.38 (m, 1H), 4.78 (s, 2H), 3.93-4.02 (m, 5H), 3.24-3.32 (m, 2H). MS obsd. (ESI⁺) [(M+H)⁺]: 338.

Example 70: 6-(3-fluoro-4-methoxy-2-pyridyl)-2-(2-pyridyl)-7,8-dihydro-5H-pyrido[4,3-d]pyrimidine, ¹H NMR (400 MHz, CDCl₃): δ 8.84-8.95 (m, 1H), 8.71 (s, 1H), 8.49-8.58 (m, 1H), 7.86-7.99 (m, 2H), 7.40-7.50 (m, 1H), 6.52-6.62 (m, 1H), 4.78 (s, 2H), 3.90-4.00 (m, 5H), 3.26-3.34 (m, 2H). MS obsd. (ESI⁺) [(M+H)⁺]: 338.

Example 72: 6-(5-fluoro-6-methoxy-2-pyridyl)-2-pyrimidin-2-yl-7,8-dihydro-5H-pyrido[4,3-d]pyrimidine

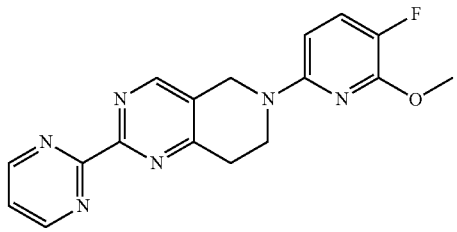 [SMILES: COc1nc(N2CCc3nc(-c4ncccn4)ncc3C2)ccc1F]

Step 1: Preparation of 3,6-difluoro-2-methoxy-pyridine

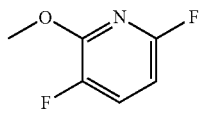

To a solution of 2,3,6-trifluoropyridine (3.0 g, 22.54 mmol) in MeOH (30 mL) was added NaH (1.08 g, 27.05 mmol, 60% wt) at 0° C. After being heated with stirring at 70° C. for 2 hrs, the resulting reaction mixture was concentrated in vacuo and the residue was dissolved in H₂O (30 mL). The solution was extracted by DCM (50 mL) twice. The combined organic layer was concentrated in vacuo to give 3,6-difluoro-2-methoxy-pyridine (1.6 g), which was used in next step directly without further purification.

Step 2: Preparation of 8-(5-fluoro-6-methoxy-2-pyridyl)-1,4-dioxa-8-azaspiro[4.5]decane

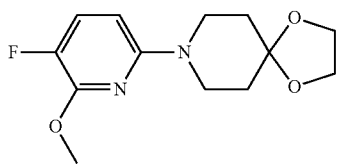 [SMILES: COc1nc(N2CCC3(CC2)OCCO3)ccc1F]

To a solution of 3,6-difluoro-2-methoxy-pyridine (2.0 g, 13.78 mmol) in DMF (20 mL) was added 1,4-dioxa-8-azaspiro[4.5]decane (2.96 g, 20.64 mmol) and Cs₂CO₃ (13.5 g, 41.34 mmol). After being heated with stirring at 120° C. for 12 hrs, the resulting reaction mixture was diluted with DCM (50 mL) and then washed with brine (40 mL) for three times. The organic layer was dried over anhydrous Na₂SO₄ and concentrated in vacuo. The residue was purified by column chromatography (eluting with 1-10% EA in PE) to give 8-(5-fluoro-6-methoxy-2-pyridyl)-1,4-dioxa-8-azaspiro[4.5]decane (600 mg) as a pale yellow oil.

Step 3: Preparation of 1-(5-fluoro-6-methoxy-2-pyridyl)piperidin-4-one

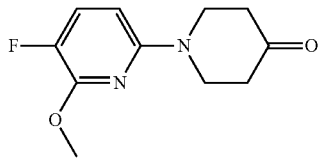 [SMILES: COc1nc(N2CCC(=O)CC2)ccc1F]

A mixture of 8-(5-fluoro-6-methoxy-2-pyridyl)-1,4-dioxa-8-azaspiro[4.5]decane (600 mg, 2.24 mmol) and 44% formic acid (10 mL) was heated with stirring at 90° C. for 2 hrs. The resulting reaction mixture was concentrated in vacuo, diluted with $H_2O$ (20 mL) and extracted with EA (30 mL) for three times. The combined organic layer was washed with brine, dried over anhydrous $Na_2SO_4$ and concentrated in vacuo. The residue was purified by silica gel column to give 1-(5-fluoro-6-methoxy-2-pyridyl)piperidin-4-one (300 mg) as a pale yellow oil.

Step 4: Preparation of 6-(5-fluoro-6-methoxy-2-pyridyl)-2-pyrimidin-2-yl-7,8-dihydro-5H-pyrido[4,3-d]pyrimidine

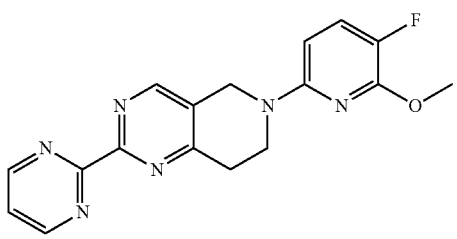 [SMILES: COc1nc(N2CCc3nc(-c4ncccn4)ncc3C2)ccc1F]

A solution of 1-(5-fluoro-6-methoxy-2-pyridyl)piperidin-4-one (300 mg, 1.34 mmol) in DMFDMA (10 mL) was heated with stirring at 120° C. for 4 hrs. The resulting reaction mixture was concentrated in vacuo and the residue was dissolved in MeOH (10 mL). To the solution was added pyridine-2-carboxamidine hydrochloride (285 mg, 1.8 mmol) and $K_2CO_3$ (745 mg, 5.4 mmol). After being heated with stirring at 60° C. for 1 hr, the resulting mixture was concentrated in vacuo. The residue was diluted with DCM (100 mL), washed with brine, dried over anhydrous $Na_2SO_4$ and concentrated in vacuo. The residue was purified by prep-TLC and further purified by prep-HPLC to give 6-(5-fluoro-6-methoxy-2-pyridyl)-2-(2-pyridyl)-7,8-dihydro-5H-pyrido[4,3-d]pyrimidine (15 mg) as a white solid. $^1H$ NMR (400 MHz, $CDCl_3$): δ 9.03-9.04 (d, 2H), 8.83 (s, 1H), 7.43-7.44 (t, 1H), 7.27-7.30 (t, 1H), 6.19-6.21 (d, 1H), 4.76 (s, 2H), 4.02 (s, 3H), 3.95-3.98 (t, 2H), 3.30-3.33 (t, 2H). MS obsd. $(ESI^+)$ $[(M+H)^+]$: 339.

Example 73: 6-(3,5-dimethoxyphenyl)-2-pyrimidin-2-yl-7,8-dihydro-5H-pyrido[4,3-d]pyrimidine

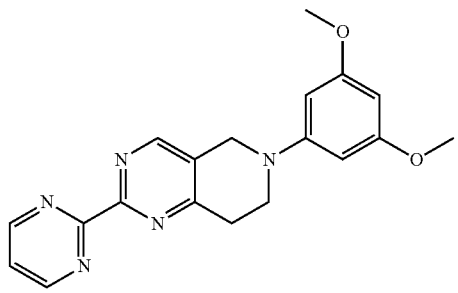 [SMILES: COc1cc(OC)cc(N2CCc3nc(-c4ncccn4)ncc3C2)c1]

Step 1: Preparation of 8-(3,5-dimethoxyphenyl)-1,4-dioxa-8-azaspiro[4.5]decane

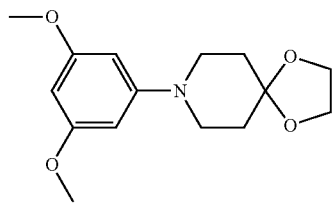 [SMILES: COc1cc(OC)cc(N2CCC3(CC2)OCCO3)c1]

To a solution of 1,4-dioxa-8-azaspiro[4.5]decane hydrochloride (1.0 g, 5.6 mmol) and 1-bromo-3,5-dimethoxybenzene (1.6 g, 7.3 mmol) in dioxane (15 mL) was added t-BuONa (1.0 g, 11.2 mmol), $Pd_2(dba)_3$ (100 mg, 0.11 mmol) and Ruphos (50 mg, 0.11 mmol) under $N_2$. After being heated with stirring at 100° C. for 12 hrs, the resulting mixture was filtered and the filtrate was concentrated in vacuo. The residue was diluted with DCM (100 mL), washed with water (30 mL) and brine (30 mL), dried over anhydrous $Na_2SO_4$ and concentrated in vacuo to give 8-(3,5-dimethoxyphenyl)-1,4-dioxa-8-azaspiro[4.5]decane (2.0 g, crude) as a yellow oil, which was used in the next step without further purification.

Step 2: Preparation of 1-(3,5-dimethoxyphenyl)piperidin-4-one

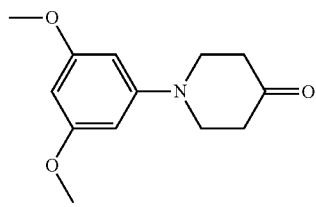 [SMILES: COc1cc(OC)cc(N2CCC(=O)CC2)c1]

A mixture of 8-(3,5-dimethoxyphenyl)-1,4-dioxa-8-azaspiro[4.5]decane (1.0 g, 3.6 mmol) and 44% formic acid (10 mL) was heated with stirring at 90° C. for 2 hrs. The resulting reaction mixture was concentrated in vacuo, diluted with sat. aqueous solution of $NaHCO_3$ and extracted with EA (30 mL) for three times. The combined organic layer was washed with water and brine, dried over anhydrous Na$_2$SO$_4$ and concentrated in vacuo to give 1-(3,5-dimethoxyphenyl)piperidin-4-one (0.9 g, crude) as a yellow oil, which was used in the next step without further purification.

Step 4: Preparation of 6-(3,5-dimethoxyphenyl)-2-pyrimidin-2-yl-7,8-dihydro-5H-pyrido[4,3-d]pyrimidine

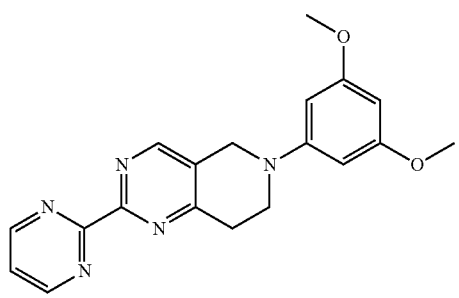 [SMILES: COc1cc(OC)cc(N2CCc3nc(-c4ncccn4)ncc3C2)c1]

A solution of 1-(3,5-dimethoxyphenyl)piperidin-4-one (0.9 g, 3.8 mmol) in DMFDMA (10 mL) was heated with stirring at 120° C. for 4 hrs. The resulting reaction mixture was concentrated in vacuo and the residue was dissolved in MeOH (10 mL). To the solution was added K$_2$CO$_3$ (1.38 g, 10 mmol) and pyrimidine-2-carboxamidine hydrochloride (550 mg, 3.4 mmol). After being heated with stirring at 70° C. for 12 hrs, the resulting mixture was filtered and the filtrate was concentrated in vacuo. The residue was purified by prep-HPLC to give 6-(3,5-dimethoxyphenyl)-2-pyrimidin-2-yl-7,8-dihydro-5H-pyrido[4,3-d]pyrimidine (6.8 mg) as a white solid. $^1$H NMR (400 MHz, MeOH-d$_4$): δ 9.02-9.01 (d, 2H), 8.82 (s, 1H), 7.64-7.61 (t, 1H), 6.24-6.24 (d, 2H), 6.05 (s, 1H), 4.48 (s, 2H), 3.76 (s, 6H), 3.70-3.68 (m, 2H), 3.22-3.19 (m, 2H). MS obsd. (ESI$^+$) [(M+H)$^+$]: 350.

Example 74: 6-(8-methoxy-3-isoquinolyl)-2-pyrimidin-2-yl-7,8-dihydro-5H-pyrido[4,3-d]pyrimidine

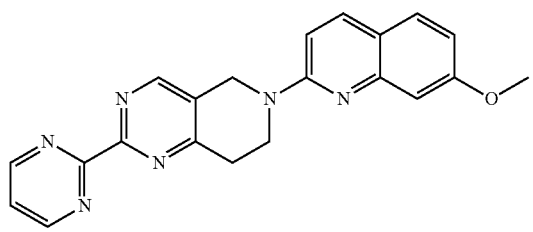 [SMILES: COc1ccc2ccc(N3CCc4nc(-c5ncccn5)ncc4C3)nc2c1]

Step 1: Preparation of 8-(8-methoxy-3-isoquinolyl)-1,4-dioxa-8-azaspiro[4.5]decane

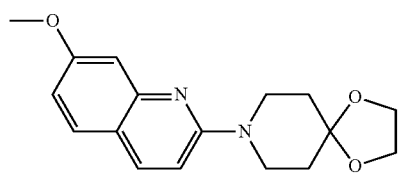 [SMILES: COc1ccc2ccc(N3CCC4(CC3)OCCO4)nc2c1]

To a solution of 2-chloro-7-methoxyquinoline (500 mg, 2.6 mmol) in DMF (1.0 mL) was added 1,4-dioxa-8-azaspiro[4.5]decane hydrochloride (1.40 g, 7.8 mmol) and K$_2$CO$_3$ (1.79 g, 13 mmol). After being heated with stirring at 90° C. for 16 hrs, the resulting reaction mixture was cooled to rt, diluted with water (30 mL) and extracted with EA (30 mL) for three times. The combined organic layer was brine (30 mL), dried over anhydrous Na$_2$SO$_4$ and concentrated in vacuo. The residue was purified by column to give 8-(8-methoxy-3-isoquinolyl)-1,4-dioxa-8-azaspiro[4.5]decane (400 mg) as a yellow oil.

Step 2: Preparation of 1-(8-methoxy-3-isoquinolyl)piperidin-4-one

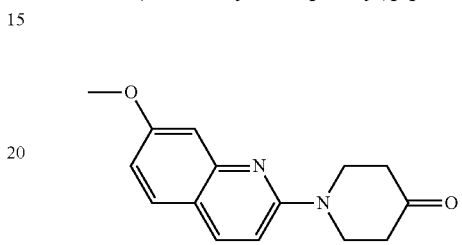

A mixture of 8-(8-methoxy-3-isoquinolyl)-1,4-dioxa-8-azaspiro[4.5]decane (380 mg, 1.27 mmol) and 44% formic acid (4 mL) was heated with stirring at 90° C. for 2 hrs. After being cooled to rt, the resulting mixture was concentrated in vacuo. The residue was diluted with EA (100 mL), washed with sat. aqueous solution of NaHCO$_3$ (30 mL) and brine (30 mL), dried over anhydrous Na$_2$SO$_4$ and concentrated in vacuo to give 1-(8-methoxy-3-isoquinolyl)piperidin-4-one (300 mg) as a yellow solid.

Step 3: Preparation of 6-(8-methoxy-3-isoquinolyl)-2-pyrimidin-2-yl-7,8-dihydro-5H-pyrido[4,3-d]pyrimidine

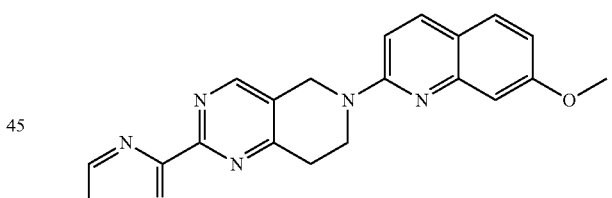

A solution of 1-(8-methoxy-3-isoquinolyl)piperidin-4-one (270 mg, 1.05 mmol) in DMFDMA (3 mL) was heated with stirring at 100° C. for 4 hrs. After being cooled to rt, the resulting mixture was concentrated in vacuo and the residue was dissolved in MeOH (10 mL). To the solution was added pyrimidine-2-carboxamidine hydrochloride (249 mg, 1.58 mmol) and K$_2$CO$_3$ (362 mg, 2.63 mmol). After being heated with stirring at 60° C. for 1 hr, the resulting reaction mixture was cooled to rt and concentrated in vacuo. The residue was diluted with DCM (50 mL), washed with sat. NaHCO$_3$ (30 mL) and brine (30 mL), dried over anhydrous Na$_2$SO$_4$ and concentrated in vacuo. The residue was purified by prep-TLC and further purified by prep-HPLC to give 6-(8-methoxy-3-isoquinolyl)-2-pyrimidin-2-yl-7,8-dihydro-5H-pyrido[4,3-d]pyrimidine (88 mg) as a yellow solid. $^1$H NMR (400 MHz, MeOH-d$_4$): δ 8.90-9.12 (m, 2H), 8.90 (s, 1H), 7.90 (d, 1H), 7.45-7.59 (m, 1H), 7.40-7.45 (m, 1H), 7.15 (s, 1H), 6.87-7.11 (m, 2H), 5.08 (s, 2H), 4.14 (t, 2H), 3.94 (s, 3H), 3.36 (t, 2H). MS obsd. (ESI⁺) [(M+H)⁺]: 371.

Example 75: 6-(2-methoxy-7-quinolyl)-2-pyrimidin-2-yl-7,8-dihydro-5H-pyrido[4,3-d]pyrimidine

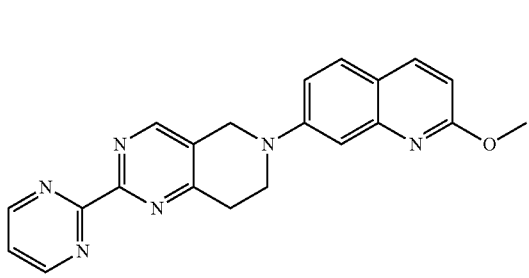 [SMILES: COc1ccc2ccc(N3CCc4nc(-c5ncccn5)ncc4C3)cc2n1]

Step 1: Preparation of 8-(2-methoxy-7-quinolyl)-1,4-dioxa-8-azaspiro[4.5]decane

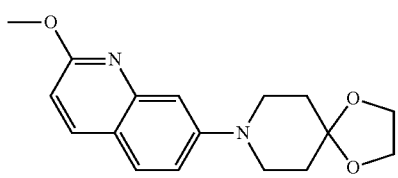 [SMILES: COc1ccc2ccc(N3CCC4(CC3)OCCO4)cc2n1]

To a solution of 1,4-dioxa-8-azaspiro[4.5]decane (550 mg, 3.06 mmol) and 7-bromo-2-methoxyquinoline (875 mg, 3.67 mmol) in dioxane (5 mL) was added t-BuONa (883 mg, 9.18 mmol) under N₂. After being heated with stirring at 100° C. for 12 hrs, the resulting reaction mixture was cooled to rt and concentrated in vacuo. The residue was diluted with H₂O (60 mL) and extracted with DCM (150 mL). The organic layer was washed with brine (60 mL), dried over anhydrous Na₂SO₄ and concentrated in vacuo. The residue was purified by flash column to give 8-(2-methoxy-7-quinolyl)-1,4-dioxa-8-azaspiro[4.5]decane (900 mg) as yellow oil.

Step 2: Preparation of 1-(2-methoxy-7-quinolyl)piperidin-4-one

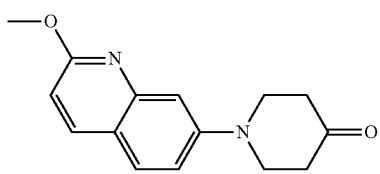 [SMILES: COc1ccc2ccc(N3CCC(=O)CC3)cc2n1]

A solution of 8-(2-methoxy-7-quinolyl)-1,4-dioxa-8-azaspiro[4.5]decane (900 mg, 3 mmol) in 44% formic acid (4 mL) was heated with stirring at 90° C. for 4 hrs. The resulting reaction mixture was concentrated in vacuo, diluted with DCM (150 mL), washed with sat. aqueous solution of NaHCO₃ (50 mL) and brine (50 mL), then dried over anhydrous Na₂SO₄ and concentrated in vacuo. The residue was purified by flash column to give 1-(2-methoxy-7-quinolyl)piperidin-4-one (730 mg) as yellow oil.

Step 3: Preparation of 6-(2-methoxy-7-quinolyl)-2-pyrimidin-2-yl-7,8-dihydro-5H-pyrido[4,3-d]pyrimidine

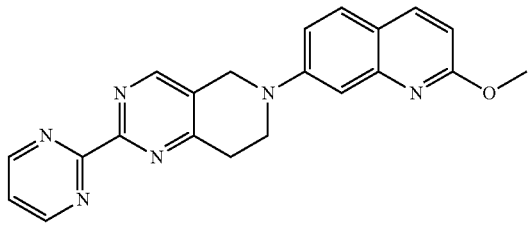 [SMILES: COc1ccc2ccc(N3CCc4nc(-c5ncccn5)ncc4C3)cc2n1]

A solution of 1-(2-methoxy-7-quinolyl)piperidin-4-one (730 mg, 2.85 mmol) in DMFDMA (5 mL) was heated with stirring at 100° C. for 4 hrs. The resulting reaction mixture was concentrated in vacuo and the residue was dissolved in MeOH (10 mL). To the solution was added pyrimidine-2-carboxamidine hydrochloride (183 mg, 1.16 mmol) and K₂CO₃ (400 mg, 2.89 mmol). After being heated with stirring at 80° C. for 0.5 hr, the resulting mixture was diluted with H₂O (20 mL) and extracted with DCM (60 mL). The organic layer was washed with brine (50 mL), dried over anhydrous Na₂SO₄ and concentrated in vacuo. The residue was purified by prep-HPLC to afford 6-(2-methoxy-7-quinolyl)-2-pyrimidin-2-yl-7,8-dihydro-5H-pyrido[4,3-d]pyrimidine (51.9 mg) as yellow solid. ¹H NMR (400 MHz, DMSO-d₆): δ 3.13 (t, 2H), 3.89 (t, 2H), 3.95 (s, 3H), 4.71 (s, 2H), 6.73 (d, 1H), 7.20 (d, 1H), 7.39 (dd, 1H), 7.63 (t, 1H), 7.74 (d, 1H), 8.04 (d, 1H), 8.91 (s, 1H), 8.99 (d, 2H). MS obsd. (ESI⁺) [(M+H)⁺]: 371.

Example 76: 3-methoxy-5-(2-pyrimidin-2-yl-7,8-dihydro-5H-pyrido[4,3-d]pyrimidin-6-yl)benzonitrile

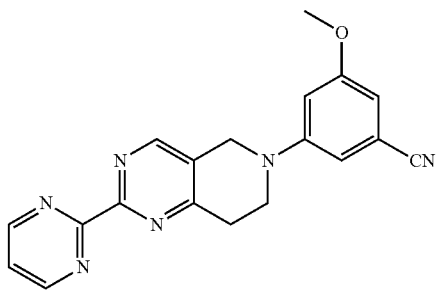 [SMILES: COc1cc(C#N)cc(N2CCc3nc(-c4ncccn4)ncc3C2)c1]

Step 1: Preparation of 3-(1,4-dioxa-8-azaspiro[4.5]decan-8-yl)-5-methoxy-benzonitrile

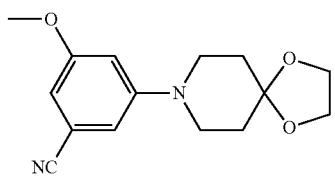 [SMILES: COc1cc(C#N)cc(N2CCC3(CC2)OCCO3)c1]

To a solution of 1,4-dioxa-8-azaspiro[4.5]decane (800 mg, 4.45 mmol) and 3-bromo-5-methoxybenzonitrile (1.13 g, 5.34 mmol) in dioxane (8 mL) was added t-BuONa (1.28 g, 13.4 mmol), Ruphos (166 mg, 0.36 mmol) and Pd₂(dba)₃ (163 mg, 0.18 mmol) under N₂. After being heated with stirring at 100° C. for 12 hrs, the resulting mixture was cooled to rt and concentrated in vacuo. The residue was diluted with H₂O (50 mL) and extracted with DCM (100 mL). The organic layer was washed with brine (50 mL), concentrated in vacuo and purified by flash column to give 3-(1,4-dioxa-8-azaspiro[4.5]decan-8-yl)-5-methoxy-benzonitrile (950 mg) as yellow oil.

Step 2: Preparation of 3-methoxy-5-(4-oxo-1-piperidyl)benzonitrile

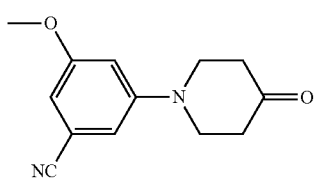 [SMILES: COc1cc(C#N)cc(N2CCC(=O)CC2)c1]

A suspension of 3-(1,4-dioxa-8-azaspiro[4.5]decan-8-yl)-5-methoxy-benzonitrile (950 mg, 3.46 mmol) in 44% formic acid (8 mL) was heated with stirring at 90° C. for 2 hrs. The resulting reaction mixture was concentrated in vacuo. The residue was diluted with DCM (150 mL), washed with sat. aqueous solution of NaHCO₃ (50 mL) and brine (50 mL) and concentrated in vacuo. The residue was purified by flash column to give 3-methoxy-5-(4-oxo-1-piperidyl)benzonitrile (630 mg) as yellow oil.

Step 3: Preparation of 3-methoxy-5-(2-pyrimidin-2-yl-7,8-dihydro-5H-pyrido[4,3-d]pyrimidin-6-yl)benzonitrile

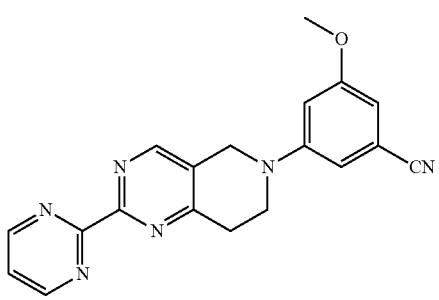 [SMILES: COc1cc(C#N)cc(N2CCc3nc(-c4ncccn4)ncc3C2)c1]

A solution of 3-methoxy-5-(4-oxo-1-piperidyl)benzonitrile (330 mg, 1.4 mmol) in DMFDMA (5 mL) was heated with stirring at 100° C. for 4 hrs. The resulting reaction mixture was concentrated in vacuo and the residue was dissolved in MeOH (5 mL). To the solution was added pyrimidine-2-carboxamidine hydrochloride (267 mg, 1.68 mmol) and K₂CO₃ (581 mg, 4.21 mmol). After being heated with stirring at 80° C. for 0.5 hr, the resulting mixture was diluted with H₂O (20 mL) and extracted with DCM (60 mL). The organic layer was washed with brine (50 mL), dried over anhydrous Na₂SO₄ and concentrated in vacuo. The residue was purified by prep-HPLC to afford 3-methoxy-5-(2-pyrimidin-2-yl-7,8-dihydro-5H-pyrido[4,3-d]pyrimidin-6-yl)benzonitrile (52 mg) as yellow solid. ¹H NMR (400 MHz, DMSO-d₆): δ 3.08 (t, 2H), 3.74-3.85 (m, 5H), 4.62 (s, 2H), 6.81 (s, 1H), 6.90 (t, 1H), 7.13 (d, J=1.00 Hz, 1H), 7.63 (t, 1H), 8.82 (s, 1H), 8.99 (d, 2H). MS obsd. (ESI⁺) [(M+H)⁺]: 345.

Example 77: 2-fluoro-6-methoxy-4-(2-pyrimidin-2-yl-7,8-dihydro-5H-pyrido[4,3-d]pyrimidin-6-yl)benzonitrile

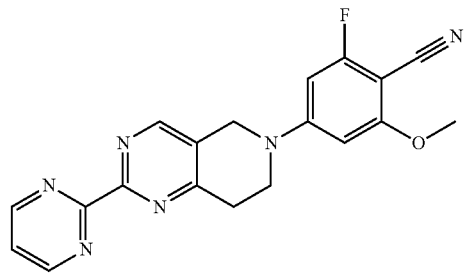 [SMILES: COc1cc(N2CCc3nc(-c4ncccn4)ncc3C2)cc(F)c1C#N]

Step 1: Preparation of 4-bromo-2-fluoro-6-methoxy-benzonitrile

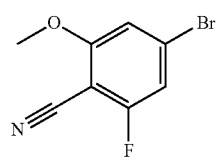

To a solution of 4-bromo-2,6-difluoro-benzonitrile (3000 mg, 13.8 mmol) in THF (40 mL) was added NaOMe (1100 mg, 20.7 mmol) at rt. The resulting mixture was stirred overnight at rt and then purified by flash column to give 4-bromo-2-fluoro-6-methoxy-benzonitrile (700 mg).

Step 2: Preparation of 4-(1,4-dioxa-8-azaspiro[4.5]decan-8-yl)-2-fluoro-6-methoxy-benzonitrile

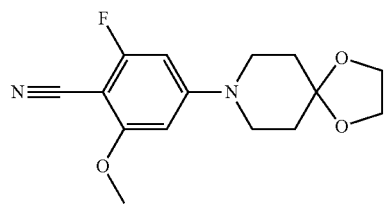 [SMILES: COc1cc(N2CCC3(CC2)OCCO3)cc(F)c1C#N]

To a mixture of 4-bromo-2-fluoro-6-methoxy-benzonitrile (700 mg, 1.75 mmol) and 1,4-dioxa-8-azaspiro[4.5]decane (276 mg, 1.93 mmol) in dioxane (15 mL) was added Cs₂CO₃ (1700 mg, 5.25 mmol), Pd₂(dba)₃ (83 mg, 0.09 mmol) and Ruphos (84 mg, 0.18 mmol) under N₂. After being heated with stirring at 100° C. overnight, the resulting mixture was cooled to rt, diluted with H₂O (30 mL) and extracted with EA (30 mL) for three times. The combined organic layer was washed with brine (30 mL), dried over anhydrous Na₂SO₄ and concentrated in vacuo to give 4-(1,4-dioxa-8-azaspiro

[4.5]decan-8-yl)-2-fluoro-6-methoxy-benzonitrile (510 mg), which was used in the next step without further purification.

Step 3: Preparation of 2-fluoro-6-methoxy-4-(4-oxo-1-piperidyl)benzonitrile

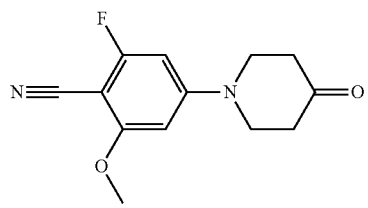 [SMILES: COc1cc(N2CCC(=O)CC2)cc(F)c1C#N]

A flask containing crude 4-(1,4-dioxa-8-azaspiro[4.5]decan-8-yl)-2-fluoro-6-methoxy-benzonitrile (510 mg, 1.75 mmol) was added 44% formic acid (10 mL). After being heated with stirring at 90° C. for 8 hrs, the resulting reaction mixture was concentrated in vacuo, diluted with sat. aqueous solution of NaHCO$_3$ (20 mL) and extracted with EA (30 mL) for three times. The combined organic layer was washed with brine (50 mL), dried over anhydrous Na$_2$SO$_4$ and concentrated in vacuo to give 2-fluoro-6-methoxy-4-(4-oxo-1-piperidyl)benzonitrile (430 mg) as brown oil, which was used in the next step without further purification.

Step 4: Preparation of 2-fluoro-6-methoxy-4-(2-pyrimidin-2-yl-7,8-dihydro-5H-pyrido[4,3-d]pyrimidin-6-yl)benzonitrile

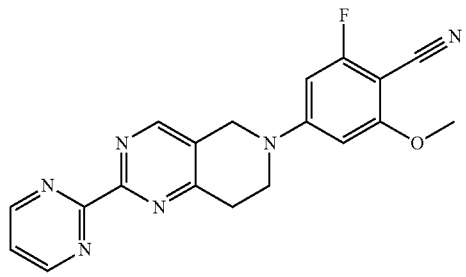 [SMILES: COc1cc(N2CCc3nc(-c4ncccn4)ncc3C2)cc(F)c1C#N]

A mixture of 2-fluoro-6-methoxy-4-(4-oxo-1-piperidyl)benzonitrile (430 mg, 1.75 mmol) and DMFDMA (10 mL) was heated with stirring at 90° C. for 3 hrs. The resulting reaction mixture was concentrated in vacuo and the residue was dissolved in EtOH (20 mL). To the solution was added pyrimidine-2-carboxamidine hydrochloride (277 mg, 1.75 mmol) and K$_2$CO$_3$ (480 mg, 3.5 mmol) successively. After being heated with stirring at 80° C. overnight, the resulting reaction mixture was cooled to rt and purified by prep-HPLC to give 2-fluoro-6-methoxy-4-(2-pyrimidin-2-yl-7,8-dihydro-5H-pyrido[4,3-d]pyrimidin-6-yl)benzonitrile (50 mg). $^1$H NMR (400 MHz, DMSO-d$_6$): δ 9.00 (d, 2H), 8.84 (s, 1H), 7.62-7.69 (m, 1H), 6.68-6.76 (m, 1H), 6.50-6.57 (m, 1H), 4.79 (s, 2H), 3.97 (s, 3H), 3.88-3.95 (m, 2H), 3.07-3.17 (m, 2H). MS obsd. (ESI$^+$) [(M+H)$^+$]: 363.

Example 78: 6-(4-chloro-3-fluoro-5-methoxy-phenyl)-2-pyrimidin-2-yl-7,8-dihydro-5H-pyrido[4,3-d]pyrimidine

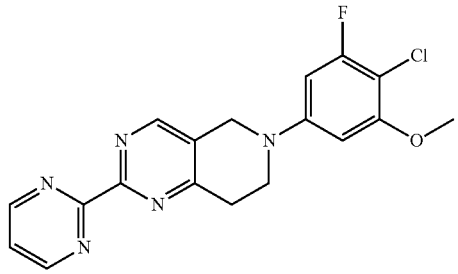 [SMILES: COc1cc(N2CCc3nc(-c4ncccn4)ncc3C2)cc(F)c1Cl]

Step 1: Preparation of 5-bromo-2-chloro-1-fluoro-3-methoxy-benzene

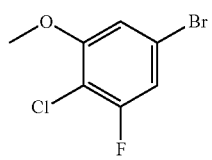

To a solution of 5-bromo-2-chloro-1,3-difluoro-benzene (7200 mg, 31.9 mmol) in MeOH (50 mL) was added NaOMe (5200 mg, 95.7 mmol) at rt. The resulting mixture was stirred overnight at rt and then purified by flash column to give 5-bromo-2-chloro-1-fluoro-3-methoxy-benzene (5.2 g).

Step 2: Preparation of 8-(4-chloro-3-fluoro-5-methoxy-phenyl)-1,4-dioxa-8-azaspiro[4.5]decane

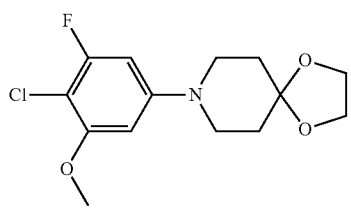 [SMILES: COc1cc(N2CCC3(CC2)OCCO3)cc(F)c1Cl]

To a mixture of 5-bromo-2-chloro-1-fluoro-3-methoxy-benzene (5200 mg, 21.85 mmol) and 1,4-dioxa-8-azaspiro[4.5]decane (3440 mg, 24.04 mmol) in dioxane (50 mL) was added t-BuONa (4200 mg, 43.7 mmol), Pd$_2$(dba)$_3$ (1000 mg, 1.09 mmol) and Ruphos (1020 mg, 2.18 mmol) under N$_2$. After being heated with stirring at 100° C. overnight, the resulting reaction mixture was cooled to rt, diluted with H$_2$O (50 mL) and extracted with EA (50 mL) for three times. The combined organic layer was washed with brine (50 mL), dried over anhydrous Na$_2$SO$_4$ and concentrated in vacuo to give 8-(4-chloro-3-fluoro-5-methoxy-phenyl)-1,4-dioxa-8-azaspiro[4.5]decane (800 mg), which was used in the next step without further purification.

Step 3: 1-(4-chloro-3-fluoro-5-methoxy-phenyl)piperidin-4-one

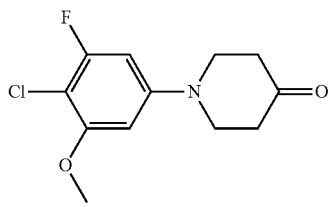 [SMILES: COc1cc(N2CCC(=O)CC2)cc(F)c1Cl]

To a flask containing crude 8-(4-chloro-3-fluoro-5-methoxy-phenyl)-1,4-dioxa-8-azaspiro[4.5]decane (800 mg, 2.65 mmol) was added 44% formic acid (10 mL). After being heated with stirring at 90° C. for 8 hrs, the resulting reaction mixture was concentrated in vacuo, diluted with sat. aqueous solution of NaHCO$_3$ (20 mL) and extracted with EA (30 mL) for three times. The combined organic layer was washed with brine (50 mL), dried over anhydrous Na$_2$SO$_4$ and concentrated in vacuo to give 1-(4-chloro-3-fluoro-5-methoxy-phenyl)piperidin-4-one (680 mg) as brown oil, which was used in the next step without further purification.

Step 4: Preparation of 6-(4-chloro-3-fluoro-5-methoxy-phenyl)-2-pyrimidin-2-yl-7,8-dihydro-5H-pyrido[4,3-d]pyrimidine

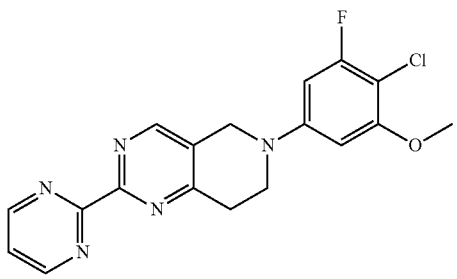 [SMILES: COc1cc(N2CCc3nc(-c4ncccn4)ncc3C2)cc(F)c1Cl]

A mixture of 1-(4-chloro-3-fluoro-5-methoxy-phenyl)piperidin-4-one (680 mg, 2.65 mmol) and DMFDMA (10 mL) was heated with stirring at 90° C. for 3 hrs. The resulting reaction mixture was concentrated in vacuo and the residue was dissolved in EtOH (20 mL). To the solution was added pyrimidine-2-carboxamidine hydrochloride (420 mg, 2.65 mmol) and K$_2$CO$_3$ (730 mg, 5.3 mmol) successively. After being heated with stirring at 80° C. overnight, the resulting reaction mixture was cooled to rt and purified by prep-HPLC to give 6-(4-chloro-3-fluoro-5-methoxy-phenyl)-2-pyrimidin-2-yl-7,8-dihydro-5H-pyrido[4,3-d]pyrimidine (250 mg). $^1$H NMR (400 MHz, DMSO-d$_6$): δ 8.96-9.00 (m, 2H), 8.72 (s, 1H), 7.62-7.68 (m, 1H), 6.95-7.07 (m, 2H), 4.33-4.41 (m, 2H), 3.82-3.86 (m, 3H), 3.43-3.52 (m, 3H), 2.98-3.06 (m, 2H). MS obsd. (ESI$^+$) [(M+H)$^+$]: 372.

Example 79: 6-(3-chloro-4-fluoro-5-methoxy-phenyl)-2-pyrimidin-2-yl-7,8-dihydro-5H-pyrido[4,3-d]pyrimidine

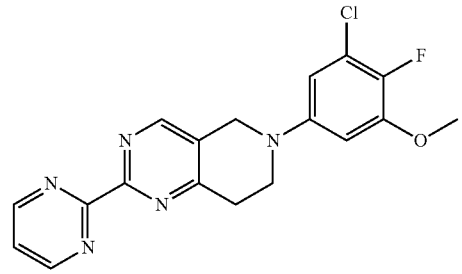

Step 1: Preparation of 8-(3-chloro-4-fluoro-5-methoxy-phenyl)-1,4-dioxa-8-azaspiro[4.5]decane

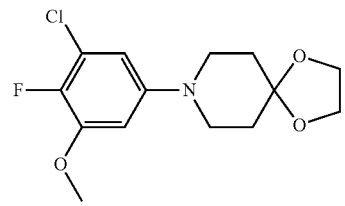 [SMILES: COc1cc(N2CCC3(CC2)OCCO3)cc(Cl)c1F]

To a mixture of 5-bromo-1-chloro-2-fluoro-3-methoxybenzene (1000 mg, 4.2 mmol) and 1,4-dioxa-8-azaspiro[4.5]decane (660 mg, 4.6 mmol) in dioxane (20 mL) was added t-BuONa (800 mg, 8.4 mmol), Pd$_2$(dba)$_3$ (184 mg, 0.2 mmol) and Ruphos (187 mg, 0.4 mmol) under N$_2$. After being heated with stirring at 100° C. overnight, the resulting reaction mixture was cooled to rt, diluted with H$_2$O (50 mL) and extracted with EA (50 mL) for three times. The combined organic layer was washed with brine (50 mL), dried over anhydrous Na$_2$SO$_4$ and concentrated in vacuo to give 8-(3-chloro-4-fluoro-5-methoxy-phenyl)-1,4-dioxa-8-azaspiro[4.5]decane (500 mg), which was used in the next step without further purification.

Step 2: Preparation of 1-(3-chloro-4-fluoro-5-methoxy-phenyl)piperidin-4-one

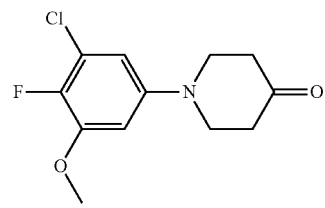 [SMILES: COc1cc(N2CCC(=O)CC2)cc(Cl)c1F]

A flask containing crude 8-(3-chloro-4-fluoro-5-methoxy-phenyl)-1,4-dioxa-8-azaspiro[4.5]decane (500 mg, 1.66 mmol) was added 44% formic acid (10 mL). After heated with stirring at 90° C. for 8 hrs, the resulting reaction mixture was concentrated in vacuo, diluted with sat. aqueous solution of NaHCO$_3$ (20 mL) and extracted with EA (30 mL)

for three times. The combined organic layer was washed with brine (50 mL), dried over anhydrous Na₂SO₄ and concentrated in vacuo to give 1-(3-chloro-4-fluoro-5-methoxy-phenyl)piperidin-4-one (420 mg) as brown oil, which was used in the next step without further purification.

Step 3: Preparation of 6-(3-chloro-4-fluoro-5-methoxy-phenyl)-2-pyrimidin-2-yl-7,8-dihydro-5H-pyrido[4,3-d]pyrimidine

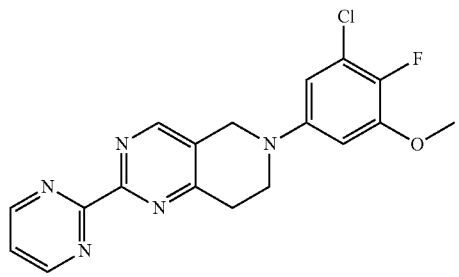

A mixture of 1-(3-chloro-4-fluoro-5-methoxy-phenyl)piperidin-4-one (420 mg, 1.66 mmol) and DMFDMA (10 mL) was heated with stirring at 90° C. for 3 hrs. The resulting reaction mixture was concentrated in vacuo and the residue was dissolved in EtOH (20 mL). To the solution was added pyrimidine-2-carboxamidine hydrochloride (260 mg, 1.66 mmol) and K₂CO₃ (458 mg, 3.32 mmol) successively. After being heated with stirring at 80° C. overnight, the resulting reaction mixture was cooled to rt and purified by prep-HPLC to give 6-(3-chloro-4-fluoro-5-methoxy-phenyl)-2-pyrimidin-2-yl-7,8-dihydro-5H-pyrido[4,3-d]pyrimidine (300 mg). ¹H NMR (400 MHz, DMSO-d₆): δ 9.00 (d, J=4.8 Hz, 2H), 8.83 (s, 1H), 7.61-7.68 (m, 1H), 6.82-6.90 (m, 1H), 6.70-6.77 (m, 1H), 4.54 (s, 2H), 3.90 (s, 3H), 3.68-3.77 (m, 2H), 3.06-3.15 (m, 2H). MS obsd. (ESI⁺) [(M+H)⁺]: 372.

Example 80: 6-(4-methylsulfonylphenyl)-2-(2-pyridyl)-3,5,7,8-tetrahydropyrido-[4,3-d]pyrimidin-4-one

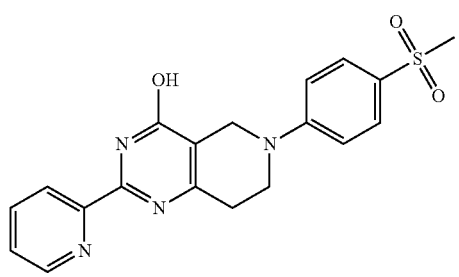 [SMILES: CS(=O)(=O)c1ccc(N2CCc3nc(-c4ccccn4)nc(O)c3C2)cc1]

Step 1: Preparation of 6-benzyl-2-(2-pyridyl)-3,5,7,8-tetrahydropyrido[4,3-d]pyrimidin-4-one

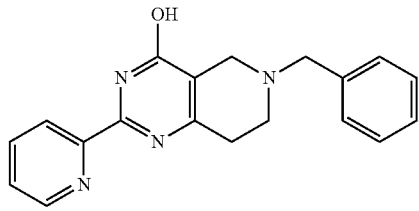 [SMILES: Oc1nc(-c2ccccn2)nc2c1CN(Cc1ccccc1)CC2]

To a solution of NaOMe (3.39 g, 73.9 mmol) in MeOH (100 mL) was added pyridine-2-carboxamidine hydrochloride (5.82 g, 36.9 mmol) followed by ethyl 1-benzyl-4-oxo-piperidine-3-carboxylate (10 g, 33.6 mmol). After being stirred at 25° C. for 16 hrs, the resulting reaction mixture was concentrated in vacuo. The residue was suspended into EA and H₂O, and the suspension was filtered. The filter cake was dried in vacuo to give 6-benzyl-2-(2-pyridyl)-3,5,7,8-tetrahydropyrido[4,3-d]pyrimidin-4-one (7.8 g) as a white solid.

Step 2: Preparation of 2-(2-pyridyl)-5,6,7,8-tetrahydro-3H-pyrido[4,3-d]pyrimidin-4-one

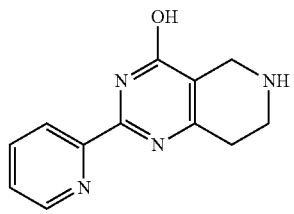 [SMILES: Oc1nc(-c2ccccn2)nc2c1CNCC2]

A solution of 6-benzyl-2-(2-pyridyl)-3,5,7,8-tetrahydropyrido[4,3-d]pyrimidin-4-one (7.8 g, 24.5 mmol) in MeOH (800 mL) was hydrogenated in the presence of Pd(OH)₂ (800 mg) at 60° C. under 30 psi of H₂ for 24 hrs. The resulting reaction mixture was filtered. The filtrate was concentrated in vacuo to give 2-(2-pyridyl)-5,6,7,8-tetrahydro-3H-pyrido[4,3-d]pyrimidin-4-one (5.4 g) as a yellow solid, which was used in the next step without further purification.

Step 3: Preparation of 6-(4-methylsulfonylphenyl)-2-(2-pyridyl)-3,5,7,8-tetrahydropyrido[4,3-d]pyrimidin-4-one

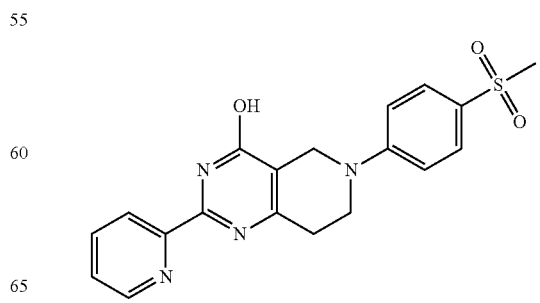

To a mixture of 2-(2-pyridyl)-5,6,7,8-tetrahydro-3H-pyrido[4,3-d]pyrimidin-4-one (12 g, 52.6 mmol) and NMP (180 mL) was added Cs$_2$CO$_3$ (25.7 g, 78.9 mmol) followed by 1-fluoro-4-methylsulfonyl-benzene (11.0 g, 63.1 mmol). After being heated with stirring at 140° C. for 16 hrs, the resulting reaction mixture was cooled to rt and purified by flash column to give 6-(4-methylsulfonylphenyl)-2-(2-pyridyl)-3,5,7,8-tetrahydropyrido[4,3-d]pyrimidin-4-one (5.0 g). 1H NMR (400 MHz, DMSO-d$_6$): δ 8.74 (d, 1H), 8.31 (d, 1H), 7.94-8.06 (m, 1H), 7.74 (d, 2H), 7.61-7.72 (m, 1H), 7.19 (d, 2H), 4.25 (s, 2H), 3.77 (t, 2H), 3.10 (s, 3H), 2.88 (t, 2H).

Example 81: 4-methoxy-6-(4-methylsulfonylphenyl)-2-pyrimidin-2-yl-7,8-dihydro-5H-pyrido[4,3-d]pyrimidine

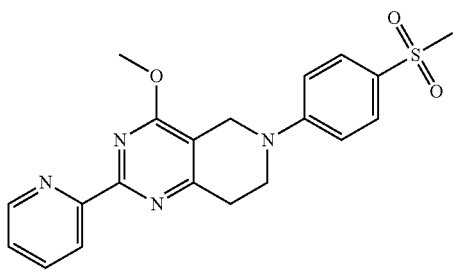 [SMILES: COc1nc(-c2ccccn2)nc2c1CN(c1ccc(S(C)(=O)=O)cc1)CC2]

Step 1: Preparation of 4-chloro-6-(4-methylsulfonylphenyl)-2-pyrimidin-2-yl-7,8-dihydro-5H-pyrido[4,3-d]pyrimidine

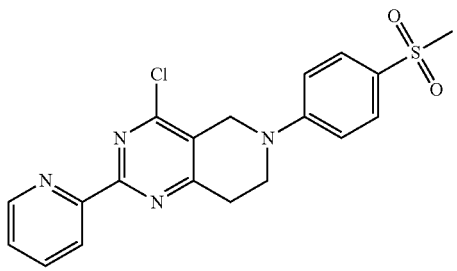

A mixture of 6-(4-methylsulfonylphenyl)-2-(2-pyridyl)-3,5,7,8-tetrahydropyrido[4,3-d]pyrimidin-4-one (5.0 g, 13 mmol) and POCl$_3$ (50 mL) was heated with stirring at 120° C. for 2 hrs. After being cooled to rt, the resulting reaction mixture was concentrated in vacuo. The residue was basified with sat. aqueous solution of NaHCO$_3$ and extracted with DCM. The organic layer was dried over anhydrous Na$_2$SO$_4$ and concentrated in vacuo. The residue was purified by column (eluting with 1% MeOH in DCM) to give 4-chloro-6-(4-methylsulfonylphenyl)-2-(2-pyridyl)-7,8-dihydro-5H-pyrido[4,3-d]pyrimidine (5.1 g) as a yellow solid.

Step 2: Preparation of 4-methoxy-6-(4-methylsulfonylphenyl)-2-pyrimidin-2-yl-7,8-dihydro-5H-pyrido[4,3-d]pyrimidine

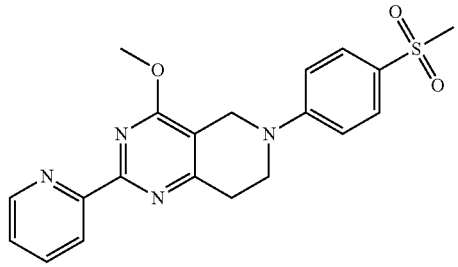

To a solution of 4-chloro-6-(4-methylsulfonylphenyl)-2-(2-pyridyl)-7,8-dihydro-5H-pyrido[4,3-d]pyrimidine (100 mg, 0.249 mmol) in MeOH (1.5 mL) was added NaOMe (27 mg, 0.50 mmol). After being stirred at rt for 16 hrs, the resulting reaction mixture was diluted with DCM, washed with water and brine, dried over anhydrous Na$_2$SO$_4$, concentrated in vacuo and lyophilized to give 4-methoxy-6-(4-methylsulfonylphenyl)-2-pyrimidin-2-yl-7,8-dihydro-5H-pyrido[4,3-d]pyrimidine (58 mg) as a light yellow solid. $^1$H NMR (400 MHz, CDCl$_3$): δ 8.85 (d, 1H), 8.50 (d, 1H), 7.82-7.93 (m, 3H), 7.42-7.48 (m, 1H), 7.06 (d, 2H), 4.45 (s, 2H), 4.21 (s, 3H), 3.82 (t, 2H), 3.25 (t, 2H), 3.04 (s, 3H). MS obsd. (ESI$^+$) [(M+H)$^+$]: 397.

Example 82: 4-ethoxy-6-(4-methylsulfonylphenyl)-2-pyrimidin-2-yl-7,8-dihydro-5H-pyrido[4,3-d]pyrimidine

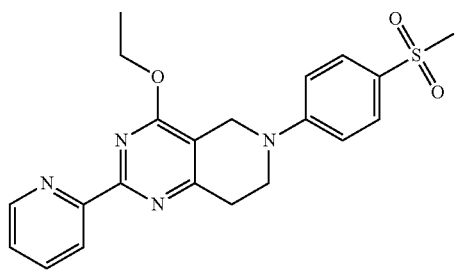 [SMILES: CCOc1nc(-c2ccccn2)nc2c1CN(c1ccc(S(C)(=O)=O)cc1)CC2]

To a solution of 4-chloro-6-(4-methylsulfonylphenyl)-2-(2-pyridyl)-7,8-dihydro-5H-pyrido[4,3-d]pyrimidine (100 mg, 0.249 mmol) in EtOH (1.5 mL) was added NaOEt (34 mg, 0.50 mmol). After being stirred at rt for 16 hrs, the resulting reaction mixture was diluted with DCM, washed with water and brine, dried over anhydrous Na$_2$SO$_4$ and concentrated in vacuo. The residue was purified by prep-HPLC to give 4-ethoxy-6-(4-methylsulfonylphenyl)-2-pyrimidin-2-yl-7,8-dihydro-5H-pyrido[4,3-d]pyrimidine (44 mg) as a light yellow solid. $^1$H NMR (400 MHz, CDCl$_3$): δ 8.85 (dd, 1H), 8.46 (d, 1H), 7.81-7.91 (m, 3H), 7.38-7.43 (m, 1H), 7.06 (d, 2H), 4.67 (q, 2H), 4.44 (s, 2H), 3.82 (t, 2H), 3.24 (t, 2H), 3.03 (s, 3H), 1.52 (t, 3H). MS obsd. (ESI$^+$) [(M+H)$^+$]: 411.

Example 83: 4-benzyloxy-6-(4-methylsulfonylphenyl)-2-pyrimidin-2-yl-7,8-dihydro-5H-pyrido[4,3-d]pyrimidine

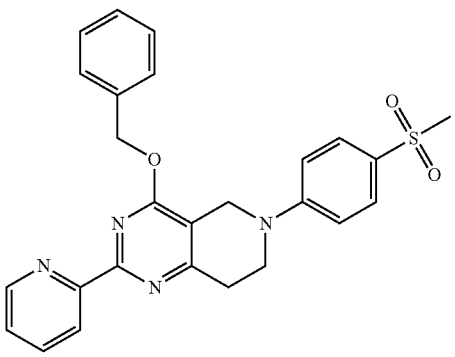 [SMILES: CS(=O)(=O)c1ccc(N2CCc3nc(-c4ccccn4)nc(OCc4ccccc4)c3C2)cc1]

To a mixture of NaH (50 mg, 1.25 mmol, 60% purity in mineral oil) and BnOH (1.5 mL) was added 4-chloro-6-(4-methylsulfonylphenyl)-2-(2-pyridyl)-7,8-dihydro-5H-pyrido[4,3-d]pyrimidine (100 mg, 0.25 mmol). After being stirred at rt for 16 hrs, the resulting reaction mixture was diluted with DCM, washed with water and brine, dried over anhydrous $Na_2SO_4$ and concentrated in vacuo. The residue was purified by prep-HPLC to give 4-benzyloxy-6-(4-methylsulfonylphenyl)-2-pyrimidin-2-yl-7,8-dihydro-5H-pyrido[4,3-d]pyrimidine (54 mg) as a light yellow solid. $^1$H NMR (400 MHz, CDCl$_3$): δ 8.87 (s, 1H), 8.47 (d, 1H), 7.80-7.89 (m, 1H), 7.53 (d, 2H), 7.42-7.51 (m, 2H), 7.37-7.41 (m, 4H), 7.04 (d, 2H), 5.68 (s, 2H), 4.48 (s, 2H), 3.82 (t, 2H), 3.26 (t, 2H), 3.03 (s, 3H). MS obsd. (ESI$^+$) [(M+H)$^+$]: 473.

Example 84: 6-(4-methylsulfonylphenyl)-4-[(E)-prop-1-enyl]-2-pyrimidin-2-yl-7,8-dihydro-5H-pyrido[4,3-d]pyrimidine

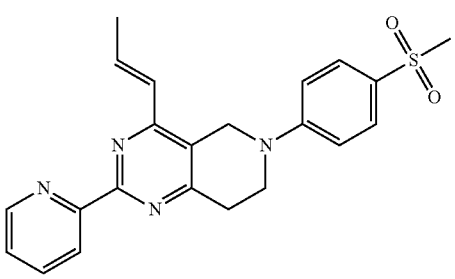

To a solution of 4-chloro-6-(4-methylsulfonylphenyl)-2-pyrimidin-2-yl-7,8-dihydro-5H-pyrido[4,3-d]pyrimidine (300 mg, 0.75 mmol) and 2-allyl-4,4,5,5-tetramethyl-1,3,2-dioxaborolane (380 mg, 2.25 mmol) in THF (15 mL) was added CsF (342 mg, 2.25 mmol), Pd(PPh$_3$)$_4$ (92 mg, 0.08 mmol) under N$_2$. After being heated under reflux under N$_2$ atmosphere overnight, the resulting reaction mixture was diluted with H$_2$O (10 mL) and extracted with EA (30 mL) for three times. The combined organic layer was dried over anhydrous Na$_2$SO$_4$ and concentrated in vacuo. The residue was purified by prep-HPLC to give 6-(4-methylsulfonylphenyl)-4-[(E)-prop-1-enyl]-2-pyrimidin-2-yl-7,8-dihydro-5H-pyrido[4,3-d]pyrimidine (50 mg). $^1$H NMR (400 MHz, CDCl$_3$): δ 8.82-8.96 (m, 1H), 8.53-8.65 (m, 1H), 7.81-7.93 (m, 3H), 7.51-7.67 (m, 1H), 7.37-7.48 (m, 1H), 7.08 (d, 2H), 6.56-6.68 (m, 1H), 4.61 (s, 2H), 3.74-3.92 (m, 2H), 3.23-3.39 (m, 2H), 3.04 (s, 3H), 1.99-2.22 (m, 3H). MS obsd. (ESI$^+$) [(M+H)$^+$]: 407.

Example 85: 6-(4-methylsulfonylphenyl)-4-propyl-2-pyrimidin-2-yl-7,8-dihydro-5H-pyrido[4,3-d]pyrimidine

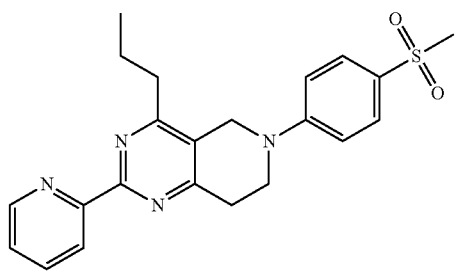 [SMILES: CCCc1nc(-c2ccccn2)nc2c1CN(c1ccc(S(C)(=O)=O)cc1)CC2]

A solution of 6-(4-methylsulfonylphenyl)-4-[(E)-prop-1-enyl]-2-pyrimidin-2-yl-7,8-dihydro-5H-pyrido[4,3-d]pyrimidine (100 mg) in MeOH (10 mL) was stirred in the presence of 10% Pd/C (50 mg) at rt under H$_2$ overnight. The resulting reaction mixture was purified by prep-HPLC to give 6-(4-methylsulfonylphenyl)-4-propyl-2-pyrimidin-2-yl-7,8-dihydro-5H-pyrido[4,3-d]pyrimidine (40 mg). $^1$H NMR (400 MHz, CDCl3): δ 8.81-8.95 (m, 1H), 8.50-8.62 (m, 1H), 7.83-7.92 (m, 3H), 7.37-7.48 (m, 1H), 7.06 (d, 2H), 4.58 (s, 2H), 3.76-3.90 (m, 2H), 3.25-3.37 (m, 2H), 3.05 (s, 3H), 2.81-2.92 (m, 2H), 1.90-2.05 (m, 2H), 1.12 (t, 3H). MS obsd. (ESI$^+$) [(M+H)$^+$]: 409.

Example 86: 4-ethyl-6-(4-methylsulfonylphenyl)-2-pyrimidin-2-yl-7,8-dihydro-5H-pyrido[4,3-d]pyrimidine

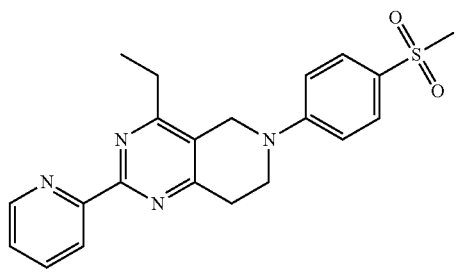 [SMILES: CCc1nc(-c2ccccn2)nc2c1CN(c1ccc(S(C)(=O)=O)cc1)CC2]

Step 1: Preparation of 6-(4-methylsulfonylphenyl)-2-pyrimidin-2-yl-4-vinyl-7,8-dihydro-5H-pyrido[4,3-d]pyrimidine

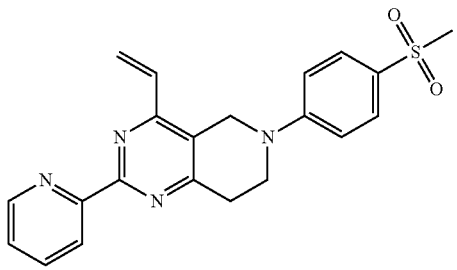 [SMILES: C=Cc1nc(-c2ccccn2)nc2c1CN(c1ccc(S(C)(=O)=O)cc1)CC2]

To a solution of 4-chloro-6-(4-methylsulfonylphenyl)-2-pyrimidin-2-yl-7,8-dihydro-5H-pyrido[4,3-d]pyrimidine (250 mg, 0.63 mmol) and 4,4,5,5-tetramethyl-2-vinyl-1,3,2-dioxaborolane (194 mg, 1.26 mmol) in dioxane (10 mL) and H$_2$O (2 mL) was added K$_2$CO$_3$ (174 mg, 1.26 mmol) and Pd(PPh$_3$)$_4$ (69 mg, 0.06 mmol) under N$_2$. After being heated under reflux overnight, the resulting reaction mixture was diluted with H$_2$O (10 mL) and extracted with EA (30 mL) for three times. The combined organic layer was dried over anhydrous Na$_2$SO$_4$ and concentrated in vacuo. The residue was purified by flash column to give 6-(4-methylsulfonylphenyl)-2-pyrimidin-2-yl-4-vinyl-7,8-dihydro-5H-pyrido[4,3-d]pyrimidine (150 mg).

Step 2: Preparation of 4-ethyl-6-(4-methylsulfonylphenyl)-2-pyrimidin-2-yl-7,8-dihydro-5H-pyrido[4,3-d]pyrimidine

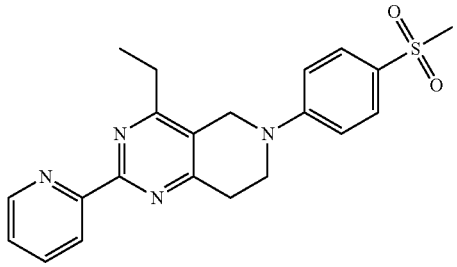 [SMILES: CCc1nc(-c2ccccn2)nc2c1CN(c1ccc(S(C)(=O)=O)cc1)CC2]

A solution of 6-(4-methylsulfonylphenyl)-2-pyrimidin-2-yl-4-vinyl-7,8-dihydro-5H-pyrido[4,3-d]pyrimidine (50 mg) in MeOH (10 mL) was stirred in the presence of 10% Pd/C (20 mg) at rt under H$_2$ overnight. The resulting reaction mixture was purified by prep-HPLC to give 4-ethyl-6-(4-methylsulfonylphenyl)-2-pyrimidin-2-yl-7,8-dihydro-5H-pyrido[4,3-d]pyrimidine (10 mg). $^1$H NMR (400 MHz, CDCl$_3$): δ 8.85-8.93 (m, 1H), 8.56-8.64 (m, 1H), 7.82-7.96 (m, 3H), 7.39-7.48 (m, 1H), 7.02-7.13 (m, 2H), 4.58 (s, 2H), 3.79-3.90 (m, 2H), 3.27-3.39 (m, 2H), 3.05 (s, 3H), 2.89-2.98 (m, 2H), 1.48 (t, 3H). MS obsd. (ESI$^+$) [(M+H)$^+$]: 395.

Example 87: 4-methyl-6-(4-methylsulfonylphenyl)-2-pyrimidin-2-yl-7,8-dihydro-5H-pyrido[4,3-d]pyrimidine

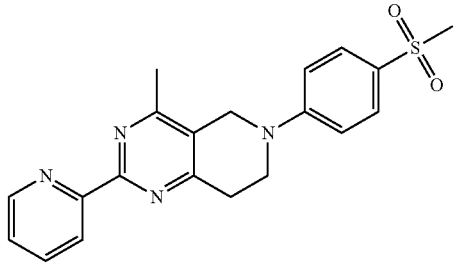 [SMILES: Cc1nc(-c2ccccn2)nc2c1CN(c1ccc(S(C)(=O)=O)cc1)CC2]

To a solution of 4-chloro-6-(4-methylsulfonylphenyl)-2-pyrimidin-2-yl-7,8-dihydro-5H-pyrido[4,3-d]pyrimidine (150 mg, 0.38 mmol) and methylboronic acid (46 mg, 0.76 mmol) in toluene (4 mL) and DMF (1 mL) was added Cs$_2$CO$_3$ (247 mg, 0.76 mmol) and Pd(PPh$_3$)$_4$ (23 mg, 0.02 mmol) under N$_2$. After being heated with stirring at 140° C. under N$_2$ atmosphere for 30 minutes in a microwave reactor, the resulting reaction mixture was filtered and the filtrate was purified by prep-HPLC to give 4-methyl-6-(4-methylsulfonylphenyl)-2-pyrimidin-2-yl-7,8-dihydro-5H-pyrido[4,3-d]pyrimidine (29 mg). $^1$H NMR (400 MHz, CDCl$_3$): δ 8.85-8.97 (m, 1H), 8.76 (s, 1H), 8.52-8.62 (m, 1H), 7.88-7.98 (m, 1H), 7.42-7.52 (m, 2H), 6.53-6.60 (m, 1H), 6.40-6.46 (m, 1H), 4.61 (s, 2H), 3.98 (s, 3H), 3.79-3.87 (m, 2H), 3.29-3.36 (m, 2H). MS obsd. (ESI$^+$) [(M+H)$^+$]: 381.

Example 88: N-methyl-6-(4-methylsulfonylphenyl)-2-pyrimidin-2-yl-7,8-dihydro-5H-pyrido[4,3-d]pyrimidin-4-amine

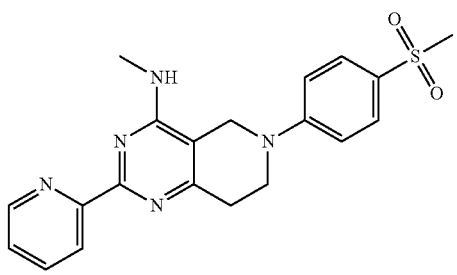 [SMILES: CNc1nc(-c2ccccn2)nc2c1CN(c1ccc(S(C)(=O)=O)cc1)CC2]

To a solution of 4-chloro-6-(4-methylsulfonylphenyl)-2-pyrimidin-2-yl-7,8-dihydro-5H-pyrido[4,3-d]pyrimidine (60 mg, 0.05 mmol) in MeOH (2 mL) was added MeNH$_2$ (0.1 mL, 33 wt. % in EtOH, 0.75 mmol). After being stirred at rt overnight, the resulting reaction mixture was filtered and the filtrate was purified by prep-HPLC to give N-methyl-6-(4-methylsulfonylphenyl)-2-pyrimidin-2-yl-7,8-dihydro-5H-pyrido[4,3-d]pyrimidin-4-amine (20 mg). $^1$H NMR (400 MHz, CDCl$_3$): δ 8.74-8.82 (m, 1H), 8.46-8.54 (m, 1H), 7.86-7.94 (m, 1H), 7.71-7.80 (m, 2H), 7.41-7.50 (m, 1H), 7.04-7.16 (m, 2H), 4.31 (s, 2H), 3.67-3.76 (m, 2H), 3.27 (s, 3H), 3.11-3.20 (m, 2H), 3.01 (s, 3H). MS obsd. (ESI$^+$) [(M+H)$^+$]: 396.

Example 89: 6-(4-methylsulfonylphenyl)-2-(2-pyridyl)-7,8-dihydro-5H-1,6-naphthyridine

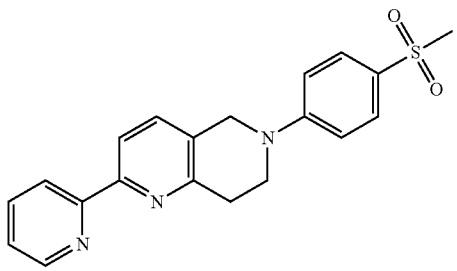 [SMILES: CS(=O)(=O)c1ccc(N2CCc3nc(-c4ccccn4)ccc3C2)cc1]

Step 1: Preparation of tert-butyl 2-(2-pyridyl)-7,8-dihydro-5H-1,6-naphthyridine-6-carboxylate

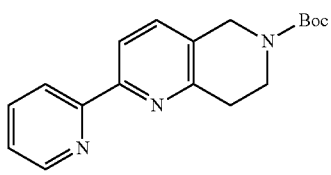 [SMILES: CC(C)(C)OC(=O)N1CCc2nc(-c3ccccn3)ccc2C1]

To a reaction vessel containing a solution of tert-butyl 2-chloro-7,8-dihydro-5H-1,6-naphthyridine-6-carboxylate (1.0 g, 3.72 mmol) in NMP (5 mL) was added tributyl(2-pyridyl)stannane (2.06 g, 5.58 mmol) and Pd$_2$Cl$_2$(PPh$_3$)$_2$ (260 mg, 0.37 mmol) under an argon atmosphere. The reaction vessel was sealed and heated at 150° C. for 30 minutes in a microwave reactor. After being cooled to rt, the resulting reaction mixture was diluted with water (10 mL) and extracted with DCM (20 mL) for three times. The combined organic layer was washed with water and brine, dried over anhydrous Na$_2$SO$_4$ and concentrated in vacuo. The residue was purified by flash column to afford tert-butyl 2-(2-pyridyl)-7,8-dihydro-5H-1,6-naphthyridine-6-carboxylate (1.1 g) as a white solid.

Step 2: Preparation of 2-(2-pyridyl)-5,6,7,8-tetrahydro-1,6-naphthyridine

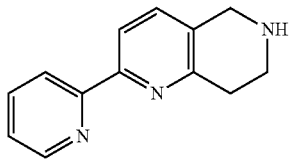 [SMILES: c1ccc(-c2ccc3c(n2)CCNC3)nc1]

A mixture of tert-butyl 2-(2-pyridyl)-7,8-dihydro-5H-1,6-naphthyridine-6-carboxylate (1.1 g, 3.53 mmol) and 2.0 N HCl/dioxane (20 mL) was stirred at rt for 16 hrs. The resulting mixture was concentrated in vacuo and the residue was diluted with H$_2$O (20 mL). The resulting mixture was stirred for 1 hr and extracted with DCM (50 mL) for two times. The combined organic layer was washed with brine and concentrated in vacuo to give 2-(2-pyridyl)-5,6,7,8-tetrahydro-1,6-naphthyridine (700 mg) as a white solid, which was used in the next step without further purification.

Step 3: Preparation of 6-(4-methylsulfonylphenyl)-2-(2-pyridyl)-7,8-dihydro-5H-1,6-naphthyridine

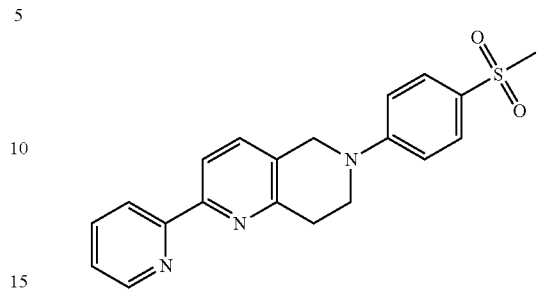

To a reaction vessel containing a solution of 2-(2-pyridyl)-5,6,7,8-tetrahydro-1,6-naphthyridine (200 mg, 0.936 mmol) in dioxane (5 mL) was added 1-bromo-4-methylsulfonyl-benzene (332 mg, 1.404 mmol), Cs$_2$CO$_3$ (892 mg, 6.56 mmol), Xantphos (20 mg, 0.04 mmol) and Pd$_2$(dba)$_3$ (20 mg, 0.02 mmol) under an argon atmosphere. The reaction vessel was sealed and heated at 120° C. for 20 minutes in a microwave reactor. The resulting reaction mixture was concentrated in vacuo and the residue was purified by the column chromatography to afford 6-(4-methylsulfonylphenyl)-2-(2-pyridyl)-7,8-dihydro-5H-1,6-naphthyridine (38 mg) as white solid. $^1$H NMR (400 MHz, CDCl$_3$): δ 3.03 (s, 3H) 3.27 (t, 2H) 3.85 (t, 2H) 4.62 (s, 2H) 7.01 (d, 2H) 7.32 (dd, 1H) 7.64 (d, 1H) 7.78-7.87 (m, 3H) 8.27 (d, 1H) 8.40 (d, 1H) 8.70 (d, 1H). MS obsd. (ESI$^+$) [(M+H)$^+$]: 366.

Example 90: 6-(4-fluoro-3-methoxy-phenyl)-2-(2-pyridyl)-7,8-dihydro-5H-pyrido[4,3-d]pyrimidine

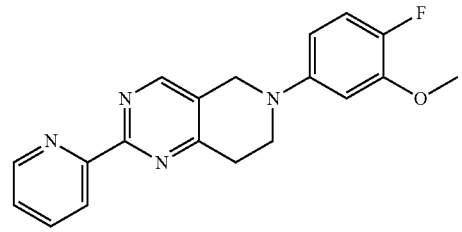 [SMILES: COc1cc(N2CCc3nc(-c4ccccn4)ncc3C2)ccc1F]

Step 1: Preparation of 8-(4-fluoro-3-methoxy-phenyl)-1,4-dioxa-8-azaspiro[4.5]decane

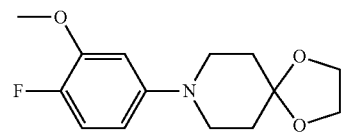 [SMILES: COc1cc(N2CCC3(CC2)OCCO3)ccc1F]

To a mixture of 4-bromo-1-fluoro-2-methoxy-benzene (1.86 g, 9.1 mmol) and 1,4-dioxa-8-azaspiro[4.5]decane (1.0 g, 7.0 mmol) in dioxane (20 mL) was added t-BuONa (1010 mg, 10.5 mmol), Pd$_2$(dba)$_3$ (128 mg, 0.14 mmol) and Ruphos (130 mg, 0.28 mmol) under N$_2$. After being heated with stirring at 100° C. overnight, the resulting reaction mixture was cooled to rt, diluted with H₂O (50 mL) and extracted with EA (50 mL) for three times. The combined organic layer was washed with brine (50 mL), dried over anhydrous Na₂SO₄ and concentrated in vacuo to give 8-(4-fluoro-3-methoxy-phenyl)-1,4-dioxa-8-azaspiro[4.5]decane (1200 mg), which was used in the next step without further purification.

Step 2: Preparation of 1-(4-fluoro-3-methoxy-phenyl)piperidin-4-one

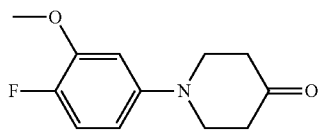 [SMILES: COc1cc(N2CCC(=O)CC2)ccc1F]

A mixture of 8-(4-fluoro-3-methoxy-phenyl)-1,4-dioxa-8-azaspiro[4.5]decane (1200 mg, 1.66 mmol) and 44% formic acid (20 mL) was heated with stirring at 90° C. for 8 hrs. The resulting reaction mixture was concentrated in vacuo, diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 1-(4-fluoro-3-methoxy-phenyl)piperidin-4-one (1000 mg) as brown oil, which was used in the next step without further purification.

Step 3: Preparation of 6-(4-fluoro-3-methoxy-phenyl)-2-(2-pyridyl)-7,8-dihydro-5H-pyrido[4,3-d]pyrimidine

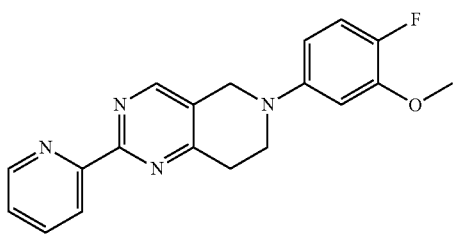 [SMILES: COc1cc(N2CCc3nc(-c4ccccn4)ncc3C2)ccc1F]

A mixture of crude 1-(4-fluoro-3-methoxy-phenyl)piperidin-4-one (1000 mg, 4.49 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (710 mg, 4.49 mmol) and K₂CO₃ (1240 mg, 8.98 mmol) successively. After being heated with stirring at 80° C. overnight, the resulting reaction mixture was cooled to rt and purified by prep-HPLC to give 6-(4-fluoro-3-methoxy-phenyl)-2-(2-pyridyl)-7,8-dihydro-5H-pyrido[4,3-d]pyrimidine (60 mg). ¹H NMR (400 MHz, CDCl₃): δ 8.88-8.87 (d, 1H), 8.71 (s, 1H), 8.54-8.52 (d, 1H), 7.91-7.87 (m, 1H), 7.44-7.28 (m, 1H), 7.07-7.02 (m, 1H), 6.71-6.70 (m, 1H), 6.69-6.54 (m, 1H), 4.41 (s, 2H), 3.95 (s, 3H), 3.65-3.63 (m, 2H), 3.25-3.30 (m, 2H). MS obsd. (ESI⁺) [(M+H)⁺]: 337.

Example 91: 6-(3-fluoro-5-methoxy-phenyl)-2-(2-pyridyl)-7,8-dihydro-5H-pyrido[4,3-d]pyrimidine

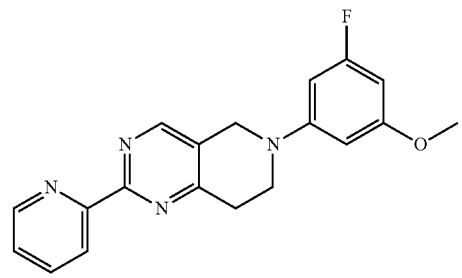 [SMILES: COc1cc(F)cc(N2CCc3nc(-c4ccccn4)ncc3C2)c1]

Step 1: Preparation of 8-(3-fluoro-5-methoxy-phenyl)-1,4-dioxa-8-azaspiro[4.5]decane

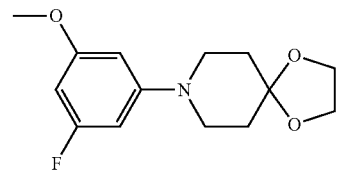 [SMILES: COc1cc(F)cc(N2CCC3(CC2)OCCO3)c1]

To a mixture of 4-bromo-1-fluoro-2-methoxy-benzene (930 mg, 9.1 mmol) and 1,4-dioxa-8-azaspiro[4.5]decane (500 mg, 3.5 mmol) in dioxane (20 mL) was added t-BuONa (500 mg, 5.2 mmol), Pd₂(dba)₃ (64 mg, 0.07 mmol) and Ruphos (65 mg, 0.14 mmol) under N₂. After being heated with stirring at 100° C. overnight, the resulting reaction mixture was cooled to rt. The resulting reaction mixture was diluted with H₂O (50 mL) and extracted with EA (50 mL) for three times. The combined organic layer was washed with brine (50 mL), dried over anhydrous Na₂SO₄ and concentrated in vacuo to give 8-(3-fluoro-5-methoxy-phenyl)-1,4-dioxa-8-azaspiro[4.5]decane (700 mg), which was used in the next step without further purification.

Step 2: Preparation of 1-(3-fluoro-5-methoxy-phenyl)piperidin-4-one

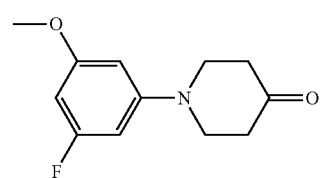 [SMILES: COc1cc(F)cc(N2CCC(=O)CC2)c1]

To a flask containing crude 8-(3-fluoro-5-methoxy-phenyl)-1,4-dioxa-8-azaspiro[4.5]decane (700 mg, 2.62 mmol) was added 44% formic acid (20 mL). After being heated with stirring at 90° C. for 8 hrs, the resulting reaction mixture was concentrated in vacuo. The residue was diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 1-(3- fluoro-5-methoxy-phenyl)piperidin-4-one (580 mg) as brown oil, which was used in the next step without further purification.

Step 3: Preparation of 6-(3-fluoro-5-methoxy-phenyl)-2-(2-pyridyl)-7,8-dihydro-5H-pyrido[4,3-d]pyrimidine

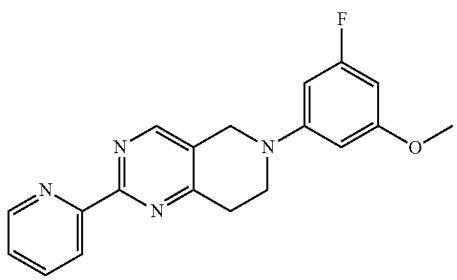 [SMILES: COc1cc(F)cc(N2CCc3nc(-c4ccccn4)ncc3C2)c1]

A mixture of 1-(3-fluoro-5-methoxy-phenyl)piperidin-4-one (580 mg, 2.62 mmol) and DMFDMA (10 mL) was heated with stirring at 90° C. for 3 hrs. The resulting reaction mixture was concentrated in vacuo and the residue was dissolved in EtOH (20 mL). To the solution was added pyridine-2-carboxamidine hydrochloride (410 mg, 2.62 mmol) and $K_2CO_3$ (720 mg, 5.24 mmol) successively. After being heated with stirring at 80° C. overnight, the resulting reaction mixture was cooled to rt and purified by prep-HPLC to give 6-(3-fluoro-5-methoxy-phenyl)-2-(2-pyridyl)-7,8-dihydro-5H-pyrido[4,3-d]pyrimidine (60 mg). $^1$H NMR (400 MHz, $CDCl_3$): δ 3.27 (t, 2H), 3.70 (t, 2H), 3.81 (s, 3H), 4.46 (s, 2H), 6.18 (d, 1H), 6.29-6.38 (m, 2H), 7.38-7.44 (m, 1H), 7.84-7.91 (m, 1H), 8.51 (d, 1H), 8.70 (s, 1H), 8.86 (d, 1H). MS obsd. (ESI$^+$) [(M+H)$^+$]: 337.

Example 92: 6-(3-methoxyphenyl)-2-(2-pyridyl)-7,8-dihydro-5H-pyrido[4,3-d]pyrimidine

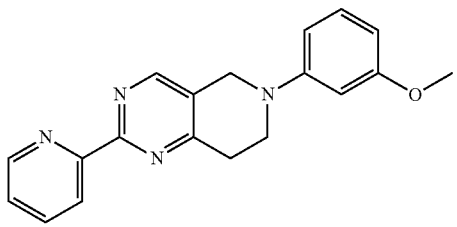 [SMILES: COc1cccc(N2CCc3nc(-c4ccccn4)ncc3C2)c1]

Step 1: Preparation of 8-(3-methoxyphenyl)-1,4-dioxa-8-azaspiro[4.5]decane

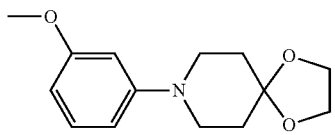 [SMILES: COc1cccc(N2CCC3(CC2)OCCO3)c1]

To a mixture of 4-bromo-1-fluoro-2-methoxy-benzene (5.09 g, 27.2 mmol) and 1,4-dioxa-8-azaspiro[4.5]decane (3.0 g, 20.9 mmol) in dioxane (20 mL) was added t-BuONa (3.02 g, 20.9 mmol), $Pd_2(dba)_3$ (600 mg, 0.66 mmol) and Ruphos (400 mg, 1.32 mmol) under $N_2$. After being heated with stirring at 100° C. overnight, the resulting reaction mixture was cooled to rt, diluted with $H_2O$ (50 mL) and extracted with EA (50 mL) for three times. The combined organic layer was washed with brine (50 mL), dried over anhydrous $Na_2SO_4$ and concentrated in vacuo to give crude 8-(3-methoxyphenyl)-1,4-dioxa-8-azaspiro[4.5]decane (3.8 g), which was used in the next step without further purification.

Step 2: Preparation of 1-(3-methoxyphenyl)piperidin-4-one

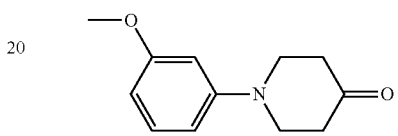

A mixture of crude 8-(3-methoxyphenyl)-1,4-dioxa-8-azaspiro[4.5]decane (3.8 g, 15.26 mmol) and 44% formic acid (30 mL) was heated with stirring at 90° C. for 8 hrs. The reaction mixture was concentrated in vacuo, diluted with sat. aqueous solution of $NaHCO_3$ (20 mL) and extracted with EA (30 mL) for three times. The combined organic layer was washed with brine (50 mL), dried over anhydrous $Na_2SO_4$ and concentrated in vacuo to give 1-(3-methoxyphenyl)-piperidin-4-one (3.1 mg) as brown oil, which was used in the next step without further purification.

Step 3: Preparation of 6-(3-methoxyphenyl)-2-(2-pyridyl)-7,8-dihydro-5H-pyrido[4,3-d]pyrimidine

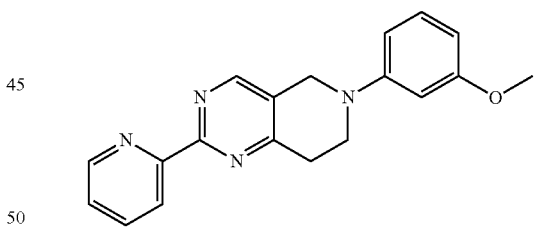

A mixture of 1-(3-methoxyphenyl)piperidin-4-one (200 mg, 0.98 mmol) and DMFDMA (10 mL) was heated with stirring at 90° C. for 3 hrs. The resulting reaction mixture was concentrated in vacuo and the residue was dissolved in EtOH (10 mL). To the solution was added pyridine-2-carboxamidine hydrochloride (155 mg, 0.98 mmol) and $K_2CO_3$ (270 mg, 1.96 mmol) successively. After being heated with stirring at 80° C. overnight, the reaction mixture was cooled to rt and purified by prep-HPLC to give 6-(3-methoxyphenyl)-2-(2-pyridyl)-7,8-dihydro-5H-pyrido[4,3-d]pyrimidine (40 mg). $^1$H NMR (400 MHz, $CDCl_3$): δ 3.11-3.17 (m, 2H), 3.68-3.77 (m, 5H), 4.53 (s, 2H), 6.36-6.46 (m, 2H), 6.42 (s, 1H), 6.61-6.70 (m, 1H), 7.16 (t, 1H), 7.66 (s, 1H), 8.11 (s, 1H), 8.51 (s, 1H), 8.76-8.84 (m, 2H). MS obsd. (ESI$^+$) [(M+H)$^+$]: 319.

Example 93: 3-[2,3-difluoro-5-[2-(2-pyridyl)-7,8-dihydro-5H-pyrido[4,3-d]pyrimidin-6-yl]phenoxy]propan-1-ol

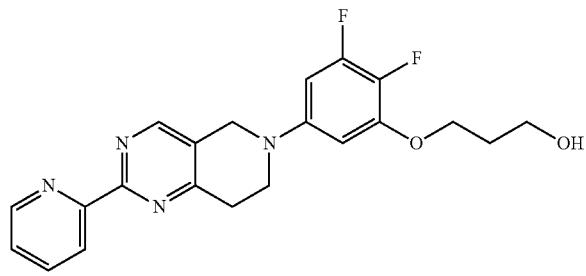 [SMILES: OCCCOc1cc(N2CCc3nc(-c4ccccn4)ncc3C2)cc(F)c1F]

Step 1: Preparation of 1-(3-benzyloxypropoxy)-5-bromo-2,3-difluoro-benzene

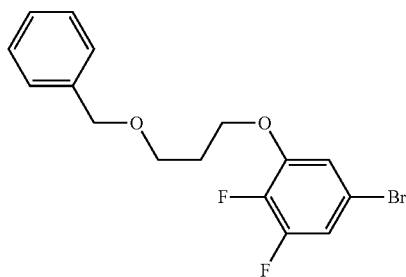 [SMILES: Fc1cc(Br)cc(OCCCOCc2ccccc2)c1F]

A mixture of 5-bromo-2,3-difluoro-phenol (1.0 g, 4.78 mmol), 3-bromopropoxy-methylbenzene (1.31 g, 5.74 mmol) and Cs₂CO₃ (2.34 g, 7.17 mmol) in MeCN (10 mL) was heated with stirring at 80° C. for 16 hrs. The resulting mixture was filtered and the filtrate was concentrated in vacuo. The residue was diluted with DCM (100 mL), washed with H₂O (30 mL) and brine (30 mL), dried over anhydrous Na₂SO₄ and concentrated in vacuo to give crude 1-(3-benzyloxypropoxy)-5-bromo-2,3-difluoro-benzene (1.25 g), which was used in the next step without further purification.

Step 2: Preparation of 8-[3-(3-benzyloxypropoxy)-4,5-difluoro-phenyl]-1,4-dioxa-8-azaspiro[4.5]decane

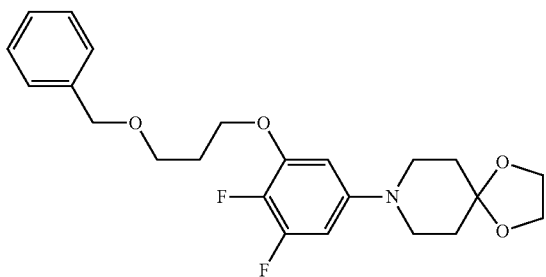 [SMILES: Fc1cc(N2CCC3(CC2)OCCO3)cc(OCCCOCc2ccccc2)c1F]

To a mixture of 1-(3-benzyloxypropoxy)-5-bromo-2,3-difluoro-benzene (1.25 g, 5.45 mmol) and 1,4-dioxa-8-azaspiro[4.5]decane (600 mg, 4.19 mmol) in dioxane (20 mL) was added t-BuONa (600 mg, 6.29 mmol), Pd₂(dba)₃ (120 mg, 0.13 mmol) and Ruphos (80 mg, 0.26 mmol) under N₂. After being heated with stirring at 100° C. overnight, the resulting reaction mixture was cooled to rt, diluted with H₂O (50 mL) and extracted with EA (50 mL) for three times. The combined organic layer was washed with brine (50 mL), dried over anhydrous Na₂SO₄ and concentrated in vacuo to give crude 8-[3-(3-benzyloxypropoxy)-4,5-difluoro-phenyl]-1,4-dioxa-8-azaspiro[4.5]decane (800 mg), which was used in the next step without further purification.

Step 3: Preparation of 1-[3-(3-benzyloxypropoxy)-4,5-difluoro-phenyl]piperidin-4-one

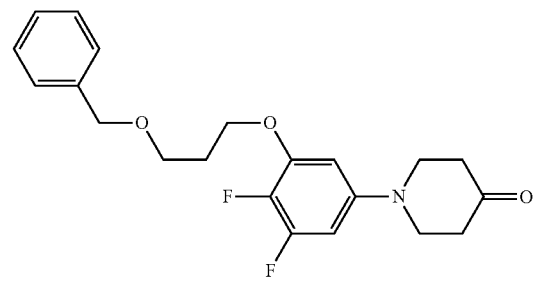 [SMILES: O=C1CCN(c2cc(F)c(F)c(OCCCOCc3ccccc3)c2)CC1]

A mixture of 8-[3-(3-benzyloxypropoxy)-4,5-difluoro-phenyl]-1,4-dioxa-8-azaspiro[4.5]decane (700 mg, 1.67 mmol) and 44% formic acid (10 mL) was heated with stirring at 90° C. for 8 hrs. The resulting reaction mixture was concentrated in vacuo, diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 1-[3-(3-benzyloxypropoxy)-4,5-difluoro-phenyl]piperidin-4-one (650 mg) as a brown oil, which was used in the next step without further purification.

Step 4: Preparation of 6-[3,4-difluoro-5-(4-phenylbutoxy)phenyl]-2-(2-pyridyl)-7,8-dihydro-5H-pyrido[4,3-d]pyrimidine

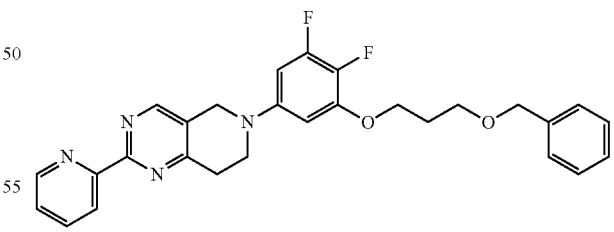

A mixture of 1-[3-(3-benzyloxypropoxy)-4,5-difluoro-phenyl]piperidin-4-one (600 mg, 1.6 mmol) and DMFDMA (10 mL) was heated with stirring at 90° C. for 3 hrs. The reaction mixture was concentrated in vacuo and the residue was dissolved in EtOH (10 mL). To the solution was added pyridine-2-carboxamidine hydrochloride (250 mg, 1.6 mmol) and K₂CO₃ (440 mg, 3.2 mmol) successively. After being heated with stirring at 80° C. overnight, the resulting reaction mixture was cooled to rt and purified by prep-HPLC to give 6-[3-(3-benzyloxypropoxy)-4,5-difluoro-phenyl]-2-(2-pyridyl)-7,8-dihydro-5H-pyrido[4,3-d]pyrimidine (400 mg).

Step 5: Preparation of 3-[2,3-difluoro-5-[2-(2-pyridyl)-7,8-dihydro-5H-pyrido[4,3-d]pyrimidin-6-yl]phenoxy]propan-1-ol

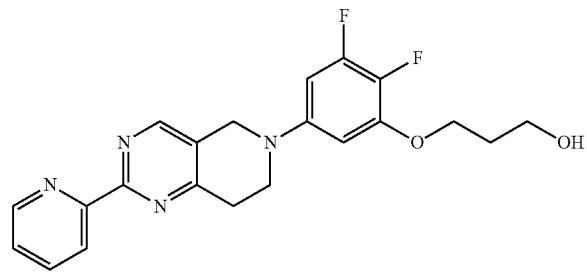 [SMILES: OCCCOc1cc(N2CCc3nc(-c4ccccn4)ncc3C2)cc(F)c1F]

To a solution of 6-[3-(3-benzyloxypropoxy)-4,5-difluoro-phenyl]-2-(2-pyridyl)-7,8-dihydro-5H-pyrido[4,3-d]pyrimidine (360 mg, 0.73 mmol) in DCM (5 mL) was added $BCl_3$ (1.46 mL, 1.46 mmol) at −70° C. After being stirred at −70° C. for 3 hrs, the reaction was quenched with sat. aqueous solution of $NaHCO_3$ (30 mL). The resulting mixture was extracted with DCM (100 mL). The organic layer was washed with brine, dried over anhydrous $Na_2SO_4$ and concentrated in vacuo. The residue was purified by prep-HPLC to give 3-[2,3-difluoro-5-[2-(2-pyridyl)-7,8-dihydro-5H-pyrido[4,3-d]pyrimidin-6-yl]phenoxy]propan-1-ol (35 mg) as a gray solid. $^1$H NMR (400 MHz, $CDCl_3$): δ 8.86 (d, 1H), 8.70 (s, 1H), 8.52 (d, 1H), 7.91-7.87 (m, 1H), 7.44-7.36 (m, 1H), 6.36-6.51 (m, 2H), 4.42 (s, 2H), 4.39 (t, 2H), 3.91 (t, 2H), 3.62 (t, 2H), 3.28 (t, 2H), 2.01-2.16 (m, 2H). MS obsd. (ESI$^+$) [(M+H)$^+$]: 399.

Example 94: 2-[2,3-difluoro-5-[2-(2-pyridyl)-7,8-dihydro-5H-pyrido[4,3-d]pyrimidin-6-yl]phenoxy]ethanol

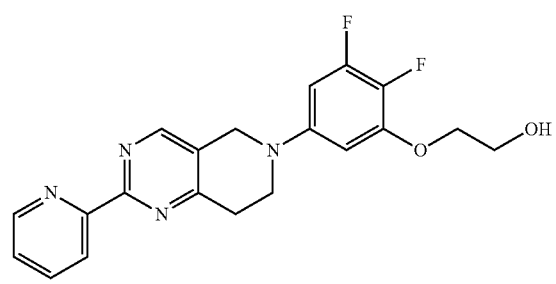 [SMILES: OCCOc1cc(N2CCc3nc(-c4ccccn4)ncc3C2)cc(F)c1F]

Step 1: Preparation of 1-(2-benzyloxyethoxy)-5-bromo-2,3-difluoro-benzene

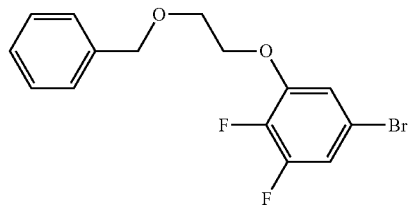 [SMILES: Fc1cc(Br)cc(OCCOCc2ccccc2)c1F]

A mixture of 5-bromo-2,3-difluoro-phenol (1.5 g, 7.21 mmol), 2-bromoethoxymethylbenzene (1.85 g, 8.65 mmol) and $Cs_2CO_3$ (3.53 g, 10.82 mmol) in MeCN (15 mL) was heated with stirring at 80° C. for 16 hrs. The mixture was filtered and the filtrate was concentrated in vacuo. The residue was diluted with DCM (100 mL), washed with $H_2O$ (30 mL) and brine (30 mL), dried over anhydrous $Na_2SO_4$ and concentrated in vacuo to give 1-(2-benzyloxyethoxy)-5-bromo-2,3-difluoro-benzene (1.6 g), which was used in the next step without further purification.

Step 2: Preparation of 8-[3-(2-benzyloxyethoxy)-4,5-difluoro-phenyl]-1,4-dioxa-8-azaspiro[4.5]decane

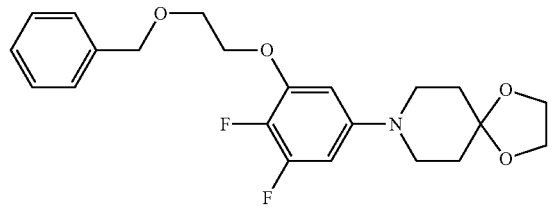 [SMILES: Fc1cc(N2CCC3(CC2)OCCO3)cc(OCCOCc2ccccc2)c1F]

To a mixture of 1-(2-benzyloxyethoxy)-5-bromo-2,3-difluoro-benzene (3.11 g, 9.09 mmol) and 1,4-dioxa-8-azaspiro[4.5]decane (1.0 g, 6.99 mmol) in dioxane (20 mL) was added t-BuONa (1.0 g, 10.49 mmol), $Pd_2(dba)_3$ (120 mg, 0.13 mmol) and Ruphos (80 mg, 0.26 mmol) under $N_2$. After being heated with stirring at 100° C. overnight, the resulting reaction mixture was cooled to rt, diluted with $H_2O$ (50 mL) and extracted with EA (50 mL) for three times. The combined organic layer was washed with brine (50 mL), dried over anhydrous $Na_2SO_4$ and concentrated in vacuo to give 8-[3-(2-benzyloxyethoxy)-4,5-difluoro-phenyl]-1,4-dioxa-8-azaspiro[4.5]decane (900 mg), which was used in the next step without further purification.

Step 3: Preparation of 1-[3-(2-benzyloxyethoxy)-4,5-difluoro-phenyl]piperidin-4-one

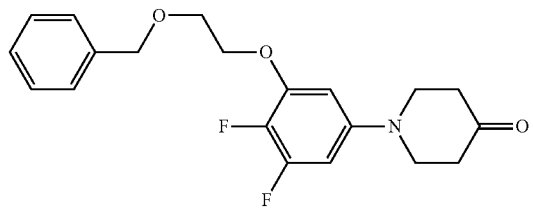 [SMILES: O=C1CCN(c2cc(F)c(F)c(OCCOCc3ccccc3)c2)CC1]

A mixture of crude 8-[3-(2-benzyloxyethoxy)-4,5-difluoro-phenyl]-1,4-dioxa-8-azaspiro[4.5]decane (850 mg, 2.1 mmol) and 44% formic acid (10 mL) was heated with stirring at 90° C. for 8 hrs. The resulting reaction mixture was concentrated in vacuo, diluted with sat. aqueous solution of NaHCO₃ (20 mL) and extracted with EA (30 mL) for three times. The combined organic layer was washed with brine (50 mL), dried over anhydrous Na₂SO₄ and concentrated in vacuo to give 1-[3-(2-benzyloxyethoxy)-4,5-difluoro-phenyl]piperidin-4-one (760 mg) as brown oil, which was used in the next step without further purification.

Step 4: Preparation of 6-[3-(2-benzyloxyethoxy)-4,5-difluoro-phenyl]-2-(2-pyridyl)-7,8-dihydro-5H-pyrido[4,3-d]pyrimidine

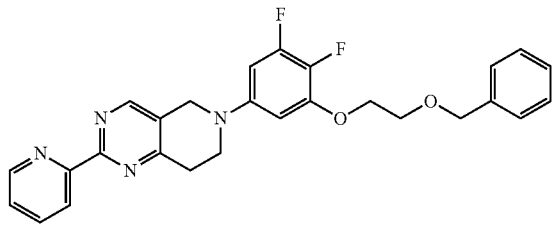 [SMILES: Fc1cc(N2CCc3nc(-c4ccccn4)ncc3C2)cc(OCCOCc2ccccc2)c1F]

A mixture of 1-[3-(2-benzyloxyethoxy)-4,5-difluoro-phenyl]piperidin-4-one (760 mg, 2.1 mmol) and DMFDMA (10 mL) was heated with stirring at 90° C. for 3 hrs. The resulting reaction mixture was concentrated in vacuo and the residue was dissolved in EtOH (10 mL). To the solution was added pyridine-2-carboxamidine hydrochloride (330 mg, 2.1 mmol) and K₂CO₃ (580 mg, 4.2 mmol) successively. After being heated with stirring at 80° C. overnight, the resulting reaction mixture was cooled to rt and purified by prep-HPLC to give 6-[3-(2-benzyloxyethoxy)-4,5-difluoro-phenyl]-2-(2-pyridyl)-7,8-dihydro-5H-pyrido[4,3-d]pyrimidine (600 mg).

Step 5: Preparation of 2-[2,3-difluoro-5-[2-(2-pyridyl)-7,8-dihydro-5H-pyrido[4,3-d]pyrimidin-6-yl]phenoxy]ethanol

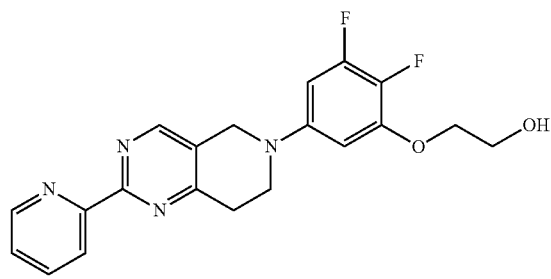 [SMILES: OCCOc1cc(N2CCc3nc(-c4ccccn4)ncc3C2)cc(F)c1F]

To a solution of 6-[3-(2-benzyloxyethoxy)-4,5-difluoro-phenyl]-2-(2-pyridyl)-7,8-dihydro-5H-pyrido[4,3-d]pyrimidine (2.0 g, crude, 0.42 mmol) in DCM (3 mL) was added BCl₃ (0.84 mmol) at −70° C. and the resulting mixture was slowly warmed to 0° C. and heated with stirring for 3 hrs at 0° C. The reaction was quenched with sat. aqueous solution of NaHCO₃. The resulting mixture was diluted with DCM, washed with water and brine, dried over anhydrous Na₂SO₄ and concentrated in vacuo. The residue was purified by prep-HPLC to give 2-[2,3-difluoro-5-[2-(2-pyridyl)-7,8-dihydro-5H-pyrido[4,3-d]pyrimidin-6-yl]phenoxy]ethanol (35 mg). ¹H NMR (400 MHz, CDCl₃): δ 3.28 (t, 2H), 3.62 (t, 2H), 3.97-4.05 (m, 2H) 4.16-4.24 (m, 2H) 4.38 (s, 2H) 6.39-6.49 (m, 2H) 7.42 (dd, 1H), 7.88 (td, 1H), 8.51 (d, 1H), 8.70 (s, 1H), 8.85 (d, 1H). MS obsd. (ESI⁺) [(M+H)⁺]: 385.

Example 95:2-(3,4-difluoro-5-methoxy-phenyl)-6-pyrimidin-2-yl-3,4-dihydro-1H-2,7-naphthyridine

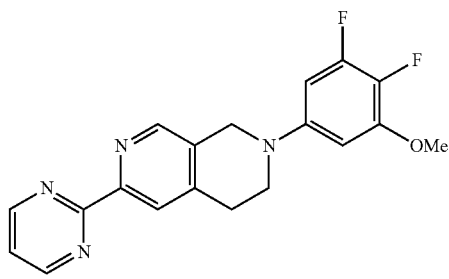 [SMILES: COc1cc(N2CCc3cc(-c4ncccn4)ncc3C2)cc(F)c1F]

Step 1: Preparation of 6-methoxypyridine-3-carbaldehyde

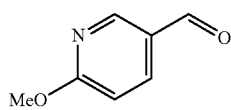

To a solution of 5-bromo-2-methoxy-pyridine (95.0 g, 0.51 mol) in THF (2.0 L) was added n-BuLi (212 ml, 0.53 mol) at −78° C. slowly. After the mixture was stirred at −78° C. for 0.5 hr, to the reaction mixture was added anhydrous DMF (44.3 g, 0.61 mmol) slowly. The reaction mixture was stirred at −78° C. for another 1 hr and then the reaction was quenched with sat. aqueous solution of NH₄Cl. The resulting mixture was extracted with EA. The organic layer was washed with brine, dried over anhydrous Na₂SO₄ and concentrated in vacuo. The residue was purified by flash column to give 6-methoxypyridine-3-carbaldehyde (66.7 g) as a light yellow solid.

Step 2: Preparation of 4-iodo-6-methoxy-pyridine-3-carbaldehyde

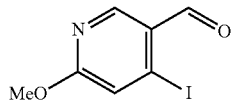

To a cooled and stirred solution of (CH₃)₂NCH₂CH₂NHCH₃ (4.5 g, 0.044 mol) in THF (50 mL) was added n-BuLi (29.0 ml, 2.5 M, 0.073 mol) at −78° C. slowly. The mixture was stirred at −78° C. for 15 minutes. To the resulting mixture was added a solution of 6-methoxypyridine-3-carbaldehyde (5.0 g, 0.036 mol) in THF (50 ml) slowly and the resulting mixture was stirred at −78° C. for 30 minutes. Then to the resulting reaction mixture was added n-BuLi (29.09 ml, 2.5 M, 0.073 mol) slowly and the resulting mixture was stirred at −78° C. for another 1 hr. The resulting reaction mixture was added into a stirred solution of I$_2$ (19.4 g, 0.077 mol) in THF (200 ml) slowly. The resulting mixture was warmed up to rt and stirred at rt for 16 hrs. The reaction was then quenched with sat. aqueous solution of NH$_4$Cl and the resulting mixture was extracted with EA. The organic layer was washed with brine dried over anhydrous Na$_2$SO$_4$ and concentrated in vacuo. The residue purified by the flash column to give 4-iodo-6-methoxy-pyridine-3-carbaldehyde (800 mg) as a yellow solid.

Step 3: Preparation of 6-methoxy-4-(2-trimethylsilylethynyl)pyridine-3-carbaldehyde

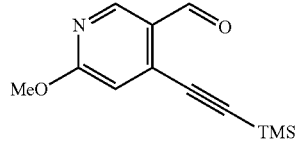 [SMILES: COc1cc(C#C[Si](C)(C)C)c(C=O)cn1]

A mixture of 4-iodo-6-methoxy-pyridine-3-carbaldehyde (2.38 g, 9.05 mmol), ethynyltrimethylsilane (1.78 g, 18.10 mmol), Et$_3$N (2.75 g, 27.15 mmol), CuI (172 mg, 0.90 mmol) and Pd(PPh$_3$)$_2$Cl$_2$ (318 mg, 0.45 mmol) in THF (50 mL) was heated with stirring at 60° C. for 2 hrs. The resulting reaction mixture was concentrated in vacuo and the residue was purified by flash column to afford 6-methoxy-4-(2-trimethylsilylethynyl)pyridine-3-carbaldehyde (1.18 g) as a yellow solid.

Step 4: preparation of 3-methoxy-2,7-naphthyridine

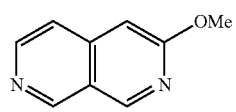 [SMILES: COc1cc2ccncc2cn1]

A mixture of 6-methoxy-4-(2-trimethylsilylethynyl)pyridine-3-carbaldehyde (5.6 g, 5.57 mmol) and sat. ammonia solution in EtOH (30 mL) was heated with stirring at 80° C. for 4 hrs. The resulting reaction mixture was concentrated in vacuo and the residue was purified by flash column to give 3-methoxy-2,7-naphthyridine (3 g) as an orange solid.

Step 5: Preparation of 6-methoxy-1,2,3,4-tetrahydro-2,7-naphthyridine

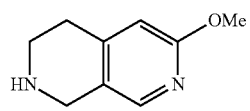

A mixture of 3-methoxy-2,7-naphthyridine (2 g, 12.5 mmol) and PtO$_2$ (200 mg) in MeOH (50 mL) was stirred at rt under H$_2$ (30 psi) for 16 hrs. The resulting reaction mixture was filtered and the filtrate was concentrated in vacuo to give 6-methoxy-1,2,3,4-tetrahydro-2,7-naphthyridine (1.7 g) as a yellow solid, which was used in the next step without further purification.

Step 6: Preparation of 2-(3,4-difluoro-5-methoxy-phenyl)-6-methoxy-3,4-dihydro-1H-2,7-naphthyridine

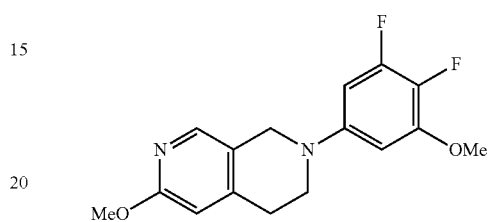

To a mixture of 6-methoxy-1,2,3,4-tetrahydro-2,7-naphthyridine (500 mg, 3.04 mmol) and 5-bromo-2,3-difluoroanisole (883 mg, 3.96 mmol) in dioxane (8 mL) was added t-BuONa (438 mg, 4.56 mmol), Pd$_2$(dba)$_3$ (40 mg, 0.04 mmol) and Ruphos (30 mg, 0.06 mmol) under N$_2$. After being heated with stirring at 100° C. for 12 hrs, the resulting reaction mixture was filtered. The filtrate was concentrated in vacuo, diluted with DCM (100 mL), washed with water (30 mL) and brine (30 mL), dried over anhydrous Na$_2$SO$_4$ and concentrated in vacuo. The residue was purified by flash column to give 2-(3,4-difluoro-5-methoxy-phenyl)-6-methoxy-3,4-dihydro-1H-2,7-naphthyridine (560 mg) as a gray solid.

Step 7: Preparation of 7-(3,4-difluoro-5-methoxy-phenyl)-6,8-dihydro-5H-2,7-naphthyridin-3-ol

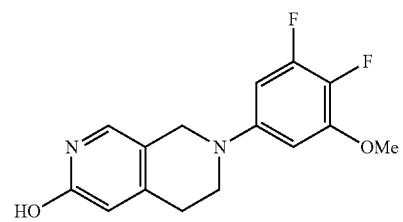 [SMILES: COc1cc(N2CCc3cc(O)ncc3C2)cc(F)c1F]

To a solution of 2-(3,4-difluoro-5-methoxy-phenyl)-6-methoxy-3,4-dihydro-1H-2,7-naphthyridine (800 mg, 2.61 mmol) in AcOH (15 mL) was added concentrated HBr (1.2 mL). The mixture was heated with stirring at 70° C. for 16 hrs. The resulting reaction mixture was concentrated in vacuo. The residue was stirred with a mixture of sat. aqueous solution of NaHCO$_3$ (50 mL) and DCM (50 mL). The formed solid was filtered and the filter cake was dried in vacuo to give 7-(3,4-difluoro-5-methoxy-phenyl)-6,8-dihydro-5H-2,7-naphthyridin-3-ol (350 mg) as a yellow solid.

Step 8: Preparation of [7-(3,4-difluoro-5-methoxy-phenyl)-6,8-dihydro-5H-2,7-naphthyridin-3-yl]trifluoromethanesulfonate

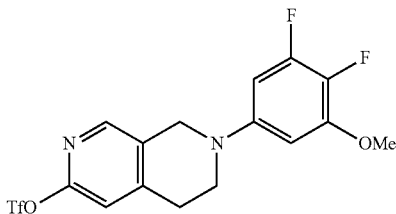 [SMILES: COc1cc(N2CCc3cc(OS(=O)(=O)C(F)(F)F)ncc3C2)cc(F)c1F]

To a solution of 7-(3,4-difluoro-5-methoxy-phenyl)-6,8-dihydro-5H-2,7-naphthyridin-3-ol (500 mg, 1.71 mmol) in DCM (10 mL) was added pyridine (675 mg, 8.55 mmol) and Tf$_2$O (1.45 g, 5.13 mmol). After being stirred at 20° C. for 3 hrs, the resulting reaction mixture was diluted with DCM (100 mL), washed with water (30 mL) and brine (30 mL), dried over anhydrous Na$_2$SO$_4$ and concentrated in vacuo. The residue was purified by flash column to give [7-(3,4-difluoro-5-methoxy-phenyl)-6,8-dihydro-5H-2,7-naphthyridin-3-yl]trifluoromethanesulfonate (350 mg) as a gray solid.

Step 9: Preparation of 2-(3,4-difluoro-5-methoxy-phenyl)-6-pyrimidin-2-yl-3,4-dihydro-1H-2,7-naphthyridine

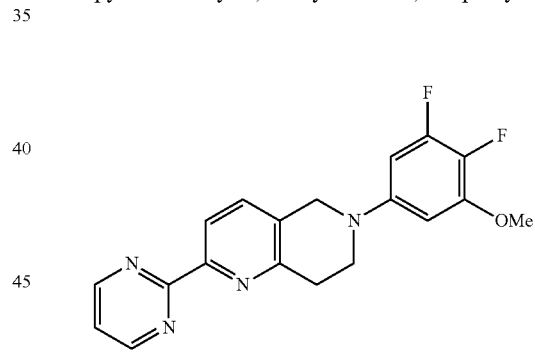

A mixture of [7-(3,4-difluoro-5-methoxy-phenyl)-6,8-dihydro-5H-2,7-naphthyridin-3-yl]trifluoromethanesulfonate (100 mg, 0.2 mmol), 2-(tributylstannyl)pyrimidine (130 mg, 0.3 mmol) and Pd(PPh$_3$)$_4$ (20 mg) in dioxane (1 mL) was heated with stirring at 130° C. for 20 minutes in a microwave reactor. The resulting mixture was filtered and the filtrate was concentrated in vacuo. The residue was purified by prep-HPLC to give 2-(3,4-difluoro-5-methoxy-phenyl)-6-pyrimidin-2-yl-3,4-dihydro-1H-2,7-naphthyridine (6 mg) as a gray solid. $^1$H NMR (400 MHz, CDCl$_3$): δ 9.07-9.14 (m, 2H), 8.95 (s, 1H), 7.71 (t, 1H), 6.54-6.68 (m, 2H), 4.67 (s, 2H), 3.93 (s, 3H), 3.71 (t, 2H), 3.41 (s, 2H). MS obsd. (ESI$^+$) [(M+H)$^+$]: 355.

Example 96: 2-(3,4-difluoro-5-methoxy-phenyl)-6-(2-pyridyl)-3,4-dihydro-1H-2,7-naphthyridine

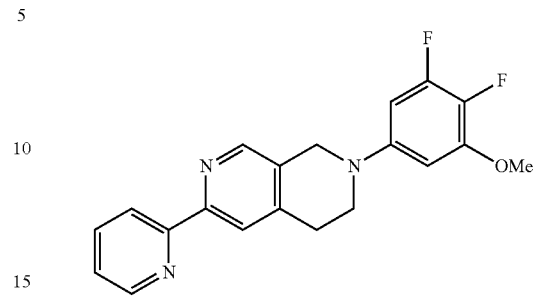

A mixture of [7-(3,4-difluoro-5-methoxy-phenyl)-6,8-dihydro-5H-2,7-naphthyridin-3-yl]trifluoromethanesulfonate (100 mg, 0.2 mmol), 2-(tributylstannyl)pyridine (130 mg, 0.3 mmol) and Pd(PPh$_3$)$_4$ (20 mg) in dioxane (1 mL) was heated with stirring at 130° C. for 20 minutes in a microwave reactor. The resulting reaction mixture was filtered and the filtrate was concentrated in vacuo. The residue was purified by prep-HPLC to give 2-(3,4-difluoro-5-methoxy-phenyl)-6-(2-pyridyl)-3,4-dihydro-1H-2,7-naphthyridine (15 mg) as a gray solid. $^1$H NMR (400 MHz, CDCl$_3$): δ 8.67 (d, 1H), 8.54 (s, 1H), 8.36 (d, 1H), 8.23 (s, 1H), 7.89-8.01 (m, 1H), 7.38-7.46 (m, 1H), 4.49 (s, 2H), 3.89 (s, 3H), 3.58 (t, J=6.0 Hz, 2H), 3.03 (t, J=6.0 Hz, 2H). MS obsd. (ESI$^+$) [(M+H)$^+$]: 354.

Example 97: 6-(3,4-difluoro-5-methoxy-phenyl)-2-pyrimidin-2-yl-7,8-dihydro-5H-1,6-naphthyridine

Step 1: Preparation of tert-butyl 2-benzyloxy-7,8-dihydro-5H-1,6-naphthyridine-6-carboxylate

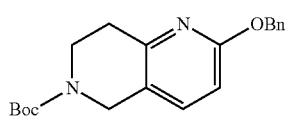 [SMILES: CC(C)(C)OC(=O)N1CCc2nc(OCc3ccccc3)ccc2C1]

To a solution of tert-butyl 2-chloro-7,8-dihydro-5H-1,6-naphthyridine-6-carboxylate (1.0 g, 3.7 mmol) in toluene (10 mL) was added KOH (0.6 g, 11.1 mmol) at 0° C. and the mixture was stirred for 0.5 hr. To the resulting mixture was added a solution of BnOH (0.34 g, 5.6 mmol) in toluene (10 mL) followed by 18-crown-6 (100 mg) at 0° C. The resulting mixture was heated with stirring at 130° C. for 2 hrs and then filtered. The filtrate was concentrated in vacuo. The residue was purified by flash column to give tert-butyl 2-benzyloxy-7,8-dihydro-5H-1,6-naphthyridine-6-carboxylate (1 g).

Step 2: Preparation of 2-benzyloxy-5,6,7,8-tetrahydro-1,6-naphthyridine

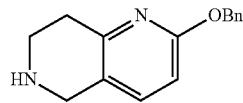 [SMILES: c1ccc(COc2ccc3c(n2)CCNC3)cc1]

A mixture of tert-butyl 2-benzyloxy-7,8-dihydro-5H-1,6-naphthyridine-6-carboxylate (800 mg, 2.4 mmol) and a solution of HCl in EA (1.0 N, 10 mL) was stirred at rt for 12 hrs. The resulting reaction mixture was concentrated in vacuo to give 2-benzyloxy-5,6,7,8-tetrahydro-1,6-naphthyridine (500 mg), which was used in the next step without further purification.

Step 3: Preparation of 2-benzyloxy-6-(3,4-difluoro-5-methoxy-phenyl)-7,8-dihydro-5H-1,6-naphthyridine

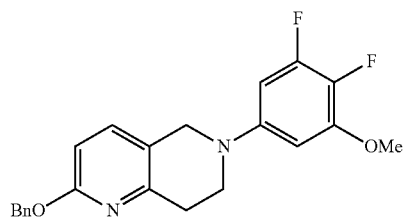 [SMILES: COc1cc(N2CCc3nc(OCc4ccccc4)ccc3C2)cc(F)c1F]

To a solution of 2-benzyloxy-5,6,7,8-tetrahydro-1,6-naphthyridine (500 mg, 2.4 mmol) and 5-bromo-1,2-difluoro-3-methoxy-benzene (696 mg, 3.1 mmol) in dioxane (10 mL) was added t-BuONa (345.6 mg, 3.6 mmol), Pd$_2$(dba)$_3$ (44 mg, 0.05 mmol) and RuPhos (34 mg, 0.07 mmol) under N$_2$. After being heated with stirring at 100° C. for 12 hrs, the resulting mixture was filtered and concentrated in vacuo. The residue was purified to give 2-benzyloxy-6-(3,4-difluoro-5-methoxy-phenyl)-7,8-dihydro-5H-1,6-naphthyridine (500 mg), which was used in the next step without further purification.

Step 4: preparation of 6-(3,4-difluoro-5-methoxy-phenyl)-7,8-dihydro-5H-1,6-naphthyridin-2-ol

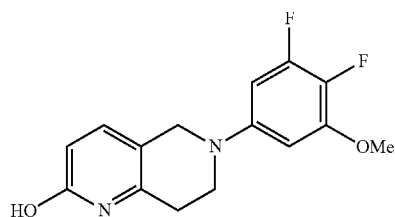 [SMILES: COc1cc(N2CCc3nc(O)ccc3C2)cc(F)c1F]

To a solution of 2-benzyloxy-6-(3,4-difluoro-5-methoxy-phenyl)-7,8-dihydro-5H-1,6-naphthyridine (400 mg, 1.04 mmol) in MeOH (3 mL) and EA (1 mL) was added Pd/C (40 mg). After being stirred at rt under H$_2$ (30 Psi) for 12 hrs, the resulting mixture was filtered and the filtrate was concentrated in vacuo to give crude 6-(3,4-difluoro-5-methoxy-phenyl)-7,8-dihydro-5H-1,6-naphthyridin-2-ol (300 mg), which was used in the next step without further purification.

Step 5: Preparation of [6-(3,4-difluoro-5-methoxy-phenyl)-7,8-dihydro-5H-1,6-naphthyridin-2-yl]trifluoromethanesulfonate

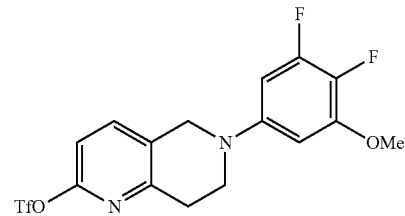 [SMILES: COc1cc(N2CCc3nc(OS(=O)(=O)C(F)(F)F)ccc3C2)cc(F)c1F]

To a solution of 6-(3,4-difluoro-5-methoxy-phenyl)-7,8-dihydro-5H-1,6-naphthyridin-2-ol (120 mg, 0.41 mmol) in DCM (2 mL) was added pyridine (2 mL) and Tf$_2$O (1.1 g, 4.1 mmol) at −30° C. After being stirred at 25° C. for 12 hrs, the reaction mixture was concentrated in vacuo and diluted with DCM. The resulting mixture was filtered and the filtrate was purified by prep-TLC to give [6-(3,4-difluoro-5-methoxy-phenyl)-7,8-dihydro-5H-1,6-naphthyridin-2-yl]trifluoromethanesulfonate (100 mg).

Step 6: Preparation o 6-(3,4-difluoro-5-methoxy-phenyl)-2-pyrimidin-2-yl-7,8-dihydro-5H-1,6-naphthyridine

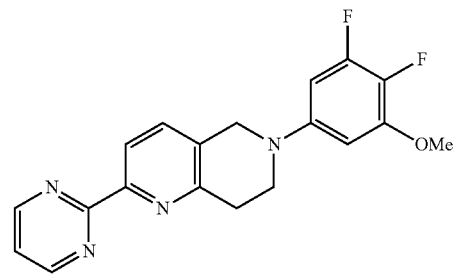 [SMILES: COc1cc(N2CCc3nc(-c4ncccn4)ccc3C2)cc(F)c1F]

To a solution of [6-(3,4-difluoro-5-methoxy-phenyl)-7,8-dihydro-5H-1,6-naphthyridin-2-yl]trifluoromethanesulfonate (160 mg, 0.37 mmol) in dioxane (2 mL) was added tributyl(pyrimidin-2-yl)stannane (139 mg, 0.57 mmol) and Pd(dppf)Cl$_2$ (16 mg) under N$_2$. The mixture was heated with stirring 130° C. for 0.5 hr in a microwave reactor. The resulting reaction mixture was purified by prep-HPLC to give 6-(3,4-difluoro-5-methoxy-phenyl)-2-pyrimidin-2-yl-7,8-dihydro-5H-1,6-naphthyridine (3.3 mg) as white solid. $^1$H NMR (400 MHz, CDCl$_3$): δ 9.14-9.13 (d, 2H), 8.92-8.90 (d, 1H), 8.63-8.61 (d, 1H), 7.75-7.72 (t, 1H), 6.69-6.62 (m, 2H), 4.68 (s, 2H), 3.95 (s, 3H), 3.81-3.78 (m, 2H), 3.56-3.53 (m, 2H). MS obsd. (ESI$^+$) [(M+H)$^+$]: 355.

Example 98: 6-(3-chloro-5-methoxy-phenyl)-2-pyrimidin-2-yl-7,8-dihydro-5H-pyrido[4,3-d]pyrimidine

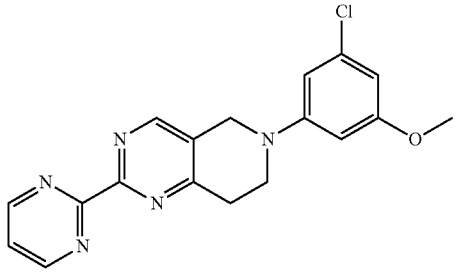

Step 1: Preparation of 8-(3-chloro-5-methoxy-phenyl)-1,4-dioxa-8-azaspiro[4.5]decane

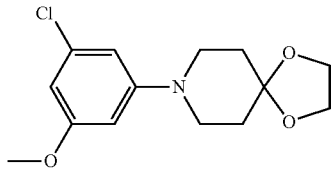 [SMILES: COc1cc(Cl)cc(N2CCC3(CC2)OCCO3)c1]

To a mixture of 1-bromo-3-chloro-5-methoxy-benzene (800 mg, 3.61 mmol) and 1,4-dioxa-8-azaspiro[4.5]decane (500 mg, 2.78 mmol) in dioxane (20 mL) was added t-BuONa (668 mg, 6.95 mmol), Pd$_2$(dba)$_3$ (51 mg, 0.05 mmol) and Ruphos (52 mg, 0.1 mmol) under N$_2$. After being heated with stirring at 100° C. overnight, the resulting reaction mixture was cooled to rt, diluted with H$_2$O (20 mL) and extracted with EA (50 mL) for three times. The combined organic layer was washed with brine (50 mL), dried over anhydrous Na$_2$SO$_4$ and concentrated in vacuo to give crude 8-(3-chloro-5-methoxy-phenyl)-1,4-dioxa-8-azaspiro[4.5]decane (700 mg), which was used in the next step without further purification.

Step 2: Preparation of 1-(3-chloro-5-methoxy-phenyl)piperidin-4-one

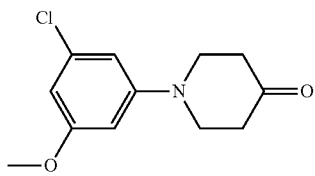 [SMILES: COc1cc(Cl)cc(N2CCC(=O)CC2)c1]

A solution of 8-(3-chloro-5-methoxy-phenyl)-1,4-dioxa-8-azaspiro[4.5]decane (700, 2.47 mmol) in 44% formic acid (30 mL) was heated with stirring at 90° C. for 2 hrs. The reaction mixture was concentrated in vacuo, diluted with sat. aqueous solution of NaHCO$_3$ and extracted with EA (30 mL) for three times. The combined organic layer was dried and concentrated in vacuo. The residue was purified by flash column to give 1-(3-chloro-5-methoxy-phenyl)piperidin-4-one (250 mg).

Step 3: Preparation of 6-(3-chloro-5-methoxy-phenyl)-2-pyrimidin-2-yl-7,8-dihydro-5H-pyrido[4,3-d]pyrimidine

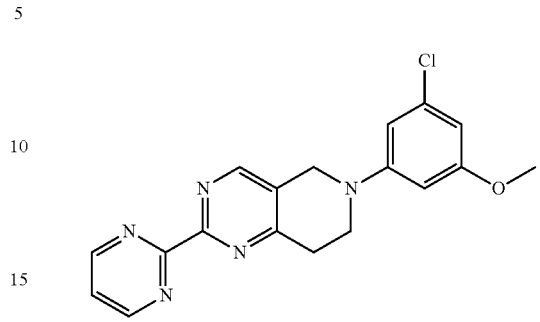

A mixture of 1-(3-chloro-5-methoxy-phenyl)piperidin-4-one (200 mg, 0.68 mmol), pyrimidine-2-carboxamidine hydrochloride (109 mg, 0.68 mmol) and K$_2$CO$_3$ (282 mg, 2.04 mmol) in MeOH (3 mL) was heated with stirring at 60° C. for 2 hrs. The resulting mixture was filtered and the filtrate was concentrated in vacuo, diluted with DCM, washed with brine, dried over anhydrous Na$_2$SO$_4$ and concentrated in vacuo. The residue was purified by prep-HPLC to give 6-(3-chloro-5-methoxy-phenyl)-2-pyrimidin-2-yl-7,8-dihydro-5H-pyrido[4,3-d]pyrimidine. $^1$H NMR (400 MHz, DMSO-d$_6$): δ 3.07 (t, 2H) 3.68-3.86 (m, 5H) 4.57 (s, 2H) 6.44 (s, 1H) 6.56 (s, 1H) 6.73 (s, 1H) 7.63 (t, 1H) 8.83 (s, 1H) 8.99 (d, 2H). MS obsd. (ESI$^+$) [(M+H)$^+$]: 354. 357.

Example 99: 6-(2-fluoro-6-methoxy-4-pyridyl)-2-pyrimidin-2-yl-7,8-dihydro-5H-pyrido[4,3-d]pyrimidine

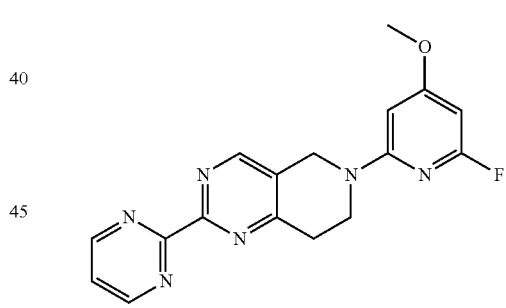

Step 1: Preparation of 2,6-difluoro-4-methoxy-pyridine

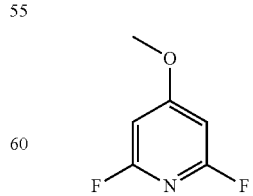

To a stirred solution of 2,4,6-trifluoropyridine (100.0 g, 0.75 mol) in MeOH (1 L) was added MeONa (81.2 g, 1.5 mol) at 0° C. After being stirred at 50° C. for 48 hrs, the resulting mixture was concentrated in vacuo. The residue was diluted with DCM (2 L) and the resulting mixture was filtered. The filtrate was washed with brine (500 mL), and then concentrated in vacuo to afford 2,6-difluoro-4-methoxy-pyridine (86.5 g) as a colorless oil which was used directly in the next step without further purification.

Step 2: Preparation of 8-(6-fluoro-4-methoxy-2-pyridyl)-1,4-dioxa-8-azaspiro[4.5]decane

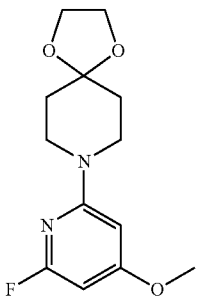 [SMILES: COc1cc(F)nc(N2CCC3(CC2)OCCO3)c1]

To a stirred solution of 1,4-dioxa-8-azaspiro[4.5]decane hydrochloride (110.0 g, 0.61 mol) in DMF (1 L) was added 2,6-difluoro-4-methoxy-pyridine (93.3 g, 0.64 mol) and K₂CO₃ (253.9 g, 1.84 mol) successively. After being heated with stirring at 90° C. for 12 hrs, the resulting mixture was diluted with EA (2.5 L), washed with H₂O (1 L) and brine (1 L), then dried over anhydrous Na₂SO₄ and concentrated in vacuo. The residue was purified by flash column to give 8-(6-fluoro-4-methoxy-2-pyridyl)-1,4-dioxa-8-azaspiro [4.5]decane (150.0 g) as a colorless oil.

Step 3: Preparation of 1-(6-fluoro-4-methoxy-2-pyridyl)piperidin-4-one

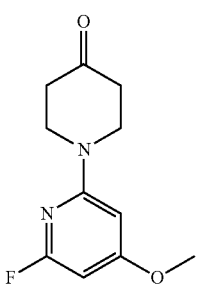 [SMILES: COc1cc(F)nc(N2CCC(=O)CC2)c1]

A mixture of 8-(6-fluoro-4-methoxy-2-pyridyl)-1,4-dioxa-8-azaspiro[4.5]decane (150.0 g, 0.56 mol), formic acid (750 mL) and H₂O (750 mL) was heated with stirring at 90° C. for 2 hrs. The resulting mixture was concentrated in vacuo and the residue was diluted with DCM (1.5 L). The resulting solution was washed with H₂O (500 mL) and brine (500 mL), then dried over anhydrous Na₂SO₄ and concentrated in vacuo. The residue was purified by flash column to give 1-(6-fluoro-4-methoxy-2-pyridyl)piperidin-4-one (100.0 g) as a colorless oil.

Step 4: Preparation of 6-(6-fluoro-4-methoxy-2-pyridyl)-2-pyrimidin-2-yl-7,8-dihydro-5H-pyrido[4,3-d]pyrimidine

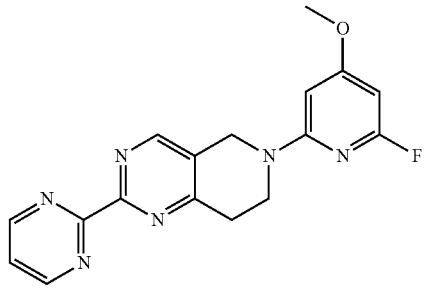 [SMILES: COc1cc(F)nc(N2CCc3nc(-c4ncccn4)ncc3C2)c1]

A solution of 1-(6-fluoro-4-methoxy-2-pyridyl)piperidin-4-one (100.0 g, 0.44 mol) in DMFDMA (1 L) was heated with stirring at 120° C. for 4 hrs. After being cooled down, the resulting reaction mixture was concentrated in vacuo. The residue was dissolved in MeOH (1.3 L) and to the solution was added pyrimidine-2-carboximidamide hydrochloride (88.6 g, 0.56 mol) and K₂CO₃ (160.8 g, 1.16 mol). After being heated with stirring at 80° C. for 2 hrs, the resulting mixture was diluted with DCM (1.5 L), then washed with H₂O (500 mL) and brine (500 mL), dried over anhydrous Na₂SO₄ and concentrated in vacuo. The residue was purified by flash column to give 6-(6-fluoro-4-methoxy-2-pyridyl)-2-pyrimidin-2-yl-7,8-dihydro-5H-pyrido[4,3-d] pyrimidine (105.0 g) as a yellow solid. ¹H NMR (400 MHz, MeOH-d4) δ: 3.20-3.28 (m, 2H), 3.37 (s, 1H), 3.86 (s, 3H), 3.93-4.01 (m, 2H), 4.60 (s, 3H), 4.62-4.62 (m, 1H), 5.82-5.92 (m, 1H), 6.09-6.18 (m, 1H), 7.51-7.61 (m, 1H), 8.76-8.87 (m, 1H), 8.96-9.06 (m, 2H). MS obsd (ESI) [(M+H)⁺]: 339.

Example 100: 6-[3-methoxy-5-(trifluoromethyl) phenyl]-2-pyrimidin-2-yl-7,8-dihydro-5H-pyrido[4,3-d]pyrimidine

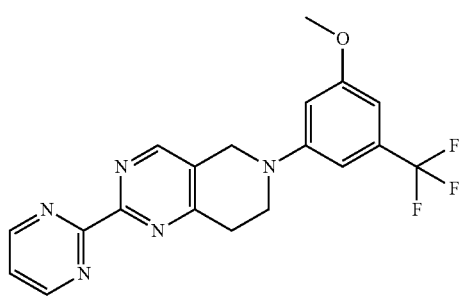 [SMILES: COc1cc(N2CCc3nc(-c4ncccn4)ncc3C2)cc(C(F)(F)F)c1]

Step 1: Preparation of 1-bromo-3-methoxy-5-(trifluoromethyl)benzene

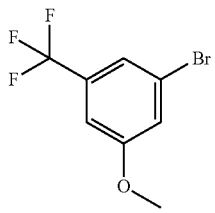

A mixture of 3-(tert-butyl)-5-methylphenol (1.5 g, 9.13 mmol), iodomethane (1.43 g, 10 mmol) and $K_2CO_3$ (1.89 g, 13.7 mmol) in acetone (20 mL) was heated with stirring at 60° C. for 3 hrs. The mixture was cooled down to rt and filtered. The filtrate was concentrated in vacuo to give crude 1-bromo-3-methoxy-5-(trifluoromethyl)benzene (1.98 g) which was used in the next step without further purification.

Step 2: Preparation of 8-[3-methoxy-5-(trifluoromethyl)phenyl]-1,4-dioxa-8-azaspiro[4.5]decane

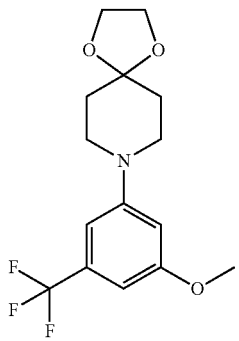 [SMILES: COc1cc(N2CCC3(CC2)OCCO3)cc(C(F)(F)F)c1]

To a mixture of 1-bromo-3-methoxy-5-(trifluoromethyl)benzene (500 mg, 1.96 mmol), 1,4-dioxa-8-azaspiro[4.5]decane (281 mg, 1.96 mmol) and sodium tert-butoxide (377 mg, 3.92 mmol) in dioxane (10 mL) was added $Pd_2(dba)_3$ (71.8 mg, 78.4 μmol) and Ruphos (18.3 mg, 39.2 μmol) under $N_2$. After being heated with stirring at 100° C. overnight, the resulting mixture was cooled down to rt, diluted with $H_2O$ (10 mL), and then extracted with EA (30 mL) for three times. The organic layers were combined, dried over anhydrous $Na_2SO_4$ and concentrated in vacuo to give crude 8-(3-methoxy-5-(trifluoromethyl)phenyl)-1,4-dioxa-8-azaspiro[4.5]decane (650 mg) which was used in the next step directly without further purification.

Step 3: Preparation of 1-[3-methoxy-5-(trifluoromethyl)phenyl]piperidin-4-one

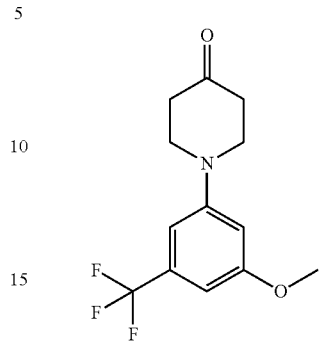

To a flask containing 8-(3-methoxy-5-(trifluoromethyl)phenyl)-1,4-dioxa-8-azaspiro[4.5]decane (600 mg, 1.89 mmol) was added formic acid (7 mL) and $H_2O$ (7 mL). After being heated with stirring at 100° C. for 2 hrs, the resulting mixture was concentrated in vacuo. The residue was diluted with sat. $NaHCO_3$ solution and extracted with EA (30 mL) for three times. The organic layers were combined, concentrated in vacuo to give crude 1-[3-methoxy-5-(trifluoromethyl)phenyl]piperidin-4-one (530 mg) which was used in the next step directly without further purification.

Step 4: Preparation of 6-[3-methoxy-5-(trifluoromethyl)phenyl]-2-pyrimidin-2-yl-7,8-dihydro-5H-pyrido[4,3-d]pyrimidine

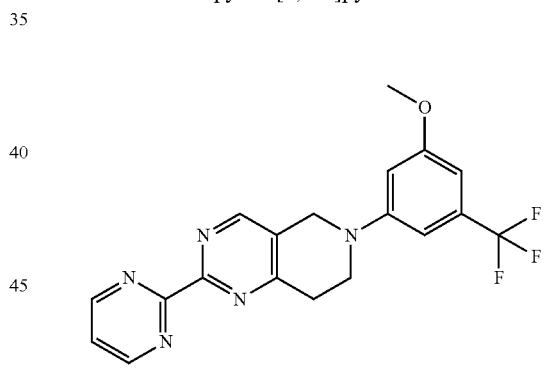

A mixture of 1-(3-methoxy-5-(trifluoromethyl)phenyl)piperidin-4-one (600 mg, 2.2 mmol) and DMFDMA (3 mL) was heated with stirring at 90° C. for 2 hrs. The resulting mixture was concentrated in vacuo and the residue was dissolved in EtOH (20 mL). To the solution was added pyrimidine-2-carboximidamide hydrochloride (348 mg, 2.2 mmol) and potassium carbonate (607 mg, 4.39 mmol). The resulting mixture was heated with stirring at 90° C. for 1 hr and then cooled down to rt. The mixture was filtered and the filtrate was concentrated in vacuo. The residue was purified by flash column to give 6-[3-methoxy-5-(trifluoromethyl)phenyl]-2-pyrimidin-2-yl-7,8-dihydro-5H-pyrido[4,3-d]pyrimidine (400 mg) as light yellow solid. $^1H$ NMR (400 MHz, DMSO-$d_6$) δ: 3.06-3.17 (m, 2H), 3.77-3.82 (m, 2H), 3.84 (s, 3H), 4.63 (s, 2H), 6.62-6.69 (m, 1H), 6.83-6.90 (m, 1H), 6.92-6.99 (m, 1H), 7.64 (s, 1H), 8.86 (s, 1H), 9.00 (d, 2H). MS obsd. (ESI) [(M+H)$^+$]: 388.

Example 101: 3-fluoro-5-(2-pyrimidin-2-yl-7,8-dihydro-5H-pyrido[4,3-d]pyrimidin-6-yl)benzonitrile

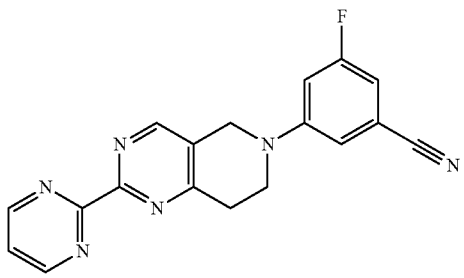 [SMILES: N#Cc1cc(F)cc(N2CCc3nc(-c4ncccn4)ncc3C2)c1]

Step 1: Preparation of 3-(1,4-dioxa-8-azaspiro[4.5]decan-8-yl)-5-fluoro-benzonitrile

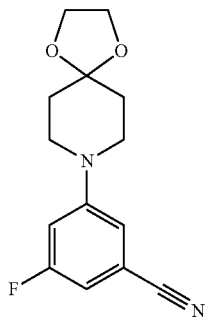 [SMILES: N#Cc1cc(F)cc(N2CCC3(CC2)OCCO3)c1]

To a solution of 1,4-dioxa-8-azaspiro[4.5]decane hydrochloride (3.5 g, 19.6 mmol) in dioxane (40 mL) was added 3-bromo-5-fluorobenzonitrile (4.3 g, 21.4 mmol) and Cs$_2$CO$_3$ (15.9 g, 48.7 mmol) followed by Pd$_2$(dba)$_3$ (357 mg, 0.39 mmol) and Ruphos (364 mg, 0.22 mmol) under N$_2$. After being stirred at 100° C. for 16 hrs, the resulting mixture was diluted with EA (500 mL), then washed with H$_2$O (150 mL) and brine (150 mL), dried over anhydrous Na$_2$SO$_4$ and concentrated in vacuo. The residue was purified by flash column to give 3-(1,4-dioxa-8-azaspiro[4.5]decan-8-yl)-5-fluoro-benzonitrile (4.0 g) as yellow solid.

Step 2: Preparation of 3-fluoro-5-(4-oxo-1-piperidyl)benzonitrile

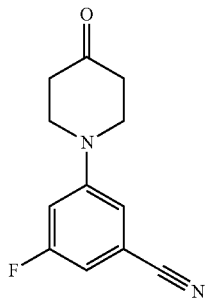 [SMILES: N#Cc1cc(F)cc(N2CCC(=O)CC2)c1]

A mixture of 3-(1,4-dioxa-8-azaspiro[4.5]decan-8-yl)-5-fluoro-benzonitrile (4.0 g, 15.3 mmol), formic acid (30 mL) and H$_2$O (30 mL/30 mL) was heated with stirring at 90° C. for 2 hrs. The reaction mixture was diluted with DCM (300 mL) and washed with saturated aqueous solution of NaHCO$_3$ (100 mL) and brine (100 mL) successively. The organic phase was dried over anhydrous Na$_2$SO$_4$ and concentrated in vacuo to afford 3-fluoro-5-(4-oxo-1-piperidyl)benzonitrile (4.1 g, crude) as a gray solid which was used directly in the next step without further purification.

Step 3: Preparation of 3-[(3Z)-3-(dimethylaminomethylene)-4-oxo-1-piperidyl]-5-fluoro-benzonitrile

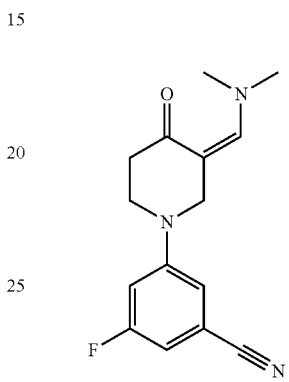

A mixture of 3-fluoro-5-(4-oxo-1-piperidyl)benzonitrile (4.1 g, 18.8 mmol) and DMFDMA (40 mL) was heated with stirring at 120° C. for 4 hrs. After being cooled, the formed yellow solid was collected by filtration, then washed with PE (50 mL) and further dried in vacuo to afford 3-[(3Z)-3-(dimethylaminomethylene)-4-oxo-1-piperidyl]-5-fluoro-benzonitrile (2.5 g) as light green solid.

Step 4: Preparation of 3-fluoro-5-(2-pyrimidin-2-yl-7,8-dihydro-5H-pyrido[4,3-d]pyrimidin-6-yl)benzonitrile

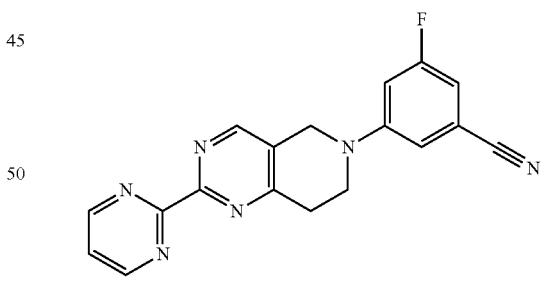

To a solution of 3-[(3Z)-3-(dimethylaminomethylene)-4-oxo-1-piperidyl]-5-fluoro-benzonitrile (500 mg, 1.83 mmol) in MeOH (10 mL) was added K$_2$CO$_3$ (758 mg, 5.49 mmol) and pyrimidine-2-carboximidamide hydrochloride (348 mg, 2.20 mmol). The resulting mixture was heated with stirring at 60° C. for 2 hrs and then diluted with DCM (100 mL). The resulting mixture was washed with brine (50 mL), dried over anhydrous Na$_2$SO$_4$ and concentrated in vacuo. The residue was purified by prep-HPLC to afford 3-fluoro-5-(2-pyrimidin-2-yl-7,8-dihydro-5H-pyrido[4,3-d]pyrimidin-6-yl)benzonitrile (32.8 mg) as white solid. $^1$H NMR (400 MHz, DMSO-d$_6$) δ: 8.99 (d, 2H), 8.81 (s, 1H), 7.64 (m, 1H), 7.38

(s, 1H), 7.28 (d, 1H), 7.10 (d, 1H), 4.68 (s, 2H), 3.84 (m, 2H), 3.08 (m, 2H). MS obsd. (ESI⁺) [(M+H)⁺]: 333.

Example 102: methyl 3-fluoro-5-(2-pyrimidin-2-yl-7,8-dihydro-5H-pyrido[4,3-d]pyrimidin-6-yl)benzoate

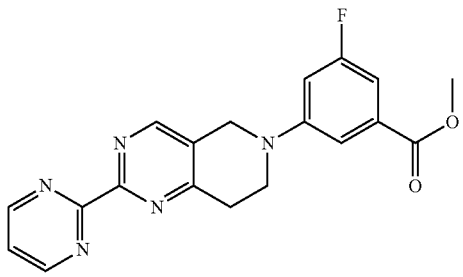 [SMILES: COC(=O)c1cc(F)cc(N2CCc3nc(-c4ncccn4)ncc3C2)c1]

Step 1: Preparation of methyl 3-(1,4-dioxa-8-azaspiro[4.5]decan-8-yl)-5-fluoro-benzoate

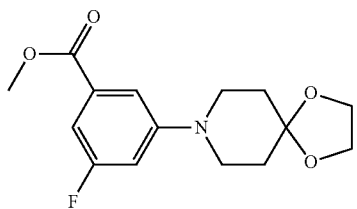 [SMILES: COC(=O)c1cc(F)cc(N2CCC3(CC2)OCCO3)c1]

To a mixture of methyl 3-bromo-5-fluorobenzoate (2.6 g, 11.2 mmol), 1,4-dioxa-8-azaspiro[4.5]decane (1.68 g, 11.7 mmol) and cesium carbonate (7.27 g, 22.3 mmol) in dioxane (50 mL) was added Pd$_2$(dba)$_3$ (204 mg, 223 µmol) and Ruphos (208 mg, 446 µmol) under N$_2$. The resulting mixture was heated with stirring at 100° C. overnight. After being cooled down to rt, the reaction mixture was diluted with saturated aqueous solution of NH$_4$Cl and then extracted with EA (50 mL) for three times. The combined organic layers were dried over anhydrous Na$_2$SO$_4$ and concentrated in vacuo to give crude methyl 3-(1,4-dioxa-8-azaspiro[4.5]decan-8-yl)-5-fluoro-benzoate as yellow oil which was used in the next step without further purification.

Step 2: Preparation of methyl 3-fluoro-5-(4-oxo-1-piperidyl)benzoate

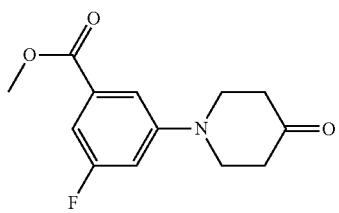 [SMILES: COC(=O)c1cc(F)cc(N2CCC(=O)CC2)c1]

A mixture of methyl 3-fluoro-5-(1,4-dioxa-8-azaspiro [4.5]decan-8-yl)benzoate (3.3 g, 11.2 mmol), formic acid (8 mL) and H$_2$O (8 mL) was heated with stirring at 90° C. for 5 hrs. The resulting mixture was concentrated in vacuo and the residue was diluted with saturated aqueous solution of NaHCO$_3$, and then extracted with EA (50 mL) for 3 times. The combined organic layers were dried over anhydrous Na$_2$SO$_4$ and concentrated in vacuo to give crude methyl 3-fluoro-5-(4-oxo-1-piperidyl)benzoate as yellow oil which was used in the next step directly without any further purification.

Step 3: Preparation of methyl 3-fluoro-5-(2-pyrimidin-2-yl-7,8-dihydro-5H-pyrido[4,3-d]pyrimidin-6-yl)benzoate

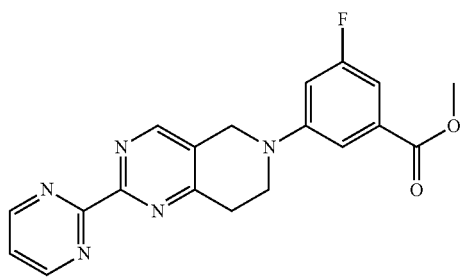 [SMILES: COC(=O)c1cc(F)cc(N2CCc3nc(-c4ncccn4)ncc3C2)c1]

A mixture of crude methyl 3-fluoro-5-(4-oxopiperidin-1-yl)benzoate (2.9 g, 11.5 mmol) and DMFDMA (5 mL) was heated with stirring at 90° C. for 3 hrs. The resulting mixture was concentrated in vacuo and the residue was dissolved in MeOH (20 mL). To the solution was added pyrimidine-2-carboximidamide hydrochloride (1.83 g, 11.5 mmol) and potassium carbonate (3.19 g, 23.1 mmol). The resulting mixture was heated with stirring at 90° C. for 4 hrs, then diluted with saturated aqueous solution of NH$_4$Cl, and extracted with EA (40 mL) for three times. The combined organic layers were dried over anhydrous Na$_2$SO$_4$ and concentrated in vacuo. The residue was purified by flash column to afford methyl 3-fluoro-5-(2-pyrimidin-2-yl-7,8-dihydro-5H-pyrido[4,3-d]pyrimidin-6-yl)benzoate (700 mg, 1.92 mmol) as yellow solid. $^1$H NMR (400 MHz, CDCl$_3$): δ 3.37 (t, 2H), 3.78 (s, 2H), 3.94 (s, 3H), 4.57 (s, 2H), 6.85-6.93 (m, 1H), 7.20-7.27 (m, 1H), 7.39-7.55 (m, 2H), 8.79-8.93 (m, 1H), 8.99-9.11 (m, 2H), 8.99-9.11 (m, 2H). MS obsd (ESI) [(M+H)⁺]: 366.

Example 103: 3-fluoro-N-methyl-5-(2-pyrimidin-2-yl-7,8-dihydro-5H-pyrido[4,3-d]pyrimidin-6-yl)benzamide

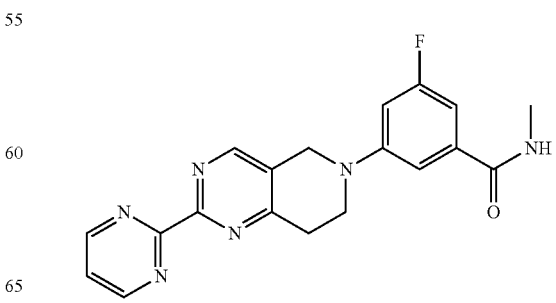

Step 1: Preparation of 3-fluoro-5-(2-pyrimidin-2-yl-7,8-dihydro-5H-pyrido[4,3-d]pyrimidin-6-yl)benzoic acid

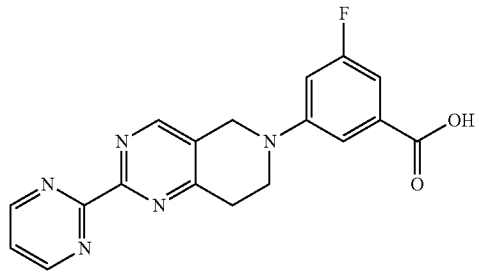 [SMILES: O=C(O)c1cc(F)cc(N2CCc3nc(-c4ncccn4)ncc3C2)c1]

To a solution of methyl 3-fluoro-5-(2-pyrimidin-2-yl-7,8-dihydro-5H-pyrido[4,3-d]pyrimidin-6-yl)benzoate (650 mg, 1.78 mmol) in MeOH (10 mL) and THF (10 mL) was added a solution of lithium hydroxide (85.2 mg, 3.56 mmol) in $H_2O$ (2 mL). The resulting mixture was stirred at rt and monitored by LC-MS. After the reaction was complete, the mixture was neutralized with 1.0 N HCl, and concentrated in vacuo. The formed precipitate was collected by suction to give 3-fluoro-5-(2-pyrimidin-2-yl-7,8-dihydro-5H-pyrido[4,3-d]pyrimidin-6-yl)benzoic acid (600 mg, 1.71 mmol) as yellow sticky solid.

Step 2: Preparation of 3-fluoro-N-methyl-5-(2-pyrimidin-2-yl-7,8-dihydro-5H-pyrido[4,3-d]pyrimidin-6-yl)benzamide

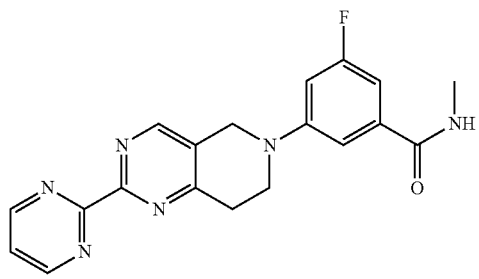 [SMILES: CNC(=O)c1cc(F)cc(N2CCc3nc(-c4ncccn4)ncc3C2)c1]

A mixture of 3-fluoro-5-(2-pyrimidin-2-yl-7,8-dihydro-5H-pyrido[4,3-d]pyrimidin-6-yl)benzoic acid (30 mg, 85.4 μmol), methylamine hydrochloride (17.3 mg, 256 μmol), HATU (64.9 mg, 171 μmol) and triethylamine (72.6 mg, 0.1 mL, 717 μmol) in DMF (2 mL) was stirred at rt overnight. The resulting mixture was purified by prep-HPLC to give 3-fluoro-N-methyl-5-(2-pyrimidin-2-yl-7,8-dihydro-5H-pyrido[4,3-d]pyrimidin-6-yl)benzamide (15 mg) as light yellow solid. $^1$H NMR (400 MHz, MeOH-d4): δ 2.94 (s, 3H), 3.22-3.30 (m, 2H), 3.79-3.88 (m, 2H), 4.57-4.68 (m, 2H), 6.93-7.08 (m, 2H), 7.35 (s, 1H), 7.61-7.72 (m, 1H), 8.42-8.56 (m, 1H), 8.99-9.12 (m, 2H). MS obsd (ESI) [(M+H)$^+$]: 365.

Example 104: 3-fluoro-5-(2-pyrimidin-2-yl-7,8-dihydro-5H-pyrido[4,3-d]pyrimidin-6-yl)-N-(2,2,2-trifluoroethyl)benzamide

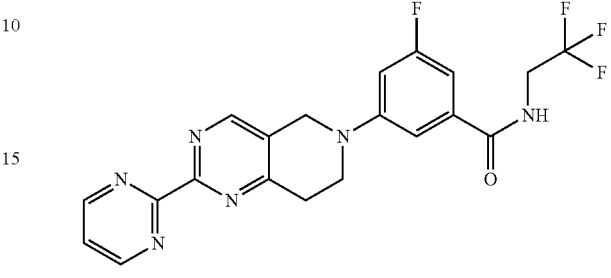

A mixture of 3-fluoro-5-(2-pyrimidin-2-yl-7,8-dihydro-5H-pyrido[4,3-d]pyrimidin-6-yl)benzoic acid (30 mg, 85.4 μmol), 2,2,2-trifluoroethanamine hydrochloride (34.7 mg, 256 μmol), triethylamine (72.6 mg, 0.1 mL, 717 μmol) and HATU (64.9 mg, 171 μmol) in DMF (2 mL) was stirred at rt overnight. The resulting mixture was filtered and the filtrate was purified by prep-HPLC to give 3-fluoro-5-(2-pyrimidin-2-yl-7,8-dihydro-5H-pyrido[4,3-d]pyrimidin-6-yl)-N-(2,2,2-trifluoroethyl)benzamide (10 mg) as light yellow solid. $^1$H NMR (400 MHz, MeOH-d$_4$): δ 3.24-3.31 (m, 2H), 3.83-3.91 (m, 2H), 4.06-4.19 (m, 2H), 4.63-4.73 (m, 2H), 7.00-7.13 (m, 2H), 7.37-7.45 (m, 1H), 7.65-7.78 (m, 1H), 8.87-8.97 (m, 1H), 9.02-9.15 (m, 2H). MS obsd (ESI) [(M+H)$^+$]: 433.

Example 105: 3-fluoro-5-(2-pyrimidin-2-yl-7,8-dihydro-5H-pyrido[4,3-d]pyrimidin-6-yl)benzamide A mixture of 3-fluoro-5-(2-pyrimidin-2-yl-7,8-dihydro-5H-pyrido[4,3-d]pyrimidin-6-yl)benzoic acid (30 mg, 85.4 μmol), ammonium chloride (13.7 mg, 256 μmol), triethylamine (72.6 mg, 0.1 mL, 717 μmol) and HATU (64.9 mg, 171 μmol) in DMF (2 mL) was stirred at rt overnight. The resulting mixture was purified by prep-HPLC to give 3-fluoro-5-(2-pyrimidin-2-yl-7,8-dihydro-5H-pyrido[4,3-d]pyrimidin-6-yl)benzamide (10 mg) as light yellow solid. $^1$H NMR (400 MHz, MeOH-d$_4$): δ 3.23-3.31 (m, 2H), 3.85 (t, 2H), 4.65 (s, 2H), 4.89 (s, 8H), 7.02-7.11 (m, 2H), 7.43 (t, 1H), 7.66 (t, 1H), 8.88 (s, 1H), 9.05 (d, 2H). MS obsd (ESI) [(M+H)$^+$]: 351.

Example 106: 3-fluoro-N-(3-methoxypropyl)-5-(2-pyrimidin-2-yl-7,8-dihydro-5H-pyrido[4,3-d]pyrimidin-6-yl)benzamide

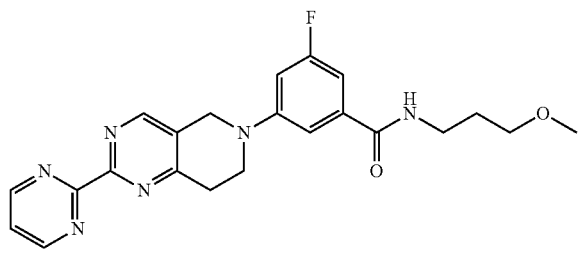 [SMILES: COCCCNC(=O)c1cc(F)cc(N2CCc3nc(-c4ncccn4)ncc3C2)c1]

A mixture of 3-fluoro-5-(2-pyrimidin-2-yl-7,8-dihydro-5H-pyrido[4,3-d]pyrimidin-6-yl)benzoic acid (45 mg, 128 μmol), 3-methoxypropan-1-amine (22.8 mg, 256 μmol), triethylamine (72.6 mg, 0.1 mL, 717 μmol) and HATU (97.4 mg, 256 μmol) in DMF (2 mL) was stirred at rt. The resulting mixture was purified by prep-HPLC to give 3-fluoro-N-(3-methoxypropyl)-5-(2-pyrimidin-2-yl-7,8-dihydro-5H-pyrido[4,3-d]pyrimidin-6-yl)benzamide (15 mg) as light yellow solid. $^1$H NMR (400 MHz, MeOH-d4) δ: 1.83-1.97 (m, 2H), 3.22-3.30 (m, 2H), 3.37 (s, 3H), 3.51 (t, 4H), 3.85 (s, 3H), 4.61-4.71 (m, 2H), 6.93-7.12 (m, 2H), 7.36 (s, 1H), 7.59-7.77 (m, 1H), 8.43-8.64 (m, 1H), 8.98-9.15 (m, 2H). MS obsd (ESI) [(M+H)$^+$]: 423.

Example 107: 3-fluoro-N-(5-hydroxypentyl)-5-(2-pyrimidin-2-yl-7,8-dihydro-5H-pyrido[4,3-d]pyrimidin-6-yl)benzamide

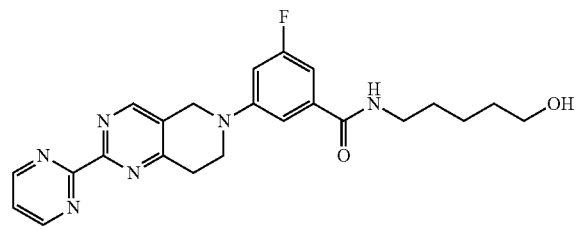 [SMILES: O=C(NCCCCCO)c1cc(F)cc(N2CCc3nc(-c4ncccn4)ncc3C2)c1]

A mixture of HATU (97.4 mg, 256 μmol), 3-fluoro-5-(2-pyrimidin-2-yl-7,8-dihydro-5H-pyrido[4,3-d]pyrimidin-6-yl)benzoic acid (45 mg, 128 μmol), 5-aminopentan-1-ol (26.4 mg, 256 μmol) and triethylamine (72.6 mg, 0.1 mL, 717 μmol) in DMF (2 mL) was stirred at rt overnight. The resulting mixture was filtered and the filtrate was purified by prep-HPLC to give 3-fluoro-N-(5-hydroxypentyl)-5-(2-pyrimidin-2-yl-7,8-dihydro-5H-pyrido[4,3-d]pyrimidin-6-yl)benzamide (15 mg) as light yellow solid. $^1$H NMR (400 MHz, MeOH-d4): δ 1.40-1.75 (m, 6H), 3.23-3.30 (m, 2H), 3.37-3.46 (m, 2H), 3.54-3.65 (m, 2H), 3.77-3.90 (m, 2H), 4.57-4.73 (m, 2H), 7.02 (s, 2H), 7.36 (s, 1H), 7.67 (br. s., 1H), 8.89 (br. s., 1H), 9.05 (d, 2H). MS obsd (ESI) [(M+H)$^+$]: 437.

Example 108: 6-(6-chloro-4-methoxy-2-pyridyl)-2-pyrimidin-2-yl-7,8-dihydro-5H-pyrido[4,3-d]pyrimidine

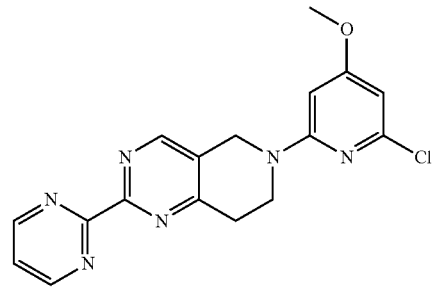 [SMILES: COc1cc(Cl)nc(N2CCc3nc(-c4ncccn4)ncc3C2)c1]

Step 1: Preparation of tert-butyl 2-pyrimidin-2-yl-7,8-dihydro-5H-pyrido[4,3-d]pyrimidine-6-carboxylate

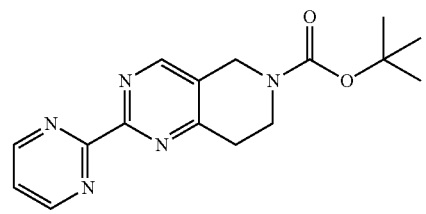 [SMILES: CC(C)(C)OC(=O)N1CCc2nc(-c3ncccn3)ncc2C1]

A solution of 1-Boc-4-piperidone (100.0 g, 0.50 mol) in DMFDMA (299.0 g, 2.5 mol) was heated with stirring at 120° C. under nitrogen for 4 hrs. The resulting reaction mixture was concentrated in vacuo. The residue was dissolved in MeOH (2.0 L), and to the solution was added 2-amidinopyrimidine hydrochloride (87.8 g, 0.55 mol) and K$_2$CO$_3$ (173.9 g, 1.26 mol) successively. After being heated with stirring at 70° C. for 3 hrs, the resulting reaction mixture was cooled to rt and filtered. The filtrate was concentrated in vacuo and the residue was diluted with DCM (2.0 L), washed with H$_2$O (500 mL) and brine (300 mL), dried over anhydrous Na$_2$SO$_4$, and concentrated in vacuo. The residue was purified by the flash column chromatography to give tert-butyl 2-pyrimidin-2-yl-7,8-dihydro-5H-pyrido[4,3-d]pyrimidine-6-carboxylate (47.7 g) as a yellow solid.

Step 2: Preparation of 2-pyrimidin-2-yl-5,6,7,8-tetrahydropyrido[4,3-d]pyrimidine

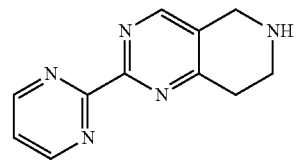 [SMILES: c1cnc(-c2ncc3c(n2)CCNC3)nc1]

To a stirred solution of tert-butyl 2-pyrimidin-2-yl-7,8-dihydro-5H-pyrido[4,3-d]pyrimidine-6-carboxylate (47.7 g, 0.15 mol) in MeOH (500 mL) was added a solution of HCl in MeOH (190 mL, 4.0 M) slowly. The resulting mixture was stirred at 15° C. for 16 hrs. The solvent was removed in vacuo and the residue was diluted with MeOH (1.0 L). To the solution was added basic resin (500 g, AMBERLYST® A21) portion wise and the resulting mixture was stirred at 15° C. for 1 hr until pH>7, and then filtered. The solid was washed with a mixture of DCM and MeOH (1200 mL, v/v=1:1). The collected filtrate was concentrated in vacuo to afford 2-pyrimidin-2-yl-5,6,7,8-tetrahydropyrido[4,3-d]pyrimidine (39.0 g) as a yellow solid.

Step 3: Preparation of 6-(6-chloro-4-methoxy-2-pyridyl)-2-pyrimidin-2-yl-7,8-dihydro-5H-pyrido[4,3-d]pyrimidine

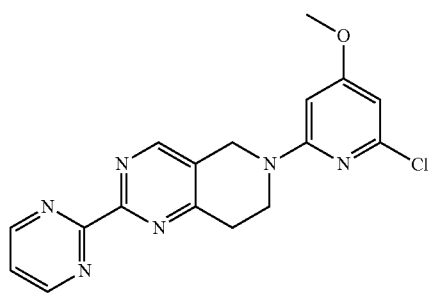 [SMILES: COc1cc(Cl)nc(N2CCc3nc(-c4ncccn4)ncc3C2)c1]

To a solution of 2,6-dichloro-4-methoxypyridine (300 mg, 1.69 mmol) in NMP (3 mL) was added K₂CO₃ (653 mg, 5.06 mmol) and 2-pyrimidin-2-yl-5,6,7,8-tetrahydropyrido[4,3-d]pyrimidine (540 mg, 2.53 mmol). Then the reaction vessel was sealed and heated in microwave at 150° C. for 1 hr. The reaction mixture was diluted with DCM (100 mL) and the resulting mixture was washed with brine (50 mL), dried over anhydrous Na₂SO₄ and concentrated in vacuo. The residue was purified by prep-HPLC to afford 6-(6-chloro-4-methoxy-2-pyridyl)-2-pyrimidin-2-yl-7,8-dihydro-5H-pyrido[4,3-d]pyrimidine (6.9 mg) as white solid. ¹H NMR (400 MHz, CDCl₃): δ 9.04 (d, 1H), 8.85 (s, 1H) 7.45 (m, 1H), 6.33 (d, 1H), 6.10 (d, 1H), 4.84 (s, 2H), 3.98 (m, 2H), 3.85 (s, 3H), 3.31 (m, 2H). MS obsd. (ESI⁺) [(M+H⁺)]: 355.

Example 109 and 110: 6-(2,6-difluoro-4-pyridyl)-2-pyrimidin-2-yl-7,8-dihydro-5H-pyrido[4,3-d]pyrimidine and 6-(4,6-difluoro-2-pyridyl)-2-pyrimidin-2-yl-7,8-dihydro-5H-pyrido[4,3-d]pyrimidine

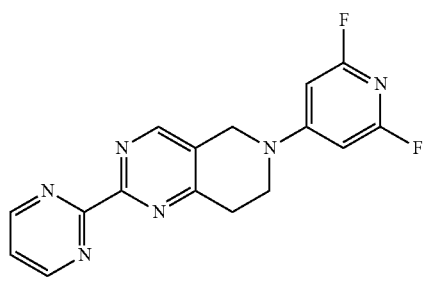

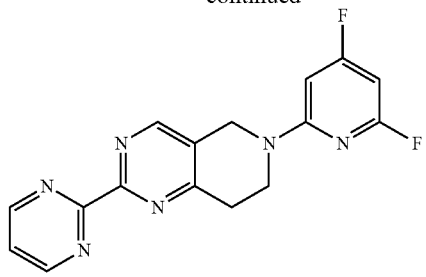

To a solution of 2,4,6-trifluoropyridine (1.0 g, 7.51 mmol) in 1-methyl-2-pyrrolidinone (15 mL) was added K₂CO₃ (3.12 g, 22.5 mmol) and 2-pyrimidin-2-yl-5,6,7,8-tetrahydropyrido[4,3-d]pyrimidine (2.44 g, 9.77 mmol). Then the reaction vessel was sealed and heated in microwave at 150° C. for 1 hr. The reaction mixture was diluted with EA (100 mL). The resulting mixture was washed with brine (50 mL), dried over anhydrous Na₂SO₄ and concentrated in vacuo. The residue was purified by prep-HPLC to afford 6-(2,6-difluoro-4-pyridyl)-2-pyrimidin-2-yl-7,8-dihydro-5H-pyrido[4,3-d]pyrimidine and (150 mg, Example 109) as yellow solid and 6-(4,6-difluoro-2-pyridyl)-2-pyrimidin-2-yl-7,8-dihydro-5H-pyrido[4,3-d]pyrimidine (150 mg, Example 110) as yellow solid.

Example 109: 6-(2,6-difluoro-4-pyridyl)-2-pyrimidin-2-yl-7,8-dihydro-5H-pyrido[4,3-d]pyrimidine and, ¹H NMR (400 MHz, CDCl₃): δ 9.06 (d, 2H), 8.87 (s, 1H), 7.47 (t, 1H), 6.24 (s, 2H), 4.67 (s, 2H), 3.83 (t, 2H), 3.37 (t, 2H). MS obsd. (ESI⁺) [(M+H)⁺]: 327.

Example 110: 6-(4,6-difluoro-2-pyridyl)-2-pyrimidin-2-yl-7,8-dihydro-5H-pyrido[4,3-d]pyrimidine, ¹H NMR (400 MHz, CDCl₃): δ 9.03 (d, 1H), 8.84 (s, 1H), 7.44 (t, 1H), 6.26 (m, 1H), 5.92-6.09 (m, 1H), 4.83 (s, 2H), 3.97 (t, 2H), 3.31 (t, 2H). MS obsd. (ESI⁺) [(M+H)⁺]: 327.

Example 111: Preparation of 6-(4-fluoro-6-methoxy-2-pyridyl)-2-pyrimidin-2-yl-7,8-dihydro-5H-pyrido[4,3-d]pyrimidine

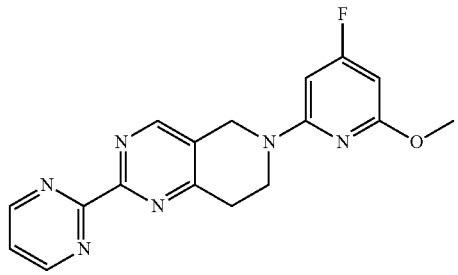

To a solution of 6-(4,6-difluoro-2-pyridyl)-2-pyrimidin-2-yl-7,8-dihydro-5H-pyrido[4,3-d]pyrimidine (50 mg, 0.15 mmol) in MeOH (2 mL) was added NaOMe (0.85 mL, 0.15 mmol). The resulting mixture was heated with stirring at 80° C. for 2 hrs and then diluted with DCM (50 mL). The resulting mixture was washed with brine (20 mL), dried over anhydrous Na₂SO₄ and concentrated in vacuo. The residue was purified by prep-HPLC to afford 6-(4-fluoro-6-methoxy-2-pyridyl)-2-pyrimidin-2-yl-7,8-dihydro-5H-pyrido[4,3-d]pyrimidine (4 mg) as white solid. ¹H NMR (400 MHz, CDCl₃): δ 9.04 (d, 2H), 8.84 (s, 1H), 7.45 (t, 1H), 6.03 (m, 1H), 5.88 (m, 1H), 4.83 (s, 2H), 4.00 (t, 2H), 3.93 (s, 3H), 3.31 (t, 2H). MS obsd. (ESI⁺) [(M+H)⁺]: 339.

Example 112: 6-(2-fluoro-6-methoxy-4-pyridyl)-2-pyrimidin-2-yl-7,8-dihydro-5H-pyrido[4,3-d]pyrimidine

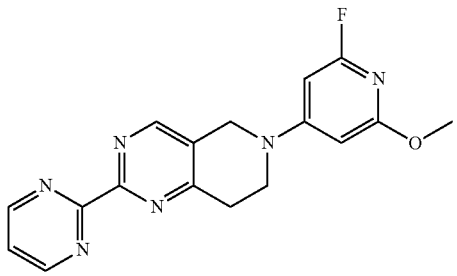

To a solution of 6-(2,6-difluoro-4-pyridyl)-2-pyrimidin-2-yl-7,8-dihydro-5H-pyrido[4,3-d]pyrimidine (50 mg, 0.15 mmol) in MeOH (2 mL) was added NaOMe (0.85 mL, 0.15 mmol). The resulting mixture was heated with stirring at 80° C. for 1 hr and then diluted with DCM (50 mL). The resulting mixture was washed with brine (20 mL), dried over anhydrous Na₂SO₄ and concentrated in vacuo. The residue was purified by prep-HPLC to afford 6-(2-fluoro-6-methoxy-4-pyridyl)-2-pyrimidin-2-yl-7,8-dihydro-5H-pyrido[4,3-d]pyrimidine (19 mg) as white solid. $^1$H NM (400 MHz, CDCl₃): δ 9.05 (d, 2H), 8.84 (s, 1H), 7.46 (m, 1H), 6.04 (s, 2H), 4.62 (s, 2H), 3.90 (s, 3H), 3.79 (t, 2H), 3.34 (t, 2H). MS obsd. (ESI⁺) [(M+H)⁺]: 339.

Example 113: 6-(4,6-dichloro-2-pyridyl)-2-pyrimidin-2-yl-7,8-dihydro-5H-pyrido[4,3-d]pyrimidine

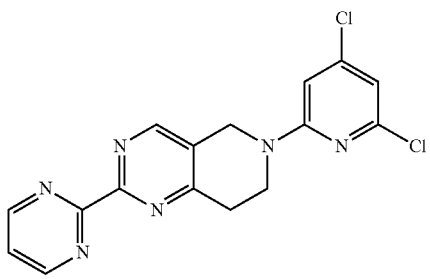 [SMILES: Clc1cc(Cl)nc(N2CCc3nc(-c4ncccn4)ncc3C2)c1]

Step 1: Preparation of 8-(2,6-dichloro-4-pyridyl)-1,4-dioxa-8-azaspiro[4.5]decane and 8-(4,6-dichloro-2-pyridyl)-1,4-dioxa-8-azaspiro[4.5]decane

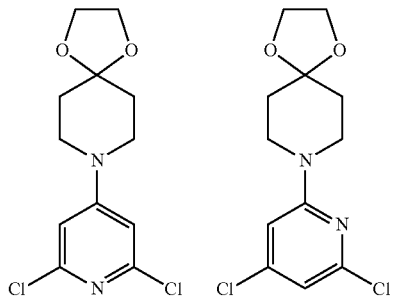 [SMILES: Clc1cc(N2CCC3(CC2)OCCO3)cc(Cl)n1 ; Clc1cc(Cl)nc(N2CCC3(CC2)OCCO3)c1]

To a solution of 1,4-dioxa-8-azaspiro[4.5]decane hydrochloride (2.0 g, 11.0 mmol) in 1-methyl-2-pyrrolidinone (20 mL) was added K₂CO₃ (3.0 g, 21.9 mmol) and 2,4,6-trichloropyridine (2.95 g, 16.4 mmol). Then the reaction vessel was sealed and heated in microwave at 150° C. for 1 hr. The resulting mixture was diluted with EA (100 mL), then washed with brine (50 mL), dried over anhydrous Na₂SO₄ and concentrated in vacuo. The residue was purified by flash column to afford 8-(2,6-dichloro-4-pyridyl)-1,4-dioxa-8-azaspiro[4.5]decane (400 mg) as yellow oil and 8-(4,6-dichloro-2-pyridyl)-1,4-dioxa-8-azaspiro[4.5]decane (300 mg) as yellow solid.

Step 2: Preparation of 1-(4,6-dichloro-2-pyridyl)piperidin-4-one

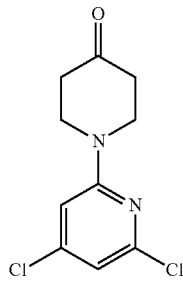 [SMILES: O=C1CCN(c2cc(Cl)cc(Cl)n2)CC1]

A mixture of 8-(4,6-dichloro-2-pyridyl)-1,4-dioxa-8-azaspiro[4.5]decane (300 mg, 1.04 mmol), formic acid (3 mL) and H₂O (3 mL) was heated with stirring at 90° C. for 2 hrs. The resulting mixture was diluted with DCM (100 mL), then washed with water (50 mL), saturated aqueous solution of NaHCO₃ (50 mL) and brine (50 mL) successively, dried over anhydrous Na₂SO₄ and concentrated in vacuo. The residue was purified by flash column to afford 1-(4,6-dichloro-2-pyridyl)piperidin-4-one (240 mg) as white solid.

Step 3: Preparation of 6-(4,6-dichloro-2-pyridyl)-2-pyrimidin-2-yl-7,8-dihydro-5H-pyrido[4,3-d]pyrimidine

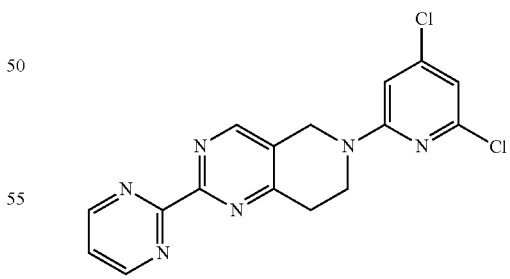

A mixture of 1-(4,6-dichloro-2-pyridyl)piperidin-4-one (170 mg, 0.69 mmol) and DMFDMA (5 mL) was heated with stirring at 120° C. for 4 hrs. After being cooled, the reaction mixture was concentrated in vacuo. The residue was dissolved in MeOH (10 mL), and to the solution was added pyrimidine-2-carboximidamide hydrochloride (290 mg, 1.83 mmol) and K₂CO₃ (575 mg, 4.16 mmol) successively. The resulting mixture was heated with stirring at 90° C. for 2 hrs, then cooled to rt and concentrated in vacuo. The residue was purified by prep-HPLC to afford 6-(4,6-dichloro-2-pyridyl)-2-pyrimidin-2-yl-7,8-dihydro-5H-pyrido[4,3-d]pyrimidine (14.3 mg) as white solid. $^1$H NMR (400 MHz, CDCl$_3$): δ 9.04 (d, 2H), 8.87 (s, 1H), 7.45 (m, 1H), 6.72 (d, 1H), 6.64 (d, 1H), 4.86 (s, 2H), 4.00 (m, 2H), 3.32 (t, 2H). MS obsd. (ESI$^+$) [(M+H)$^+$]: 359.

Example 114: 6-(2,6-dichloro-4-pyridyl)-2-pyrimidin-2-yl-7,8-dihydro-5H-pyrido[4,3-d]pyrimidine

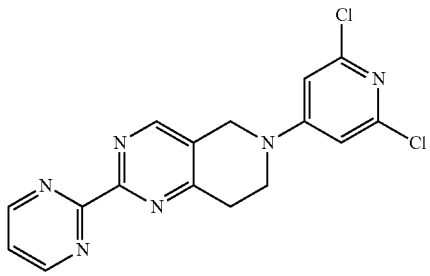 [SMILES: Clc1cc(N2CCc3nc(-c4ncccn4)ncc3C2)cc(Cl)n1]

Step 1: Preparation of 1-(2,6-dichloro-4-pyridyl)piperidin-4-one

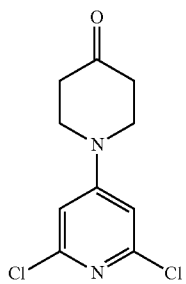 [SMILES: O=C1CCN(c2cc(Cl)nc(Cl)c2)CC1]

A mixture of 8-(2,6-dichloro-4-pyridyl)-1,4-dioxa-8-azaspiro[4.5]decane (400 mg, 1.38 mmol) in formic acid (3 mL) and H$_2$O (3 mL) was heated with stirring at 90° C. for 2 hrs. The resulting mixture was diluted with DCM (100 mL), then washed with water (50 mL), saturated aqueous solution of NaHCO$_3$ (50 mL) and brine (50 mL) successively, dried over anhydrous Na$_2$SO$_4$ and concentrated in vacuo. The residue was purified by the flash column to afford 1-(2,6-dichloro-4-pyridyl)piperidin-4-one (210 mg) as white solid.

Step 2: Preparation of 6-(2,6-dichloro-4-pyridyl)-2-pyrimidin-2-yl-7,8-dihydro-5H-pyrido[4,3-d]pyrimidine

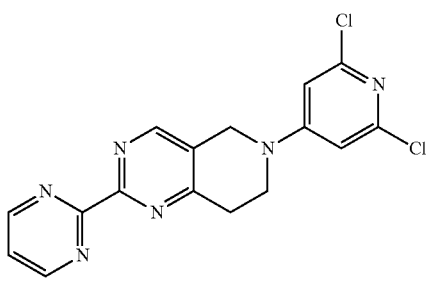 [SMILES: Clc1cc(N2CCc3nc(-c4ncccn4)ncc3C2)cc(Cl)n1]

A mixture of 1-(2,6-dichloro-4-pyridyl)piperidin-4-one (210 mg, 0.86 mmol) in DMFDMA (5 mL) was heated with stirring at 120° C. for 4 hrs. After being cooled, the resulting reaction mixture was concentrated in vacuo. The residue was dissolved in MeOH (10 mL) and to the solution was added pyrimidine-2-carboximidamide hydrochloride (290 mg, 1.83 mmol) and K$_2$CO$_3$ (575 mg, 4.16 mmol). The resulting mixture was heated with stirring at 90° C. for 2 hrs, then cooled to rt and concentrated in vacuo. The residue was purified by prep-HPLC to afford 6-(2,6-dichloro-4-pyridyl)-2-pyrimidin-2-yl-7,8-dihydro-5H-pyrido[4,3-d]pyrimidine (14 mg) as yellow solid. $^1$H NMR (400 MHz, CDCl$_3$): δ 9.06 (d, 2H), 8.87 (s, 1H), 7.47 (t, 1H), 6.74 (s, 2H), 4.65 (s, 2H), 3.82 (t, 2H), 3.37 (t, 2H). MS obsd. (ESI$^+$) [(M+H)$^+$]: 359.

Example 115 and 116: 6-(4-chloro-6-methoxy-2-pyridyl)-2-pyrimidin-2-yl-7,8-dihydro-5H-pyrido[4,3-d]pyrimidine and 6-(2-chloro-6-methoxy-4-pyridyl)-2-pyrimidin-2-yl-7,8-dihydro-5H-pyrido[4,3-d]pyrimidine

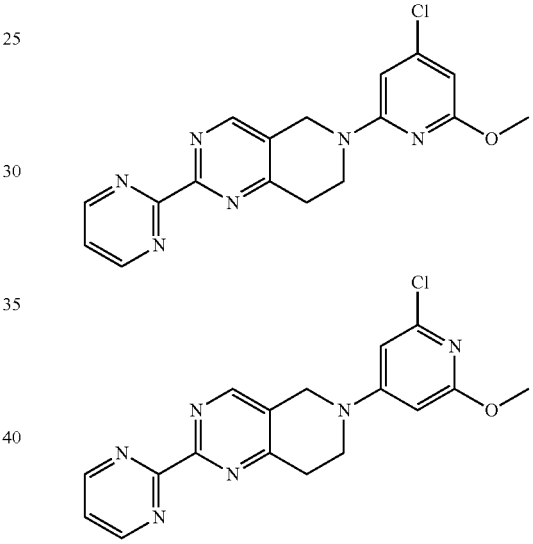

To a solution of 2,4-dichloro-6-methoxypyridine (150 mg, 0.84 mmol) in 1-methyl-2-pyrrolidinone (2 mL) was added K$_2$CO$_3$ (233 mg, 1.69 mmol) and 2-pyrimidin-2-yl-5,6,7,8-tetrahydropyrido[4,3-d]pyrimidine (269 mg, 1.26 mmol). Then the reaction vessel was sealed and heated in microwave reactor at 150° C. for 1 hr. The reaction mixture was diluted with EA (100 mL) and the resulting mixture was washed with brine (30 mL), dried over anhydrous Na$_2$SO$_4$ and concentrated in vacuo. The residue was purified by prep-HPLC to afford 6-(4-chloro-6-methoxy-2-pyridyl)-2-pyrimidin-2-yl-7,8-dihydro-5H-pyrido[4,3-d]pyrimidine (11.5 mg) and 6-(2-chloro-6-methoxy-4-pyridyl)-2-pyrimidin-2-yl-7,8-dihydro-5H-pyrido[4,3-d]pyrimidine (7.4 mg) both as white solid.

Example 115: 6-(4-chloro-6-methoxy-2-pyridyl)-2-pyrimidin-2-yl-7,8-dihydro-5H-pyrido[4,3-d]pyrimidine, $^1$H NMR (400 MHz, CDCl$_3$): δ 8.53-9.33 (m, 3H), 7.46 (br. s., 1H), 6.30 (s, 1H), 6.17 (d, 1H), 4.83 (s, 2H), 4.00 (t, 2H), 3.92 (s, 3H), 3.31 (t, 2H). MS obsd. (ESI$^+$) [(M+H)$^+$]: 355.

Example 116: 6-(2-chloro-6-methoxy-4-pyridyl)-2-pyrimidin-2-yl-7,8-dihydro-5H-pyrido[4,3-d]pyrimidine, 1H NMR (400 MHz, CDCl3): δ 9.05 (d, 2H), 8.84 (s, 1H), 7.46

(t, 1H), 6.53 (d, 1H), 6.07 (d, 1H), 4.60 (s, 2H), 3.92 (s, 3H), 3.78 (t, 2H), 3.33 (t, 2H). MS obsd. (ESI⁺) [(M+H)⁺]: 355.

Example 117: 6-(3-fluoro-5-methoxy-phenyl)-2-pyrimidin-2-yl-7,8-dihydro-5H-pyrido[4,3-d]pyrimidine

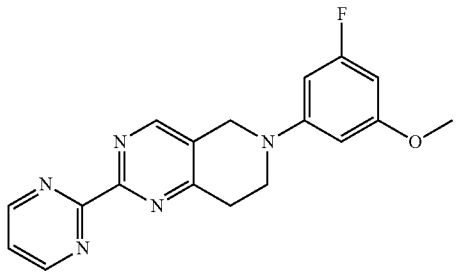

Step 1: Preparation of 8-(3-fluoro-5-methoxy-phenyl)-1,4-dioxa-8-azaspiro[4.5]decane

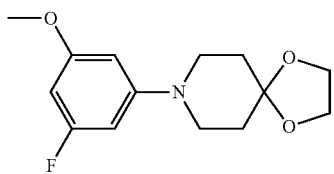 [SMILES: COc1cc(F)cc(N2CCC3(CC2)OCCO3)c1]

A mixture of 3-bromo-5-fluoroanisole (87.6 g, 0.49 mol), 1,4-dioxa-8-azaspiro[4.5]decane hydrochloride (100.0 g, 0.49 mol), tert-BuONa (117.2 g, 1.22 mol), BINAP (12.1 g, 0.02 mol) and Pd₂dba₃ (8.9 g, 0.01 mol) in toluene (1.3 L) was heated with stirring at 100° C. under nitrogen for 16 hrs. The reaction mixture was cooled to rt and filtered. The filtrate was diluted with DCM (3.0 L), washed with H₂O (500 mL) and brine (200 mL), dried over anhydrous Na₂SO₄ and concentrated in vacuo. The residue was purified by the flash column chromatography to give 8-(3-fluoro-5-methoxy-phenyl)-1,4-dioxa-8-azaspiro[4.5]decane (78.2 g) as a yellow oil.

Step 2: Preparation of 1-(3-fluoro-5-methoxy-phenyl)piperidin-4-one

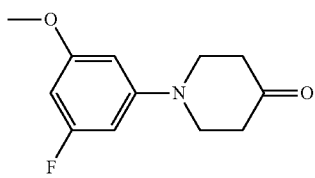 [SMILES: COc1cc(F)cc(N2CCC(=O)CC2)c1]

A mixture of 8-(3-fluoro-5-methoxy-phenyl)-1,4-dioxa-8-azaspiro[4.5]decane (78.2 g, 0.29 mol), formic acid (400 mL) and H₂O (400 mL) was heated with stirring at 90° C. for 3 hrs. The resulting reaction mixture was concentrated in vacuo. The residue was diluted with DCM (1.0 L), washed with saturated aqueous solution of Na₂CO₃ (200 mL) and brine (200 mL), then dried over anhydrous Na₂SO₄ and concentrated in vacuo. The residue was purified by the flash column chromatography to give 1-(3-fluoro-5-methoxy-phenyl)piperidin-4-one (42.0 g) as a yellow solid.

Step 3: Preparation of 6-(3-fluoro-5-methoxy-phenyl)-2-pyrimidin-2-yl-7,8-dihydro-5H-pyrido[4,3-d]pyrimidine

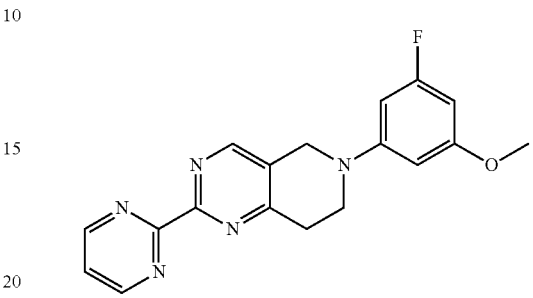

A mixture of 1-(3-fluoro-5-methoxy-phenyl)piperidin-4-one (42.0 g, 0.15 mol) and DMFDMA (400 mL) was heated with stirring at 120° C. for 4 hrs. The resulting reaction mixture was concentrated in vacuo and the residue was dissolved in MeOH (700 mL). To the solution was added pyrimidine-2-carboximidamide hydrochloride (26.2 g, 0.17 mol) and K₂CO₃ (50.3 g, 0.36 mol). The resulting mixture was heated with stirring at 60° C. for 2 hrs, then cooled to rt and filtered. The filtrate was concentrated in vacuo. The residue was diluted with DCM (1.0 L), washed H₂O (200 mL) and brine (200 mL), dried over anhydrous Na₂SO₄ and concentrated in vacuo. The residue was purified by the flash column chromatography to give 6-(3-fluoro-5-methoxy-phenyl)-2-pyrimidin-2-yl-7,8-dihydro-5H-pyrido[4,3-d]pyrimidine (30.8 g) as a light yellow solid. ¹H NMR (400 MHz, CDCl₃): δ 9.03 (d, 2H), 8.79 (s, 1H), 7.37-7.48 (m, 1H), 6.27-6.38 (m, 2H), 6.17 (dt, 1H), 4.48 (s, 2H), 3.79 (s, 3H), 3.69 (t, 2H), 3.32 (t, 2H). MS obsd. (ESI⁺) [(M+H)⁺]: 338.

Example 118: 6-[3-fluoro-5-(trifluoromethoxy)phenyl]-2-pyrimidin-2-yl-7,8-dihydro-5H-pyrido[4,3-d]pyrimidine

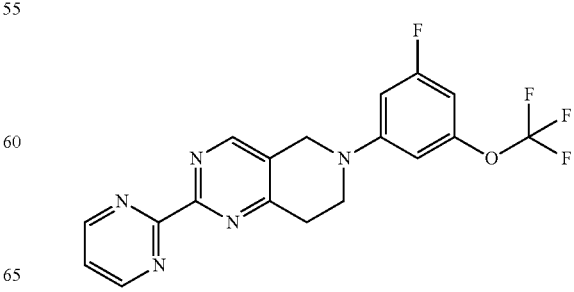

Step 1: Preparation of 1-bromo-3-fluoro-5-(trifluoromethoxy)benzene

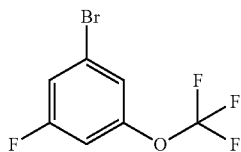

A mixture of 3-fluoro-5-(trifluoromethoxy)aniline (4.0 g, 20.5 mmol) in H₂SO₄ (90 mL, 30%) was cooled to 0° C. and to the mixture was added NaNO₂ (2.83 g, 41.0 mmol). After being stirred at 0° C. for 0.5 hr, the resulting mixture was added slowly to a solution of CuBr (5.86 g, 41.0 mmol), CuBr₂ (9.14 g, 41.0 mmol) in HBr (50 mL). The resulting mixture was stirred at 10° C. for 16 hrs, then diluted with EA (200 mL), washed with water (50 mL) and brine (50 mL), dried over anhydrous Na₂SO₄ and concentrated in vacuo to give crude 1-bromo-3-fluoro-5-(trifluoromethoxy)benzene (2.9 g), which was used directly in the next step without any further purification.

Step 2: Preparation of 8-[3-fluoro-5-(trifluoromethoxy)phenyl]-1,4-dioxa-8-azaspiro[4.5]decane

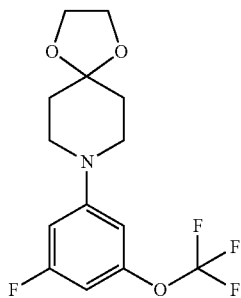

A mixture of 1-bromo-3-fluoro-5-(trifluoromethoxy)benzene (2.9 g, 16.2 mmol), 1,4-dioxa-8-azaspiro[4.5]decane hydrochloride (4.24 g, 16.4 mmol), tert-BuONa (3.89 g, 40.5 mmol), Ruphos (120 mg) and Pd₂dba₃ (80 mg) in dioxane (50 mL) was heated with stirring at 100° C. under nitrogen for 16 hrs. The resulting mixture was concentrated in vacuo. The residue was diluted with EA (200 mL), washed with water (50 mL) and brine (50 mL), dried over anhydrous Na₂SO₄ and concentrated in vacuo. The residue was purified by flash column to give 8-[3-fluoro-5-(trifluoromethoxy)phenyl]-1,4-dioxa-8-azaspiro[4.5]decane (1.6 g) as a yellow oil.

Step 3: Preparation of 1-[3-fluoro-5-(trifluoromethoxy)phenyl]piperidin-4-one

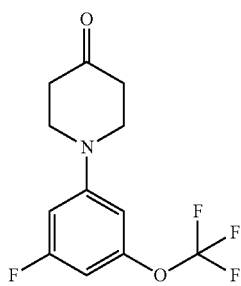

A mixture of 8-[3-fluoro-5-(trifluoromethoxy)phenyl]-1,4-dioxa-8-azaspiro[4.5]decane (1.6 g, 5.0 mol) in formic acid (15 mL) and H₂O (15 mL) was heated with stirring at 90° C. for 2 hrs. The resulting mixture was concentrated in vacuo. The residue was diluted with DCM (100 mL), then washed with water (30 mL) and brine (30 mL), dried over anhydrous Na₂SO₄ and concentrated in vacuo. The residue was purified by flash column to give 1-[3-fluoro-5-(trifluoromethoxy)phenyl]piperidin-4-one (930 mg) as a yellow oil.

Step 4: Preparation of 6-[3-fluoro-5-(trifluoromethoxy)phenyl]-2-pyrimidin-2-yl-7,8-dihydro-5H-pyrido[4,3-d]pyrimidine

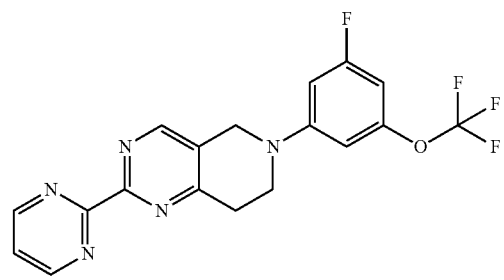 [SMILES: Fc1cc(OC(F)(F)F)cc(N2CCc3nc(-c4ncccn4)ncc3C2)c1]

A mixture of 1-[3-fluoro-5-(trifluoromethoxy)phenyl]piperidin-4-one (830 mg. 3.00 mmol) in DMFDMA (10 mL) was heated with stirring at 100° C. for 4 hrs. The resulting mixture was concentrated in vacuo. The residue was dissolved in MeOH (10 mL) and to the solution was added 2-amidinopyrimidine hydrochloride (500 mg, 3.15 mmol) and K₂CO₃ (911 mg, 6.6 mmol). The resulting mixture was heated with stirring at 60° C. for 2 hrs and concentrated in vacuo. The residue was diluted with DCM (100 mL), washed with H₂O (30 mL) and brine (30 mL), dried over anhydrous Na₂SO₄ and concentrated in vacuo. The residue was purified by flash column to give 6-[3-fluoro-5-(trifluoromethoxy)phenyl]-2-pyrimidin-2-yl-7,8-dihydro-5H-pyrido[4,3-d]pyrimidine (800 mg, yield: 68.4%) as a light yellow solid. ¹H NMR (400 MHz, CDCl₃): δ 9.05 (d, 2H), 8.79 (s, 1H), 7.45 (t, 1H), 7.11 (dd, 1H), 6.79-6.97 (m, 2H), 4.43 (s, 2H), 3.54-3.68 (m, 2H), 3.38 (t, 2H). MS obsd (ESI) [(M+H)⁺]: 392.

Example 119: 2-(2-pyrimidin-2-yl-7,8-dihydro-5H-pyrido[4,3-d]pyrimidin-6-yl)thiazole

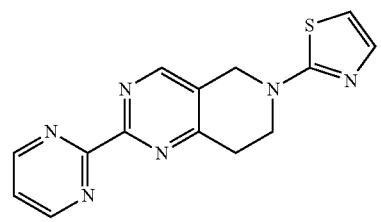 [SMILES: c1cnc(-c2ncc3c(n2)CCN(c2nccs2)C3)nc1]

Step 1: Preparation of 1-thiazol-2-ylpiperidin-4-ol

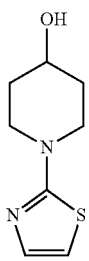

To a solution of 2-bromothiazole (10.0 g, 60.97 mmol) in THF (100 mL) was added N,N-diisopropylethylamine (17.3 g, 134.2 mmol) and 4-hydroxypiperidine (9.3 g, 91.45 mmol). The resulting mixture was heated with stirring at 80° C. for 16 hrs. The reaction mixture was dissolved in EA (300 mL), washed with water (100 mL) and brine (100 mL), dried over anhydrous $Na_2SO_4$ and concentrated in vacuo. The residue was purified by column chromatography to give 1-thiazol-2-ylpiperidin-4-ol (2.3 g) as a yellow oil.

Step 2: Preparation of 1-thiazol-2-ylpiperidin-4-one

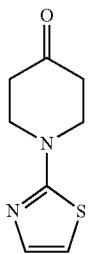

A solution of 1-thiazol-2-ylpiperidin-4-ol (2.10 g, 11.40 mmol) in EA (25 mL) was added 2-iodylbenzoic acid (3.51 g, 12.54 mmol). After being heated with stirring at 80° C. for 16 hrs, the resulting mixture was diluted with EA (500 mL), washed with saturated aqueous solution of $Na_2SO_3$ (200 mL) and brine (200 mL), dried over anhydrous $Na_2SO_4$ and concentrated in vacuo. The residue was purified by column chromatography to give 1-thiazol-2-ylpiperidin-4-one (450 mg) as a yellow oil.

Step 3: Preparation of 2-(2-pyrimidin-2-yl-7,8-dihydro-5H-pyrido[4,3-d]pyrimidin-6-yl)thiazole

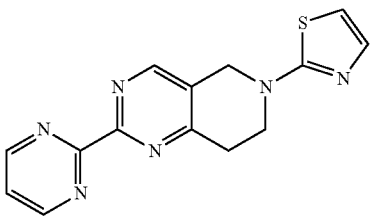 [SMILES: c1cnc(-c2ncc3c(n2)CCN(c2nccs2)C3)nc1]

A mixture of 1-thiazol-2-ylpiperidin-4-one (450 mg, 2.47 mmol) and DMFDMA (5 mL) was heated with stirring at 120° C. for 4 hrs. The resulting mixture was concentrated in vacuo. The residue was dissolved in MeOH (8 mL) and to the solution was added $K_2CO_3$ (705 mg, 5.060 mmol) and pyrimidine-2-carboximidamide hydrochloride (368 mg, 2.318 mmol). The resulting mixture was heated with stirring at 70° C. for 2 hrs and then concentrated in vacuo. The residue was purified by prep-HPLC to give 2-(2-pyrimidin-2-yl-7,8-dihydro-5H-pyrido[4,3-d]pyrimidin-6-yl)thiazole (33 mg) as a pale yellow solid. $^1H$ NMR (400 MHz, DMSO-d6): δ 8.99 (d, 2H), 8.90 (s, 1H), 7.64 (t, 1H), 7.23 (d, 1H), 6.93 (d, 1H), 4.77 (s, 2H), 3.91 (t, 2H), 3.13 (t, 2H). MS obsd. (ESI$^+$) [(M+H)$^+$]: 297.

BIOLOGICAL EXAMPLES

Example 120 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 µL/well culture supernatant was used and HBsAg was quantified using HBsAg chemiluminescence immunoassay (CLIA) kit (Autobio Diagnostics Co., Zhengzhou, China, Catalog number: CL0310-2), 50 µL of the supernatant was transferred to the CLIA assay plate and 50 µL of enzyme conjugate reagent was added into each well. The plates were sealed and gently agitated for 1 hour at room temperature. The supernatant-enzyme-mixture was discarded and wells were washed 6 times with 300 µL of PBS. The residual liquid was removed by plating the CLIA plate right side down on absorbent tissue paper. 25 µL of substrates A and B were added to each well. Luminance was measured using a luminometer (Mithras LB 940 Multimode Microplate Reader) after 10 minutes incubation. Dose-response curves were generated and the IC$_{50}$ value was extrapolated by using the E-WorkBook Suite (ID Business Solutions Ltd., Guildford, UK). The IC$_{50}$ was defined as the compound concentration (or conditioned media log dilution) at which HBsAg secretion was reduced by 50% compared to the no drug control.

The compounds according to formula I were tested for their capacity to inhibit HBsAg as described herein. The Examples were tested in the above assay and found to have IC$_{50}$ below 50 µM. Particular compounds of formula I were found to have IC$_{50}$ below 0.50 µM. Results of HBsAg assay are given in Table 1.

Results of HBsAg assay are given in Table 1.

TABLE 1

Activity data of examples in HBsAg assay

| Example No. | IC$_{50}$ (µM) |
|---|---|
| 1 | 4.243 |
| 2 | 10.168 |
| 3 | 9.223 |
| 4 | 17.824 |
| 5 | 42.101 |
| 6 | 18.786 |
| 7 | 5.17 |

TABLE 1-continued

Activity data of examples in HBsAg assay

| Example No. | IC$_{50}$ (µM) |
|---|---|
| 8 | 4.176 |
| 9 | 16.859 |
| 10 | 2.687 |
| 11 | 17.411 |
| 12 | 13.323 |
| 13 | 1.042 |
| 14 | 9.51 |
| 15 | 9.229 |
| 16 | 13.675 |
| 17 | 0.154 |
| 18 | 22.001 |
| 19 | 0.461 |
| 20 | 2.837 |
| 21 | 0.321 |
| 22 | 0.75 |
| 23 | 0.549 |
| 24 | 1.863 |
| 25 | 16.01 |
| 26 | 0.061 |
| 27 | 3.163 |
| 28 | 0.455 |
| 29 | 4.164 |
| 30 | 9.486 |
| 31 | 16.921 |
| 32 | 9.75 |
| 33 | 0.39 |
| 34 | 0.874 |
| 35 | 8.215 |
| 36 | 1.535 |
| 37 | 4.451 |
| 38 | 17.682 |
| 39 | 9.115 |
| 40 | 0.669 |
| 41 | 0.5 |
| 42 | 0.566 |
| 43 | 1.858 |
| 44 | 18.932 |
| 45 | 3.228 |
| 46 | 8.787 |
| 47 | 11.395 |
| 48 | 1.375 |
| 49 | 1.073 |
| 50 | 21.863 |
| 51 | 5.355 |
| 52 | 1.972 |
| 53 | 1.56 |
| 54 | 3.911 |
| 55 | 1.175 |
| 56 | 1.837 |
| 57 | 2.17 |
| 58 | 20.249 |
| 59 | 9.058 |
| 60 | 0.371 |
| 61 | 3.026 |
| 62 | 1.341 |
| 63 | 1.935 |
| 64 | 1.819 |
| 65 | 18.413 |
| 66 | 13.23 |
| 67 | 7.795 |
| 68 | 1.466 |
| 69 | 0.999 |
| 70 | 1.55 |
| 71 | 0.33 |
| 72 | 1.427 |
| 73 | 1.958 |
| 74 | 2.094 |
| 75 | 2.016 |
| 76 | 1.513 |
| 77 | 0.265 |
| 78 | 19.05 |
| 79 | 0.288 |
| 80 | 5.943 |
| 81 | 11.258 |
| 82 | 3.352 |
| 83 | 20.013 |
| 84 | 8.559 |
| 85 | 8.29 |
| 86 | 22.098 |
| 87 | 10.257 |
| 88 | 26.369 |
| 89 | 6.717 |
| 90 | 0.933 |
| 91 | 0.198 |
| 92 | 2.888 |
| 93 | 0.314 |
| 94 | 0.66 |
| 95 | 0.061 |
| 96 | 0.162 |
| 97 | 16.425 |
| 98 | 0.268 |
| 99 | 0.1 |
| 100 | 0.278 |
| 101 | 0.674 |
| 102 | 11.92 |
| 103 | 2.769 |
| 104 | 1.244 |
| 105 | 18.06 |
| 106 | 1.342 |
| 107 | 7.122 |
| 108 | 0.263 |
| 109 | 4.086 |
| 110 | 1.437 |
| 111 | 0.362 |
| 112 | 0.553 |
| 113 | 0.161 |
| 114 | 1.166 |
| 115 | 0.352 |
| 116 | 0.53 |
| 117 | 0.157 |
| 118 | 4.981 |
| 119 | 6.076 |

HBV DNA Assay

The assay employs real-time qPCR (TaqMan) to directly measure extracellular HBV DNA copy number. HepG2.2.15 cells were plated in 96-well microtiter plates. Only the interior wells were utilized to reduce "edge effects" observed during cell culture, the exterior wells were filled with complete medium to help minimize sample evaporation. On the following day, the HepG2.2.15 cells were washed and the medium was replaced with complete medium containing various concentrations of a test compound in triplicate. 3TC was used as the positive control, while media alone was added to cells as a negative control (virus control, VC). Three days later, the culture medium was replaced with fresh medium containing the appropriately diluted drug. Six days following the initial administration of the test compound, the cell culture supernatant was collected, treated with pronase and then used in a real-time qPCR/TaqMan assay to determine HBV DNA copy numbers. Antiviral activity was calculated from the reduction in HBV DNA levels (IC$_{50}$).

The compounds of the present invention were tested for their capacity to inhibit HBV DNA as described herein. The Examples were tested in the above assay and found to have $IC_{50}$ below 50 μM.

Results of HBV DNA assay are given in Table 2.

TABLE 2

| Anti HBV DNA production activity in HepG2.2.15 cells | |
| --- | --- |
| Example No. | $IC_{50}$ (μM) |
| 80 | 0.16 |

The invention claimed is:

1. A method for the treatment or prophylaxis of HBV infection, which method comprises administering an effective amount of a compound of formula I

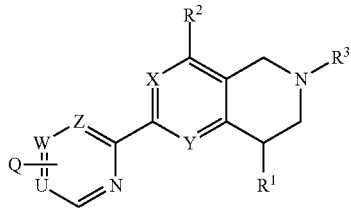

(I)

wherein
- $R^1$ is hydrogen, $C_{1-6}$alkyl, or halo$C_{1-6}$alkyl;
- $R^2$ is $C_{1-6}$alkyl, $C_{2-6}$alkenyl, $C_{1-6}$alkoxy, hydrogen, hydroxy, halo$C_{1-6}$alkyl, phenyl$C_{1-6}$alkoxy, amino, $C_{1-6}$alkylamino, or di$C_{1-6}$alkylamino;
- $R^3$ is phenyl; phenyl substituted by one, two, or three substituents independently selected from $C_{1-6}$alkyl, $C_{3-7}$cycloalkyl, halogen, halo$C_{1-6}$alkyl, cyano, nitro, —C(=O)OR$^4$, —OR$^5$, —SO$_2$R$^6$, and —C(=O)NR$^7$R$^8$; thiophenyl; thiophenyl substituted by one, two, or three substituents independently selected from $C_{1-6}$alkyl, $C_{1-6}$alkyoxy, and halogen; furanyl; furanyl substituted by one, two, or three substituents independently selected from $C_{1-6}$alky, $C_{1-6}$alkyoxy, and halogen; N-containing heteroaryl; or N-containing heteroaryl substituted with one, two, or three substituents independently selected from $C_{1-6}$alky, $C_{1-6}$alkyoxy, halogen, halo$C_{1-6}$alkyl, cyano, nitro, —C(=O)OR$^4$, —OR$^5$, and —SO$_2$R$^6$; wherein,
- $R^4$ is hydrogen or $C_{1-6}$alkyl;
- $R^5$ is hydrogen, $C_{1-6}$alkyl, halo$C_{1-6}$alkyl, hydroxy$C_{1-6}$alkyl, $C_{1-6}$alkoxy$C_{1-6}$alkyl, or phenyl$C_{1-6}$alkyl;
- $R^6$ is $C_{1-6}$alkyl, halo$C_{1-6}$alkyl, amino, $C_{1-6}$alkyamino, or di$C_{1-6}$alkyamino;
- $R^7$ and $R^8$ are independently selected from hydrogen, $C_{1-6}$alkyl, halo$C_{1-6}$alkyl, hydroxy$C_{1-6}$alkyl, and $C_{1-6}$alkoxy$C_{1-6}$alkyl;
- Q is hydrogen, $C_{1-6}$alkyl, $C_{1-6}$alkoxy, halogen, or halo$C_{1-6}$alkyl;
- U and W, are C;
- Z is C or N; and
- X and Y are N;
- or a pharmaceutically acceptable salt or enantiomer thereof.

2. A compound of formula I,

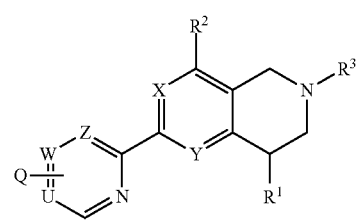

(I)

wherein
- $R^1$ is hydrogen, $C_{1-6}$alkyl, or halo$C_{1-6}$alkyl;
- $R^2$ is $C_{1-6}$alkyl, $C_{2-6}$alkenyl, $C_{1-6}$alkoxy, hydrogen, hydroxy, halo$C_{1-6}$alkyl, phenyl$C_{1-6}$alkoxy, amino, $C_{1-6}$alkylamino, or di$C_{1-6}$alkylamino;
- $R^3$ is phenyl; phenyl substituted by one, two, or three substituents independently selected from $C_{1-6}$alkyl, $C_{3-7}$cycloalkyl, halogen, halo$C_{1-6}$alkyl, cyano, nitro, —C(=O)OR$^4$, —OR$^5$, —SO$_2$R$^6$, and —C(=O)NR$^7$R$^8$; thiophenyl; thiophenyl substituted by one, two, or three substituents independently selected from $C_{1-6}$alkyl, $C_{1-6}$alkyoxy, and halogen; furanyl; furanyl substituted by one, two, or three substituents independently selected from $C_{1-6}$alky, $C_{1-6}$alkyoxy, and halogen; N-containing heteroaryl; or N-containing heteroaryl substituted with one, two, or three substituents independently selected from $C_{1-6}$alky, $C_{1-6}$alkyoxy, halogen, halo$C_{1-6}$alkyl, cyano, nitro, —C(=O)OR$^4$, —OR$^5$, and —SO$_2$R$^6$; wherein,
- $R^4$ is hydrogen or $C_{1-6}$alkyl;
- $R^5$ is hydrogen, $C_{1-6}$alkyl, halo$C_{1-6}$alkyl, hydroxy$C_{1-6}$alkyl, $C_{1-6}$alkoxy$C_{1-6}$alkyl, or phenyl$C_{1-6}$alkyl;
- $R^6$ is $C_{1-6}$alkyl, halo$C_{1-6}$alkyl, amino, $C_{1-6}$alkyamino, or di$C_{1-6}$alkyamino;
- $R^7$ and $R^8$ are independently selected from hydrogen, $C_{1-6}$alkyl, halo$C_{1-6}$alkyl, hydroxy$C_{1-6}$alkyl, and $C_{1-6}$alkoxy$C_{1-6}$alkyl;
- Q is hydrogen, $C_{1-6}$alkyl, $C_{1-6}$alkoxy, halogen, or halo$C_{1-6}$alkyl;
- U and W, are C;
- Z is C or N; and
- X and Y are N;
- with the proviso that 6-(4-nitrophenyl)-2-(2-pyridyl)-7,8-dihydro-5H-pyrido[4,3-d]pyrimidine is excluded;
- or a pharmaceutically acceptable salt or enantiomer thereof.

3. A compound according to claim 2, or a pharmaceutically acceptable salt or enantiomer thereof, wherein $R^1$ is hydrogen, $R^2$ is hydrogen, and Q is hydrogen.

4. A compound according to claim 2, or a pharmaceutically acceptable salt or enantiomer thereof, wherein $R^3$ is phenyl substituted by one, two, or three substituents independently selected from halogen, cyano, nitro, carboxy, —OR$^5$, and —SO$_2$R$^6$, wherein $R^5$ is $C_{1-6}$alkyl, halo$C_{1-6}$alkyl, hydroxy$C_{1-6}$alkyl, $C_{1-6}$alkoxy$C_{1-6}$alkyl, or phenyl$C_{1-6}$alkyl, and $R^6$ is $C_{1-6}$alkyl; or pyridinyl substituted by one or two substituents independently selected from halogen and $C_{1-6}$alkoxy.

5. A compound according to claim 2, or a pharmaceutically acceptable salt or enantiomer thereof, wherein $R^3$ is phenyl substituted by one, two, or three substituents independently selected from fluoro, chloro, cyano, nitro, carboxy, methoxy, ethoxy, propoxy, difluoromethoxy, trifluoromethoxy, hydroxyethoxy, hydroxypropoxy, methoxyethoxy, methoxypropoxy, benzyloxy, and methylsulfonyl; or pyridinyl substituted by one or two substituents independently selected from fluoro, chloro, and methoxy.

6. A compound according to claim 2 wherein
$R^1$ is hydrogen;
$R^2$ is hydrogen;
$R^3$ is phenyl substituted by one, two, or three substituents independently selected from halogen, cyano and —$OR^5$, wherein $R^5$ is $C_{1-6}$alkyl, hydroxy$C_{1-6}$alkyl, or $C_{1-6}$alkoxy$C_{1-6}$alkyl; or pyridinyl substituted by one or two substituents independently selected from halogen and $C_{1-6}$alkoxy;
Q is hydrogen;
U is C;
W is C;
Z is N or C;
X is N;
Y is N;
or a pharmaceutically acceptable salt or enantiomer thereof.

7. A compound according to claim 2, wherein
$R^1$ is hydrogen;
$R^2$ is hydrogen;
$R^3$ is phenyl substituted by one, two, or three substituents independently selected from fluoro, chloro, cyano, methoxy, ethoxy, hydroxypropoxy, and methoxypropoxy; or pyridinyl substituted by one or two substituents independently selected from fluoro, chloro, and methoxy;
Q is hydrogen;
U is C;
W is C;
Z is N or C;
X is N;
Y is N;
or a pharmaceutically acceptable salt or enantiomer thereof.

8. A compound according to claim 2, selected from
6-(4-Methylsulfonylphenyl)-2-(2-pyridyl)-7,8-dihydro-5H-pyrido[4,3-d]pyrimidine;
2-(5-Fluoro-2-pyridyl)-6-(4-methylsulfonylphenyl)-7,8-dihydro-5H-pyrido[4,3-d]pyrimidine;
2-(5-Methyl-2-pyridyl)-6-(4-methylsulfonylphenyl)-7,8-dihydro-5H-pyrido[4,3-d]pyrimidine;
2-(3-Methyl-2-pyridyl)-6-(4-methylsulfonylphenyl)-7,8-dihydro-5H-pyrido[4,3-d]pyrimidine;
2-(5-Methoxy-2-pyridyl)-6-(4-methylsulfonylphenyl)-7,8-dihydro-5H-pyrido[4,3-d]pyrimidine;
2-(5-Chloro-2-pyridyl)-6-(4-methylsulfonylphenyl)-7,8-dihydro-5H-pyrido[4,3-d]pyrimidine;
8-Ethyl-6-(4-methylsulfonylphenyl)-2-(2-pyridyl)-7,8-dihydro-5H-pyrido[4,3-d]pyrimidine;
N-Methyl-4-[2-(2-pyridyl)-7,8-dihydro-5H-pyrido[4,3-d]pyrimidin-6-yl]benzenesulfonamide;
N,N-Dimethyl-4-[2-(2-pyridyl)-7,8-dihydro-5H-pyrido[4,3-d]pyrimidin-6-yl]benzenesulfonamide;
6-(3,4-Difluorophenyl)-2-(2-pyridyl)-7,8-dihydro-5H-pyrido[4,3-d]pyrimidine;
6-(3-Methylsulfonylphenyl)-2-(2-pyridyl)-7,8-dihydro-5H-pyrido[4,3-d]pyrimidine;
2-(2-Pyridyl)-6-[4-(trifluoromethylsulfonyl)phenyl]-7,8-dihydro-5H-pyrido[4,3-d]pyrimidine;
6-(3,5-Difluorophenyl)-2-(2-pyridyl)-7,8-dihydro-5H-pyrido[4,3-d]pyrimidine;
6-(2,4-Difluorophenyl)-2-(2-pyridyl)-7,8-dihydro-5H-pyrido[4,3-d]pyrimidine;
Methyl 2-fluoro-4-[2-(2-pyridyl)-7,8-dihydro-5H-pyrido[4,3-d]pyrimidin-6-yl]benzoate;
Methyl 5-bromo-2-[2-(2-pyridyl)-7,8-dihydro-5H-pyrido[4,3-d]pyrimidin-6-yl]benzoate;
6-(3,4-Difluoro-5-methoxy-phenyl)-2-(2-pyridyl)-7,8-dihydro-5H-pyrido[4,3-d]pyrimidine;
2,3-Difluoro-5-[2-(2-pyridyl)-7,8-dihydro-5H-pyrido[4,3-d]pyrimidin-6-yl]phenol;
6-[3,4-Difluoro-5-(3-methoxypropoxy)phenyl]-2-(2-pyridyl)-7,8-dihydro-5H-pyrido[4,3-d]pyrimidine;
6-(3-Benzyloxy-4,5-difluoro-phenyl)-2-(2-pyridyl)-7,8-dihydro-5H-pyrido[4,3-d]pyrimidine;
6-(3-Ethoxy-4,5-difluoro-phenyl)-2-(2-pyridyl)-7,8-dihydro-5H-pyrido[4,3-d]pyrimidine;
6-(3,4-Difluoro-5-propoxy-phenyl)-2-(2-pyridyl)-7,8-dihydro-5H-pyrido[4,3-d]pyrimidine;
6-[3,4-Difluoro-5-(2-methoxyethoxy)phenyl]-2-(2-pyridyl)-7,8-dihydro-5H-pyrido[4,3-d]pyrimidine;
6-(3,4-Difluoro-5-methoxy-phenyl)-2-(4-methoxy-2-pyridyl)-7,8-dihydro-5H-pyrido[4,3-d]pyrimidine;
6-(3,4-Difluoro-5-methoxy-phenyl)-2-(6-methoxy-2-pyridyl)-7,8-dihydro-5H-pyrido[4,3-d]pyrimidine;
6-(3,4-Difluoro-5-methoxy-phenyl)-2-pyrimidin-2-yl-7,8-dihydro-5H-pyrido[4,3-d]pyrimidine;
6-(4,5-Difluoro-2-methoxy-phenyl)-2-(2-pyridyl)-7,8-dihydro-5H-pyrido[4,3-d]pyrimidine;
6-(3,4-Difluoro-2-methoxy-phenyl)-2-(2-pyridyl)-7,8-dihydro-5H-pyrido[4,3-d]pyrimidine;
Ethyl 4-[2-(2-pyridyl)-7,8-dihydro-5H-pyrido[4,3-d]pyrimidin-6-yl]benzoate;
4-[2-(2-Pyridyl)-7,8-dihydro-5H-pyrido[4,3-d]pyrimidin-6-yl]benzoic acid;
6-(2-Nitrophenyl)-2-(2-pyridyl)-7,8-dihydro-5H-pyrido[4,3-d]pyrimidine;
6-(2-Methoxy-4-nitro-phenyl)-2-(2-pyridyl)-7,8-dihydro-5H-pyrido[4,3-d]pyrimidine;
2,6-Bis(2-pyridyl)-7,8-dihydro-5H-pyrido[4,3-d]pyrimidine;
6-(5-Chloro-2-pyridyl)-2-(2-pyridyl)-7,8-dihydro-5H-pyrido[4,3-d]pyrimidine;
2-(2-Pyridyl)-6-pyrimidin-2-yl-7,8-dihydro-5H-pyrido[4,3-d]pyrimidine;
6-(2-Benzyloxy-4-fluoro-phenyl)-2-(2-pyridyl)-7,8-dihydro-5H-pyrido[4,3-d]pyrimidine;
2-(2-Pyridyl)-6-(3-pyridyl)-7,8-dihydro-5H-pyrido[4,3-d]pyrimidine;
6-(3-Fluoro-5-methyl-phenyl)-2-(2-pyridyl)-7,8-dihydro-5H-pyrido[4,3-d]pyrimidine;
6-(3-Bromo-5-fluoro-phenyl)-2-pyrimidin-2-yl-7,8-dihydro-5H-pyrido[4,3-d]pyrimidine;
6-(3-Cyclopropyl-5-fluoro-phenyl)-2-pyrimidin-2-yl-7,8-dihydro-5H-pyrido[4,3-d]pyrimidine;
2-Pyrimidin-2-yl-6-[3-(trifluoromethoxy)phenyl]-7,8-dihydro-5H-pyrido[4,3-d]pyrimidine;
6-[3-Methoxy-4-(3-methoxypropoxy)phenyl]-2-(2-pyridyl)-7,8-dihydro-5H-pyrido[4,3-d]pyrimidine;
6-(4-Chlorophenyl)-2-(2-pyridyl)-7,8-dihydro-5H-pyrido[4,3-d]pyrimidine;
6-(4-Benzyloxyphenyl)-2-(2-pyridyl)-7,8-dihydro-5H-pyrido[4,3-d]pyrimidine;
6-(p-Tolyl)-2-(2-pyridyl)-7,8-dihydro-5H-pyrido[4,3-d]pyrimidine;
8-Methyl-6-(4-nitrophenyl)-2-(2-pyridyl)-7,8-dihydro-5H-pyrido[4,3-d]pyrimidine;

6-(3,4-Dichlorophenyl)-2-(2-pyridyl)-7,8-dihydro-5H-pyrido[4,3-d]pyrimidine;
6-(4-Methoxyphenyl)-2-(2-pyridyl)-7,8-dihydro-5H-pyrido[4,3-d]pyrimidine;
6-(3-Bromo-4-fluoro-phenyl)-2-(2-pyridyl)-7,8-dihydro-5H-pyrido[4,3-d]pyrimidine;
6-(4-Bromo-3-fluoro-phenyl)-2-(2-pyridyl)-7,8-dihydro-5H-pyrido[4,3-d]pyrimidine;
6-(4-Benzyloxy-3-fluoro-phenyl)-2-(2-pyridyl)-7,8-dihydro-5H-pyrido[4,3-d]pyrimidine;
6-(4-Ethoxy-3-fluoro-phenyl)-2-(2-pyridyl)-7,8-dihydro-5H-pyrido[4,3-d]pyrimidine;
6-(3-Fluoro-4-propoxy-phenyl)-2-(2-pyridyl)-7,8-dihydro-5H-pyrido[4,3-d]pyrimidine;
6-[3-Fluoro-4-(3-methoxypropoxy)phenyl]-2-(2-pyridyl)-7,8-dihydro-5H-pyrido[4,3-d]pyrimidine;
6-[3-Methoxy-4-(2-methoxyethoxy)phenyl]-2-(2-pyridyl)-7,8-dihydro-5H-pyrido[4,3-d]pyrimidine;
6-[4-Methoxy-3-(2-methoxyethoxy)phenyl]-2-(2-pyridyl)-7,8-dihydro-5H-pyrido[4,3-d]pyrimidine;
6-(3,4-Dimethoxyphenyl)-2-(2-pyridyl)-7,8-dihydro-5H-pyrido[4,3-d]pyrimidine;
2-Methoxy-4-[2-(2-pyridyl)-7,8-dihydro-5H-pyrido[4,3-d]pyrimidin-6-yl]benzonitrile;
6-(2,3-Difluoro-4-methoxy-phenyl)-2-pyrimidin-2-yl-7,8-dihydro-5H-pyrido[4,3-d]pyrimidine;
6-(4-Chloro-3-methoxy-phenyl)-2-(2-pyridyl)-7,8-dihydro-5H-pyrido[4,3-d]pyrimidine;
6-[3-(Difluoromethoxy)phenyl]-2-pyrimidin-2-yl-7,8-dihydro-5H-pyrido[4,3-d]pyrimidine;
6-(4-Benzyloxy-3,5-difluoro-phenyl)-2-(2-pyridyl)-7,8-dihydro-5H-pyrido[4,3-d]pyrimidine;
2-Methoxy-4-[2-(2-pyridyl)-7,8-dihydro-5H-pyrido[4,3-d]pyrimidin-6-yl]benzoic acid;
2-Ethoxy-4-[2-(2-pyridyl)-7,8-dihydro-5H-pyrido[4,3-d]pyrimidin-6-yl]benzoic acid;
2-Butoxy-4-[2-(2-pyridyl)-7,8-dihydro-5H-pyrido[4,3-d]pyrimidin-6-yl]benzoic acid;
6-(5-Chloro-4-methoxy-pyrimidin-2-yl)-2-(2-pyridyl)-7,8-dihydro-5H-pyrido[4,3-d]pyrimidine;
6-(5-Chloro-2-methoxy-pyrimidin-4-yl)-2-(2-pyridyl)-7,8-dihydro-5H-pyrido[4,3-d]pyrimidine;
6-(3-Fluoro-4-methoxy-2-pyridyl)-2-(2-pyridyl)-7,8-dihydro-5H-pyrido[4,3-d]pyrimidine;
6-(5-Fluoro-4-methoxy-2-pyridyl)-2-(2-pyridyl)-7,8-dihydro-5H-pyrido[4,3-d]pyrimidine;
6-(5-Fluoro-6-methoxy-2-pyridyl)-2-pyrimidin-2-yl-7,8-dihydro-5H-pyrido[4,3-d]pyrimidine;
6-(3,5-Dimethoxyphenyl)-2-pyrimidin-2-yl-7,8-dihydro-5H-pyrido[4,3-d]pyrimidine;
6-(8-Methoxy-3-isoquinolyl)-2-pyrimidin-2-yl-7,8-dihydro-5H-pyrido[4,3-d]pyrimidine;
6-(2-Methoxy-7-quinolyl)-2-pyrimidin-2-yl-7,8-dihydro-5H-pyrido[4,3-d]pyrimidine;
3-Methoxy-5-(2-pyrimidin-2-yl-7,8-dihydro-5H-pyrido[4,3-d]pyrimidin-6-yl)benzonitrile;
2-Fluoro-6-methoxy-4-(2-pyrimidin-2-yl-7,8-dihydro-5H-pyrido[4,3-d]pyrimidin-6-yl)benzonitrile;
6-(4-Chloro-3-fluoro-5-methoxy-phenyl)-2-pyrimidin-2-yl-7,8-dihydro-5H-pyrido[4,3-d]pyrimidine;
6-(3-Chloro-4-fluoro-5-methoxy-phenyl)-2-pyrimidin-2-yl-7,8-dihydro-5H-pyrido[4,3-d]pyrimidine;
6-(4-Methylsulfonylphenyl)-2-(2-pyridyl)-3,5,7,8-tetrahydropyrido[4,3-d]pyrimidin-4-one;
4-Methoxy-6-(4-methylsulfonylphenyl)-2-pyrimidin-2-yl-7,8-dihydro-5H-pyrido[4,3-d]pyrimidine;
4-Ethoxy-6-(4-methylsulfonylphenyl)-2-pyrimidin-2-yl-7,8-dihydro-5H-pyrido[4,3-d]pyrimidine;
4-Benzyloxy-6-(4-methylsulfonylphenyl)-2-pyrimidin-2-yl-7,8-dihydro-5H-pyrido[4,3-d]pyrimidine;
6-(4-Methylsulfonylphenyl)-4-[(E)-prop-1-enyl]-2-pyrimidin-2-yl-7,8-dihydro-5H-pyrido[4,3-d]pyrimidine;
6-(4-Methylsulfonylphenyl)-4-propyl-2-pyrimidin-2-yl-7,8-dihydro-5H-pyrido[4,3-d]pyrimidine;
4-Ethyl-6-(4-methylsulfonylphenyl)-2-pyrimidin-2-yl-7,8-dihydro-5H-pyrido[4,3-d]pyrimidine;
4-Methyl-6-(4-methylsulfonylphenyl)-2-pyrimidin-2-yl-7,8-dihydro-5H-pyrido[4,3-d]pyrimidine;
N-Methyl-6-(4-methylsulfonylphenyl)-2-pyrimidin-2-yl-7,8-dihydro-5H-pyrido[4,3-d]pyrimidin-4-amine;
6-(4-Methylsulfonylphenyl)-2-(2-pyridyl)-7,8-dihydro-5H-1,6-naphthyridine;
6-(4-Fluoro-3-methoxy-phenyl)-2-(2-pyridyl)-7,8-dihydro-5H-pyrido[4,3-d]pyrimidine;
6-(3-Fluoro-5-methoxy-phenyl)-2-(2-pyridyl)-7,8-dihydro-5H-pyrido[4,3-d]pyrimidine;
6-(3-Methoxyphenyl)-2-(2-pyridyl)-7,8-dihydro-5H-pyrido[4,3-d]pyrimidine;
3-[2,3-Difluoro-5-[2-(2-pyridyl)-7,8-dihydro-5H-pyrido[4,3-d]pyrimidin-6-yl]phenoxy]propan-1-ol;
2-[2,3-Difluoro-5-[2-(2-pyridyl)-7,8-dihydro-5H-pyrido[4,3-d]pyrimidin-6-yl]phenoxy]ethanol;
2-(3,4-Difluoro-5-methoxy-phenyl)-6-pyrimidin-2-yl-3,4-dihydro-1H-2,7-naphthyridine;
2-(3,4-Difluoro-5-methoxy-phenyl)-6-(2-pyridyl)-3,4-dihydro-1H-2,7-naphthyridine;
6-(3,4-Difluoro-5-methoxy-phenyl)-2-pyrimidin-2-yl-7,8-dihydro-5H-1,6-naphthyridine;
6-(3-Chloro-5-methoxy-phenyl)-2-pyrimidin-2-yl-7,8-dihydro-5H-pyrido[4,3-d]pyrimidine;
6-(6-Fluoro-4-methoxy-2-pyridyl)-2-pyrimidin-2-yl-7,8-dihydro-5H-pyrido[4,3-d]pyrimidine;
6-[3-Methoxy-5-(trifluoromethyl)phenyl]-2-pyrimidin-2-yl-7,8-dihydro-5H-pyrido[4,3-d]pyrimidine;
3-Fluoro-5-(2-pyrimidin-2-yl-7,8-dihydro-5H-pyrido[4,3-d]pyrimidin-6-yl)benzonitrile;
Methyl 3-fluoro-5-(2-pyrimidin-2-yl-7,8-dihydro-5H-pyrido[4,3-d]pyrimidin-6-yl)benzoate;
3-Fluoro-N-methyl-5-(2-pyrimidin-2-yl-7,8-dihydro-5H-pyrido[4,3-d]pyrimidin-6-yl)benzamide;
3-Fluoro-5-(2-pyrimidin-2-yl-7,8-dihydro-5H-pyrido[4,3-d]pyrimidin-6-yl)-N-(2,2,2-trifluoroethyl)benzamide;
3-Fluoro-5-(2-pyrimidin-2-yl-7,8-dihydro-5H-pyrido[4,3-d]pyrimidin-6-yl)benzamide;
3-Fluoro-N-(3-methoxypropyl)-5-(2-pyrimidin-2-yl-7,8-dihydro-5H-pyrido[4,3-d]pyrimidin-6-yl)benzamide;
3-Fluoro-N-(5-hydroxypentyl)-5-(2-pyrimidin-2-yl-7,8-dihydro-5H-pyrido[4,3-d]pyrimidin-6-yl)benzamide;
6-(6-Chloro-4-methoxy-2-pyridyl)-2-pyrimidin-2-yl-7,8-dihydro-5H-pyrido[4,3-d]pyrimidine;
6-(4,6-Difluoro-2-pyridyl)-2-pyrimidin-2-yl-7,8-dihydro-5H-pyrido[4,3-d]pyrimidine;
6-(4-Fluoro-6-methoxy-2-pyridyl)-2-pyrimidin-2-yl-7,8-dihydro-5H-pyrido[4,3-d]pyrimidine;
6-(4,6-Dichloro-2-pyridyl)-2-pyrimidin-2-yl-7,8-dihydro-5H-pyrido[4,3-d]pyrimidine;
6-(4-Chloro-6-methoxy-2-pyridyl)-2-pyrimidin-2-yl-7,8-dihydro-5H-pyrido[4,3-d]pyrimidine;
6-(3-Fluoro-5-methoxy-phenyl)-2-pyrimidin-2-yl-7,8-dihydro-5H-pyrido[4,3-d]pyrimidine;
6-[3-Fluoro-5-(trifluoromethoxy)phenyl]-2-pyrimidin-2-yl-7,8-dihydro-5H-pyrido[4,3-d]pyrimidine; and 2-(2-Pyrimidin-2-yl-7,8-dihydro-5H-pyrido[4,3-d]pyrimidin-6-yl)thiazole;

or a pharmaceutically acceptable salt or enantiomer thereof.

9. A compound according to claim 2, selected from 6-(3,4-Difluoro-5-methoxy-phenyl)-2-(2-pyridyl)-7,8-dihydro-5H-pyrido[4,3-d]pyrimidine;

6-[3,4-Difluoro-5-(3-methoxypropoxy)phenyl]-2-(2-pyridyl)-7,8-dihydro-5H-pyrido[4,3-d]pyrimidine;

6-(3-Ethoxy-4,5-difluoro-phenyl)-2-(2-pyridyl)-7,8-dihydro-5H-pyrido[4,3-d]pyrimidine;

6-(3,4-Difluoro-5-methoxy-phenyl)-2-pyrimidin-2-yl-7,8-dihydro-5H-pyrido[4,3-d]pyrimidine;

2-Methoxy-4-[2-(2-pyridyl)-7,8-dihydro-5H-pyrido[4,3-d]pyrimidin-6-yl]benzonitrile;

6-(5-Fluoro-4-methoxy-2-pyridyl)-2-(2-pyridyl)-7,8-dihydro-5H-pyrido[4,3-d]pyrimidine;

2-Fluoro-6-methoxy-4-(2-pyrimidin-2-yl-7,8-dihydro-5H-pyrido[4,3-d]pyrimidin-6-yl)benzonitrile;

6-(3-Chloro-4-fluoro-5-methoxy-phenyl)-2-pyrimidin-2-yl-7,8-dihydro-5H-pyrido[4,3-d]pyrimidine;

6-(3-Fluoro-5-methoxy-phenyl)-2-(2-pyridyl)-7,8-dihydro-5H-pyrido[4,3-d]pyrimidine;

3-[2,3-Difluoro-5-[2-(2-pyridyl)-7,8-dihydro-5H-pyrido[4,3-d]pyrimidin-6-yl]phenoxy]propan-1-ol;

2-(3,4-Difluoro-5-methoxy-phenyl)-6-pyrimidin-2-yl-3,4-dihydro-1H-2,7-naphthyridine;

2-(3,4-Difluoro-5-methoxy-phenyl)-6-(2-pyridyl)-3,4-dihydro-1H-2,7-naphthyridine;

6-(3-Chloro-5-methoxy-phenyl)-2-pyrimidin-2-yl-7,8-dihydro-5H-pyrido[4,3-d]pyrimidine;

6-(6-Fluoro-4-methoxy-2-pyridyl)-2-pyrimidin-2-yl-7,8-dihydro-5H-pyrido[4,3-d]pyrimidine;

6-(6-Chloro-4-methoxy-2-pyridyl)-2-pyrimidin-2-yl-7,8-dihydro-5H-pyrido[4,3-d]pyrimidine;

6-(4,6-Dichloro-2-pyridyl)-2-pyrimidin-2-yl-7,8-dihydro-5H-pyrido[4,3-d]pyrimidine; and 6-(3-Fluoro-5-methoxy-phenyl)-2-pyrimidin-2-yl-7,8-dihydro-5H-pyrido[4,3-d]pyrimidine;

or a pharmaceutically acceptable salt or enantiomer thereof.

10. A pharmaceutical composition comprising a compound according to claim 2, or a pharmaceutically acceptable salt or enantiomer thereof and a therapeutically inert carrier.

11. A method for the treatment or prophylaxis of HBV infection, which method comprises administering an effective amount of a compound according to claim 2, or a pharmaceutically acceptable salt or enantiomer thereof.

12. A process for the preparation of a compound according to claim 2, or a pharmaceutically acceptable salt or enantiomer thereof, comprising cyclization of a compound of formula (A) with a compound of formula (B) to afford a compound of formula (J)

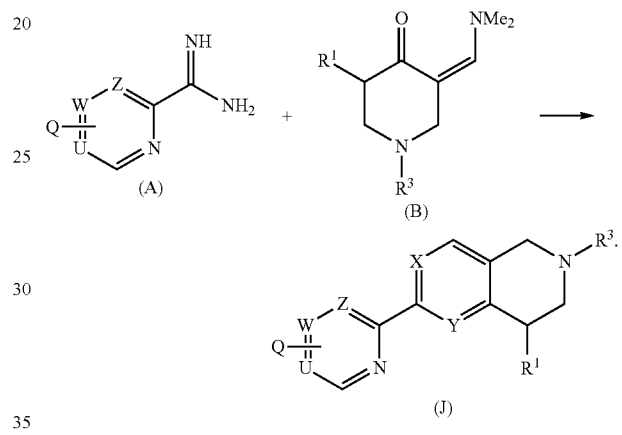

* * * * *